(12) United States Patent
Comer et al.

(10) Patent No.: US 12,065,496 B2
(45) Date of Patent: Aug. 20, 2024

(54) ANTIBODY MOLECULES AND CONJUGATES

(71) Applicant: ASTRAZENECA AB, Södertälje (SE)

(72) Inventors: Frank Irvine Comer, Gaithersburg, MD (US); Yariv Mazor, Gaithersburg, MD (US); Srinath Kasturirangan, Gaithersburg, MD (US); Qun Du, Gaithersburg, MD (US); Chunning Yang, Gaithersburg, MD (US); Andrew Grier Buchanan, Cambridge (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 18/053,955

(22) Filed: Nov. 9, 2022

(65) Prior Publication Data

US 2023/0183358 A1 Jun. 15, 2023

Related U.S. Application Data

(60) Provisional application No. 63/263,835, filed on Nov. 10, 2021.

(51) Int. Cl.
| | |
|---|---|
| *C07K 16/28* | (2006.01) |
| *A61K 47/68* | (2017.01) |
| *A61P 1/18* | (2006.01) |
| *A61P 35/00* | (2006.01) |
| *A61K 39/00* | (2006.01) |

(52) U.S. Cl.
CPC .... *C07K 16/2863* (2013.01); *A61K 47/68037* (2023.08); *A61K 47/6849* (2017.08); *A61P 1/18* (2018.01); *A61P 35/00* (2018.01); *A61K 2039/505* (2013.01); *C07K 2317/31* (2013.01); *C07K 2317/33* (2013.01); *C07K 2317/35* (2013.01); *C07K 2317/52* (2013.01); *C07K 2317/565* (2013.01); *C07K 2317/77* (2013.01); *C07K 2317/92* (2013.01)

(58) Field of Classification Search
None
See application file for complete search history.

(56) References Cited

U.S. PATENT DOCUMENTS

2020/0231681 A1    7/2020  Moon et al.

FOREIGN PATENT DOCUMENTS

| WO | 2012/019123 A1 | 2/2012 |
| WO | 2015/016559 A1 | 2/2015 |
| WO | 2015/157594 A1 | 10/2015 |
| WO | 2017/076492 A1 | 5/2017 |

OTHER PUBLICATIONS

Culang et al. The structural basis of antibody-antigen recognition. Front. Immunol., Oct. 8, 2013. Sec. B Cell Biology. vol. 4—2013. https://doi.org/10.3389/fimmu.2013.00302.) (Year: 2013).*

(Continued)

*Primary Examiner* — Daniel E Kolker
*Assistant Examiner* — Hilary Ann Petrash

(57) ABSTRACT

The present disclosure relates to antibody molecules that bind epidermal growth factor receptor (EGFR) and/or c-Met and conjugates containing these antibody molecules. The antibody molecules and conjugates find application in the treatment of cancer, for example.

27 Claims, 29 Drawing Sheets

Specification includes a Sequence Listing.

(56) References Cited

OTHER PUBLICATIONS

Westphal, M., Maire, C.L. & Lamszus, K. EGFR as a Target for Glioblastoma Treatment: An Unfulfilled Promise. CNS Drugs 31, 723-735 (2017). https://doi.org/10.1007/s40263-017-0456-6 (Year: 2017).*
American Lung Association. EGFR and Lung Cancer. Last updated: Nov. 17, 2022. Accessed Dec. 7, 2023. https://www.lung.org/lung-health-diseases/lung-disease-lookup/lung-cancer/symptoms-diagnosis/biomarker-testing/egfr. (Year: 2022).*
Sellmann et al. BalancingSelectivity and Efficacy of Bispecific Epidermal Growth Factor Receptor (EGFR) x c-MET Antibodies and Antibody-Drug Conjugates. Immunology| vol. 291, Issue 48, p. 25106-25119, Nov. 2016. https://doi.org/10.1074/jbc.M116.753491 (Year: 2016).*
Majeed et al. Targeted therapy in advanced non-small cell lung cancer: current advances and future trends. J Hematol Oncol. Jul. 8, 2021;14(1):108. doi: 10.1186/s13045-021-01121-2. PMID: 34238332; PMCID: PMC8264982 (Year: 2021).*
Altschul S.F. et al., "Basic local alignment search tool"., Journal of Molecular Biology, 1990, 215(3):403-10.
Altschul S.F. et al., "Gapped BLAST and PSI-BLAST: a new generation of protein database search programs", Nucleic Acids Research, 1997, 25 3389-3402.
Andreev, J., et al., "Bispecific Antibodies and Antibody-Drug Conjugates (ADCs) Bridging HER2 and Prolactin Receptor Improve Efficacy of HER2 ADCs", Molecular Cancer Therapeutics, 2017, 16(4): 681-693.
Angevin, E., et al., "Phase I study of ABBV-399, a c-Met antibody-drug conjugate (ADC), as monotherapy and in combination with erlotinib in patients (pts) with non-small cell lung cancer (NSCLC)", Journal of Clinical Oncology, 2017, 35(15_suppl): p. 2509-2509.
Ariyawutyakorn et al., "Understanding and Targeting MET Signaling in Solid Tumors—Are We There Yet?", Journal of Cancer, 2016, 7(6): p. 633-649.
Arteaga, C.L. et al., "ERBB receptors: from oncogene discovery to basic science to mechanism-based cancer therapeutics", Cancer Cell, 2014, 25(3): p. 282-303.
Bachleitner-Hofmann, T., et al., "HER kinase activation confers resistance to MET tyrosine kinase inhibition in MET oncogene-addicted gastric cancer cells", Molecular Cancer Therapeutics, 2008, 7: p. 3499-3508.
Haura et al., "Signaling Control by Epidermal Growth Factor Receptor and MET: Rationale for Cotargeting Strategies in Lung Cancer", Journal of Clinical Oncology, 2013, 31(32): p. 4148-4150.
Bardelli et al., "Amplification of the MET Receptor Drives Resistance to Anti-EGFR Therapies in Colorectal Cancer", Cancer Discovery, 2013, 3(6): p. 658-673.
Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer", Journal of Clinical Oncology, 2017, 35(19):2141-2148.
Bean J., et al., "MET amplification occurs with or without T790M mutations in EGFR mutant lung tumors with acquired resistance to gefitinib or erlotinib", Proceedings of the National Academy of Sciences of the United States of America, 2007, 104(52): p. 20932-20937.
Beck, A., et al., "Strategies and challenges for the next generation of antibody-drug conjugates", Nature Reviews Drug Discovery, 2017, 16, pp. 315-337.
Belalcazar, A., et al., "Targeting the Met pathway in lung cancer", Expert Review of Anticancer Therapy, 2012, 12 (4): p. 519-528.
Benedettini, E., et al., "Met activation in non-small cell lung cancer is associated with de novo resistance to EGFR inhibitors and the development of brain metastasis", The American Journal of Pathology, 2010, 177(1): p. 415-423.
Bertotti, A. et al., "Molecular Pathways: Sensitivity and Resistance to Anti-EGFR Antibodies", Clinical Cancer Research, 2015, 21 (15): 3377-3383.

Birchmeier, C., et al., "Met, metastasis, motility and more", Nature Reviews Molecular Cell Biology, 2003, 4: p. 915-925.
Boccaccio et al., "MET-Mediated Resistance to EGFR Inhibitors: An Old Liaison Rooted in Colorectal Cancer Stem Cells", Cancer Research, 2014, p. 3647-3651.
Bouattour, M., et al., "Recent developments of c-Met as a therapeutic target in hepatocellular carcinoma", Hepatology, 2018, 67(3): p. 1132-1149.
Bouchard et al., "Antibody-drug conjugates—A new wave of cancer drugs", Bioorganic and Medicinal Chemistry Letters, 2014, 24(23): p. 5357-63.
Brinkmann, U. et al., "The making of bispecific antibodies", mAbs, 2017. 9(2): p. 182-212.
Calvo, E., et al., "Preliminary results from a phase 1 study of the antibody-drug conjugate ABBV-221 in patients with solid tumors likely to express EGFR", Journal of Clinical Oncology, 2017, 35(15_suppl): p. 2510-2510.
Cappuzzo, F., et al., "Increased MET gene copy number negatively affects survival of surgically resected non-small-cell lung cancer patients", Journal of Clinical Oncology, 2009, 27(10): p. 1667-1674.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjugate Chemistry, 2015, 26 (5):919-931.
Cecchi et al., "Targeting the HGF/Met signaling pathway in cancer therapy", Expert Opinion on Therapeutic Targets, 2012, 16(6): p. 553-572.
Chan et al., "Epidermal growth factor receptor (EGFR) inhibitors for metastatic colorectal cancer" The Cochrane Database of Systematic Reviews, 2017, 6: p. CD007047.
Chong, C.R. et al., "The quest to overcome resistance to EGFR-targeted therapies in cancer" Nature Medicine, 2013, 19(11): p. 1389-1400.
Chothia et al., "Canonical structures for the hypervariable regions of immunoglobulins", Journal of Molecular Biology, 1987, 196:901-917.
Choueiri, T.K., et al., "Biomarker-Based Phase II Trial of Savolitinib in Patients With Advanced Papillary Renal Cell Cancer", Journal of Clinical Oncology, 2017, 35(26): p. 2993-3001.
Comer et al., "Bispecific and Biparatopic Antibody Drug Conjugates", Innovations for Next-Generation Antibody-Drug Conjugates, Cancer Drug Discovery and Development, M. Damelin, Editor. 2018, p. 267-280.
Corso, S., et al., "Activation of HER family members in gastric carcinoma cells mediates resistance to MET inhibition", Molecular Cancer, 2010, 9(1): p. 121.
Cunningham, D., et al., "Cetuximab monotherapy and cetuximab plus irinotecan in irinotecan-refractory metastatic colorectal cancer", The New England Journal of Medicine, 2004, 351(4): p. 337-345.
De Bacco, F., et al., "The MET Oncogene Is a Functional Marker of a Glioblastoma Stem Cell Subtype", Cancer Research, 2012, 72(17): p. 4537-4550.
De Goeij et al., "New developments for antibody-drug conjugate-based therapeutic approaches", Current Opinion in Immunology, 2016, 40: p. 14-23.
Dimasi et al., "Efficient Preparation of Site-Specific Antibody-Drug Conjugates Using Cysteine Insertion", Molecular Pharmaceutics, 2017, 14(5) 1501-1516.
Dokala et al., "Extracellular region of epidermal growth factor receptor: a potential target for anti-EGFR drug discovery" Oncogene, 2016, 36: p. 2337.
Domling et al., "Myxobacterial epothilones and tubulysins as promising anticancer agents", Molecular Diversity, 2005 9:141-147.
Donaghy, H., "Effects of antibody, drug and linker on the preclinical and clinical toxicities of antibody-drug conjugates", mAbs, 2016, 8(4): p. 659-71.
Dornan et al., "Therapeutic potential of an anti-CD79b antibody-drug conjugate, anti-CD79b-vc-MMAE, for the treatment of non-Hodgkin lymphoma", Blood, 2009, 114(13):2721-2729.
Dubowchik et al., "Cathepsin B-labile dipeptide linkers for lysosomal release of doxorubicin from internalizing immunoconjugates: model

(56) References Cited

OTHER PUBLICATIONS studies of enzymatic drug release and antigen-specific in vitro anticancer activity", Bioconjugate Chemistry, 2002, 13,855-869.

Engelman, J.A., et al., "MET amplification leads to gefitinib resistance in lung cancer by activating ERBB3 signaling", Science, 2007, 316: p. 1039-1043.

Fan, G.W., et al., "Bispecific antibodies and their applications", Journal of Hematology & Oncology, 2015, 8:130.

Garber, K., "MET inhibitors start on road to recovery", Nature Reviews Drug Discovery, 2014, 13(8): p. 563-565.

Gherardi et al., "Functional map and domain structure of MET, the product of the co-met protooncogene and receptor for hepatocyte growth factor/scatter factor", Proceedings of the National Academy of Sciences of the United States of America, 2003, 100(21): 12039-12044.

Giordano, S., et al., "Tyrosine kinase receptor indistinguishable from the c-met protein", Nature, 1989, 339: p. 155-156.

Gisterek, I., et al., "Prognostic role of c-met expression in breast cancer patients", Reports of Practical Oncology and Radiotherapy, 2011, 16(5): p. 173-177.

Gou, L.Y., et al., "The coexistence of MET over-expression and an EGFR T790M mutation is related to acquired resistance to EGFR tyrosine kinase inhibitors in advanced non-small cell lung cancer" Oncotarget, 2016, 7(32): 51311-51319.

Guo, A., et al., "Signaling networks assembled by oncogenic EGFR and c-Met", Proceedings of the National Academy of Sciences of the United States of America, 2008, 105(2): p. 692-697.

Guo, B., et al., "Prognostic value of MET gene copy number and protein expression in patients with surgically resected non-small cell lung cancer: a meta-analysis of published literatures", PLoS One, 2014, 9(6): p. e99399.

Hamblett et al., "Effects of drug loading on the antitumor activity of a monoclonal antibody drug conjugate", Clinical Cancer Research, 2004, 10:7063-7070.

Zucali et al., "Role of cMET expression in non-small-cell lung cancer patients treated with EGFR tyrosine kinase inhibitors", Annals of Oncology, 2008, 19(9): p. 1605-1612.

Hay et al., "Targeting CD73 in the tumor microenvironment with MEDI9447", Oncoimmunology, 2016 5(8):e1208875.

Hinrichs et al., "Antibody Drug Conjugates: Nonclinical Safety Considerations", The AAPS Journal, 2015, 17(5): p. 1055-64.

Huang, L., et al., "MET expression plays differing roles in non-small-cell lung cancer patients with or without EGFR mutation", Journal of Thoracic Oncology, 2014, 9(5): p. 725-728.

Jimeno, A., et al., "KRAS mutations and sensitivity to epidermal growth factor receptor inhibitors in colorectal cancer: practical application of patient selection" Journal of Clinical Oncology, 2009, 27(7): p. 1130-1136.

Jun et al., "Inhibition of EGFR induces a c-MET driven stem cell population in Glioblastoma", Stem Cells, 2013, 32 (2):338-48.

Junutula, et al., "Site-specific conjugation of a cytotoxic drug to an antibody improves the therapeutic index" Nature Biotechnology, 2008, 26(8):925-932.

Junutula, et al., "Next-Generation Antibody-Drug Conjugates (ADCs) for Cancer Therapy", ACS Medicinal Chemistry Letters, 2016, 7(11): p. 972-973.

Puri et al., "Synergism of EGFR and c-Met pathways, cross-talk and inhibition, in non-small cell lung cancer" Journal of Carcinogenesis, 2008, 7:9.

Karamouzis et al., "Targeting MET as a strategy to overcome crosstalk-related resistance to EGFR inhibitors", The Lancet Oncology, 2009, 10(7): p. 709-717.

Kim et al., "Clinicopathological impacts of high c-Met expression in head and neck squamous cell carcinoma: a meta-analysis and review", Oncotarget, 2017, 8(68): p. 113120-113128.

Kim et al., "Clinicopathological impacts of high c-Met expression in renal cell carcinoma: a meta-analysis and review", Oncotarget, 2017, 8(43): p. 75478-75487.

Kim et al., "Prognostic value of c-Met overexpression in hepatocellular carcinoma: a meta-analysis and review", Oncotarget, 2017, 8(52): p. 90351-90357.

Klein et al., "Progress in overcoming the chain association issue in bispecific heterodimeric IgG antibodies", mAbs, 2012, 4:653-663.

Knickelbein et al., "Mutant KRAS as a critical determinant of the therapeutic response of colorectal cancer" Genes & Diseases, 2015, 2(1): p. 4-12.

Kondo, S., et al., "Clinical impact of c-Met expression and its gene amplification in hepatocellular carcinoma" International Journal of Clinical Oncology, 2013, 18(2): p. 207-213.

Kontermann et al., "Bispecific antibodies", Drug Discovery Today, 2015, 20(7): p. 838-47.

Lacouture, "Mechanisms of cutaneous toxicities to EGFR inhibitor", Nature Reviews: Cancer, 2006, 6(10): p. 803-812.

Lambert et al., "Antibody-Drug Conjugates (ADCs) for Personalized Treatment of Solid Tumors: A Review", Advances in Therapy, 2017, 34(5): p. 1015-1035.

Ledermann et al., "A phase-I study of repeated therapy with radiolabelled antibody to carcinoembryonic antigen using intermittent or continuous administration of cyclosporin A to suppress the immune response", International Journal of Cancer, 1991, 47: 659-664.

Lefranc et al., "IMGT®, the international ImMunoGeneTics information system® 25 years on", Nucleic Acids Research, 2015, 43(Database issue):D413-22.

Li et al., "c-Met Is a Marker of Pancreatic Cancer Stem Cells and Therapeutic Target", Gastroenterology, 2011, 141(6): p. 2218-2227. e5.

Liska et al., "HGF Rescues Colorectal Cancer Cells from EGFR Inhibition via MET Activation", Clinical Cancer Research, 2011, 17(3): p. 472-482.

Liu et al., "Prognostic value of c-Met in colorectal cancer: a meta-analysis", World Journal of Gastroenterology, 2015, 21(12): p. 3706-3710.

Peters et al., "MET: a promising anticancer therapeutic target", Nature Reviews: Clinical Oncology, 2012, 9(6): p. 314-326.

Luraghi, P., et al., "MET Signaling in Colon Cancer Stem-like Cells Blunts the Therapeutic Response to EGFR Inhibitors" Cancer Research, 2014, 74(6): p. 1857-1869.

Madoz-Gurpide et al., "Activation of MET pathway predicts poor outcome to cetuximab in patients with recurrent or metastatic head and neck cancer", Journal of Translational Medicine, 2015, p. 1-13.

Phillips et al., "Characterization of ABBV-221, a Tumor-Selective EGFR Targeting Antibody Drug Conjugate", Molecular Cancer Therapeutics, 2018, 17 (4): 795-805.

Mazor et al., "Enhanced tumor-targeting selectivity by modulating bispecific antibody binding affinity and format valence", Scientific Reports, 2017, 7: p. 40098.

Mazor et al., "Insights into the molecular basis of a bispecific antibody's target selectivity", mAbs, 2015, 7(3): p. 461-469.

Mazor et al., "Improving target cell specificity using a novel monovalent bispecific IgG design", mAbs, 2016, 7:2, 377-389.

McDermott et al., "Acquired Resistance of Non-Small Cell Lung Cancer Cells to MET Kinase Inhibition Is Mediated by a Switch to Epidermal Growth Factor Receptor Dependency", Cancer Research, 2010, 70(4): p. 1625-1634.

Miyamoto et al., "Prognostic significance of overexpression of c-Met oncoprotein in cholangiocarcinoma", British Journal of Cancer, 2011, 105(1): p. 131-138.

Mo et al., "Targeting MET in cancer therapy", Chronic Diseases and Translational Medicine, 2017, 3(3): p. 148-153.

Moores et al., "A Novel Bispecific Antibody Targeting EGFR and cMet that is Effective Against EGFR Inhibitor-Resistant Lung Tumors", Cancer Research, 2016, 76(13), 3942-3953.

Nasiri et al., "Antibody-drug conjugates: promising and efficient tools for targeted cancer therapy", Journal of Cellular Physiology, 2018.

Phillips et al., "ABT-414, an Antibody-Drug Conjugate Targeting a Tumor-Selective EGFR Epitope", Molecular Cancer Therapeutics, 2016, 15(4): p. 661-669.

Nicholson et al., "EGFR and cancer prognosis", European Journal of Cancer, 2001, 37: p. 9-15.

(56) References Cited

OTHER PUBLICATIONS

Ogitani et al., "Wide application of a novel topoisomerase I inhibitor-based drug conjugation technology", Bioorganic & Medicinal Chemistry Letters, 2016, 26(20):5069-5072.

Ogitani et al., "DS-8201a, A Novel HER2-Targeting ADC with a Novel DNA Topoisomerase I Inhibitor, Demonstrates a Promising Antitumor Efficacy with Differentiation from T-DM1", Clinical Cancer Research, 2016, 22(20):5097-5108.

Organ et al., "An overview of the c-MET signaling pathway", Therapeutic Advances in Medical Oncology, 2011, 3(1 Suppl): p. S7-S19.

Oganesyan et al., "Structural characterization of a human Fc fragment engineered for lack of effector functions", Acta Crystallographica Section D Structural Biology, 2008 ;64(Pt 6):700-4.

Ou et al., "High MET amplification level as a resistance mechanism to osimertinib (AZD9291) in a patient that symptomatically responded to crizotinib treatment post-osimertinib progression", Lung Cancer, 2016, 98(Supplement C): p. 59-61.

Park et al., "Amivantamab in EGFR Exon 20 Insertion-Mutated Non-Small-Cell Lung Cancer Progressing on Platinum Chemotherapy: Initial Results From the Chrysalis Phase I Study", Journal of Clinical Oncology, 2021, 39:3391-3402.

Pearson et al., "Improved tools for biological sequence comparison" Proceedings of the National Academy of Sciences of the United States of America, 1988, 85: 2444-2448.

Persic et al., "An integrated vector system for the eukaryotic expression of antibodies or their fragments after selection from phage display libraries", Gene, 1997, 187: 9-18.

Zhang, "Promise and challenges on the horizon of MET-targeted cancer therapeutics", World Journal of Biological Chemistry, 2015, 6(2): p. 16-27.

Zhang et al., "Biomarker development in MET-targeted therapy", Oncotarget, 2016, 7(24): p. 37370-37389.

Yan et al., "Prognostic significance of c-Met in breast cancer: a meta-analysis of 6010 cases", Diagnostic Pathology, 2015, 10: p. 62.

Xu et al., "C-Met as a Molecular Marker for Esophageal Squamous Cell Carcinoma and Its Association with Clinical Outcome", Journal of Cancer, 2016, 7(5): p. 587-594.

Wu et al., "Does c-Met remain a rational target for therapy in patients with EGFR TKI-resistant non-small cell lung cancer?", Cancer Treatment Reviews, 2017, 61: p. 70-81.

Remon et al., "Osimertinib and other third-generation EGFR TKI in EGFR-mutant NSCLC patients", Annals of Oncology, 2018, 29(suppl_1): p. 120-127.

Retter et al., "VBASE2, an integrative V gene database", Nucleic Acids Research, 2005, 33 (suppl 1): D671-D674.

Rho et al., "The role of MET activation in determining the sensitivity to epidermal growth factor receptor tyrosine kinase inhibitors", Molecular Cancer Research, 2009, 7(10): p. 1736-1743.

Wang et al., "ABBV-399, a c-Met Antibody-Drug Conjugate that Targets Both MET-Amplified and c-Met-Overexpressing Tumors, Irrespective of MET Pathway Dependence", Clinical Cancer Research, 2017, 23(4): p. 992-1000.

Rocha-Lima et al., "EGFR targeting of solid tumors", Cancer Control: Journal of the Moffitt Cancer Center, 2007, 14 (3): p. 295-304.

Sacco et al., "Dysregulation of the Met pathway in non-small cell lung cancer: implications for drug targeting and resistance", Translational Lung Cancer Research, 2015, 4(3): p. 242-52.

Saltz et al., "Phase II trial of cetuximab in patients with refractory colorectal cancer that expresses the epidermal growth factor receptor", Journal of Clinical Oncology, 2004, 22(7): p. 1201-1208.

Sanderson et al., "In vivo drug-linker stability of an anti-CD30 dipeptide-linked auristatin immunoconjugate", Clinical Cancer Research, 2005, 11:843-852.

Sau et al., "Advances in antibody-drug conjugates: A new era of targeted cancer therapy", Drug Discovery Today, 2017, 22(10): p. 1547-1556.

Sellmann et al., "Balancing Selectivity and Efficacy of Bispecific EGFR x c-MET Antibodies and Antibody-Drug Conjugates", Journal of Biological Chemistry, 2016, 291(48):25106-25119.

Seshacharyulu, et al., "Targeting the EGFR signaling pathway in cancer therapy", Expert Opinion on Therapeutic Targets, 2012, 16(1): p. 15-31.

Sierra et al., "c-MET as a potential therapeutic target and biomarker in cancer", Therapeutic Advances in Medical Oncology, 2011, 3(1 suppl): p. S21-S35.

Smith et al., "Identification of common molecular subsequences", Journal of Molecular Biology, 1981, 147: 195-197.

Sohn et al., "cMET Activation and EGFR-Directed Therapy Resistance in Triple-Negative Breast Cancer", Journal of Cancer, 2014, 5(9): p. 745-753.

Suda et al., "Reciprocal and complementary role of MET amplification and EGFR T790M mutation in acquired resistance to kinase inhibitors in lung cancer", Clinical Cancer Research, 2010,16(22): p. 5489-5498.

Thompson et al., "Rational design, biophysical and biological characterization of site-specific antibody-tubulysin conjugates with improved stability, efficacy and pharmacokinetics", Journal of Controlled Release, 2016, 236:100-116.

Tolcher, et al., "A phase 1/2 study evaluating the safety, pharmacokinetics and efficacy of ABT-414 in subjects with advanced solid tumors likely to over-express the epidermal growth factor receptor (EGFR)", European Journal of Cancer, 2014. 50: p. 111.

Tolcher, "Antibody drug conjugates: lessons from 20 years of clinical experience", Annals of Oncology, 2016, 27 (12):2168-2172.

Troiani et al., "Therapeutic value of EGFR inhibition in CRC and NSCLC: 15 years of clinical evidence" ESMO Open, 2016, 1(5): p. e000088.

Trusolino et al., "MET signalling: principles and functions in development, organ regeneration and cancer", Nature Reviews: Molecular Cell Biology, 2010, 11(12): p. 834.

Vainshtein et al., "Quantitative measurement of the target-mediated internalization kinetics of biopharmaceuticals", Pharmaceutical Research, 2015, 32: 286-299.

Vaughan et al., "Human antibodies with sub-nanomolar affinities isolated from a large non-immunized phage display library", Nature Biotechnology, 1996, 14: p. 309.

Vecchione et al., "EGFR-targeted therapy", Experimental Cell Research, 2011, 317(19): p. 2765-2771.

Vsiansky et al., "Prognostic role of c-Met in head and neck squamous cell cancer tissues: a meta-analysis", Scientific Reports, 2018, 8(1): p. 10370.

Wang et al., "IgG Fc engineering to modulate antibody effector functions", Protein & Cell, 2018;9(1):63-73.

Rieker, "Targeted Combination Therapy: Discovery and Evaluation of Synergistic Anticancer Effects of Anti-HER2-Duocarmycin Antibody-Drug Conjugates Combined with ATR Inhibitors", Dissertation of Technische Universitat Darmstadt, 2018.

Lee et al., "Novel strategy for a bispecific antibody: induction of dual target internalization and degradation", Oncogene, 2016, vol. 35, No. 34, p. 4437-4446.

Jarantow et al., "Impact of Cell-surface Antigen Expression on Target Engagement and Function of an Epidermal Growth Factor Receptor x c-MET Bispecific Antibody", Journal of Biological Chemistry, 2015, vol. 290, No. 41, p. 24689-24704.

Castoldi et al., "A novel bispecific EGFR/Met antibody blocks tumor-promoting phenotypic effects induced by resistance to EGFR inhibition and has potent antitumor activity", Oncogene, 2013, vol. 32, No. 50, p. 5593-5601.

\* cited by examiner

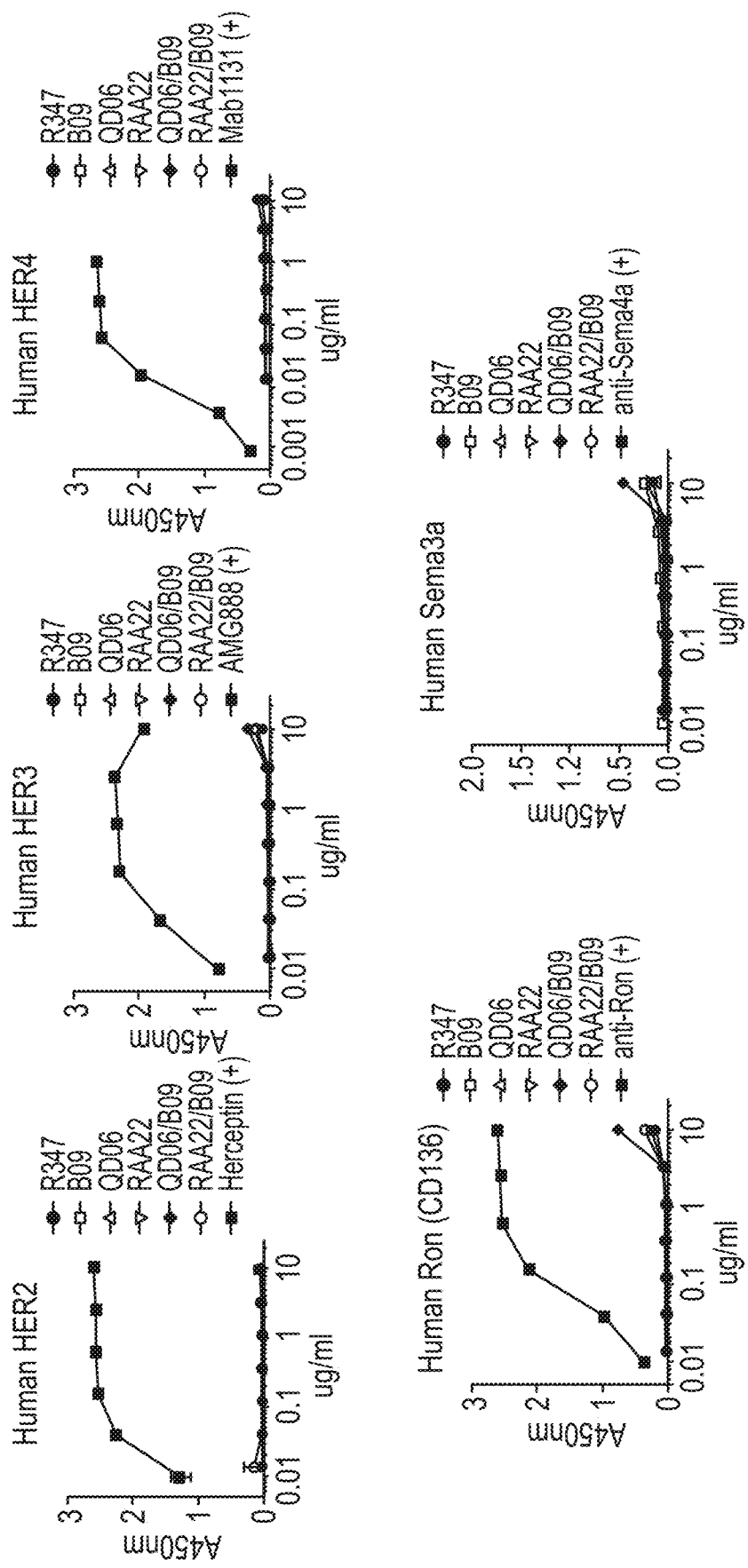

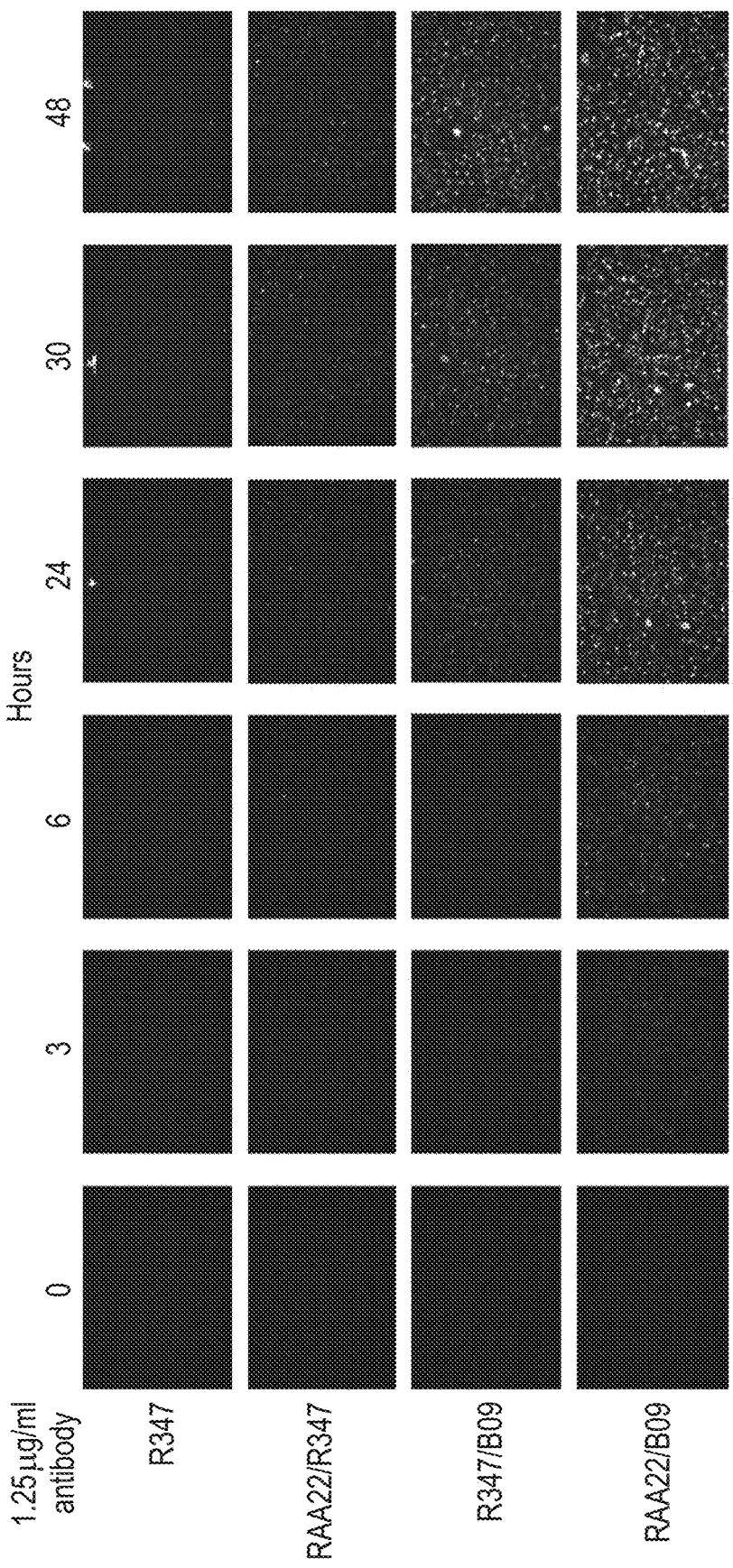

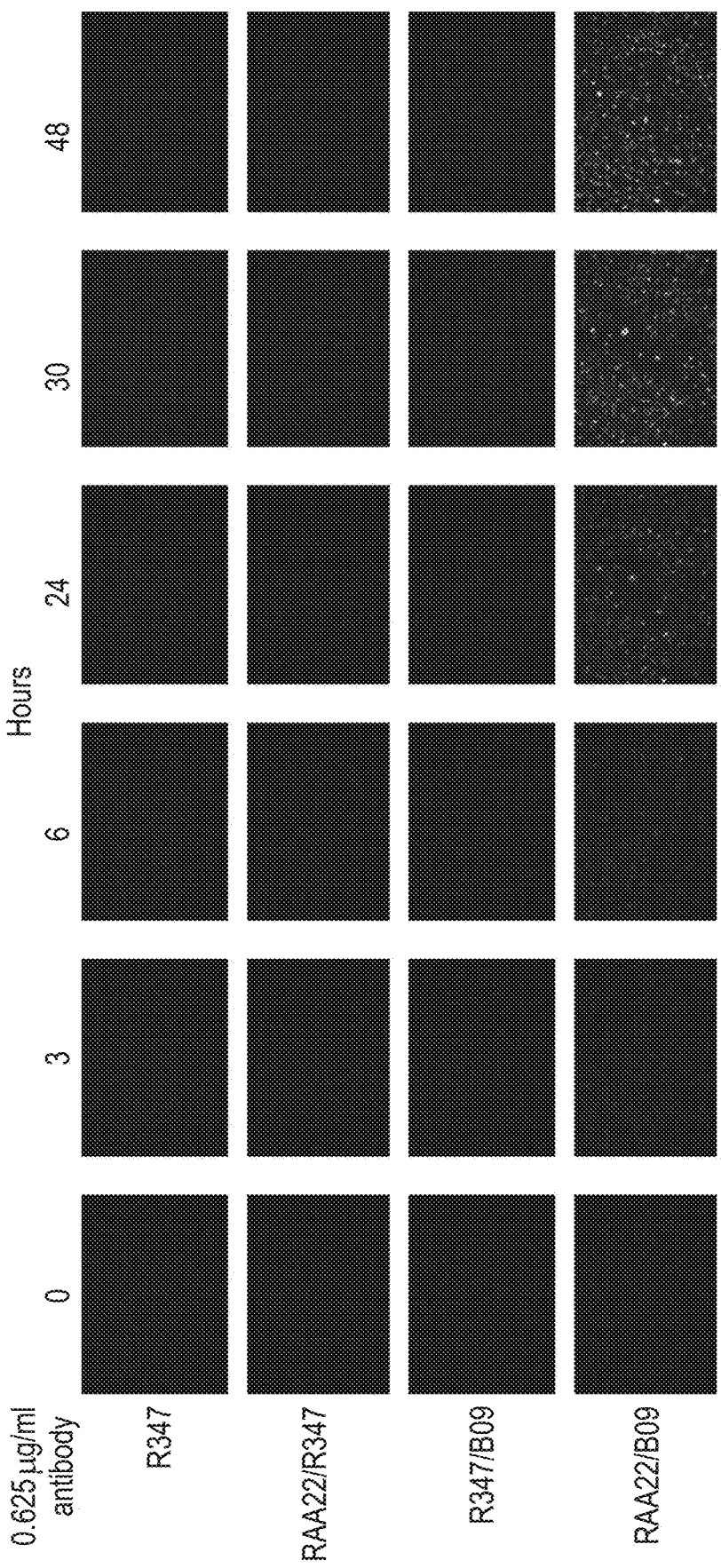

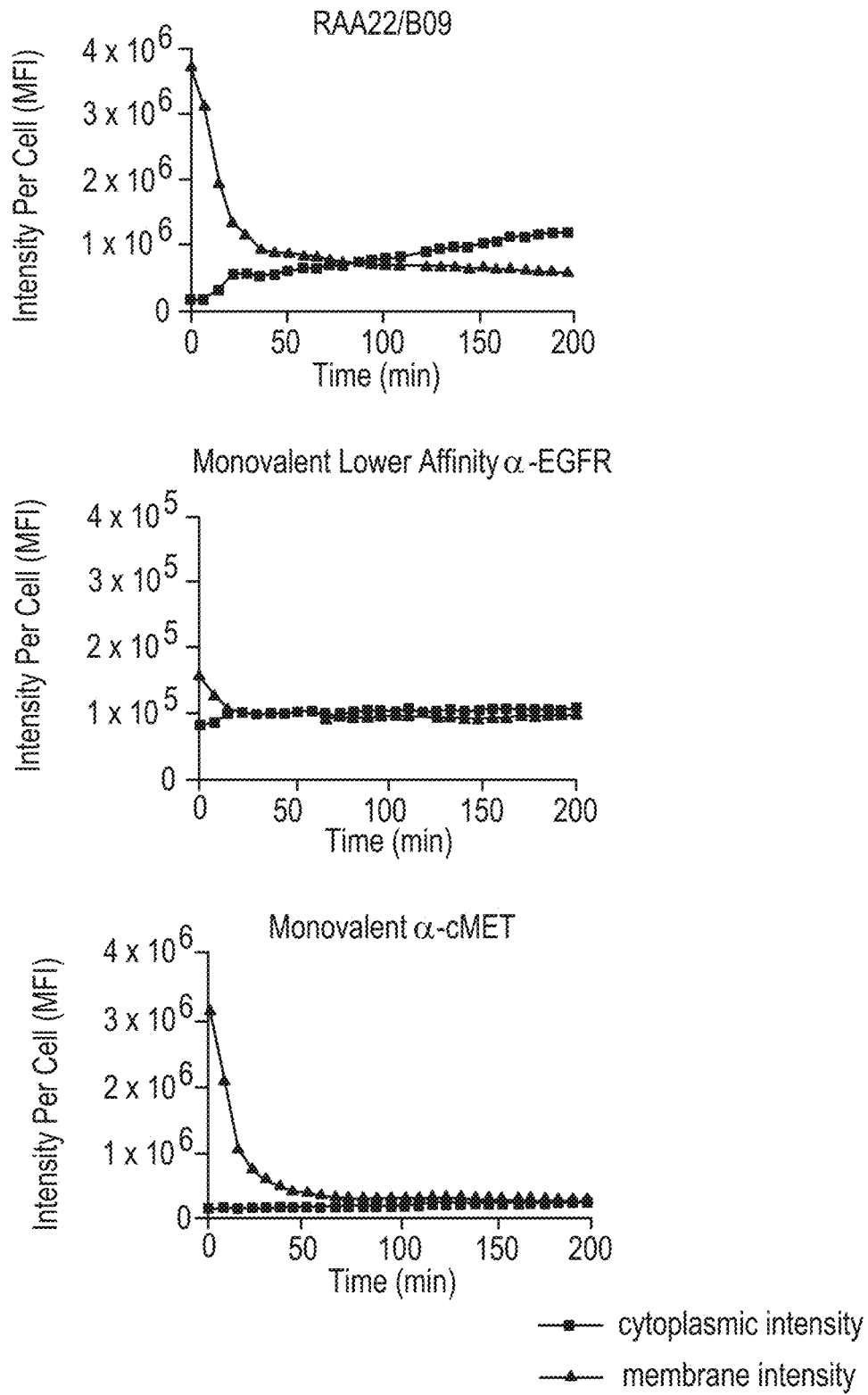

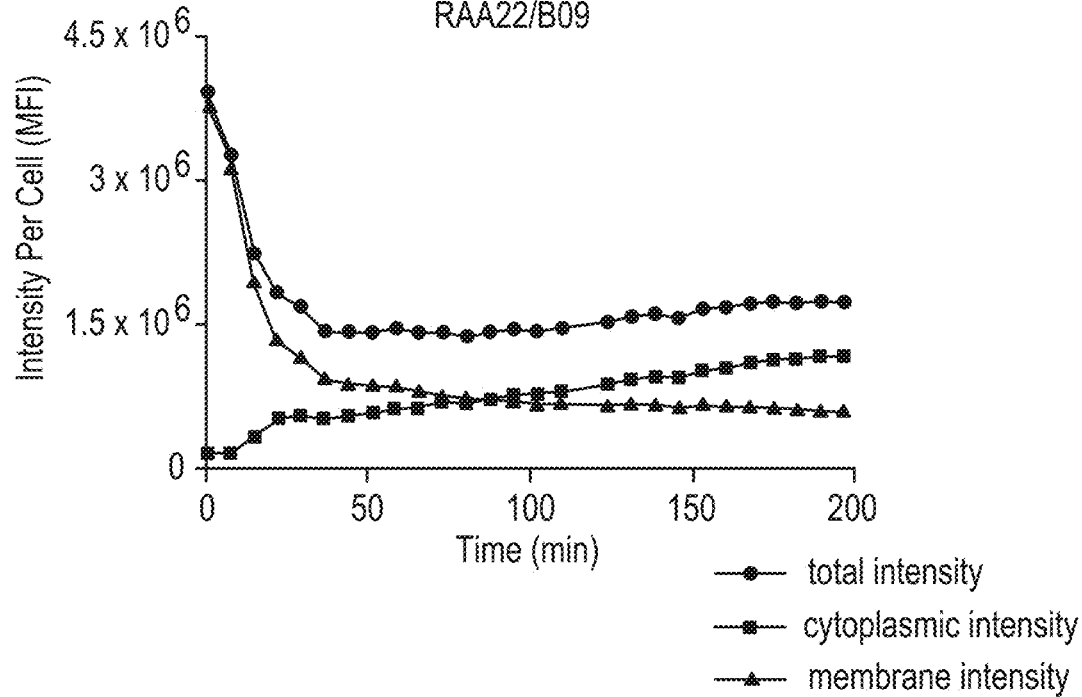
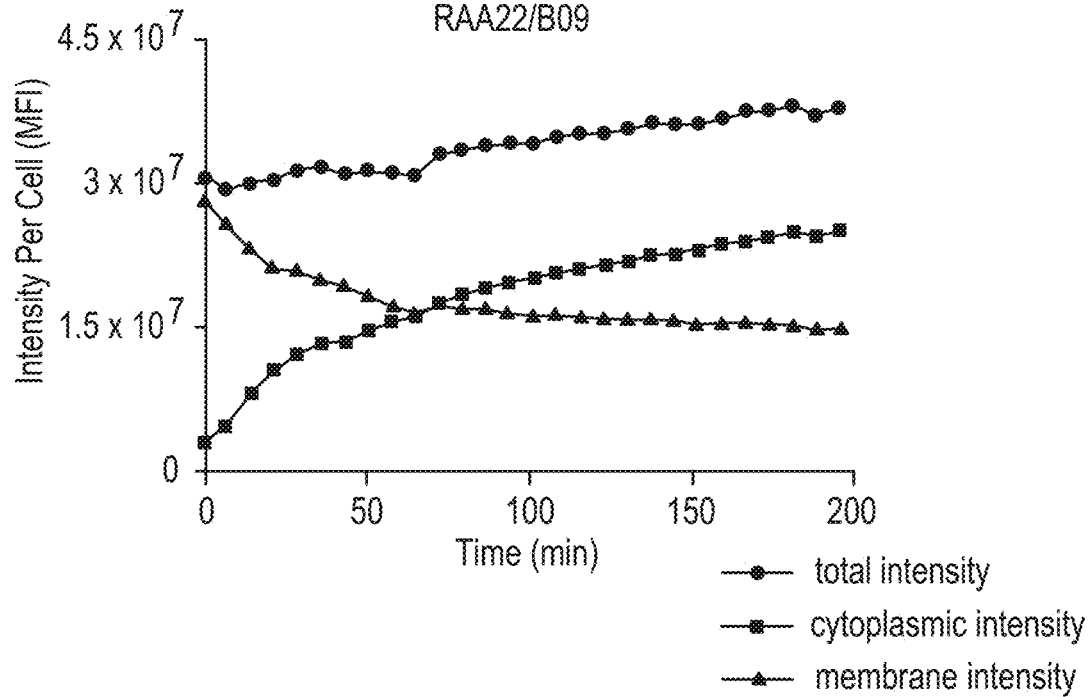

HCC827 Cells
Monovalent Lower Affinity α-EGFR

HCC827 Cells
Monovalent α-cMET

Monovalent ADC's Against EGFR or cMET Have Reduced Activity In Vitro Compared to Bispecific EGFR-cMET ADC

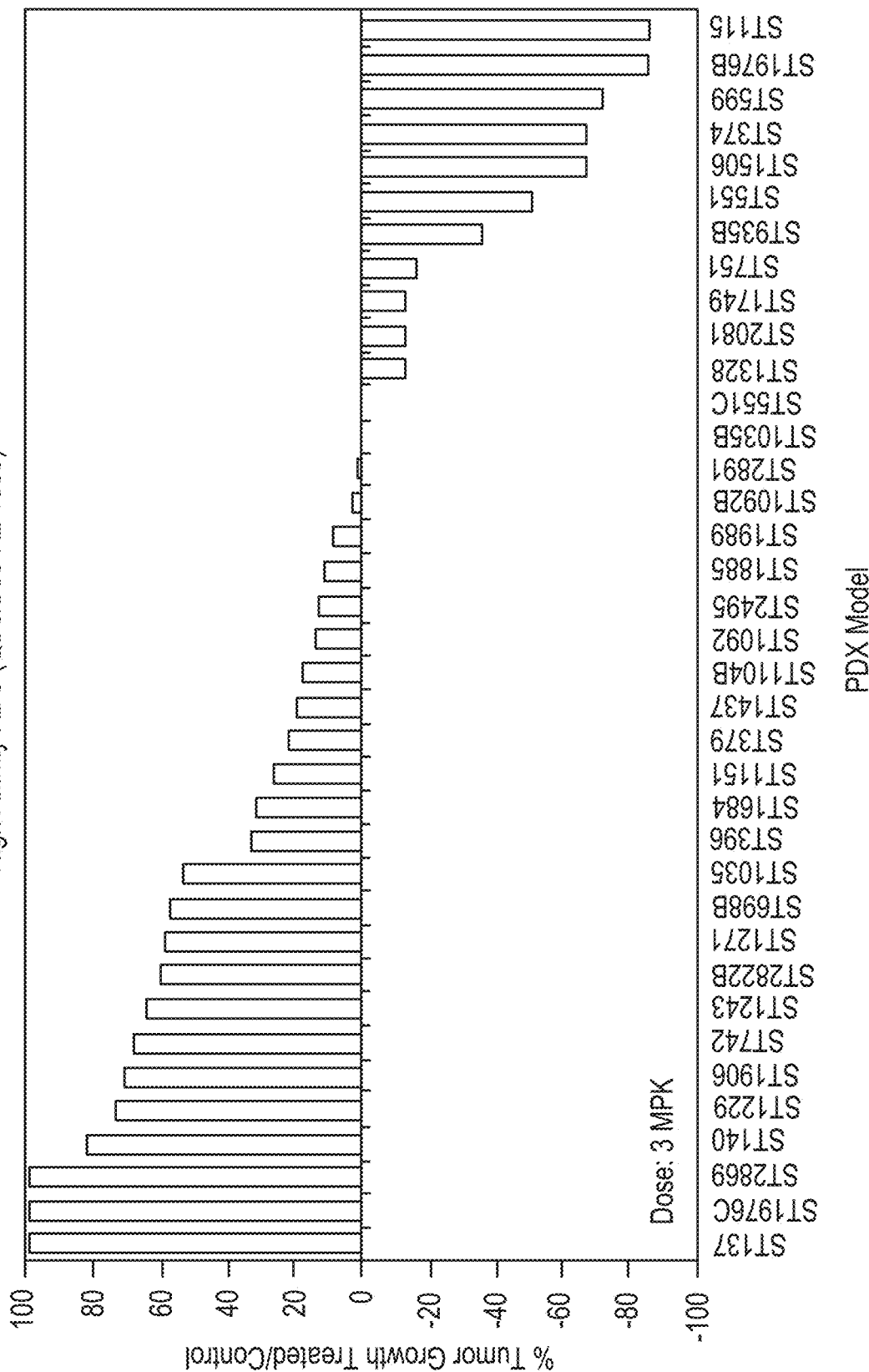

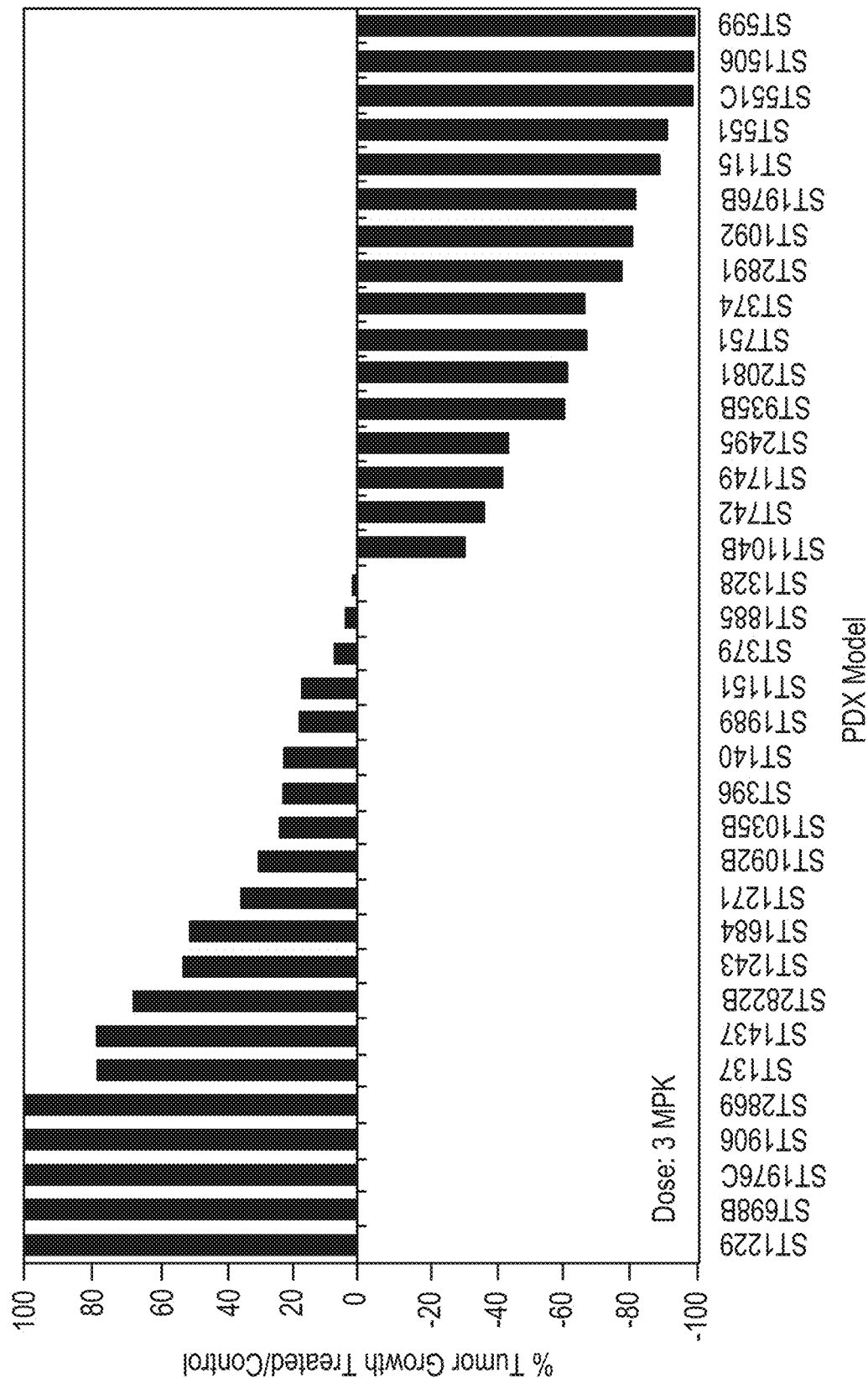

High Affinity EGFR

Low Affinity EGFR

RAA22/B09-57-AZ1508

QD6/B09-57-AZ1508

RAA22/B09-57-AZ1508

| QD6/B09-57-AZ1508 PK Parameters | | | |
|---|---|---|---|
| Dose (mg/kg) | 1 | 2 | 3 |
| $C_{max}$ (µg/mL) | 20.4 | 51.4 | 73.3 |
| AUC (µg*day/mL) | 14.5 | 52.2 | 94.4 |
| t1/2 (day) | 0.491 | 1.11 | 0.969 |
| CL (mL/kg/day) | 67.8 | 38.1 | 31.6 |

PDX Model SQHN-02

PDX Model PANC-08

ANTIBODY MOLECULES AND CONJUGATES

CROSS-REFERENCE TO RELATED APPLICATIONS

This application claims benefit under 35 U.S.C. § 119(e) of U.S. Provisional Patent Application No. 63/263,835, filed Nov. 10, 2021, which is incorporated by reference herein in its entirety for all purposes.

REFERENCE TO THE SEQUENCE LISTING

This application incorporates by reference a Sequence Listing submitted with this application as text file entitled 'EGFCM-100_Sequence_Listing.xml' created on Nov. 3, 2022, and having a size of 91,134 Bytes.

FIELD OF THE DISCLOSURE

The present disclosure relates to antibody molecules that bind epidermal growth factor receptor (EGFR) and/or c-Met and conjugates containing these antibody molecules. The antibody molecules and conjugates find application in the treatment of cancer, for example.

BACKGROUND

Overcoming drug resistance is a major challenge facing targeted cancer therapies. There are multiple drugs directed toward EGFR and c-MET that are either approved or in clinical development, but de novo and acquired resistance limits their long-term efficacy (Ou, 2016; Boccaccio, 2014; Karamouzis, 2009; Corso, 2010; Chong, 2013; Bertotti, 2015; Benedettini, 2010; Bean, 2007; Bardelli, 2013; Bachleitner-Hofmann, 2008). Mechanisms of resistance include secondary mutations, activation of oncogenic downstream signaling modules such as KRAS, ligand upregulation, and amplification of alternate growth factor receptors. For example, MET amplification or protein overexpression has been well established as an important mechanism of clinical resistance to EGFR inhibitors. Likewise, emerging evidence suggests that EGFR pathway activation can confer resistance to c-MET targeted inhibitors (Engelman, 2007; Bertotti, 2015; Benedettini, 2010; Bean, 2007; Bardelli, 2013). Antibody drug conjugates (ADC's) are a growing class of targeted therapies designed to selectively deliver cytotoxic drugs directly to tumor cells (Angevin, 2017; Junutula, 2016; Lambert, 2017; Nasiri, 2018; Sau, 2017; Phillips, 2016). In this context, the antigen targeted by the antibody is primarily used as a handle for delivery of the cytotoxic drug and the mechanism of killing is generally distinct from the biology of the target. Therefore, ADC's have the potential to largely avoid resistance due to activation of alternative receptors or downstream signaling pathways, provided that the target is present. However, adverse events due to engagement of the target on normal cells can limit the therapeutic index of ADC's (Hinrichs, 2015; Donaghy, 2016; Sau, 2017). Bispecific antibody technology may confer additional specificity to ADC's by engaging two distinct targets on tumor cells to effectively deliver the cytotoxic payload when both targets are present (Comer, 2018; Andreev, 2017; Kontermann, 2015; Lü, 2017; Brinkmann, 2017; Fan, 2015; Mazor, 2017). However, simply targeting two antigens does not guarantee improved selectivity for tumor cells compared to normal non-target cells, with multiple factors influencing the properties of a given bispecific antibody (Mazor, 2017; Mazor, 2015). Therefore, it would be desirable to develop bispecific ADC's that have improved targeting of tumor cells while sparing normal tissue. Such an ADC would have the potential to overcome resistance to targeted therapies due to pathway alterations, while maintaining a therapeutic window by capitalizing on selective targeting afforded by the bispecific antibody.

The Epidermal Growth Factor Receptor (EGFR, HER1, Erbb1) is the founding member of the Human Epidermal Growth Factor Receptor (HER) tyrosine kinase family, which also includes HER2/Erbb2, HER3/Erbb3, and HER4/Erbb4 (Arteaga, 2014; Rocha-Lima, 2007; Seshacharyulu, 2012; Vecchione, 2011; Nicholson, 2001). Numerous therapies directed against EGFR have been approved, in both the biologics and small molecule tyrosine kinase inhibitor (TKI) classes (Troiani, 2016; Chong, 2013; Chan, 2017; Remon, 2018; Dokala, 2016). Despite these successes, the clinical benefit realized by these therapies falls short of what one might expect based on the broad expression profile of EGFR in many cancer types. There are several factors that contribute to the observed clinical limitations, involving both intrinsic and acquired resistance mechanisms that are largely attributable to signaling pathway alterations (Chong, 2013). For example, in colorectal cancer (CRC), EGFR is overexpressed in 65-75% or more of patients, yet the objective response rate of anti-EGFR antibodies, such as cetuximab and panitumumab, were only in the ~10% range when administered as monotherapy in unselected patient populations (Cunningham, 2004; Saltz, 2004). These antibodies are only efficacious for patients whose tumors express wild type KRAS (~50-55% of patients), which defines the treatable patient population (Jimeno, 2009; Knickelbein, 2015). Moreover, due to additional resistance mechanisms, only about half of the eligible patients respond to treatment and all eventually fail therapy. Treatment of patients with EGFR targeted agents is frequently associated with moderate to severe cutaneous toxicities, which occur in 65-90% of patients (Lacouture, 2006). These skin toxicities can be of Grade 3 to 4 in severity (NCI-CTCAE criteria), and may lead to dose modifications or treatment discontinuation. Therefore, although it is highly expressed in a wide range of tumor types, EGFR represents a challenging target for an ADC approach, which could exacerbate these observed toxicities. Development of ADC's that can effectively target EGFR expressing tumors without provoking unacceptable EGFR associated toxicities would have the potential to treat a broader segment of the EGFR positive patient population compared to existing therapies.

c-MET is the gene product of the proto-oncogene, MET, which is encoded on chromosome 7. The c-MET protein is a receptor tyrosine kinase, expressed primarily on the surface of epithelial cells, which recognizes only one known ligand, the hepatocyte growth factor (HGF), also known as scatter factor (Giordano, 1989; Prat, 1991). The c-MET/HGF signaling axis has an essential role in regulating proliferation, differentiation, motility, and morphogenesis in a number of normal processes, including wound healing, tissue regeneration and organogenesis during development (Organ, 2011). Aberrant expression and dysregulation of the c-MET pathway has been reported for a wide variety of human cancers, including non-small cell lung, colorectal, gastrointestinal, head and neck, pancreatic, renal, and hepatocellular cancers, among many others (Organ, 2011; Birchmeier, 2003; Mo, 2017; Sierra, 2011; Trusolino, 2010; Peters, 2012; Vsiansky, 2018). For many of these cancer indications, c-MET overexpression is negatively associated with prognosis and survival (Yan, 2015; Kim, 2017a; Kim, 2017b; Kim, 2017c; Li, 2011; Kondo, 2013; Miyamoto, 2011; Liu, 2015; Miyamoto, 2011; Xu, 2016; Sacco, 2015; Gisterek, 2011; Belalcazar, 2012; Guo, 2014; Cappuzzo, 2009). Furthermore, in some cancer types, c-MET is associated with a cancer stem cell phenotype, which has been implicated in resistance to EGFR targeted therapies (Li, 2011; Boccaccio, 2014; Luraghi, 2014; June, 2013; De Bacco, 2012). There is a large and growing body of literature demonstrating that there is cross talk and direct interaction between the EGFR and c-MET signaling pathways, and that this cross talk functionally translates into resistance to EGFR and c-MET targeted therapies in the clinic (McDermott, 2010; Moores, 2016; Suda, 2010; Zucali, 2008; Liska, 2011; Huang, 2014; Boccaccio, 2014; Madoz-Gúrpide, 2016; Sohn, 2014; Rho, 2009; Puri, 2008; Peters, 2012; Karamouzis, 2009; June, 2013; Haura, 2013; Guo, 2008; Gou, 2016; Engelman, 2007; Cecchi, 2012; Bardelli, 2013). Based on the ample evidence of a role for c-MET as an independent negative prognostic indicator in many tumor types and its implication as a mechanism of resistance to EGFR inhibitors, there have been multiple efforts to develop c-MET inhibitors as cancer therapeutics. Nevertheless, despite the high frequency of c-MET expression in multiple tumor types, development of effective c-MET inhibitors has met with substantial challenges and setbacks in the clinic Zhang, 2015; Wu, 2017; Ariyawutyakorn, 2016; Marano, 2015; Garber, 2014). For example, while crizotinib, a dual inhibitor of c-MET and ALK, has been approved for treatment of non-small cell lung cancer, other c-MET targeting drugs, such as the one-armed c-MET antibody, MetMAb (onartuzumab), and the small molecule inhibitor, tivantinib, have failed in late stage Phase III clinical trials due to lack of efficacy (Mo, 2017; Zhang, 2015; Wu, 2017; Company press releases). A plausible hypothesis for the discrepancy between the broad c-MET expression profile and the limited clinical response of c-MET inhibitors is that only a subset of these tumors are driven by the c-MET pathway, and thus, many c-MET expressing tumors are insensitive to inhibitors that block c-MET signaling activity. There are several c-MET inhibitors in ongoing clinical development, and some of these programs are seeking to employ a biomarker driven strategy to identify the fraction of patients whose tumors are dependent on c-MET (Choueiri, 2017; Zhang, 2016; Bouattour, 2018). The clinical experience to date suggests that, as with EGFR inhibitors, successful development of new c-MET signal blocking inhibitors will benefit only a subset of the total population of patients with c-MET expressing tumors. Development of an efficacious c-MET directed ADC could overcome some of the limitations of signal blocking c-MET inhibitors.

The concept of antibody drug conjugates (ADC's) is simple, with the goal to produce a drug that has a broad therapeutic window by using the exquisite specificity of antibodies to precisely deliver a cytotoxic warhead to cancer cells while causing minimal damage to normal tissue (Comer, 2018; Nasiri, 2018; Sau, 2017; de Goeij, 2016; Bouchard, 2014; Junutula, 2016; Lambert, 2017). Although the concept is simple, achieving the ideal combination of ADC properties has proven challenging, as reflected by the limited number of ADC's that have been approved to date (Tolcher, 2016). Recent years have witnessed a growing field, with clinical stage ADC's currently numbering more than 70 drug candidates in development. Despite the successes to date and the prospect of new ADC's reaching patients in the coming years, many challenges remain and there is substantial room for improvement. Ultimately, the key challenge in developing an ADC is balancing its efficacy and safety. Currently, there is one EGFR directed ADC, depatuxizumab mafodotin (ABT-414), in Phase III clinical development by AbbVie for glioblastoma (Phillips, 2016). ABT-414 was previously tested in Phase II trials for multiple additional solid tumor indications (ClinicalTrials.gov: NCT01741727). The ADC showed limited efficacy at tolerated doses in these indications, and concerning ocular toxicities were frequently observed in treated patients (Tolcher, 2014). A second generation EGFR ADC, ABBV-221 was in clinical development but was discontinued due to safety concerns (Phillips, 2018; Calvo, 2017; company presentation). Currently, there is one c-MET targeted ADC, Telisotuzumab Vedotin (ABBV-399), which is entering Phase II clinical development for non-small cell lung cancer (NSCLC) patients whose tumors express high levels of c-MET, both as monotherapy and in combination with the EGFR inhibitor, erlotinib (Angevin, 2017; Wang, 2017). The c-MET ADC+EGFR TKI combination has shown clinical activity in Phase I trials in this selected patient population, with peripheral neuropathy and skin rash as the most frequent treatment related adverse events (Angevin, 2017; Calvo, 2017). The nature of bispecific antibodies allows for fine tuning of the interactions between each target to impact the overall properties of the molecule, which could produce an ADC with an acceptable therapeutic window (Comer, 2018). This concept has been tested for EGFR and c-MET in vitro, but investigators have yet to demonstrate proof of concept in vivo of an improvement in safety or efficacy compared to the EGFR and c-MET ADC's noted above (Sellmann, 2016). Therefore, it would be beneficial take advantage of bispecific antibody strategies to develop an EGFR-cMET ADC that demonstrates both efficacy and an acceptable safety profile.

The present disclosure has been devised in light of the above considerations.

SUMMARY OF THE DISCLOSURE

The present disclosure provides antibody molecules and conjugates having combinations of desirable biophysical and/or functional properties as compared to antibody molecules disclosed in the prior art.

Aspects of the disclosure relate to an antibody molecule capable of binding both EGFR and c-Met. EGFR and c-Met are co-expressed in many cancer types and antibody molecules that target both molecules ("bispecific antibody molecules") provide an opportunity for broad clinical benefit across multiple indications. The antibody molecule represents an improved treatment for cancers as compared to monospecific EGFR or c-Met antibodies of the prior art, because the bispecific antibody molecules described herein are capable of binding to both targets simultaneously and therefore have increased selectively for tumours co-expressing EGFR and c-MET as compared to normal tissues.

Thus, in one aspect the disclosure provides an antibody molecule comprising:
  a first antigen-binding domain that binds epidermal growth factor receptor (EGFR); and
  a second antigen-binding domain that binds c-Met,
  wherein the first antigen-binding domain comprises:
    (i) a heavy chain variable (VH) region comprising the following complementarity determining regions (CDRs):
      HCDR1 having the amino acid sequence of SEQ ID NO: 1
      HCDR2 having the amino acid sequence of SEQ ID NO: 2
      HCDR3 having the amino acid sequence of SEQ ID NO: 3, or a variant thereof in which one or two or three amino acids in one or more of HCDR1, HCDR2, or HCDR3 are substituted with another amino acid; and (ii) a light chain variable (VL) region comprising the following CDRs:
LCDR1 having the amino acid sequence of SEQ ID NO: 4
LCDR2 having the amino acid sequence of SEQ ID NO: 5
LCDR3 having the amino acid sequence of SEQ ID NO: 6,
or a variant thereof in which one or two or three amino acids in one or more of HCDR1, HCDR2, or HCDR3 are substituted with another amino acid.

In particular, conjugates containing this antibody molecule are able to selectively deliver a drug (also referred to as a "payload" or "warhead") to tumours co-expressing these targets and treat these tumours with a high degree of efficacy. The examples demonstrate that different conjugates comprising alternative warheads (e.g. a tubulysin or a topoisomerase I inhibitor) display robust cytotoxic activity in both in vitro cytotoxicity assays and in vivo models of cancer treatment.

Thus, in another aspect, the disclosure provides a conjugate comprising an antibody molecule described herein conjugated to a drug. In some instances, the drug is a topoisomerase I inhibitor, e.g. a topoisomerase inhibitor having formula A*

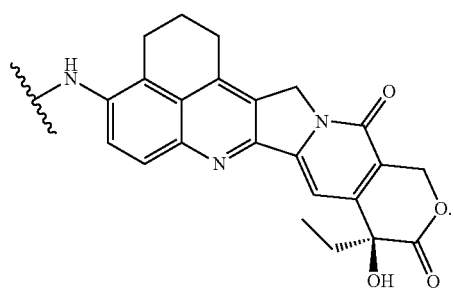

A*

In some instances, the antibody molecule is conjugated to a topoisomerase I inhibitor having the following formula:

In some instances, the antibody molecule comprises a first antigen-binding domain that binds to human EGFR with a "low affinity". As used herein, "low affinity" refers to a first antigen-binding domain that binds to human EGFR with a dissociation constant (Kd) that is equal to or higher than 10 nM. As demonstrated herein, antibodies and conjugates disclosed herein comprising such a low affinity EGFR antigen-binding domain display reduced on-target toxicity in normal tissues such as skin toxicity and therefore have an improved safety profile compared to conjugates comprising an EGFR antigen-binding domain that binds human EGFR with a "higher affinity". As used herein, "higher affinity" or "high affinity" refers to a first antigen binding domain that binds to human EGFR with a Kd that is lower than 10 nM. Furthermore, the disclosure demonstrates that conjugates comprising a low affinity EGFR antigen-binding domain are more efficacious at treating cancer compared to conjugates comprising a higher affinity EGFR antigen-binding domain (e.g., FIG. 12).

The disclosure also provides antibody molecules comprising a first antigen-binding domain that binds EGFR and antibody molecules comprising a second antigen-binding domain that binds c-Met, as defined herein.

Further, the disclosure provides pharmaceutical compositions comprising the antibody molecules defined herein or the conjugates defined herein.

The disclosure provides antibody molecules, conjugates and pharmaceutical compositions, all as defined herein, for use in a method of treatment of the human or animal body, such as a method of treatment of a cancer. The disclosure provides methods of treating cancer comprising administering an antibody molecule, conjugate or pharmaceutical composition as defined herein. In particular, the disclosure provides methods of treating a cancer selected from pancreatic cancer, colorectal cancer, non-small cell lung cancer (NSCLC) and squamous head and neck carcinoma (SQHN), comprising administering an antibody molecule, conjugate or pharmaceutical composition as defined herein. In some instances, the cancer for treatment is NSCLC.

The disclosure also provides nucleic acids, vectors and host cells as defined herein. Further, the disclosure provides a method of producing an antibody molecule as defined herein.

(SG3932)

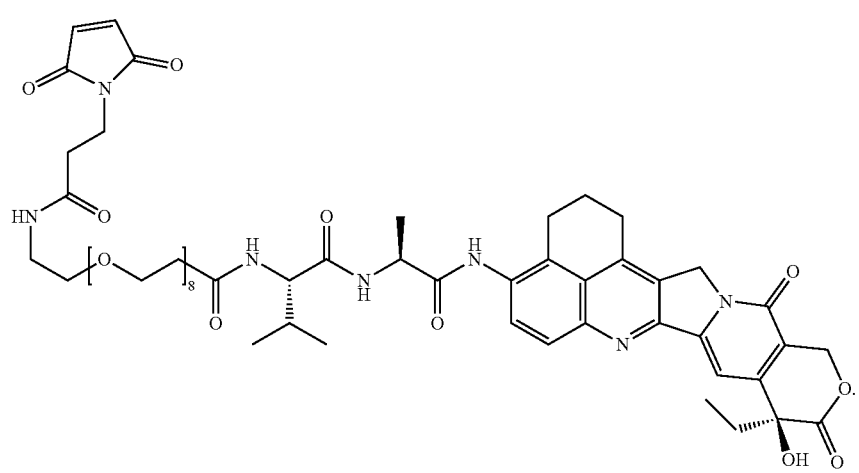

The disclosure includes the combination of the aspects and preferred features described except where such a combination is clearly impermissible or expressly avoided.

SUMMARY OF THE FIGURES

Instances and experiments illustrating the principles of the disclosure will now be discussed with reference to the accompanying figures in which:

FIG. 3B ELISA results showing EGFR and c-Met family specificity. None of the antibodies tested showed any appreciable binding to any of the EGFR HER family proteins (HER2, HER3, or HER4) or any of the c-Met family members (Ron (CD136) or Semaphorin 3a).

FIG. 4 Internalization of RAA22/B09 bispecific mAb and trafficking to acidified intracellular compartments was visualized using antibodies labeled with pHAb pH sensitive dye (Promega). Control antibodies included R347 isotype control and the monovalent bispecific control antibodies anti-EGFR RAA22/R347 and anti-cMET B09/R347. The pHAb labelled antibodies were incubated with NCI-H1975 lung cancer cells at a concentration of 1.25 ug/mL in a humidified incubator at 37° C. and 5% $CO_2$. Fluorescent images were captured at the indicated time points on an Operetta High Content Imaging system using the Cy3 filter. Increased cellular fluorescence intensity over time was deemed evidence of internalization and trafficking to acidic intracellular compartments as measured by the pH sensitive fluor.

FIG. 5 As in FIG. 4, internalization of RAA22/B09 bispecific mAb and trafficking to acidified intracellular compartments was visualized using antibodies labeled with pHAb pH sensitive dye, but the cells were treated with antibodies at the lower concentration of 0.625 ug/mL.

FIG. 7B. Internalization profiles of RAA22/B09 DuetMab and its respective single-arm control antibodies. Internalization profiles are displayed via time course of the respective membrane and cytoplasm signals for each construct. The set was acquired using a Zeiss spinning-disc confocal fluorescence microscope.

Identical profiles for QD6/B09 and QD6/IgG indicate internalization mode driven by EGFR-arm of QD6/B09 DuetMab, whereas RAA22/B09 DuetMab requires engagement of both EGFR and c-MET arms for efficient internalization.

FIG. 8A. Internalization profile of RAA22/B09-AZD1508 ADC in cells expressing moderate and high target c-MET and EGFR cell surface receptors. Shown are membrane, cytoplasm and total signals for RAA22/B09-AF647 ADC in H1975 cells. One representative experiment of 2 is shown. H1975 cells show concurrent drop in total and membrane intensities indicating dissociation of antibody from the cell surface.

FIG. 8B is equivalent to FIG. 8A but in HCC827 cells. HCC827 cells have stable total signal over experimental time course. Decrease of membrane signal is derived antibody internalization.

Figure 9A:
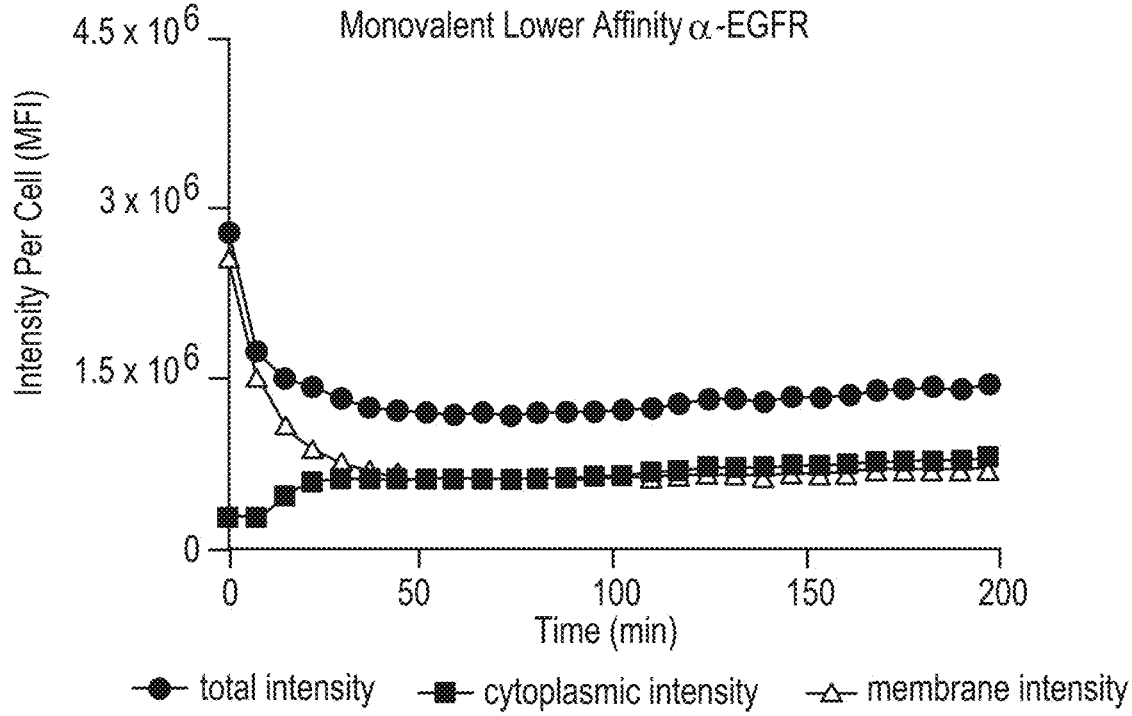
Figure 9B:
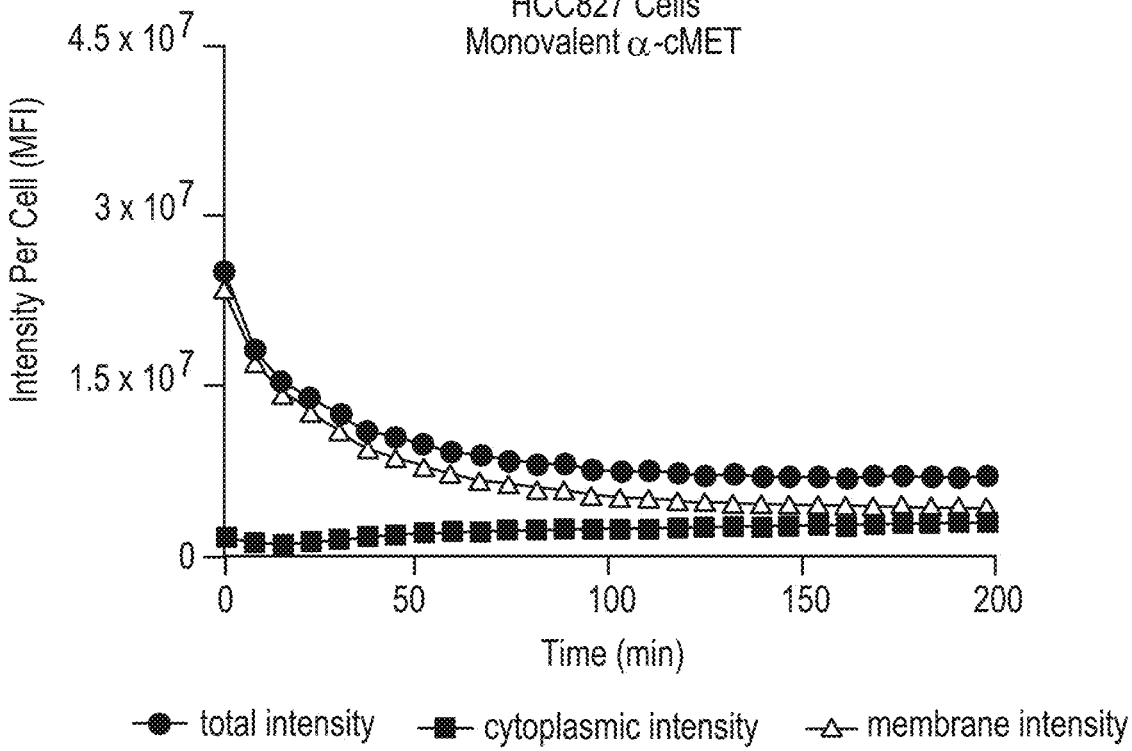

FIG. 9A. Internalization of RAA22/B09-AZD1508 ADC single arm control antibodies in HCC827 cells. Intensity profiles of the RAA22/IgG single arm is ~10 fold lower than RAA22/B09 due to weaker binding to EGFR through single arm binding FIG. 9B B09/IgG single arm dissociates from cell membrane as signaled by simultaneous drop in total and membrane signals over time.

Figure 10:
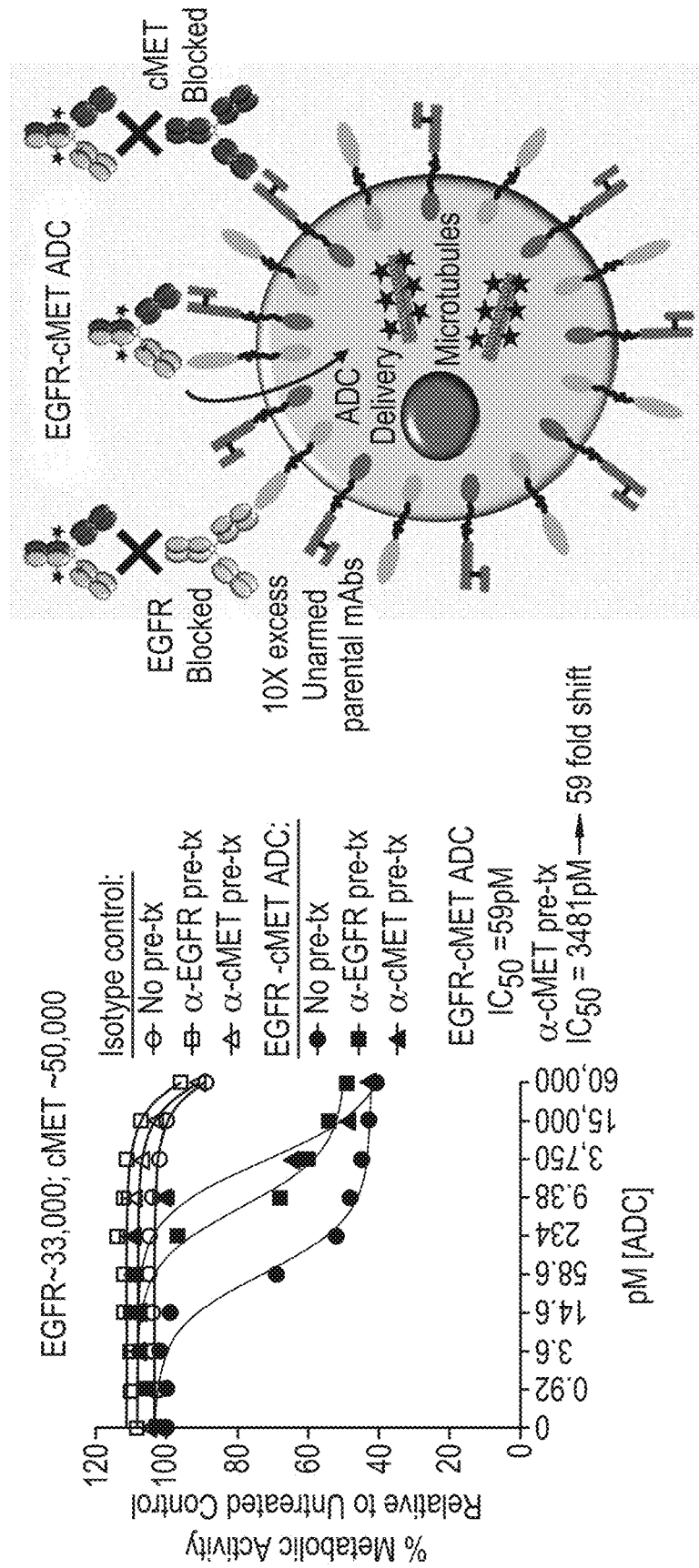

FIG. 10. Blockade of EGFR or cMETR reduces bispecific ADC activity in vitro. NCI H1975 cells were pretreated with an excess of unarmed parental antibodies to block either EGFR or cMET. Next, EGFR-cMET ADC (RAA22/B09-AZ1508) was added to cells in a 4× serial dilution series with a final concentration ranging from 67 nM down to 0.0009 nM. The treated cells were cultured for 72 hours in a humidified incubator at 37° C. and 5% $CO_2$. The metabolic activity was determined using CellTiter-Glo Luminescent Viability Assay (Promega). Data are plotted as percent metabolic activity relative to untreated control. IC50 values were determined using logistic non-linear regression analysis between the maximal viability (untreated cells) and the maximal response (peak inhibition) with GraphPad Prism software.

Figure 11:
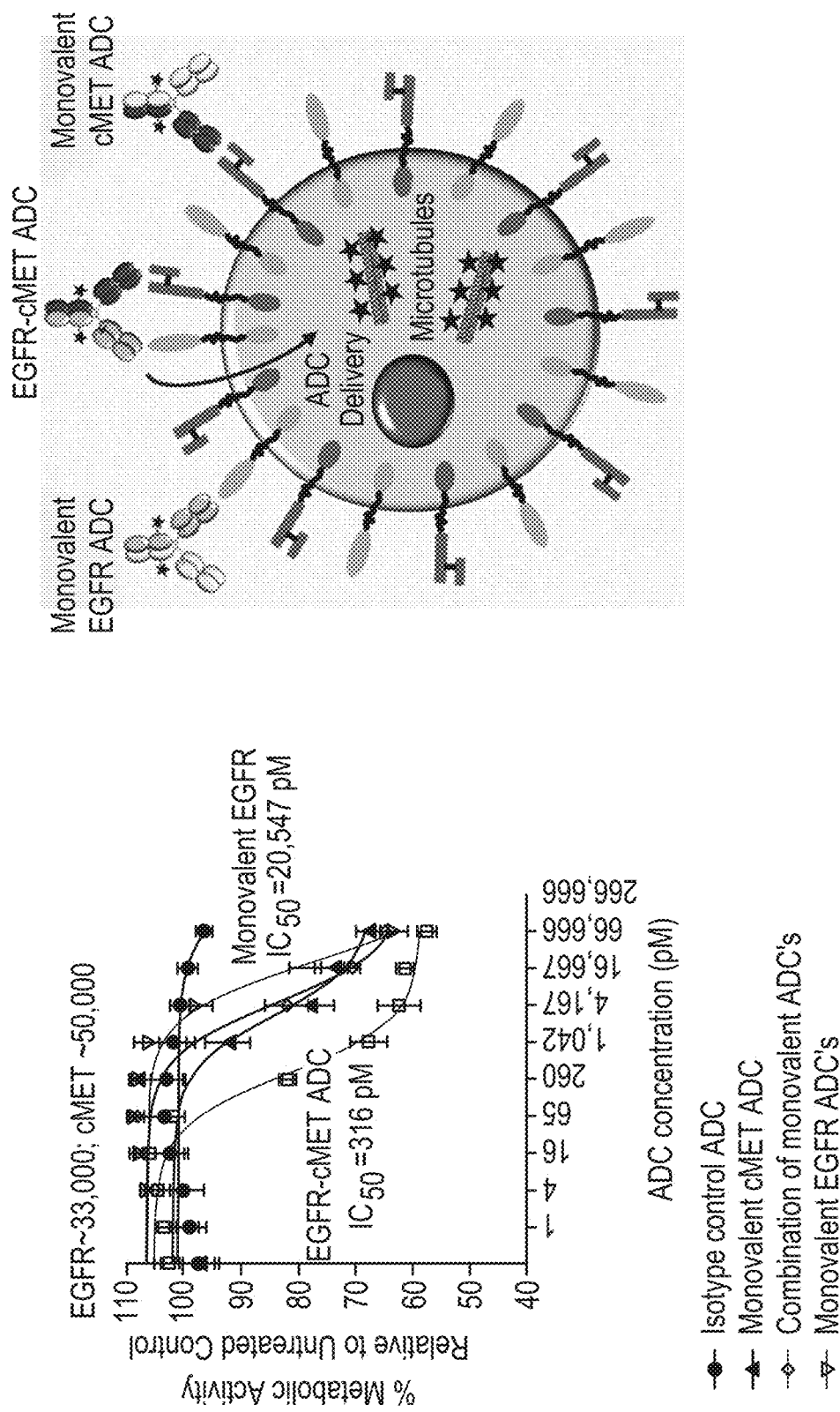

FIG. 11. Monovalent ADCs against EGFR or cMET have reduced activity in vitro compared to bispecific EGFR/cMET ADC. Monovalent ADCs were constructed by pairing each binding arm with a non-binding isotype control arm (R347) to produce EGFR ADC (RAA22/R347-AZ1508) and anti-cMET ADC (B09/R347-AZ1508), The ADCs were added to NCI H1975 cells in a 4× serial dilution series with a final concentration ranging from 67 nM down to 0.0009 nM. Percent metabolic activity was determined as described in FIG. 9.

Figure 12A:
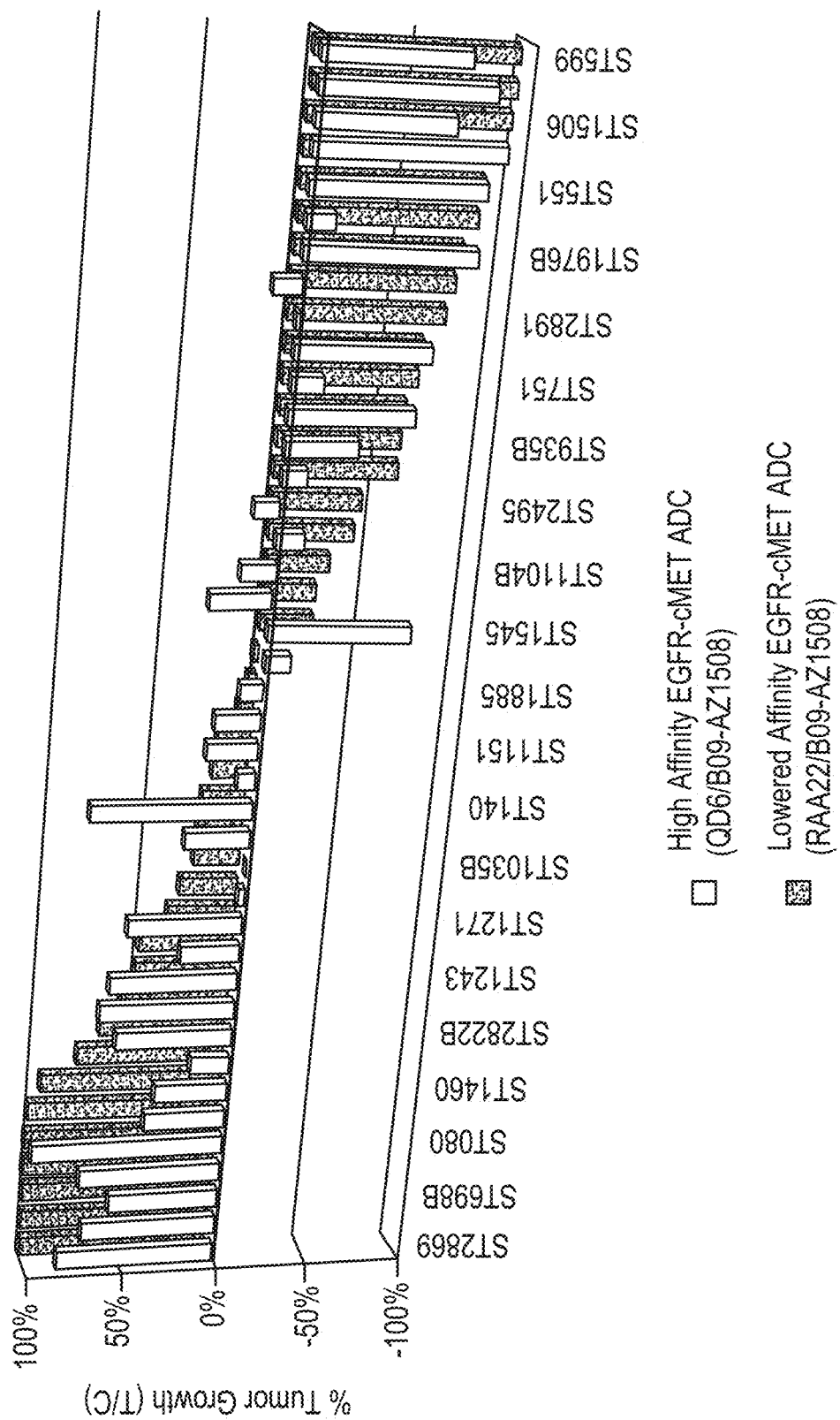

FIG. 12A Shows results of mouse PDX trials carried out to determine the efficacy of high affinity (QD6/B09-AZ1508) and low affinity (RAA22/B09-AZ1508) EGFR-cMET ADCs in a large number of patient derived xenograft (PDX) models of human cancer in immunodeficient mice. Each compound was tested at a single dose level of 3 mg/kg in a single mouse for each PDX model representing a different human tumor. Percent tumor growth relative to untreated control tumors (% T/C) was calculated for tumors that grew larger than the initial volume and percent tumor regression was calculated for tumors that showed a reduction in size compared to the initial tumor volume. (A) shows the direct comparison of the high and low affinity ADCs in each model and FIG. 12B shows waterfall plots for QD6/B09-AZ1508 in rank order of efficacy FIG. 12C shows waterfall plots for RAA22/B09-AZ1508 in rank order of efficacy FIG. 13. Dose range finding in vivo efficacy studies in PDX models were carried out in athymic nude mice implanted unilaterally on the flank with tumor fragments harvested from host animals. The high affinity EGFR-cMET ADC, QD6/B09-AZ1508, was tested at dose levels of 1 and 2 mg/kg and the variant with lowered affinity for EGFR, RAA22/B09-AZ1508, was tested at 1, 2, and 3 mg/kg, as indicated in the figure. Tumor volume measurements were taken twice weekly following the initiation of dosing and plotted as line graphs of tumor volume over time. Error bars represent standard error of the means (SEM) and the inset images show the immunohistochemical staining of EGFR and cMET for each model, from tumor tissue taken from an earlier passage of the model.

Figure 14A:
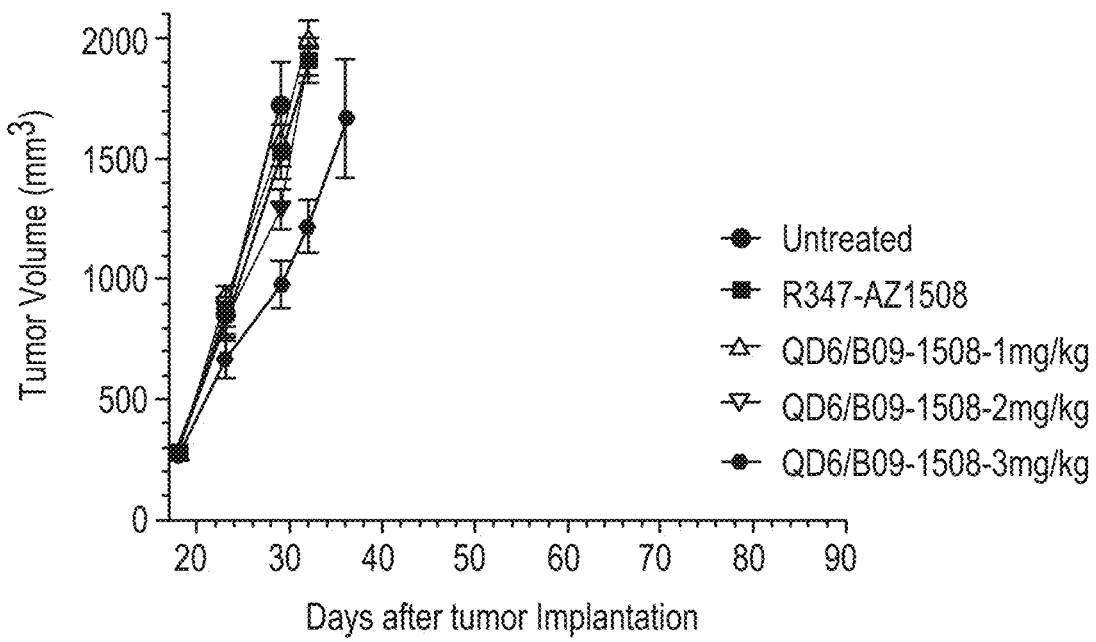

FIG. 14A In vivo efficacy of EGFR-cMET bispecific ADCs in a subcutaneous and orthotopic Pancreatic PDX model. A) In vivo efficacy of the High Affinity QD6/B09 ADC in the subcutaneous MEDI-PANC-08 PDX model, ●—Untreated, ■—R347-AZ1508 (3 mg/kg—Q1Wx4), ▲—QD6/B09-1508 (1 mg/kg—Q1Wx4), ▼—QD6/B09-1508 (2 mg/kg—Q1Wx4) and ◆—QD6/B09-1508 (3 mg/kg—Q1Wx4). Tumor volumes were measure twice a week.

Figure 14B:
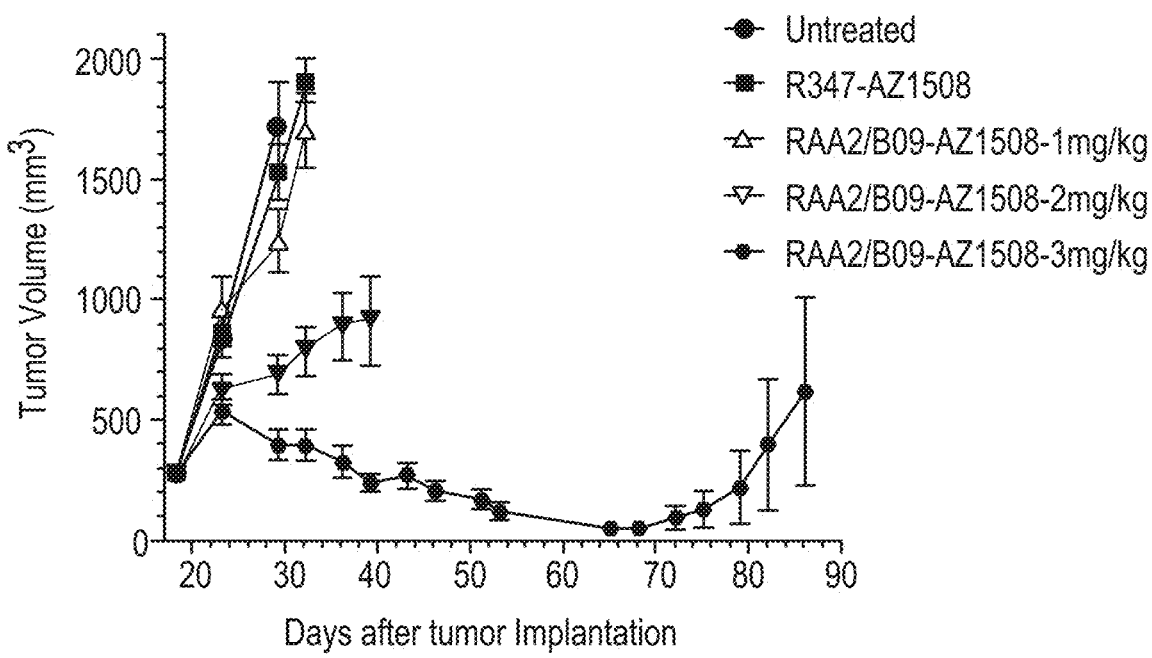

FIG. 14B In vivo efficacy of the Low Affinity RAA2/B09 ADC in the subcutaneous MEDI-PANC-08 PDX model. ●—Untreated, ■—R347-AZ1508 (3 mg/kg—Q1Wx4), ▲—RAA2/B09-1508 (1 mg/kg—Q1Wx4), ▼—RAA2/B09-1508 (2 mg/kg—Q1Wx4) and ◆—RAA2/B09-1508 (3 mg/kg—Q1Wx4). Tumor volumes were measure twice a week.

Figure 14C:
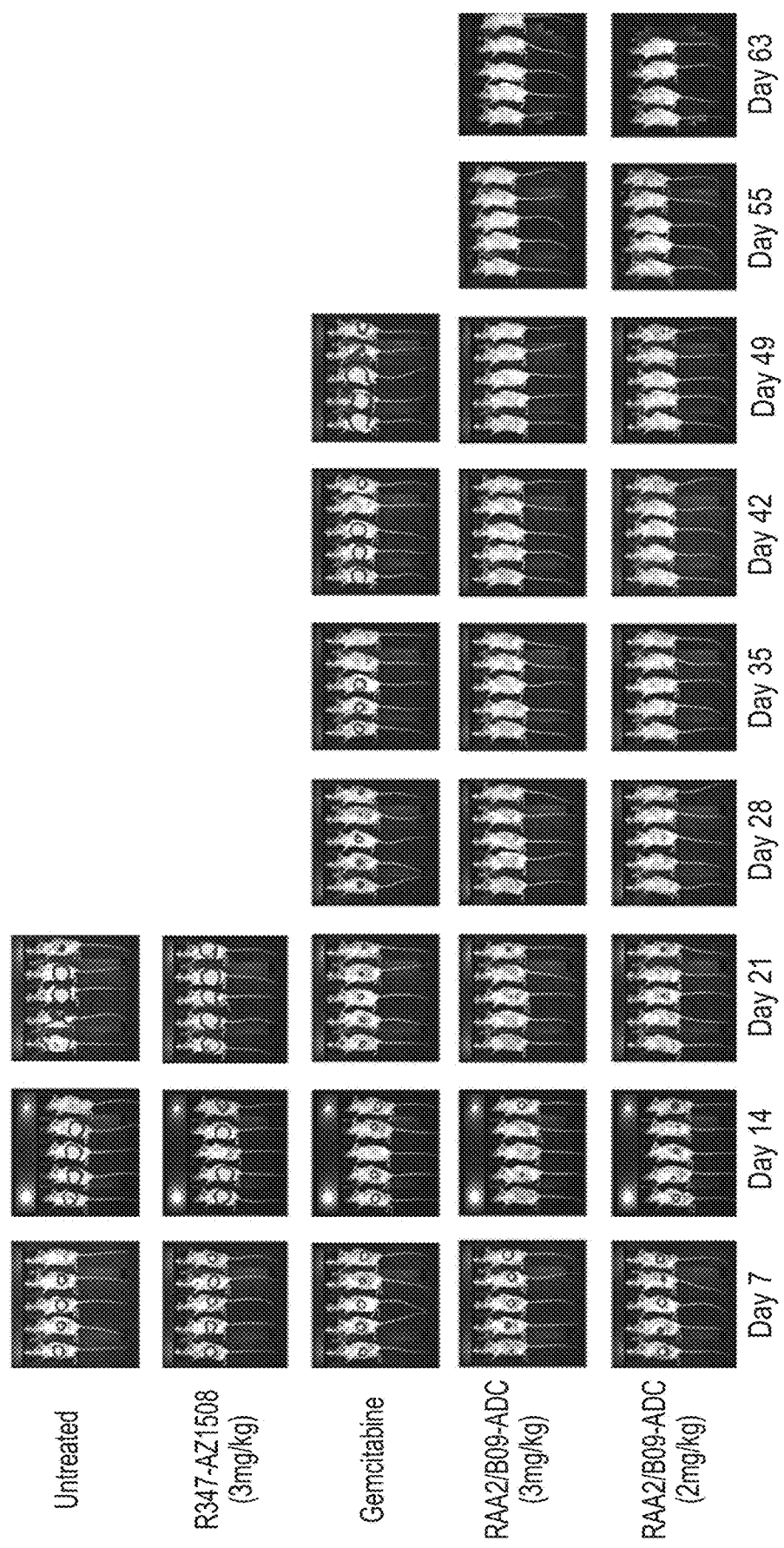

FIG. 14C Luciferase imaging of the orthotopic MEDI-PANC-08$^{LUC}$ (luciferase expressing) PDX model. Mice were imaged weekly using the IVIS Spectrum In vivo Imaging system. The images are normalized across all groups and timepoints with the radiance scale (Avg Radiance [p/s/cm2/sr]) set between the max signal (Day 21 Control Gp) and background.

Figure 14D:
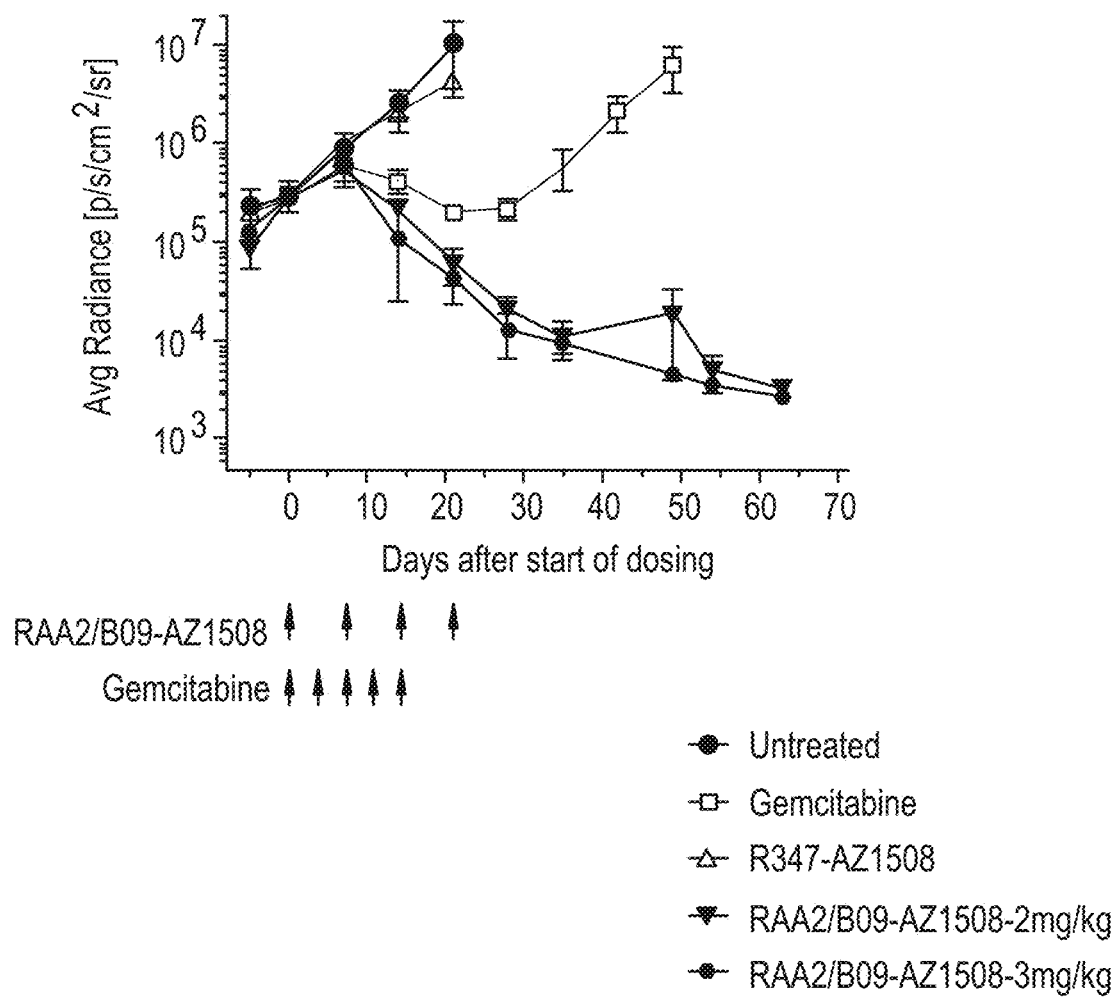

FIG. 14D In vivo efficacy of the Low Affinity RAA2/B09 ADC in the subcutaneous MEDI-PANC-08 PDX model. ●—Untreated, ■—Gemcitabine (75 mg/kg—Q3/4Dx5), ▲—R347-AZ1508 (3 mg/kg—Q1Wx4), ▼—RAA2/B09-1508 (2 mg/kg—Q1Wx4) and ◆—RAA2/B09-1508 (3 mg/kg—Q1Wx4). Treatment days are indicated by the arrows, tumor volumes were measure twice a week. The data displayed in panels A and B are the group mean tumor volume ($mm^3$)±SEM, in panel D group mean Radiance [p/s/cm²/sr]±SEM.

Figure 15A:
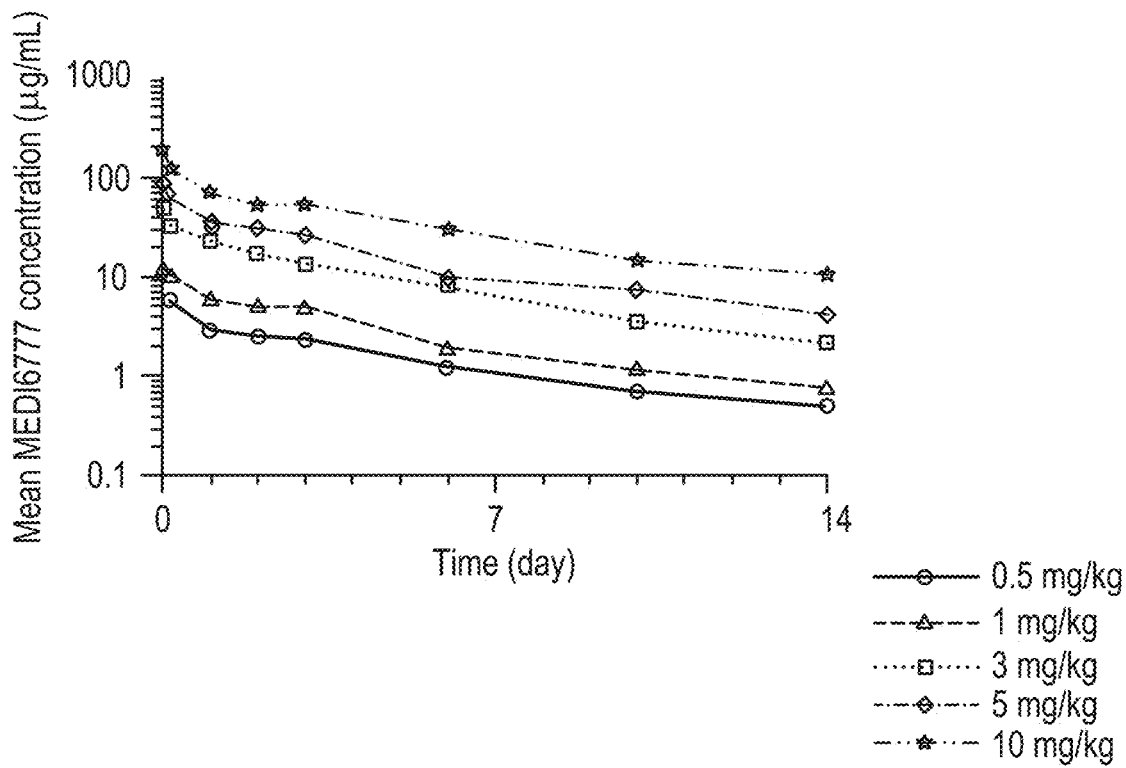
Figure 15B:
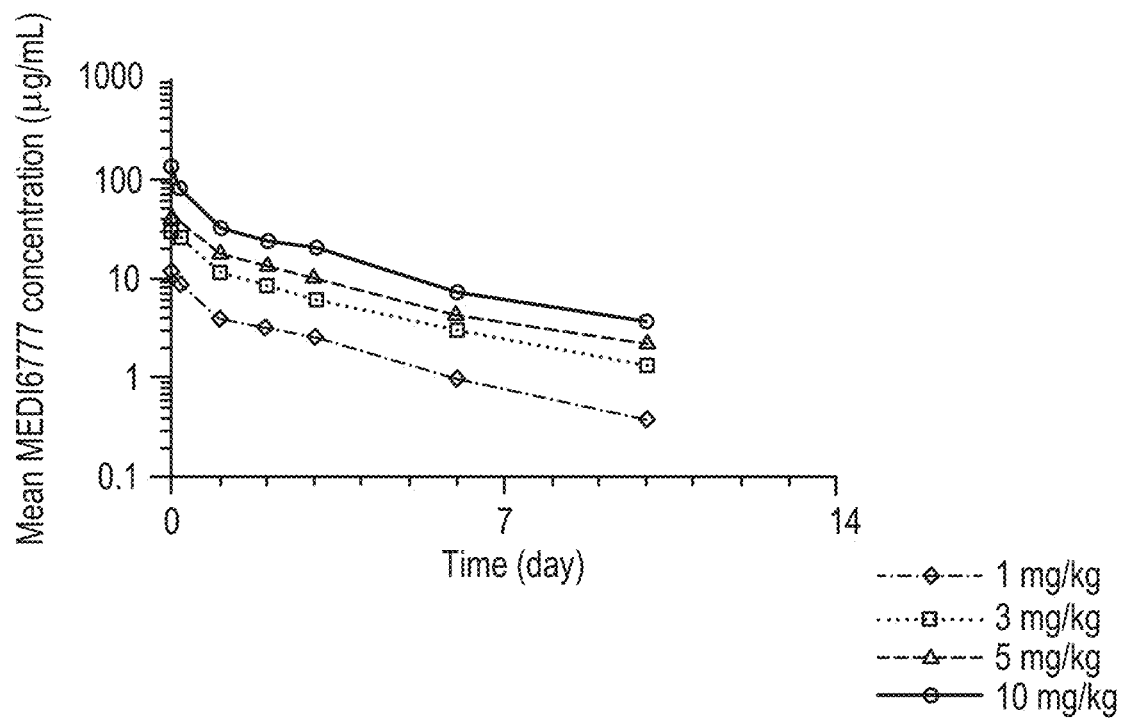

FIG. 15A Mean concentrations-time profiles and mean NCA PK parameters for RAA22/B09-57-AZ1508 in Mice. The target compound concentration and the total antibody concentration were measured with an immuno capture LC-MS/MS assay. FIG. 15B Mean concentrations-time profiles and mean NCA PK parameters for QD6/B09-57-AZ1508 in Mice. The target compound concentration and the total antibody concentration were measured with an immuno capture LC-MS/MS assay.

The signature tryptic peptide on the human antibody Fc region and the cleaved warhead was separated using reversed phase chromatography (RPLC) followed with detection using multiple reaction monitoring (MRM). The signature peptide on the Fc region (VVSVLTVLHQDWLNGK) was used to calculate total Ab, while the digestion released warhead was used to calculate the RAA22/B09 ADC. The internal standard used in this experiment are isotopically labeled peptide or protein (SiluMAb, Sigma-Aldrich) or isotopically labeled warhead. The peak area ratio of the analyte against the internal standards was used to calculate against the standard curve.

The standard curves and QCs are prepared by spiking RAA22/B09 ADC at different levels into the same matrix as the samples. The quantification range covers 100 ng/mL-15,000 ng/mL, with the dilution QC covering up to 525,000 ng/mL. The standard curve was fitted with the simplest possible model. The accuracy and precision of the assay is within 20% for all levels except the LLOQ, which is at 25%.

Figure 16A:
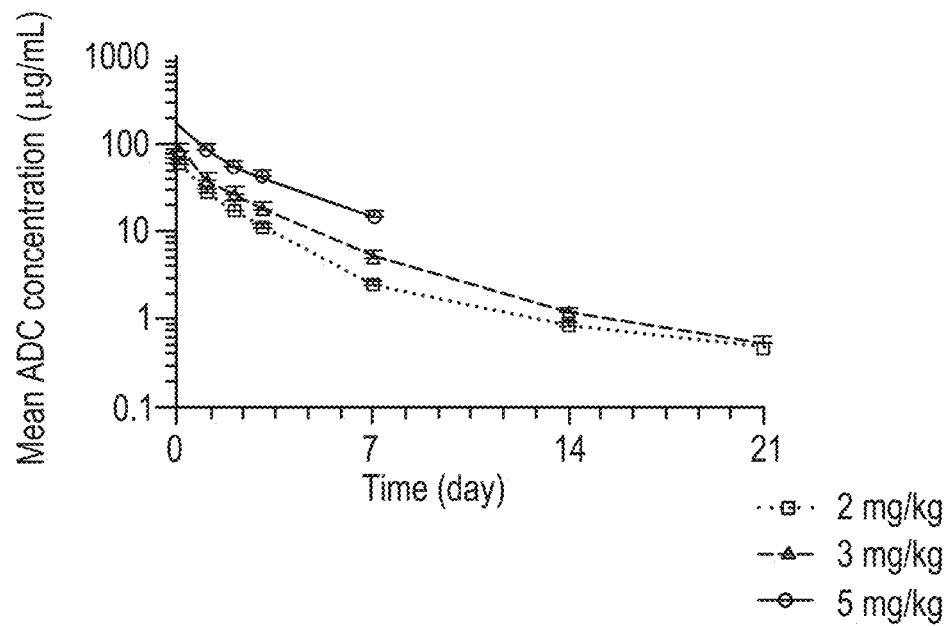

FIG. 16A Mean concentrations-time profiles for RAA22/B09-57-AZ1508 in Monkeys. Cynomolgus monkey plasma samples were collected and processed using the immuno capture LC-MS/MS assay and non-compartmental PK analysis as described in FIG. 15.

Figure 16B:
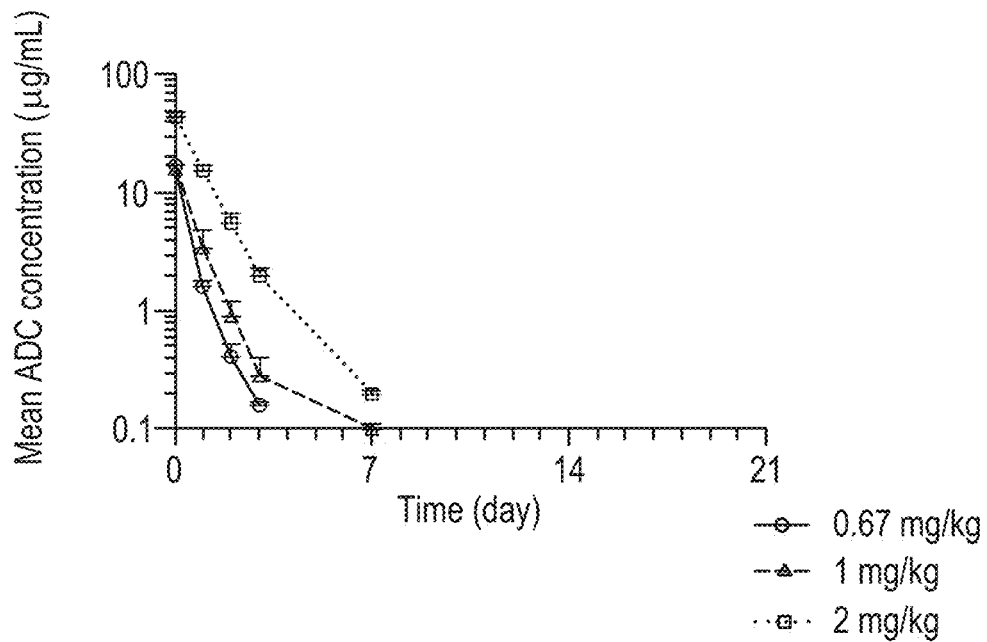

FIG. 16B Mean concentrations-time profiles for QD6/B09-57-AZ1508 in Monkeys. Cynomolgus monkey plasma samples were collected and processed using the immuno capture LC-MS/MS assay and non-compartmental PK analysis as described in FIG. 15.

Figure 17:
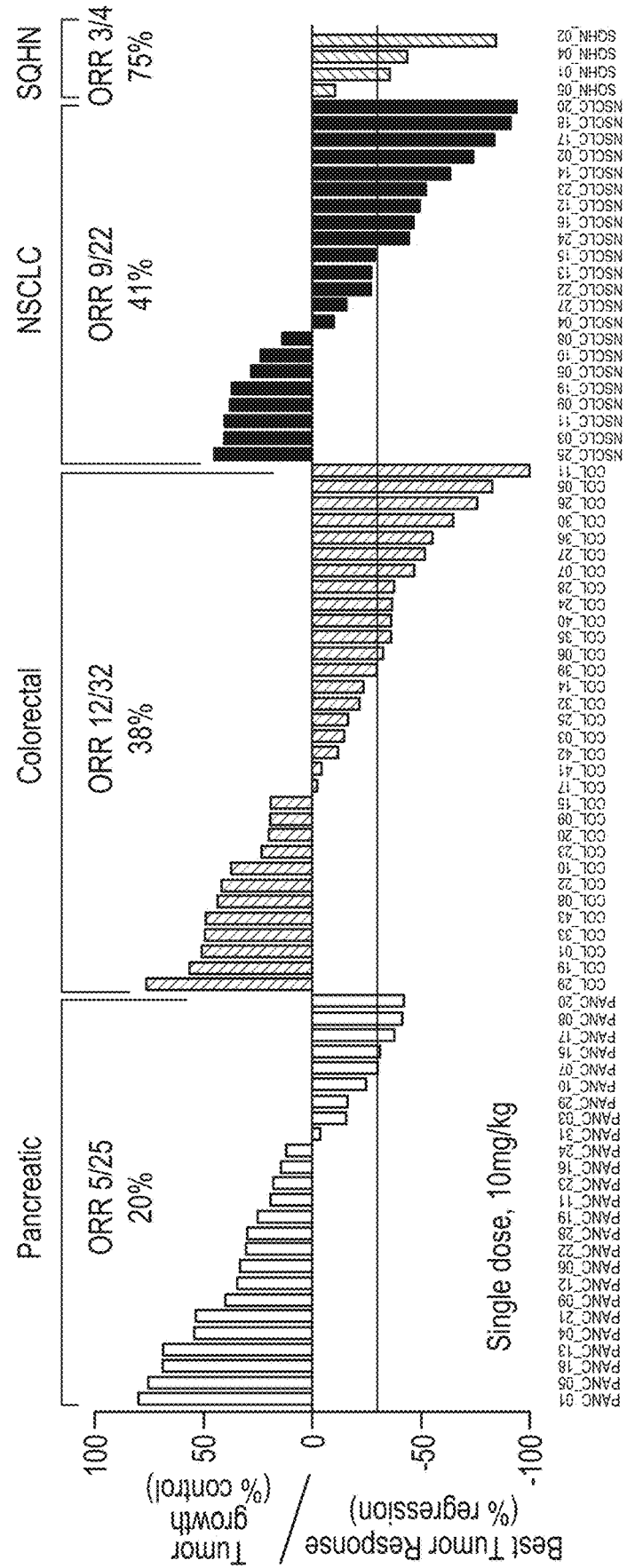

FIG. 16C mean NCA PK parameters for QD6/B09-57-AZ1508 in Monkeys. NCA PK parameters for QD6/B09-57-AZ1508 at 3 mg/kg in 20067312 was based on PK data following second dose. All other results were based on PK data following first dose. Cynomolgus monkey plasma samples were collected and processed using the immuno capture LC-MS/MS assay and non-compartmental PK analysis as described in FIG. 15. FIG. 17 EGFR-cMET Maia Topoi ADC was evaluated in patient derived xenograft (PDX) models representing multiple types of human cancer in immunodeficient mice as a PDX trial. Compound was tested at a dose level of 10 mg/kg in a single mouse for each PDX model representing a unique human tumor. Percent tumor growth relative to untreated control tumors (% T/C) was calculated for tumors that grew larger than the initial volume (Tumor growth inhibition (% TGI) was defined as Percent stumor growth versus Day 0 between treatment (TX) and control (C) groups, according to the formula: % TGI=1−(TXfinal−TXinitial)/(Cfinal−Cinitial)). and percent tumor regression was calculated for tumors that showed a reduction in size compared to the initial tumor volume (Percent Tumor Regression was defined as the percentage tumor reduction of tumors in treated animals relative to the Day 0 tumor volume (day of initial dose), calculated at study endpoint according to the following formula: % Regression=(TXfinal avg−TXinitial avg)/(TXinitial avg)×100).

Figure 18:
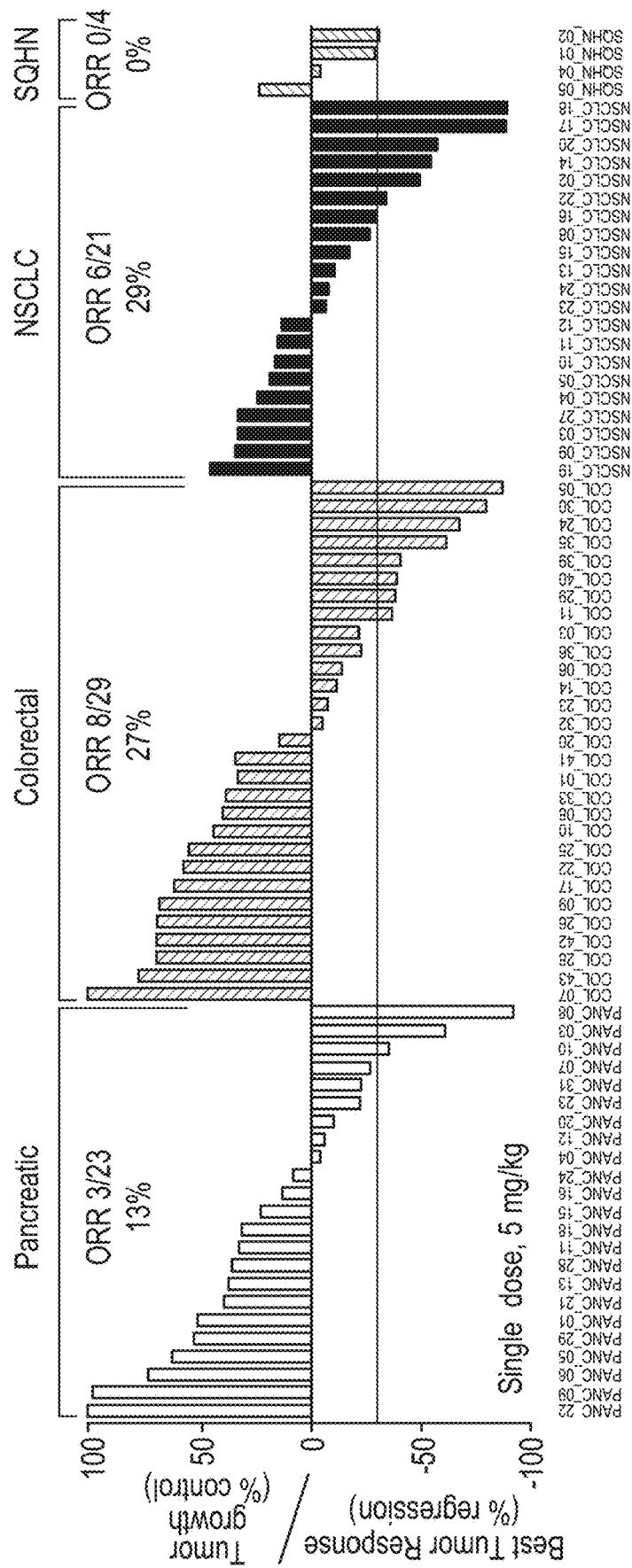

FIG. 18 EGFR-cMET Topoi TM ADC was evaluated in patient derived xenograft (PDX) models representing multiple types of human cancer in immunodeficient mice as a PDX trial. Compound was tested at a dose level of 5 mg/kg in a single mouse for each PDX model representing a unique human tumor. Percent tumor growth relative to untreated control tumors (% T/C) was calculated for tumors that grew larger than the initial volume (Tumor growth inhibition (% TGI) was defined as Percent stumor growth versus Day 0 between treatment (TX) and control (C) groups, according to the formula: % TGI=1−(TXfinal−TXinitial)/(Cfinal−Cinitial)). and percent tumor regression was calculated for tumors that showed a reduction in size compared to the initial tumor volume (Percent Tumor Regression was defined as the percentage tumor reduction of tumors in treated animals relative to the Day 0 tumor volume (day of initial dose), calculated at study endpoint according to the following formula: % Regression=(TXfinal avg−TXinitial avg)/(TXinitial avg)×100).

Figure 19A:
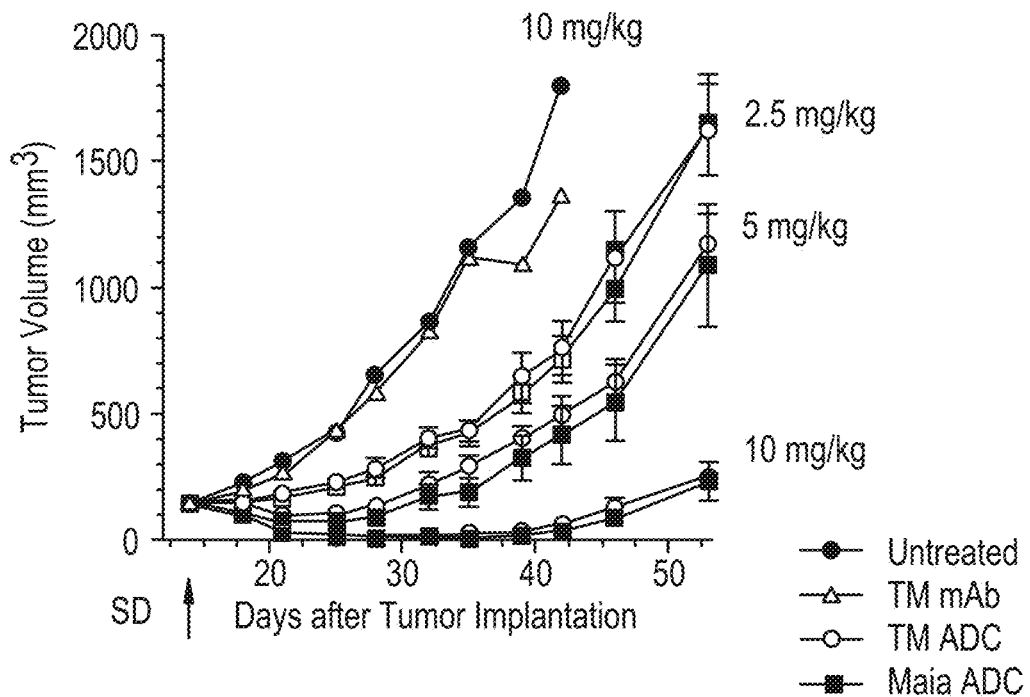

FIG. 19A Two different EGFR-cMET ADCs with different IgG Fc formats (Maia and TM) were evaluated for comparability in the SQHN-02 PDX model. The ADCs were tested at 3 dose levels: 2.5, 5, and 10 mg/kg and tumor growth was compared against untreated control animals. A total of 10 animals were treated per treatment and control group.

Figure 19B:
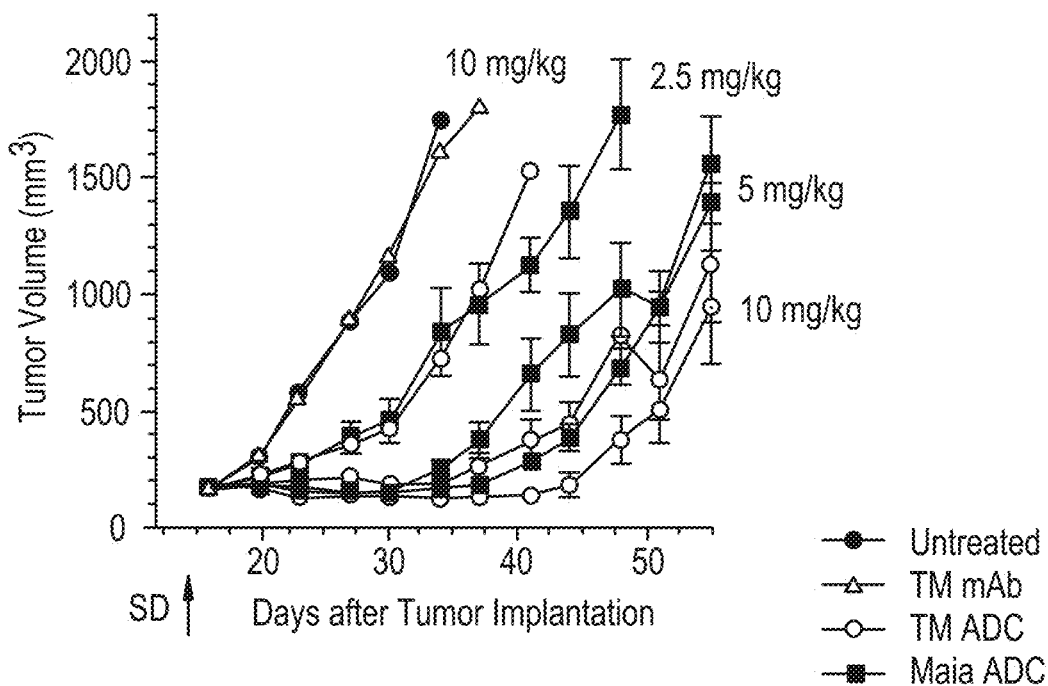

FIG. 19B Two different EGFR-cMET ADCs with different IgG Fc formats (Maia and TM) were evaluated for comparability in the Panc-08 PDX model. The ADCs were tested at 3 dose levels: 2.5, 5, and 10 mg/kg and tumor growth was compared against untreated control animals. A total of 10 animals were treated per treatment and control group.

Figure 20:
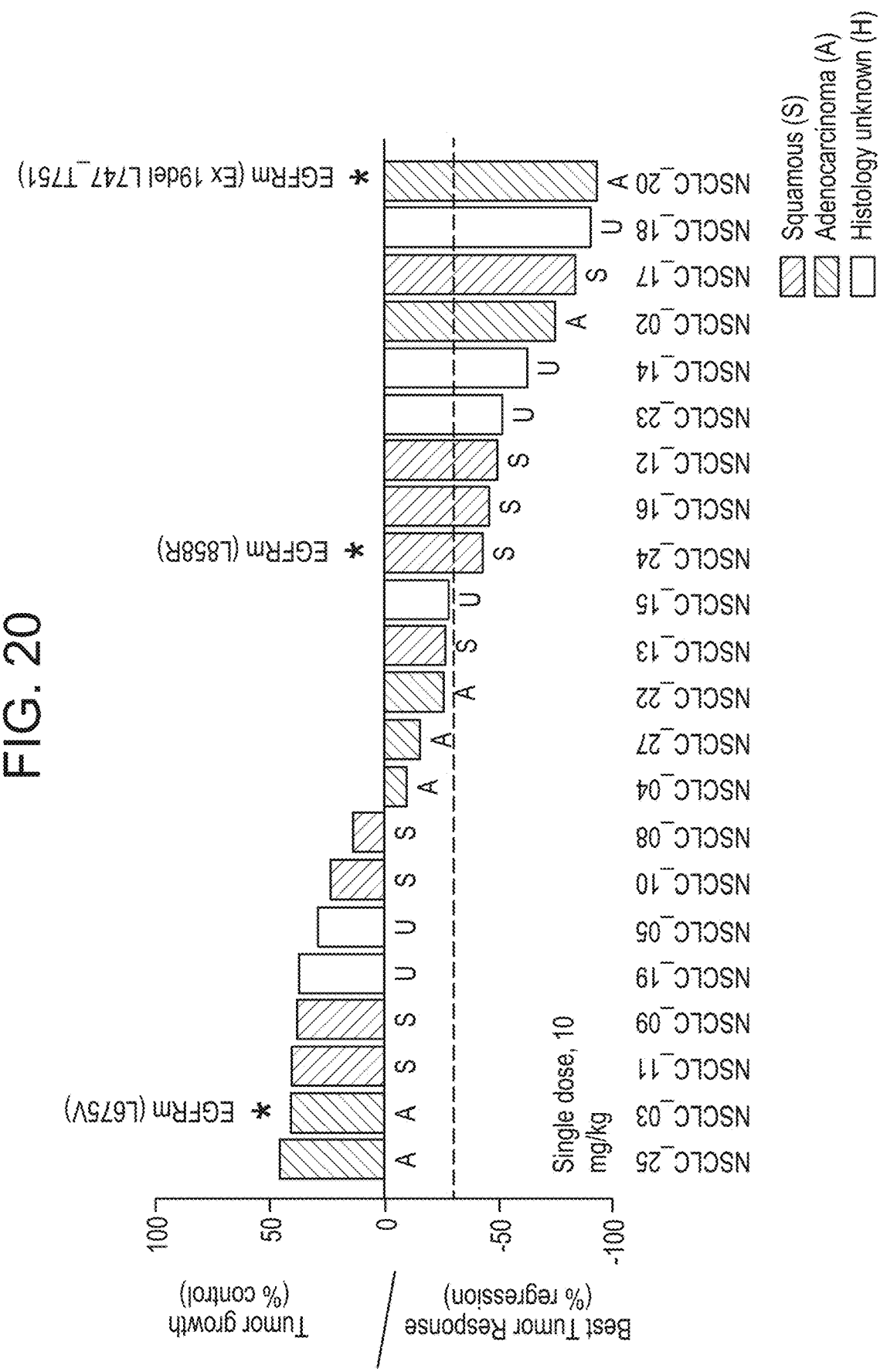

FIG. 20 depicts the results of the non-small cell lung cancer NSCLC PDX models from FIG. 17 above, highlighting the EGFR mutation status and histology, where known.

Figure 21:
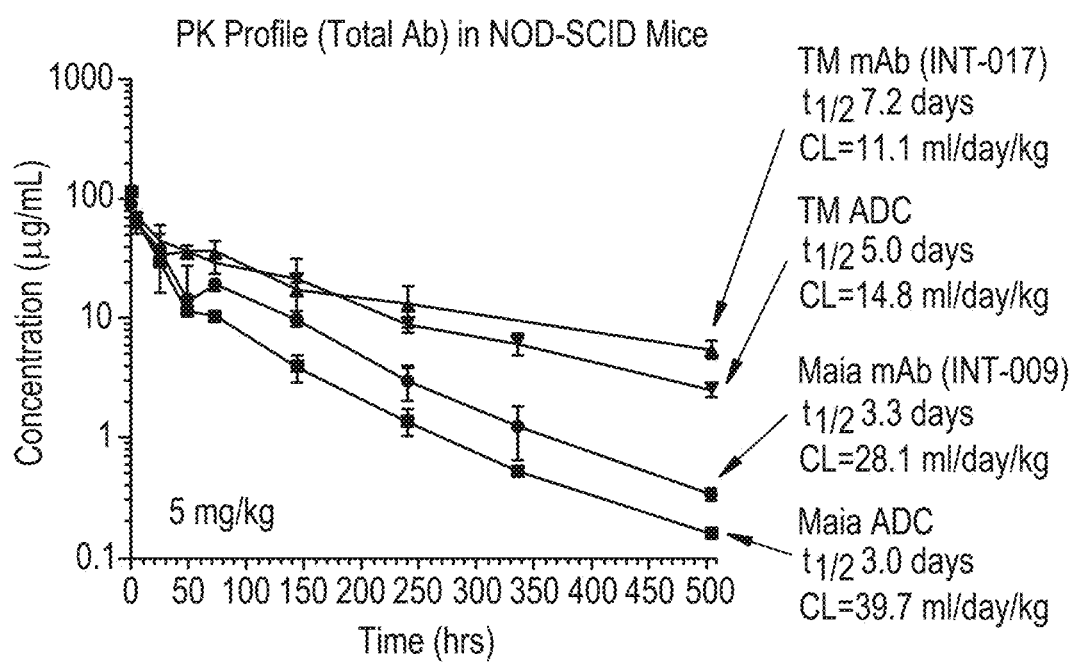

FIG. 21 The pharmacokinetic profiles of EGFR-cMET bispecific antibodies INT-009 (RAA22/B09-Maia naked mAb) and INT-009-SG3932 DAR8 ADC ("MAIA ADC") were compared to B09/RAA2-IgG1-TM mirror mAb (INT-017) and TM-mirror-SG3932 DAR6 ADC ("TM ADC") in NOD-SCID mice at therapeutic doses of 5 mg/kg.

Figure 22:
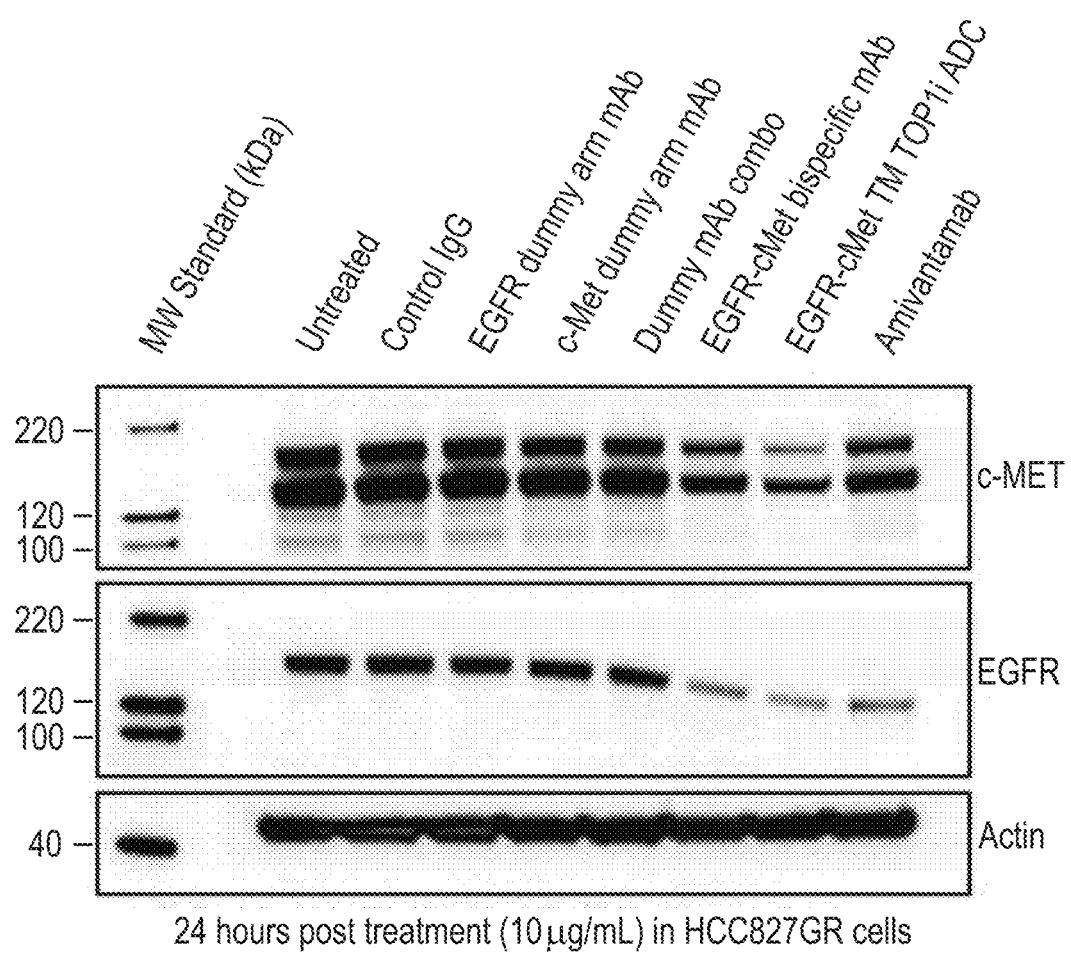

FIG. 22 shows a comparison of EGFR and cMet receptor degradation after treatment with EGFR-cMET Topoi TM ADC vs Amivantamab

DETAILED DESCRIPTION

Aspects and instances of the present disclosure will now be discussed with reference to the accompanying figures. Further aspects and disclosure will be apparent to those skilled in the art. All documents mentioned in this text are incorporated herein by reference.

Targets
EGFR

Human EGFR (also known as proto-oncogene c-ErbB-1, receptor tyrosine-protein kinase erbB-1 and EC 2.7.10.1) is the protein identified by UniProt P00533. Alternative splicing of mRNA encoded by the human EGFR gene (also known as ERBB, ERBB1 and HER1) yields four isoforms: isoform 1 (UniProt: P00533-1, v2 (last sequence update: Nov. 1, 1997)); isoform 2 (UniProt: P00533-2, v1), which comprises the substitutions F404L and L405S relative to isoform 1, and which lacks the amino acid sequence corresponding to positions 406 to 1210 of isoform 1; isoform 3 (UniProt: P00533-3, v1), which comprises substitutions at position 628 to 705 of isoform 1, and which lacks the amino acid sequence corresponding to positions 706 to 1210 of isoform 1; and isoform 4 (UniProt: P00533-4), which comprises the substitution C628S relative to isoform 1, and which lacks the amino acid sequence corresponding to positions 629 to 1210 of isoform 1.

The structure and function of EGFR is reviewed e.g. in Ferguson, Annu Rev Biophys. (2008) 37: 353-373. EGFR is a transmembrane protein that is a receptor for members of the epidermal growth factor family (EGF family) The receptor comprises a large extracellular region, a single spanning transmembrane domain, an intracellular juxtamembrane domain, a tyrosine kinase domain and a C-terminal regulatory region. Binding of EGFR to a ligand induces receptor dimerization and autophosphorylation of several tyrosine residues (Y992, Y1045, Y1068, Y1148 and Y1173) in the C-terminal regulatory region of EGFR.

Aberrant EGFR expression/activity is implicated in many diseases, including nervous system disorders and many cancers.

In this specification "EGFR" refers to EGFR from any species and includes EGFR isoforms, fragments, variants or homologues from any species.

c-Met

Human c-Met (also known as Hepatocyte growth factor receptor (HGFR) or tyrosine-protein kinase Met) is the protein identified by UniProt P08581. Alternative splicing of mRNA encoded by the human MET gene yields three isoforms: isoform 1 (UniProt: P08581-1, v4 (last sequence update: Jul. 7, 2009)); isoform 2 (UniProt: P08581-2), in which the amino acid sequence "STWWKE-PLNIVSFLFCFAS" is inserted at position 755 of isoform 1; and isoform 3 (UniProt: P08581-3) also known as Soluble met variant 4, in which the amino acid sequence corresponding to positions 755 to 764 of isoform 1 are substituted with "RHVNIALIQR" and which further lacks the amino acid sequence corresponding to positions 765 to 1390 of isoform 1.

The structure of c-Met is reviewed e.g. in Gherardi, 2003, which is herein incorporated by reference in its entirety. c-Met is a heterodimer made of an alpha chain (50 kDa) and a beta chain (145 kDa), which are disulphide linked. c-Met comprises a N-terminal Sema domain, which mediates binding to hepatocyte growth factor (HGF) and an intracellular kinase domain. Ligand binding at the cell surface induces autophosphorylation of c-Met on its intracellular domain that provides docking sites for downstream signalling molecules and the activation of several signalling cascades.

c-Met is expressed in normal tissues on the surface of epithelial cells. c-Met overexpression is observed in many human tumors and cancers, which is frequently associated with a metastatic phenotype and poor prognosis. Examples of cancers where high levels of c-Met expression has been observed includes non-small cell lung cancer, pancreatic cancer, colorectal cancer, head and neck squamous cell carcinoma, breast cancer and esophageal-gastric cancer. In these cancers, co-expression of EGFR and c-Met is often observed.

Antibody Molecules

The present disclosure provides antibody molecules. Antibody molecules according to the present disclosure may be provided in isolated form, in the sense of being free from contaminants, such as antibodies able to bind other polypeptides and/or serum components.

The term "antibody molecule" describes an immunoglobulin whether natural or partly or wholly synthetically produced. The antibody molecule may be human or humanised. The antibody molecule is preferably a monoclonal antibody molecule. Examples of antibodies are the immunoglobulin isotypes, such as immunoglobulin G (IgG), and their isotypic subclasses, such as IgG1, IgG2, IgG3 and IgG4, as well as fragments thereof.

The term "antibody molecule", as used herein, thus includes antibody fragments, as long as they display binding to the relevant target molecule(s). Examples of antibody fragments include Fv, scFv, Fab, scFab, F(ab')$_2$, Fab$_2$, diabodies, triabodies, scFv-Fc, minibodies and single domain antibodies (e.g. VhH), etc.). Unless the context requires otherwise, the term "antibody molecule", as used herein, is thus equivalent to "antibody molecule or fragment thereof".

Antibody molecules and methods for their construction and use are well-known in the art and are described in, for example, Holliger & Hudson, Nature Biotechnology 23(9): 1126-1136 (2005). It is possible to take monoclonal and other antibody molecules and use techniques of recombinant DNA technology to produce other antibody or chimeric molecules which retain the specificity of the original antibody. Such techniques may involve introducing CDRs or variable regions of one antibody molecule into a different antibody molecule (EP-A-184187, GB 2188638A and EP-A-239400).

In view of today's techniques in relation to monoclonal antibody technology, antibody molecules can be prepared to most antigens. The antigen-binding domain may be a part of an antibody (for example a Fab fragment) or a synthetic antibody fragment (for example a single chain Fv fragment (ScFv)). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger, 1988.

Antibody molecules according to the present disclosure comprise an antigen-binding domain. An "antigen-binding domain" describes the part of a molecule that binds to all or part of the target antigen. Where an antigen is large, an antibody may only bind to a particular part of the antigen, which part is termed an epitope. An antibody antigen-binding site may be provided by one or more antibody variable domains. An antibody antigen-binding site preferably comprises a variable light (VL) region and variable heavy (VH) region. The VH and VL region of an antigen-binding domain together constitute the Fv region.

An antigen-binding domain generally comprises six complementarity-determining regions (CDRs); three in the VH region: HCDR1, HCDR2 and HCDR3, and three in the VL region: LCDR1, LCDR2, and LCDR3. The six CDRs together define the paratope of the antigen-binding domain, which is the part of the antigen-binding domain which binds to the target antigen.

The VH region and VL region comprise framework regions (FRs) either side of each CDR, which provide a scaffold for the CDRs. From N-terminus to C-terminus, VH regions comprise the following structure: N term-[HFR1]-[HCDR1]-[HFR2]-[HCDR2]-[HFR3]-[HCDR3]-[HFR4]-C term; and VL regions comprise the following structure: N term-[LFR1]-[LCDR1]-[LFR2]-[LCDR2]-[LFR3]-[LCDR3]-[LFR4]-C term.

There are several different conventions for defining antibody CDRs and FRs, such as those described in Kabat, 1991, Chothia, 1987, IMGT numbering as described in LeFranc, 2015, and VBASE2, as described in Retter, 2005. The CDRs and FRs of the VH regions and VL regions of the antibody molecules described herein were defined according to Kabat (Kabat, 1991).

Antibody molecules that comprise at least two antigen-binding domains, each of which being capable of binding to a different target may be termed "bispecific antibody molecules". In contrast, antibody molecules that only bind a single target (e.g. EGFR or c-Met) are termed "monospecific antibody molecules". The present disclosure provides a bispecific antibody molecule that comprises a first antigen binding domain that binds EGFR and a second antigen-binding domain that binds c-Met.

Anti-EGFR Antigen-Binding Domains

The antigen-binding domain that binds EGFR comprises the CDRs of an antibody molecule which is capable of binding to EGFR. In some instances, the antigen-binding domain that binds EGFR additionally comprises the FRs of an antibody molecule which is capable of binding to EGFR. That is, in some instances the antigen-binding domain that binds EGFR comprises the VH region and the VL region of an antibody molecule which is capable of binding to EGFR.

In some instances the antigen-binding domain that binds EGFR comprises a VH region and a VL region which is, or which is derived from, the VH/VL region of an EGFR-binding antibody clone described herein (i.e. anti-EGFR antibody clones RAA22 or QD6). Preferably, the antigen-binding domain that binds EGFR comprises a VH region and a VL region which is, or which is derived from, the VH/VL region of RAA22.

In some instances, the antigen-binding domain that binds EGFR comprises the three HCDRs or three LCDRs, preferably the three VH CDRs and the three VL CDRs, of anti-EGFR antibody clones RAA22 or QD6, preferably RAA22. The VH and VL domain sequences of antibodies RAA22 and QD6 are described herein, and the three VH and three VL domain CDRs of said antibodies may thus be determined from said sequences.

In some instances, the antigen-binding domain that binds EGFR comprises a VH region according to (1) or (2) below:
 (1) a VH region comprising the following CDRs:
   HCDR1 having the amino acid sequence of SEQ ID NO: 1
   HCDR2 having the amino acid sequence of SEQ ID NO: 2
   HCDR3 having the amino acid sequence of SEQ ID NO: 3,
   or a variant thereof in which one or two or three amino acids in one or more of HCDR1, HCDR2, or HCDR3 are substituted with another amino acid, or
 (2) a VH region comprising the following CDRs:
   HCDR1 having the amino acid sequence of SEQ ID NO: 1
   HCDR2 having the amino acid sequence of SEQ ID NO: 7

HCDR3 having the amino acid sequence of SEQ ID NO: 3,
or a variant thereof in which one or two or three amino acids in one or more of HCDR1, HCDR2, or HCDR3 are substituted with another amino acid.

Preferably, the antigen-binding domain that binds EGFR comprises a VH region according to (1) above.

In some instances, the antigen-binding domain that binds EGFR comprises a VH region according to (1) or (2) above, wherein the VH region additionally comprises the FRs according to (3) below:
(3) HFR1 having the amino acid sequence of SEQ ID NO: 8
HFR2 having the amino acid sequence of SEQ ID NO: 9
HFR3 having the amino acid sequence of SEQ ID NO: 10
HFR4 having the amino acid sequence of SEQ ID NO: 11,
or a variant thereof in which one or two or three amino acids in one or more of HFR1, HFR2, HFR3, or HFR4 are substituted with another amino acid.

In some instances the antigen-binding domain that binds EGFR comprises a VH region comprising the CDRs according to (1) or (2) above, and the FRs according to (3) above.

In some instances the antigen-binding domain that binds EGFR comprises a VH region according to (4) or (5) below:
(4) a VH region comprising the CDRs according to (1) and the FRs according to (3),
(5) a VH region comprising the CDRs according to (2) and the FRs according to (3).

Preferably, the antigen-binding domain that binds EGFR comprises a VH region according to (4) above.

In some instances the antigen-binding domain that binds EGFR comprises a VH region according to (6) or (7) below:
(6) a VH region comprising an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 16.
(7) a VH region comprising an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 18.

Preferably, the antigen-binding domain that binds EGFR comprises a VH region according to (6) above.

In some instances the antigen-binding domain that binds EGFR comprises a VL region according to (8) or (9) below:
(8) a VL region comprising the following CDRs:
LCDR1 having the amino acid sequence of SEQ ID NO: 4
LCDR2 having the amino acid sequence of SEQ ID NO: 5
LCDR3 having the amino acid sequence of SEQ ID NO: 6,
or a variant thereof in which one or two or three amino acids in one or more of LCDR1, LCDR2, or LCDR3 are substituted with another amino acid.
(9) a VL region comprising the following CDRs:
LCDR1 having the amino acid sequence of SEQ ID NO: 4
LCDR2 having the amino acid sequence of SEQ ID NO: 66
LCDR3 having the amino acid sequence of SEQ ID NO: 67,
or a variant thereof in which one or two or three amino acids in one or more of LCDR1, LCDR2, or LCDR3 are substituted with another amino acid.

Preferably, the antigen-binding domain that binds EGFR comprises a VL region according to (8) above.

In some instances, the antigen-binding domain that binds EGFR comprises a VL region according to (8) or (9) above, wherein the VL region additionally comprises the I-Rs according to (10) below:
(10) LFR1 having the amino acid sequence of SEQ ID NO: 12
LFR2 having the amino acid sequence of SEQ ID NO: 13
LFR3 having the amino acid sequence of SEQ ID NO: 14
LFR4 having the amino acid sequence of SEQ ID NO: 15,
or a variant thereof in which one or two or three amino acids in one or more of LFR1, LFR2, LFR3, or LFR4 are substituted with another amino acid.

In some instances the antigen-binding domain that binds EGFR comprises a VL region comprising the CDRs according to (8) or (9) above, and the FRs according to (10) above.

In some instances the antigen-binding domain that binds EGFR comprises a VL region according to (11) or (12) below:
(11) a VL region comprising the CDRs according to (8) and the FRs according to (10).
(12) a VL region comprising the CDRs according to (9) and the FRs according to (10).

Preferably, the antigen-binding domain that binds EGFR comprises a VL region according to (11) above.

In some instances the antigen-binding domain that binds EGFR comprises a VL region according to (13) or (14) below:
(13) a VL region comprising an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 20.
(14) a VL region comprising an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 22.

Preferably, the antigen-binding domain that binds EGFR comprises a VL region according to (13) above.

In some instances the antigen-binding domain that binds EGFR comprises a VH region according to any one of (1) to (7) above, and a VL region according to any one of (8) to (14) above. In some preferred instances, the antigen-binding domain comprises a VH region according to any one of (1), (4) and (6) and a VL region according to any one of (8), (11) and (13). In other instances, the antigen-binding domain comprises a VH region according to any one of (2), (5) and (7) and a VL region according to any one of (9), (12), and (14).

Anti-c-Met Antigen-Binding Domains

The antigen-binding domain that binds c-Met comprises the CDRs of an antibody molecule which is capable of binding to c-Met. In some instances, the antigen-binding domain that binds c-Met additionally comprises the FRs of an antibody molecule which is capable of binding to c-Met.

That is, in some instances the antigen-binding domain that binds c-Met comprises the VH region and the VL region of an antibody molecule which is capable of binding to c-Met.

In some instances the antigen-binding domain that binds c-Met comprises a VH region and a VL region which is, or which is derived from, the VH/VL region of a c-Met-binding antibody clone described herein (i.e. anti-c-Met antibody clone B09-GL).

In some instances the antigen-binding domain that binds c-Met comprises the three HCDRs or three LCDRs, preferably the three VH CDRs and the three VL CDRs, of c-Met-binding antibody clone B09-GL. The VH and VL domain sequences of antibodies B09-GL are described herein, and the three VH and three VL domain CDRs of said antibodies may thus be determined from said sequences.

In some instances, the antigen-binding domain that binds c-Met comprises a VH region according to (15) below:
  (15) a VH region comprising the following CDRs:
    HCDR1 having the amino acid sequence of SEQ ID NO: 24
    HCDR2 having the amino acid sequence of SEQ ID NO: 25
    HCDR3 having the amino acid sequence of SEQ ID NO: 26,
    or a variant thereof in which one or two or three amino acids in one or more of HCDR1, HCDR2, or HCDR3 are substituted with another amino acid.

In some instances, the antigen-binding domain that binds c-Met comprises a VH region according to (15) above, wherein the VH region additionally comprises the FRs according to (16) below:
  (16) HFR1 having the amino acid sequence of SEQ ID NO: 30
    HFR2 having the amino acid sequence of SEQ ID NO: 31
    HFR3 having the amino acid sequence of SEQ ID NO: 32
    HFR4 having the amino acid sequence of SEQ ID NO: 33,
    or a variant thereof in which one or two or three amino acids in one or more of HFR1, HFR2, HFR3, or HFR4 are substituted with another amino acid.

In some instances the antigen-binding domain that binds c-Met comprises a VH according to (17) below:
  (17) a VH region comprising the CDRs according to (15) and the FRs according to (16).

In some instances the antigen-binding domain that binds c-Met comprises a VH region according to (18) below:
  (18) a VH region comprising an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 38.

In some instances the antigen-binding domain that binds c-Met comprises a VL region according to (19) below:
  (19) a VL region comprising the following CDRs:
    LCDR1 having the amino acid sequence of SEQ ID NO: 27
    LCDR2 having the amino acid sequence of SEQ ID NO: 28
    LCDR3 having the amino acid sequence of SEQ ID NO: 29,
    or a variant thereof in which one or two or three amino acids in one or more of LCDR1, LCDR2, or LCDR3 are substituted with another amino acid.

In some instances, the antigen-binding domain that binds c-Met comprises a VL region according to (19) above, wherein the VL region additionally comprises the FRs according to (20) below:
  (20) LFR1 having the amino acid sequence of SEQ ID NO: 34
    LFR2 having the amino acid sequence of SEQ ID NO: 35
    LFR3 having the amino acid sequence of SEQ ID NO: 36
    LFR4 having the amino acid sequence of SEQ ID NO: 37,
    or a variant thereof in which one or two or three amino acids in one or more of LFR1, LFR2, LFR3, or LFR4 are substituted with another amino acid.

In some instances the antigen-binding domain that binds c-Met comprises a VL region according to (21) below:
  (21) a VL region comprising the CDRs according to (19) and the FRs according to (20).

In some instances the antigen-binding domain that binds c-Met comprises a VL region according to (22) below:
  (22) a VL region comprising an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 40.

In some instances the antigen-binding domain that binds c-Met comprises a VH region according to any one of (15) to (18) above, and a VL region according to any one of (19) to (22) above.

Antigen-Binding Domains of a Bispecific Antibody Molecule

The invention provides an antibody molecule (i.e. a bispecific antibody molecule) comprising a first antigen-binding domain that comprises the CDRs of an antigen-binding domain which is capable of binding to EGFR, and a second antigen-binding domain that comprises the CDRs of an antigen-binding domain which is capable of binding to c-Met. In some instances, the first antigen-binding domain comprises the CDRs and the FRs of an antigen-binding domain which is capable of binding to EGFR and the second antigen-binding domain comprises the CDRs and the FRs of an antigen-binding domain which is capable of binding to c-Met. That is, in some instances the antibody molecule comprises a first antigen-binding domain comprising the VH region and the VL region of an antigen-binding domain which is capable of binding to EGFR and a second antigen-binding domain comprising the VH region and the VL region of an antigen-binding domain which is capable of binding to c-Met.

In some instances the first antigen-binding domain that binds EGFR comprises VH region and a VL region which is, or which is derived from, the VH/VL region of a EGFR-binding antibody clone described herein (e.g., anti-EGFR antibody clones RAA22 or QD6, preferably RAA22) and the second antigen-binding domain that binds c-Met comprises a VH region and a VL region which is, or which is derived from, the VH/VL region of a c-Met-binding antibody clone described herein (e.g., anti-c-Met antibody clone B09-GL). A bispecific antibody comprising a first antigen-binding domain that binds EGFR and comprises a VH region and a VL region which is, or which is derived from, the VH/VL region of EGFR-binding antibody clone RAA22, and a second antigen-binding domain that binds c-Met and comprises a VH region and a VL region which is, or which is derived from, the VH/VL region of c-Met-binding antibody clone B09-GL may be termed "RAA22/B09" or "RAA22/B09 bispecific antibody molecule".

In some instances the first antigen-binding domain comprises:
a VH region according to any one of (1) to (7) above and a VL region according to any one of (8) to (14) above; and
the second antigen-binding domain comprises:
a VH region according to any one of (15) to (18) above, and a VL region according to any one of (19) to (22) above.

In some preferred instances the first antigen-binding domain comprises:
a VH region according to any of (1), (4) and (6) above and a VL region according to any of (8), (11) and (13) above; and
the second antigen-binding domain comprises:
a VH region according to any of (15) to (18) above, and a VL region according to any of (19) to (22) above.

For example, in a preferred instance, an antibody molecule of the disclosure comprises:
a first antigen-binding domain that binds epidermal growth factor receptor (EGFR); and
a second antigen-binding domain that binds c-Met,
wherein the first antigen-binding domain comprises:
(i) a heavy chain variable (VH) region comprising the following complementarity determining regions (CDRs):
HCDR1 having the amino acid sequence of SEQ ID NO: 1
HCDR2 having the amino acid sequence of SEQ ID NO: 2
HCDR3 having the amino acid sequence of SEQ ID NO: 3,
or a variant thereof in which one or two or three amino acids in one or more of HCDR1, HCDR2, or HCDR3 are substituted with another amino acid; and
(ii) a light chain variable (VL) region comprising the following CDRs:
LCDR1 having the amino acid sequence of SEQ ID NO: 4
LCDR2 having the amino acid sequence of SEQ ID NO: 5
LCDR3 having the amino acid sequence of SEQ ID NO: 6,
or a variant thereof in which one or two or three amino acids in one or more of HCDR1, HCDR2, or HCDR3 are substituted with another amino acid.

In an additionally preferred instance, the first antigen-binding domain comprises:
a VH region comprising an amino acid sequence having at least 70% sequence identity to the amino acid sequence of SEQ ID NO: 16; and
a VL region comprising an amino acid sequence having at least 70% sequence identity to the amino acid sequence of SEQ ID NO: 20, and/or the second antigen-binding domain comprises:
a VH region comprising an amino acid sequence having at least 70% sequence identity to the amino acid sequence of SEQ ID NO: 38; and
a VL region comprising an amino acid sequence having at least 70% sequence identity to the amino acid sequence of SEQ ID NO: 40.

CDR Substitutions

In instances in accordance with the present disclosure in which one or more amino acids are substituted with another amino acid, the substitutions may conservative substitutions, for example according to the following Table. In some instances, amino acids in the same block in the middle column are substituted, i.e. a non-polar amino acid is substituted for another non-polar amino acid for example. In some instances, amino acids in the same line in the rightmost column are substituted, i.e. G is substituted for A or P for example.

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some instances, substitution(s) may be functionally conservative. That is, in some instances the substitution may not affect (or may not substantially affect) one or more functional properties (e.g. binding affinity) of the antigen-binding domain comprising the substitution as compared to the equivalent unsubstituted antigen-binding domain Constant Region In some instances the antibody molecule described herein comprises an immunoglobulin heavy chain constant (CH) region. In some instances the CH is, or is derived from, the heavy chain constant sequence of an IgG (e.g. IgG1, IgG2, IgG3, IgG4), IgA (e.g. IgA1, IgA2), IgD, IgE or IgM.

In some instances the CH region is human immunoglobulin G1 constant (IGHG1; UniProt: P01857-1, v1; SEQ ID NO: 42) or a fragment thereof.

In some instances, the CH region comprises an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 42, 43, 44, 45, 46, 63 or 64. In preferred instances, the CH region comprises an amino acid sequence having at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO: 63 or 64.

In some instances, the antibody molecule comprises a heavy chain that comprises or consists of a VH region as described herein and a CH region as described herein.

In some instances, the antibody molecule described herein comprises an immunoglobulin light chain constant (CL) region or a fragment thereof. In some instances, the CL region is, or is derived from a kappa CL region set forth in SEQ ID NO: 47 or SEQ ID NO: 48. In some instances, the CL region is, or is derived from a lambda CL region set forth in SEQ ID NO: 49 or SEQ ID NO: 65. In some instances, the antibody molecule comprises: a first CL region that is, or is derived from, a kappa CL region set forth in SEQ ID NO: 47 or 48; and a second CL region that is, or is derived from, a lambda CL region set forth in SEQ ID NO: 49 or 65.

In some instances, the antibody molecule described herein comprises:
a first heavy chain, wherein the first heavy chain comprises the VH region of the first antigen-binding domain, and a first heavy chain constant (CH) region or a fragment thereof;
a first light chain, wherein the first light chain comprises the VL region of the first antigen-binding domain, and a first light chain constant (CL) region or a fragment thereof;

a second heavy chain, wherein the second heavy chain comprises the VH region of the second antigen-binding domain, and a second heavy chain constant (CH) region or a fragment thereof; and a second light chain, wherein the second light chain comprises the VL region of the second antigen-binding domain, and a second light chain constant (CL) region or a fragment thereof.

The first and second CH region may be identical or different. In other words the first and second CH region may form a homodimer or heterodimer. For example, asymmetrical bispecific antibody molecules have different first and second CH regions, as described in more detail below. The first and second CL regions may be identical or different. In some instances, the first CL region is, or is derived from, a kappa CL region set forth in SEQ ID NO: 47 or 48; and a second CL region that is, or is derived from, a lambda CL region set forth in SEQ ID NO: 49 or 65.

It will be understood that when an antibody molecule comprises a first VH region and a first CH region, that these regions together form a first heavy chain of the antibody molecule, that is that the first VH and first CH regions are connected to each other. Similarly, a second VH region and a second CH region forms a second heavy chain of the antibody molecule; a first VL region and a first CL region form a first light chain of the antibody molecule; and a second VL region and a second CL region form a second light chain of the antibody molecule.

In some instances, the antibody molecule comprises a heavy chain having an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the B-09-GL heavy chain set forth in SEQ ID NO: 50, the QD6 heavy chain set forth in SEQ ID NO: 53, the RAA22 heavy chain set forth in SEQ ID NO: 56, the heavy chain set forth in SEQ ID NO: 59, or the heavy chain set forth in SEQ ID NO: 60.

In some instances, the antibody molecule comprises a first and second heavy chain, wherein
(i) the first heavy chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the B-09-GL heavy chain set forth in SEQ ID NO: 56; and
(ii) the second heavy chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the RAA22 heavy chain set forth in SEQ ID NO: 50.

In some instances, the antibody molecule comprises a first and second heavy chain, wherein
(i) the first heavy chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the heavy chain set forth in SEQ ID NO: 59; and
(ii) the second heavy chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the heavy chain set forth in SEQ ID NO: 60.

In some instances, the antibody molecule described herein comprises a light chain that comprises or consists of a VL region as described herein and a CL region as described herein.

In some instances, the antibody molecule described herein comprises a light chain having an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the B-09-GL light chain set forth in SEQ ID NO: 52, the QD6 light chain set forth in SEQ ID NO: 55, the RAA22 light chain set forth in SEQ ID NO: 58, the light chain set forth in SEQ ID NO: 61, or the light chain set forth in SEQ ID NO: 62.

In some instances, the antibody molecule described herein comprises a first and second light chain, wherein
(i) the first light chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the RAA22 light chain set forth in SEQ ID NO: 58; and
(ii) the second light chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the B-09-GL light chain set forth in SEQ ID NO: 52

In some instances, the antibody molecule described herein comprises a first and second light chain, wherein
(i) the first light chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the light chain set forth in SEQ ID NO: 61; and
(ii) the second light chain comprises an amino acid sequence which has at least 70% sequence identity, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of the light chain set forth in SEQ ID NO: 62.

The CH, CL, heavy chain and/or light chain of the antibody molecules described herein may comprise one or more modifications, for example to abrogate or reduce Fc effector functions, promote formation of a heterodimeric antibody molecule, to increase the efficacy of cognate heavy and light chain pairing, and/or to assist with conjugate formation as described in more detail below. A CH, CL, heavy chain and light chain that has been modified may be referred to as a modified CH, CL, heavy chain and light chain, respectively.

The antibody molecule may comprise a mutation in the CH region(s) of the heavy chain(s) to reduce or abrogate binding of the antibody molecule to one or more Fcγ receptors, such as FcγRI, FcγRIIa, FcγRIIb, FcγRIII and/or to complement. Such mutations abrogate or reduce Fc effector functions. Mutations for reduce or abrogate binding of antibody molecule to one or more Fcγ receptors and complement are known and include the "triple mutation" or "TM" of L234F/L235E/P331S described for example in Organesyan, 2008. Other mutations that are known to modulate antibody effector function are described for example in Wang, 2018.

Thus, in some instances the first and/or second heavy chain (preferably both) comprise phenylalanine (F) at position 234, glutamic acid (E) at position 235, and serine (S) at position 331, wherein the numbering is as per the EU index. For example, one or both (preferably both) of the first and second heavy chains may comprise a CH region having an amino acid sequence having at least 70%, at least 80%, at least 90%, at least 95% sequence identity to the sequence set forth in SEQ ID NO: 42 and comprise a phenylalanine (F) at position 234, glutamic acid (E) at position 235, and serine (S) at position 331, wherein the numbering is as per the EU index. As demonstrated in the examples (e.g. Example 12), including the TM in the heavy chain was demonstrated to improve pharmacokinetic properties of the exemplified antibody molecules and ADCs.

Examples of CH regions comprising the triple mutation are SEQ ID NOs: 63 and 64. Thus, in some instances, one of the first and second heavy chains comprises a CH region having an amino acid sequence having at least 70%, at least 80%, at least 90%, at least 95%, or 100% sequence identity to the sequence set forth in SEQ ID NO: 63 and the other heavy chain comprises a CH region having an amino acid sequence having at least 70%, at least 80%, at least 90%, at least 95%, or 100% sequence identity to the sequence set forth in SEQ ID NO: 64, wherein one or both (preferably both) of the CH regions comprise a phenylalanine at position 234, glutamic acid at position 235, and serine at position 331, wherein the numbering is as per the EU index.

Examples of heavy chains comprising a CH region containing the triple mutation are SEQ ID NOs: 59 and 60. Thus, in some instances, one of the first and second heavy chains has an amino acid sequence having at least 70%, at least 80%, at least 90%, at least 95%, or 100% sequence identity to the sequence set forth in SEQ ID NO: 59 and the other heavy chain has an amino acid sequence having at least 70%, at least 80%, at least 90%, at least 95%, or 100% sequence identity to the sequence set forth in SEQ ID NO: 60, wherein one or both (preferably both) of the have chains comprise a phenylalanine at position 234, glutamic acid at position 235, and serine at position 331, wherein the numbering is as per the EU index.

The VL and CL region, and the VH region and CH1 region of an antibody molecule together constitute the Fab region. The remainder of the antibody molecule constitute the Fc region.

Unless otherwise specified, amino acid residue positions in the constant domain, including the position of amino acid sequences, substitutions, deletions and insertions as described herein, are numbered according to EU numbering (Edelman, 2007).

Bispecific Formats

Bispecific antibody molecules may be provided in any suitable format. Suitable formats for a bispecific antibody molecule described herein, and methods for producing the same, are described in Kontermann, MAbs 2012, 4(2):182-197 and Kontermann and Brinkmann 2015, 20(7): 838-847, both of which are herein incorporated by reference in their entirety. See in particular FIG. 2 of Kontermann MAbs 2012, 4(2): 182-19.

Bispecific antibody molecules can also be generated from existing antibodies by chemical conjugation. For example, two IgG molecules or two Fab' fragments can be coupled using homo- or hetero-bifunctional coupling reagents, e.g. as described in Graziano and Guptill, Methods Mol Biol. 2004; 283:71-85.

In some instances, the bispecific antibody molecules may be an immunoglobulin G-like (IgG-like) bispecific antibody molecule. IgG-like bispecific antibody molecule may comprise an Fv region, Fab region or sVD specific for one antigen, an Fv/Fab/sVD specific for another antigen, and an Fc region. IgG-like bispecific antibody molecules may be either symmetrical or asymmetrical. The bispecific antibody molecule is preferably asymmetrical.

Symmetrical IgG-like bispecific antibody molecules generally contain an antigen-binding domain that is fused to the N- or C-terminus of the heavy of light chain of an IgG molecule, e.g. in the form of a scFv fragment or a variable single domain. A characteristic property of these symmetrical IgG-like bispecific antibody molecules is that they contain a two identical heavy chains. Furthermore, symmetrical IgG-like bispecific antibody molecules are typically bivalent for each epitope. Valency as used herein refers to the number of antigen-binding regions in the antibody molecule that are able to bind a single epitope. A monoclonal monospecific IgG antibody molecule is bivalent for a single epitope—it contains two antigen-binding domains, each of which are able to bind an epitope on a single target molecule. A symmetrical IgG-like bispecific antibody molecule is bivalent for each epitope—it typically contains four antigen-binding domains, two of which are able to bind a first epitope on a target molecule and two of which are able to bind to a second epitope on a target molecule.

Examples of symmetrical IgG-like bispecific antibody molecules include DVD-IgG, IgG-scFv, scFv-IgG, scFv$_4$-Ig, IgG-scFab, scFab-IgG, IgG-sVD, sVD-IgG, 2 in 1-IgG, mAb$^2$, tandemab common LC. These can be formed by methods known in the art, for example chemical crosslinking, somatic hybridisation or the redox method.

Asymmetrical IgG-like bispecific antibody molecules, in contrast, are typically monovalent for each target. As described in, for example, Klein, 2012, the concept of monovalent bispecific IgG is thought to have a unique therapeutic niche in that they (i) do not cause receptor homodimerization, (ii) potentially have reduced toxicity on non-target tissues due to loss of avidity for each antigen, and (iii) have better selectivity when both antigens are either selectively restricted or abundantly expressed on target cells. Thus, in some instances, the antibody molecule is an asymmetrical IgG-like bispecific antibody molecule.

Asymmetrical IgG-like bispecific antibody molecules involve heterodimerization of two distinct heavy chain and correct pairing of the cognate light chain and heavy chain. Heterodimerization of the heavy chains can be addressed by several techniques, such as knobs-into-holes, electrostatic steering of CH3, CH3 strand exchanged engineered domains and leucine zippers. The pairing of the correct light and heavy chain can be ensured by using one of these heavy chain heterodimerization techniques along with the use of a common light chain, domain cross-over between CH1 and CL, coupling of the heavy and light chains with a linker, in vitro assembly of heavy chain-light chain dimers from two separate monoclonals, interface engineering of an entire Fab domain, or disulfide engineering of the CH1/CL interface.

Examples of asymmetrical IgG-like bispecific antibody molecules include DuetMab, kih IgG, kih IgG common LC, CrossMab, kih IgG-scFab, mAb-Fv, charge pairs and SEED-body.

In some instances, the antibody molecules comprise one or more modifications in one or more of the CH1, CH2 and CH3 domains that promotes formation of a heterodimeric antibody molecule. For example, the DuetMab antibody molecule described above may additionally comprise one or more modifications in one or more of the CH1, CH2 and CH3 domains that promotes formation of a heterodimeric antibody molecule. This may involve a Knobs into Holes (KiH) strategy based on single amino acid substitutions in the CH3 domains that promote heavy chain heterodimerization is described in Ridgway, 1996. The knob variant heavy chain CH3 has a small amino acid has been replaced with a larger one, and the hole variant has a large amino acid has replaced with a smaller one. Additional modifications may also introduced to stabilise the association between the heavy chains.

CH3 modifications to enhance heterodimerization include, for example, Y407V/T366S/L368A on one heavy chain and T366W on the other heavy chain; and S354C/T366W on one heavy chain and Y349C/Y407V/T366S/L368A on the other heavy chain, wherein the numbering of the constant region is as per the EU index.

Other examples of CH3 modification to enhance heterodimerization are described in, e.g. Table 1 of Brinkmann and Kontermann, 2017 MABS 9(2), 182-212, which is herein specifically incorporated by reference.

In some instances, the antibody molecule comprises a first and second heavy chain that form a heterodimer, wherein one of the first and second heavy chains comprises a cysteine (C) residue at position 354 and a tryptophan (W) residue at position 366 and the other heavy chain comprises a cysteine (C) residue at position 349, a valine (V) residue at position 407, a serine (S) at position 366 and an alanine (A) at position 368, wherein the numbering of the constant region is as per the EU index. For example, the one of the first and second heavy chains may have the sequence set forth in SEQ ID NO: 42 and further comprise a cysteine (C) residue at position 354 and a tryptophan (W) residue at position 366, and the other heavy chain have the sequence set forth in SEQ ID NO: 42 and further comprise a cysteine (C) residue at position 349, a valine (V) residue at position 407, a serine (S) at position 366 and an alanine (A) at position 368, wherein the numbering of the constant region is as per the EU index.

In some instances, the antibody molecule comprises:
  (i) a first heavy chain comprising a first modified CH3 region, wherein the first modified CH3 region comprises a cysteine (C) residue at position 354 and a tryptophan (W) residue at position 366; and
  (ii) a second heavy chain comprising a second modified CH3 region, wherein the second modified CH3 region comprises a cysteine (C) residue at position 349, a valine (V) residue at position 407, a serine (S) at position 366 and an alanine (A) at position 368,
  wherein the numbering of the constant region is as per the EU index.

A particular exemplified format of asymmetrical IgG-like bispecific antibody molecules is referred to as "DuetMab". DuetMab antibody molecules uses KIH technology for heterodimerization of 2 distinct heavy chains and increases the efficacy of cognate heavy and light chain pairing by replacing the native disulphide bond in one of the CH1-CL interfaces with an engineered disulphide bond. Disclosure related to DuetMab can found e.g., in U.S. Pat. No. 9,527,927 and Mazor, 2015, which are herein incorporated by reference in their entirety.

In some instances, the antibody molecule comprises:
  (a) a modified CH region, wherein the modified heavy chain comprises a substitution of a native non-cysteine amino acid to a cysteine amino acid; and
  (b) a modified corresponding CL region, wherein the modified CL comprises a substitution of a native non-cysteine amino acid to a cysteine amino acid,
  wherein either:
  (i) the first heavy chain comprises the modified CH region and the first light chain comprises the modified corresponding CL region; or
  (ii) the second heavy chain comprises the modified CH region and the second light chain comprises the modified corresponding CL region.

In some instances, the substituted cysteine of the modified CH region, resulting from the substitution of the native non-cysteine amino acid to the cysteine amino acid, and the substituted cysteine of the modified corresponding CL region, resulting from the substitution of the native non-cysteine amino acid to the cysteine amino acid, can form a disulphide bond.

In some instances, the modified CH region comprises a substitution of a native non-cysteine amino acid to a cysteine amino acid at position 126; and the modified corresponding CL region comprises a substitution of a native non-cysteine amino acid to a cysteine at position 121, wherein the numbering of the constant region is as per the EU index.

In some instances, the modified CH region comprises a substitution of a native non-cysteine amino acid to a cysteine amino acid at position 126 and a substitution of a native cysteine amino acid to a non-cysteine amino acid at position 219, for example to a valine; and the modified corresponding CL region comprises a substitution of a native non-cysteine amino acid to a cysteine at position 121 and a substitution of a native cysteine amino acid to a non-cysteine amino acid at position 214, for example to a valine, where the numbering of the constant region is as per the EU index.

In some instances, the antibody molecule comprises a second CH region and a second corresponding light chain, wherein the second CH region and second corresponding CL do not comprise a substitution of a native non-cysteine amino acid to a cysteine amino acid and do not comprise a substitution of a native cysteine to a non-cysteine amino acid.

Conjugates

The antibody molecule may be conjugated to a drug. In this case, the antibody molecule may be referred to as a "conjugate" or an "antibody drug conjugate". Such conjugates find application in the treatment and/or diagnosis of diseases as described herein. As used herein, the drug may be referred to as a "payload" or "warhead".

In some instances, the drug comprises a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, a chelating agent, or combinations thereof.

A cytotoxin is a compound that is able to include death of the cell that is being targeted. Typically, in the context of antibody drug conjugates, a cytotoxin is delivered to a cell targeted by the antibody molecule, where it is released into the cell and induces cell death. The use of cytotoxins in antibody drug conjugates is described, for example, in Chalouni and Doll 2018 J Exp Clin Cancer Res. 37(1):20. In some instances, cytotoxin is a tubulysin, an auristatin, a maytansinoid, a topoisomerase inhibitor or a pyrrolobenzodiazepine (PBD).

In particular instances, the cytotoxin is or comprises a tubulysin. Tubulysins are a class of cytostatic tetrapeptides which contain isoleucine and three other complex unnatural amino acids Mep (R—N-Mepipecolic acid), Tuv (tubuvaline) and Tut (tubulyrosine) or Tup (tubuphenylalanine). Tubulysins are extremely potent cytotoxic molecules and are potent against multidrug resistant cell lines (Domling, 2005). These compounds show high cytotoxicity tested against a panel of cancer cell lines with IC50 values in the low picomolar range; thus, they are of interest as anticancer therapeutics. See, e.g., WO2012019123. Tubulysin conjugates are disclosed, e.g., in U.S. Pat. No. 7,776,814. In some instances, the tubulysin is tubulysin A having the following chemical structure:

refers to a cytotoxic agent that inhibits the activity of one or more of the topoisomerase enzymes (topoisomerase I and II), which are enzymes that play an important role in DNA replication and transcription by regulating DNA supercoiling. Antibody drug conjugates comprising a topoisomerase inhibitor as a cytotoxin are therefore expected to interfere with normal processes involving DNA, therefore leading to cell death. Conjugates containing topoisomerase inhibitors have been demonstrated to be effective against a variety of tumor containing cell lines as well as having anticancer activity in clinical trials. See for example Ogitani, 2016a; Ogitani, 2016b; Cardillo, 2015; and Bardia, 2017.

It is preferred that the antibody molecule is conjugated to a topoisomerase I inhibitor. Representative examples of topoisomerase I inhibitors include, but are not limited to, camptothecins and its analogues topotecan, irinotecan, belotecan, exatecan, lurotecan and sinotecan. Representative

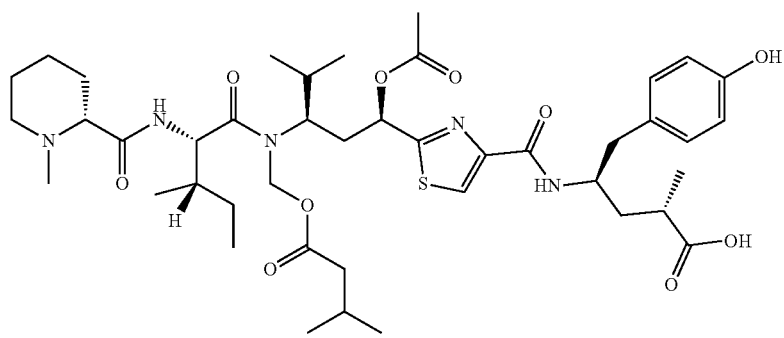 [SMILES: CC[C@H](C)[C@H](NC(=O)[C@H]1CCCCN1C)C(=O)N(COC(=O)CC(C)C)[C@H](C[C@@H](OC(C)=O)c1nc(C(=O)N[C@@H](Cc2ccc(O)cc2)C[C@H](C)C(=O)O)cs1)C(C)C]

In some instances, the tubulysin is tubulysin 1508, also referred to as "AZ1508" and described in more detail in WO 2015157594. Tubulysin 1508 has the following chemical structure:

examples of topoisomerase II inhibitors include, but are not limited to, amsacrine, daunorubicin, doxorubicin, epipodophyllotoxins, ellipticines, epirubicin, etoposide, razoxane, and teniposide.

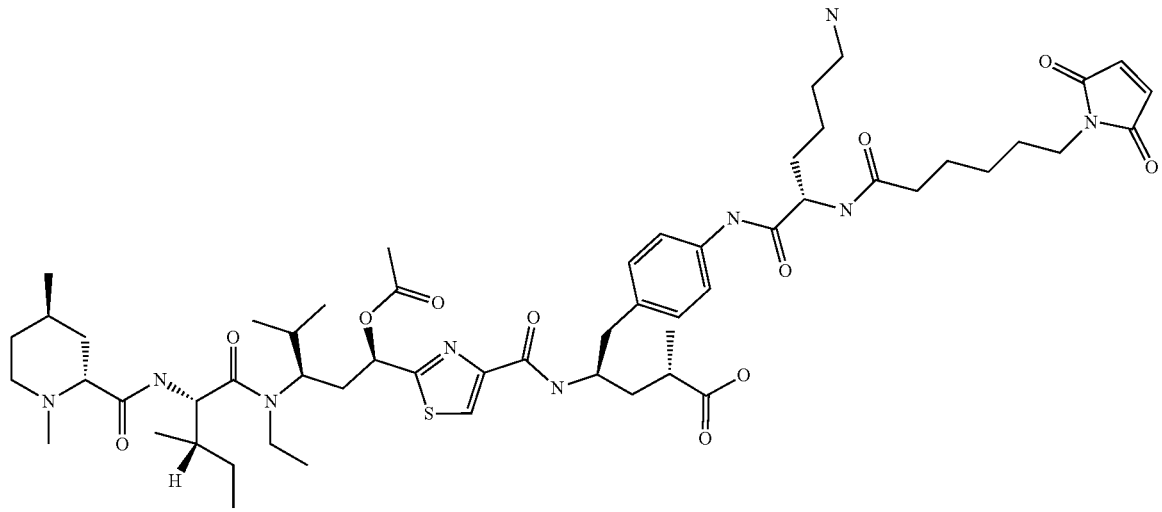 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

Preferably, the cytotoxin is or comprises a topoisomerase inhibitor. The term 'topoisomerase inhibitor' as used herein An example of the camptothecin chemical structure is as follows:

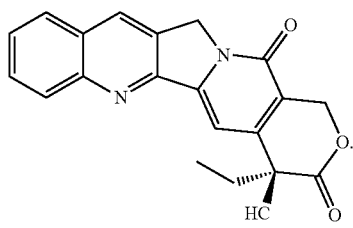 [SMILES: CC[C@@]1(C)C(=O)OCc2c1cc1n(c2=O)Cc2cc3ccccc3nc2-1]

A general example of a suitable topoisomerase I inhibitor is represented by the following compound:

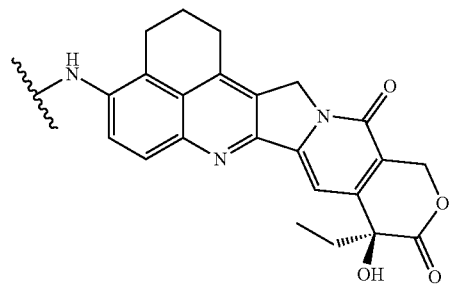

A*

Said compound is denoted as A*.

The compound (e.g. A*) is preferably provided with a linker for connecting (preferably conjugating) to an antibody molecule described herein (which may be referred to as a "Ligand Unit" or alternatively a "Cell Binding Agent" (CBA)). Suitably, the linker is attached (e.g. conjugated) in a cleavable manner to an amino residue, for example, an amino acid of an antibody molecule described herein.

The design and selection of linkers to be used in conjugates is known in the art and is described for example in Beck, 2017. The linker used herein may be any of the linkers described in Beck, 2017.

More particularly, an example of a suitable topoisomerase I inhibitor is represented by the following compound, with the formula "I":

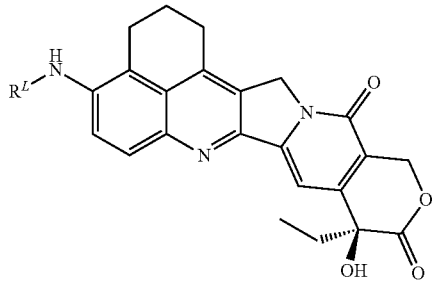

I and salts and solvates thereof, wherein $R^L$ is a linker for connection to an antibody molecule described herein, wherein said linker is preferably selected from:

(ia):

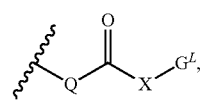

Ia wherein

Q is:

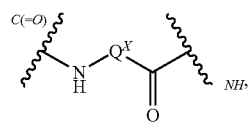

where $Q^X$ is such that Q is an amino-acid residue, a dipeptide residue, a tripeptide residue or a tetrapeptide residue;

X is:

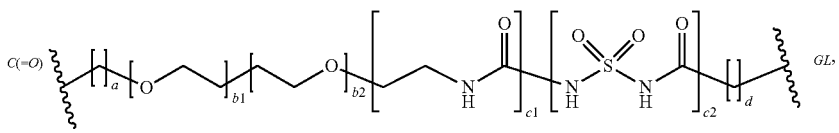

where a=0 to 5, b1=0 to 16, b2=0 to 16, c1=0 or 1, c2=0 or 1, d=0 to 5, wherein at least b1 or b2=0 (i.e. only one of b1 and b2 may not be 0) and at least c1 or c2=0 (i.e. only one of c1 and c2 may not be 0);

$G^L$ is a linker for connecting to an antibody or antigen binding fragment thereof described herein (e.g. the Ligand Unit or Cell Binding Agent); or (ib):

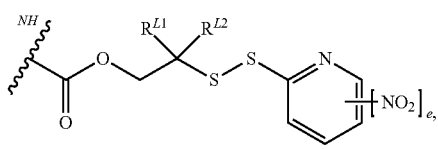

Ib where $R^{L1}$ and $R^{L2}$ are independently selected from H and methyl, or together with the carbon atom to which they are bound form a cyclopropylene or cyclobutylene group; and e is 0 or 1.

It will be understood by the person skilled in the art that more than one of said agent(s) (e.g. topoisomerase I inhibitor) may be conjugated to the antibody molecule.

For example, a conjugate (e.g. antibody-drug conjugate) of the disclosure may be of the general formula IV:

$$L\text{-}(D^L)_p \qquad (IV)$$

or a pharmaceutically acceptable salt or solvate thereof, wherein L is an antibody molecule described herein (e.g. the Ligand Unit or CBA), $D^L$ is drug having a linker (e.g. a Drug Linker Unit), and p is a integer of from 1 to 20.

Preferably, $D^L$ is a topoisomerase I inhibitor having a linker that is of formula III:

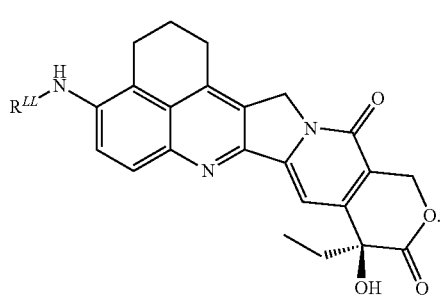

III $R^{LL}$ is a linker connected to an antibody molecule described herein (e.g. the Ligand Unit), wherein the linker is preferably selected from (ia'):

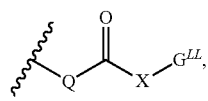

Ia' where Q and X are as defined above and $G^{LL}$ is a linker connected to an antibody molecule described herein (e.g. the Ligand Unit or CBA); and (ib'):

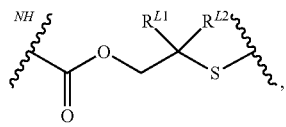

Ib' where $R^{L1}$ and $R^{L2}$ are as defined above.

The drug loading is represented by p, the number of topoisomerase I inhibitor(s) (e.g. Drug units) per antibody molecule (e.g. Ligand Unit). Drug loading may range from 1 to 20 Drug units (D) per Ligand unit. For compositions, p represents the average drug loading of the conjugates in the composition, and p ranges from 1 to 20. In some instances, where the drug is a topoisomerase inhibitor, the p range is selected from 2 to 8, preferably 4 to 8, even more preferably 5 to 7, still more preferably 5.5 to 6.5. As described in the examples, an ADC comprising topoisomerase I inhibitor SG3932 was produced with an average DAR of 6+/−6%.

Accordingly, the disclosure embraces a conjugate comprising an antibody molecule described herein (e.g. the Ligand Unit or CBA) covalently linked to at least one topoisomerase I inhibitor (e.g. Drug unit, such as A* illustrated above). Said inhibitor is preferably linked to the antibody molecule by a linker (e.g. Linker unit), such as a linker described above as $R^L$ and/or $R^{LL}$. In other words, the disclosure embraces an antibody molecule described herein (e.g. the Ligand Unit or CBA) with one or more topoisomerase I inhibitors attached, preferably via a linker (e.g. Drug-Linker units). The antibody molecule (representing a Ligand unit or CBA), described more fully above, is a targeting agent that binds to a target moiety. More particularly, this antibody molecule can, for example, specifically binds to a EGFR and cMET on a target cell, to which the Drug unit is thus delivered. Accordingly, the present disclosure also provides methods for the treatment of, for example, various cancers and other disorders with an ADC (e.g. cancers/disorders which are associated with the presence of cells, preferably cancerous cells, which express EGFR and cMET). Such methods are described in more detail below Certain features of the topoisomerase I inhibitors described above are particularly preferred and may be defined in more detail as set out below. By way of example, a preferred instance of feature $Q^X$ (e.g. within the linker of 1a described above) will be outlined.

The following preferences may apply to all aspects of the disclosure as described above, or may relate to a single aspect. The preferences may be combined together in any combination.

$Q^X$

In one instance, Q is an amino acid residue. The amino acid may be a natural amino acid or a non-natural amino acid. For example, Q may be selected from: Phe, Lys, Val, Ala, Cit, Leu, Ile, Arg, and Trp, where Cit is citrulline.

In one instance, Q comprises a dipeptide residue. The amino acids in the dipeptide may be any combination of natural amino acids and non-natural amino acids. In some instances, the dipeptide comprises natural amino acids. Where the linker is a cathepsin labile linker, the dipeptide is the site of action for cathepsin-mediated cleavage. The dipeptide then is a recognition site for cathepsin.

In one instance, Q is selected from:
$^{NH}$-Phe-Lys-$^{C=O}$,
$^{NH}$-Val-Ala-$^{C=O}$,
$^{NH}$-Val-Lys-$^{C=O}$,
$^{NH}$-Ala-Lys-$^{C=O}$,
$^{NH}$-Val-Cit-$^{C=O}$,
$^{NH}$-Phe-Cit-$^{C=O}$,
$^{NH}$-Leu-Cit-$^{C=O}$,
$^{NH}$-Ile-Cit-$^{C=O}$,
$^{NH}$-Phe-Arg-$^{C=O}$,
$^{NH}$-Trp-Cit-$^{C=O}$, and
$^{NH}$-Gly-Val-$^{C=O}$;
where Cit is citrulline.

Preferably, Q is selected from:
$^{NH}$-Phe-Lys-$^{C=O}$,
$^{NH}$-Val-Ala-$^{C=O}$,
$^{NH}$-Val-Lys-$^{C=O}$,
$^{NH}$-Ala-Lys-$^{C=O}$, and
$^{NH}$-Val-Cit-$^{C=O}$.

More preferably, Q is selected from NH-Phe-Lys-$^{C=O}$, $^{NH}$-Val-Cit-$^{C=O}$ or $^{NH}$-Val-Ala-$^{C=O}$.

Other suitable dipeptide combinations include:
$^{NH}$-Gly-Gly-$^{C=O}$,
$^{NH}$-Gly-Val-$^{C=O}$
$^{NH}$-Pro-Pro-$^{C=O}$, and
$^{NH}$-Val-Glu-$^{C=O}$.

Other dipeptide combinations may be used, including those described by Dubowchik et al., *Bioconjugate Chemistry*, 2002, 13, 855-869, which is incorporated herein by reference.

In some instances, Q is a tripeptide residue. The amino acids in the tripeptide may be any combination of natural amino acids and non-natural amino acids. In some instances, the tripeptide comprises natural amino acids. Where the linker is a cathepsin labile linker, the tripeptide is the site of action for cathepsin-mediated cleavage. The tripeptide then is a recognition site for cathepsin. Tripeptide linkers of particular interest are:

$^{NH}$-Glu-Val-Ala-$^{C=O}$
$^{NH}$-Glu-Val-Cit-$^{C=O}$
$^{NH}$-αGlu-Val-Ala-$^{C=O}$
$^{NH}$-αGlu-Val-Cit-$^{C=O}$

In some instances, Q is a tetrapeptide residue. The amino acids in the tetrapeptide may be any combination of natural amino acids and non-natural amino acids. In some instances, the tetrapeptide comprises natural amino acids. Where the linker is a cathepsin labile linker, the tetrapeptide is the site of action for cathepsin-mediated cleavage. The tetrapeptide then is a recognition site for cathepsin. Tetrapeptide linkers of particular interest are:

$^{NH}$-Gly-Gly-Phe-Gly$^{C=O}$; and
$^{NH}$-Gly-Phe-Gly-Gly$^{C=O}$.

In some instances, the tetrapeptide is:
$^{NH}$-Gly-Gly-Phe-Gly$^{C=O}$.

In the above representations of peptide residues, $^{NH}$— represents the N-terminus, and —$^{C=O}$ represents the C-terminus of the residue. The C-terminus binds to the NH of A*.

Glu represents the residue of glutamic acid, i.e.:

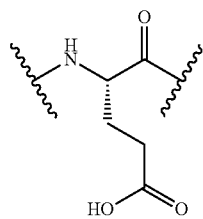 [SMILES: *N[C@@H](CCC(=O)O)C(*)=O]

αGlu represents the residue of glutamic acid when bound via the α-chain, i.e.:

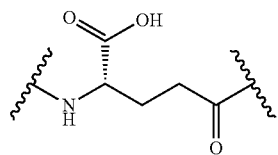 [SMILES: *N[C@@H](CCC(*)=O)C(=O)O]

In one instance, the amino acid side chain is chemically protected, where appropriate. The side chain protecting group may be a group as discussed above. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

$G^L$ $G^L$ may be selected from:

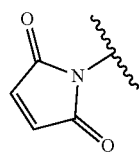

(G$^{L1-1}$)

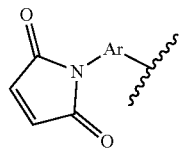

(G$^{L1-2}$)

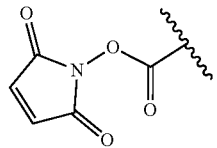

(G$^{L2}$)

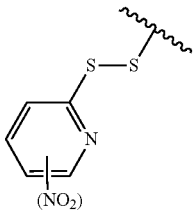

(G$^{L3-1}$)

where the NO$_2$ group is optional

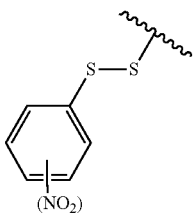

(G$^{L3-2}$)

where the NO$_2$ group is optional

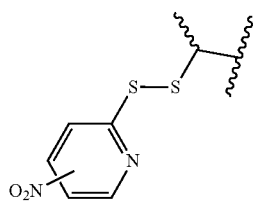

(G$^{L3-3}$)

where the NO$_2$ group is optional

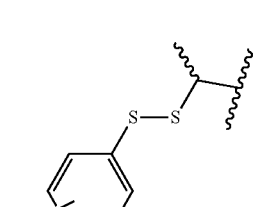

(G$^{L3-4}$)

where the NO$_2$ group is optional

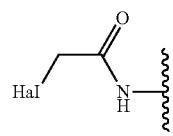

(G$^{L4}$)

Where Hal = I, Br, Cl

-continued
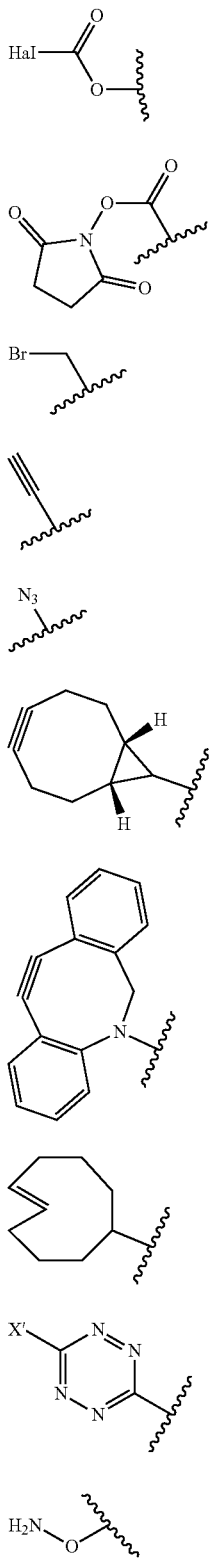
where Ar represents a $C_{5-6}$ arylene group, e.g. phenylene, and X' represents $C_{1-4}$ alkyl.
In some instances, $G^L$ is selected from $G^{L1-1}$ and $G^{L1-2}$. In some of these instances, $G^L$ is $G^{L1-1}$.
$G^{LL}$
$G^{LL}$ may be selected from:
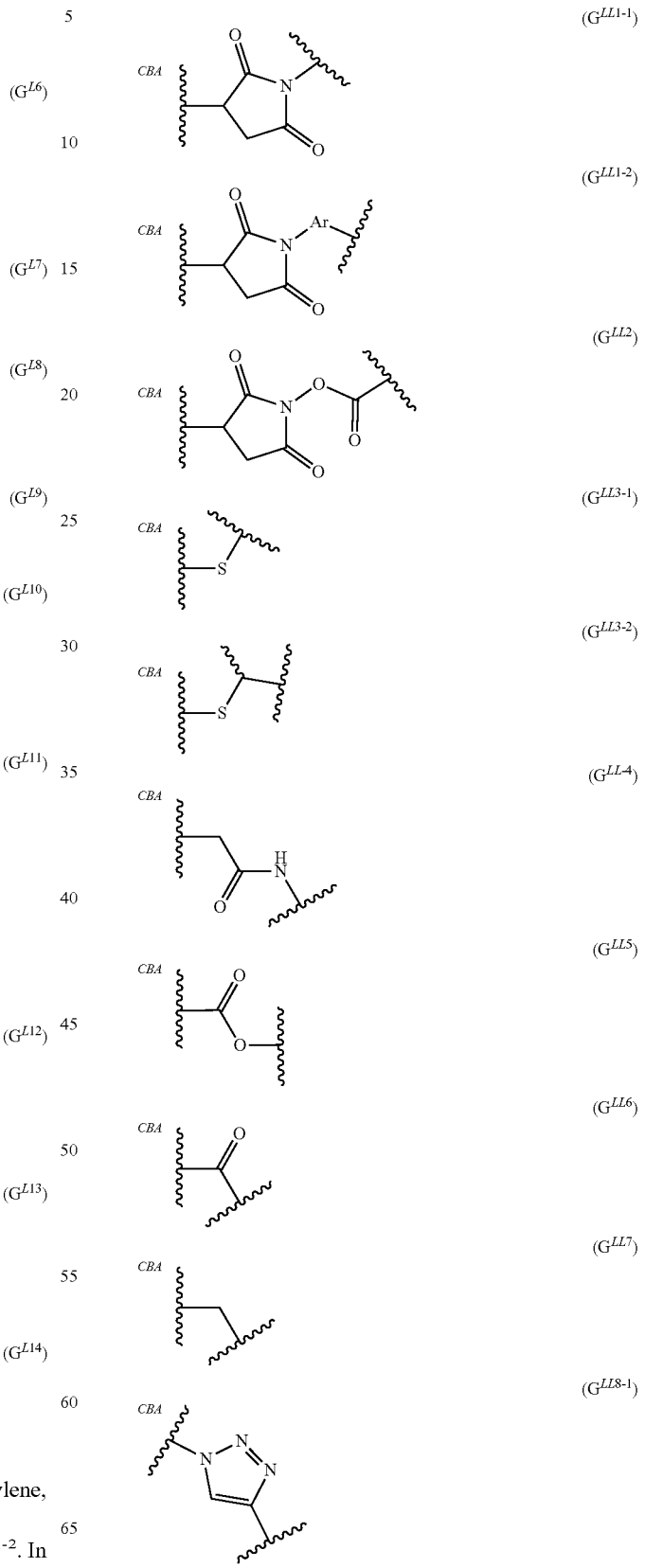

(G^{LL8-2})
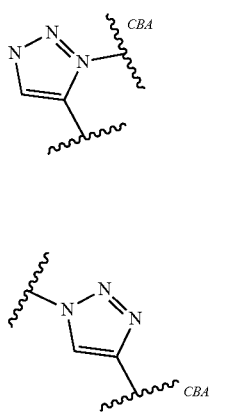
(G^{LL9-1})
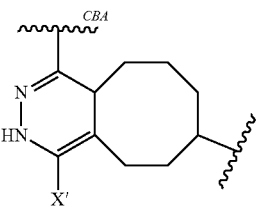
(G^{LL9-2})
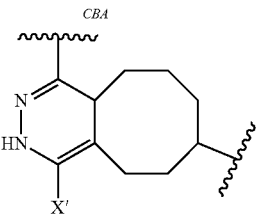
(G^{LL10})
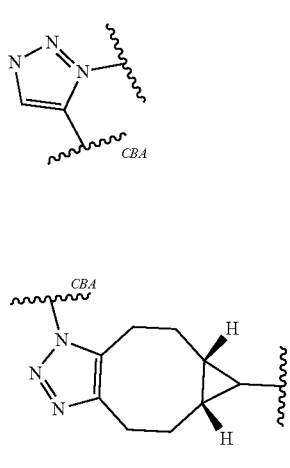
(G^{LL11})
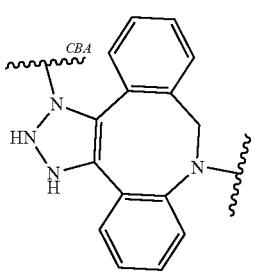
(G^{LL12})
(G^{LL13})
(G^{LL14})
where Ar represents a $C_{5-6}$ arylene group, e.g. phenylene and X' represents $C_{1-4}$ alkyl. CBA represents the Cell Binding Agent or Ligand Unit.
In some instances, $G^{LL}$ is selected from $G^{LL1-1}$ and $G^{LL1-2}$. In some of these instances, $G^{LL}$ is $G^{LL1-1}$.
X
X is preferably:
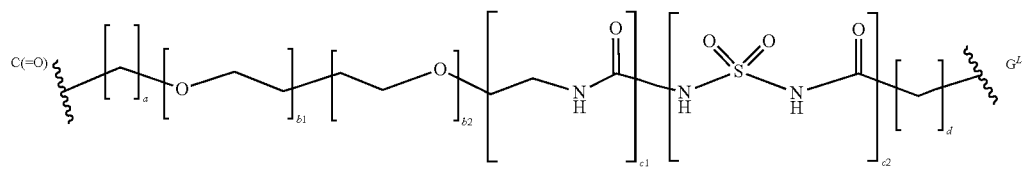

where a=0 to 5, b1=0 to 16, b2=0 to 16, c=0 or 1, d=0 to 5, wherein at least b1 or b2=0 and at least c1 or c2=0.

a may be 0, 1, 2, 3, 4 or 5. In some instances, a is 0 to 3. In some of these instances, a is 0 or 1. In further instances, a is 0.

b1 may be 0, 1, 2, 3, 4, 5, 6, 7, 8, 9, 10, 11, 12, 13, 14, 15 or 16. In some instances, b1 is 0 to 12. In some of these instances, b1 is 0 to 8, and may be 0, 2, 3, 4, 5 or 8.

b2 may be 0, 1, 2, 3, 4, 5, 6, 7, 8, 9, 10, 11, 12, 13, 14, 15 or 16. In some instances, b2 is 0 to 12. In some of these instances, b2 is 0 to 8, and may be 0, 2, 3, 4, 5 or 8. Preferably, only one of b1 and b2 may not be 0.

c1 may be 0 or 1. c2 may be 0 or 1. Preferably, only one of c1 and c2 may not be 0.

d may be 0, 1, 2, 3, 4 or 5. In some instances, d is 0 to 3. In some of these instances, d is 1 or 2. In further instances, d is 2. In further instances, d is 5.

In some instances of X, a is 0, b1 is 0, c1 is 1, c2 is 0 and d is 2, and b2 may be from 0 to 8. In some of these instances, b2 is 0, 2, 3, 4, 5 or 8. In some instances of X, a is 1, b2 is 0, c1 is 0, c2 is 0 and d is 0, and b1 may be from 0 to 8. In some of these instances, b1 is 0, 2, 3, 4, 5 or 8. In some instances of X, a is 0, b1 is 0, c1 is 0, c2 is 0 and d is 1, and b2 may be from 0 to 8. In some of these instances, b2 is 0, 2, 3, 4, 5 or 8. In some instances of X, b1 is 0, b2 is 0, c1 is 0, c2 is 0 and one of a and d is 0. The other of a and d is from 1 to 5. In some of these instances, the other of a and d is 1. In other of these instances, the other of a and d is 5. In some instances of X, a is 1, b2 is 0, c1 is 0, c2 is 1, d is 2, and b1 may be from 0 to 8. In some of these instances, b2 is 0, 2, 3, 4, 5 or 8.

In some instances, $R^L$ is of formula Ib. In some instances, $R^{LL}$ is of formula Ib'.

$R^{L1}$ and $R^{L2}$ may be independently selected from H and methyl, or together with the carbon atom to which they are bound form a cyclopropylene or cyclobutylene group.

In some instances, both $R^{L1}$ and $R^{L2}$ are H. In some instances, $R^{L1}$ is H and $R^{L2}$ is methyl. In some instances, both $R^{L1}$ and $R^{L2}$ are methyl.

In some instances, $R^{L1}$ and $R^{L2}$ together with the carbon atom to which they are bound form a cyclopropylene group. In some instances, $R^{L1}$ and $R^{L2}$ together with the carbon atom to which they are bound form a cyclobutylene group.

In the group Ib, in some instances, e is 0. In other instances, e is 1 and the nitro group may be in any available position of the ring. In some of these instances, it is in the ortho position. In others of these instances, it is in the para position.

In some instances where compounds described herein are provided in a single enantiomer or in an enantiomerically enriched form, the enantiomerically enriched form has an enantiomeric ratio greater than 60:40, 70:30; 80:20 or 90:10. In further instances, the enantiomeric ratio is greater than 95:5, 97:3 or 99:1.

In some instances, $R^L$ is selected from:

(ix)

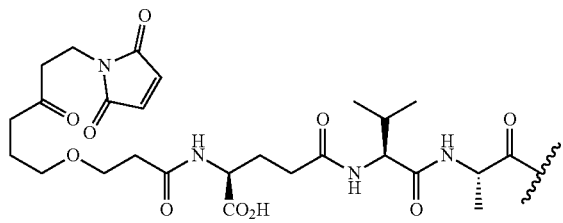

In some instances, $R^{LL}$ is a group derived from the $R^L$ groups above.

Having outlined said preferences above, certain preferred topoisomerase I-linker (e.g. Drug Linker unit) formulas are now described.

In some instances, the compound of formula I is of the formula IP:

$I^P$

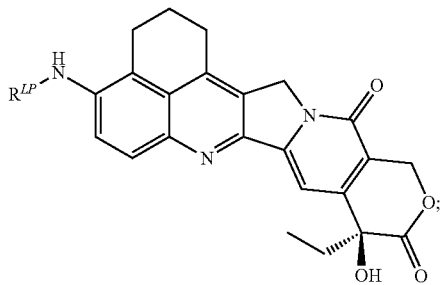

and salts and solvates thereof, wherein $R^{LP}$ is a linker for connection to an antibody or antigen binding fragment thereof described herein, wherein said linker is selected from:

(ia):

$Ia^P$

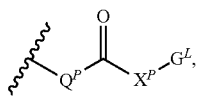

wherein
$Q^P$ is:

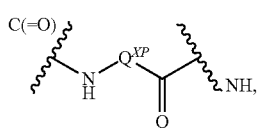

where $Q^{XP}$ is such that $Q^P$ is an amino-acid residue, a dipeptide residue or a tripeptide residue;

$X^P$ is:

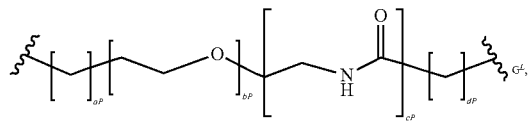

where aP=0 to 5, bP=0 to 16, cP=0 or 1, dP=0 to 5;
$G^L$ is a linker for connecting to an antibody or antigen binding fragment thereof described herein (e.g. Ligand Unit);

(ib):

Ib

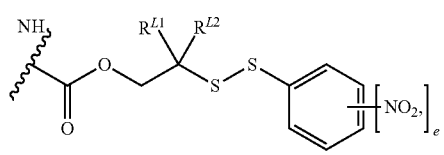

where $R^{L1}$ and $R^{L2}$ are independently selected from H and methyl, or together with the carbon atom to which they are bound form a cyclopropylene or cyclobutylene group; and
e is 0 or 1.

aP may be 0, 1, 2, 3, 4 or 5. In some instances, aP is 0 to 3. In some of these instances, aP is 0 or 1. In further instances, aP is 0.

bP may be 0, 1, 2, 3, 4, 5, 6, 7, 8, 9, 10, 11, 12, 13, 14, 15 or 16. In some instances, b is 0 to 12. In some of these instances, bP is 0 to 8, and may be 0, 2, 4 or 8.

cP may be 0 or 1.

dP may be 0, 1, 2, 3, 4 or 5. In some instances, dP is 0 to 3. In some of these instances, dP is 1 or 2. In further instances, dP is 2.

In some instances of $X^P$, aP is 0, cP is 1 and dP is 2, and bP may be from 0 to 8. In some of these instances, bP is 0, 4 or 8.

The preferences for $Q^X$ above for compounds of Formula I may apply to $Q^{XP}$ (for example, where appropriate).

The preferences for $G^L$, $R^{L1}$, $R^{L2}$ and e above for compounds of Formula I may apply to compounds of Formula $I^P$.

In some instances, the conjugate of formula IV is of the formula $IV^P$:

$$L\text{-}(D^{LP})_p \quad (IV^P)$$

or a pharmaceutically acceptable salt or solvate thereof, wherein L is an antibody or antigen binding fragment thereof described herein (e.g. Ligand Unit), $D^{LP}$ is a topoisomerase I inhibitor (e.g. Drug Linker unit) that is of formula $III^P$:

$III^P$

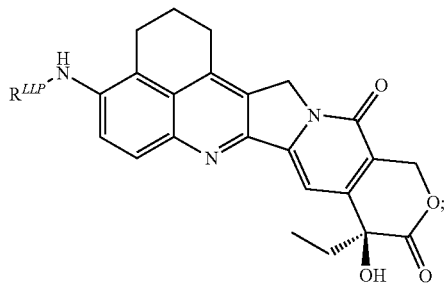

$R^{LLP}$ is a linker connected to the antibody or antigen binding fragment thereof (e.g. Ligand unit), wherein said linker is selected from (ia'):

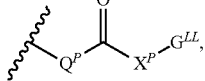

Ia$^P$ where $Q^P$ and $X^P$ are as defined above and $G^{LL}$ is a linker connected to an antibody or antigen binding fragment thereof described herein (e.g. Ligand Unit); and (ib'):

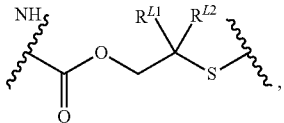

Ib where $R^{L1}$ and $R^{L2}$ are as defined above; and
p is an integer of from 1 to 20.

In some instances, the compound of formula I is of the formula I$^{P2}$:

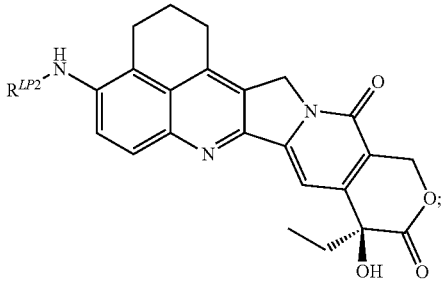

I$^{P2}$ and salts and solvates thereof, wherein $R^{LP2}$ is a linker for connection to an antibody or antigen binding fragment thereof described herein, wherein said linker is selected from:

(ia):

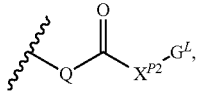

Ia$^{P2}$ wherein
Q is:

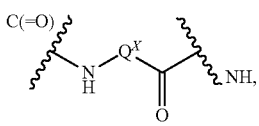

where $Q^X$ is such that Q is an amino-acid residue, a dipeptide residue, a tripeptide residue or a tetrapeptide residue;

$X^{P2}$ is:

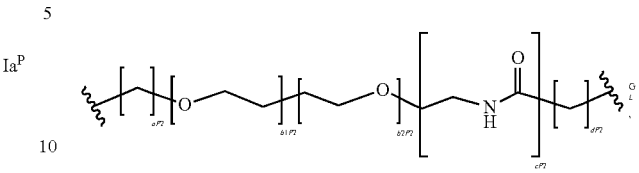

where aP2=0 to 5, b1P2=0 to 16, b2P2=0 to 16, cP2=0 or 1, dP2=0 to 5, wherein at least b1P2 or b2P2=0 (i.e. only one of b1 and b2 may not be 0);

$G^L$ is a linker for connecting to an antibody or antigen binding fragment thereof described herein (e.g. Ligand Unit);

(ib):

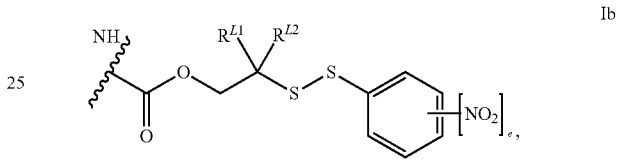

Ib where $R^{L1}$ and $R^{L2}$ are independently selected from H and methyl, or together with the carbon atom to which they are bound form a cyclopropylene or cyclobutylene group; and e is 0 or 1.

aP2 may be 0, 1, 2, 3, 4 or 5. In some instances, aP2 is 0 to 3. In some of these instances, aP2 is 0 or 1. In further instances, aP2 is 0.

b1P2 may be 0, 1, 2, 3, 4, 5, 6, 7, 8, 9, 10, 11, 12, 13, 14, 15 or 16. In some instances, b1P2 is 0 to 12. In some of these instances, b1P2 is 0 to 8, and may be 0, 2, 3, 4, 5 or 8.

b2P2 may be 0, 1, 2, 3, 4, 5, 6, 7, 8, 9, 10, 11, 12, 13, 14, 15 or 16. In some instances, b2P2 is 0 to 12. In some of these instances, b2P2 is 0 to 8, and may be 0, 2, 3, 4, 5 or 8. Preferably, only one of b1P2 and b2P2 may not be 0.

cP2 may be 0 or 1.

dP2 may be 0, 1, 2, 3, 4 or 5. In some instances, dP2 is 0 to 3. In some of these instances, dP2 is 1 or 2. In further instances, dP2 is 2. In further instances, dP2 is 5.

In some instances of $X^{P2}$, aP2 is 0, b1P2 is 0, cP2 is 1 and dP2 is 2, and b2P2 may be from 0 to 8. In some of these instances, b2P2 is 0, 2, 3, 4, 5 or 8. In some instances of $X^{P2}$, aP2 is 1, b2P2 is 0, cP2 is 0 and dP2 is 0, and b1P2 may be from 0 to 8. In some of these instances, b1P2 is 0, 2, 3, 4, 5 or 8. In some instances of $X^{P2}$, aP2 is 0, b1P2 is 0, cP2 is 0 and dP2 is 1, and b2P2 may be from 0 to 8. In some of these instances, b2P2 is 0, 2, 3, 4, 5 or 8. In some instances of $X^{P2}$, b1P2 is 0, b2P2 is 0, cP2 is 0 and one of aP2 and dP2 is 0. The other of aP2 and d is from 1 to 5. In some of these instances, the other of aP2 and d is 1. In other of these instances, the other of aP2 and dP2 is 5.

The preferences for $Q^X$ above for compounds of Formula I may apply to $Q^X$ in Formula Ia$^{P2}$ (e.g. where appropriate).

The preferences for $G^L$, $R^{L1}$, $R^{L2}$ and e above for compounds of Formula I may apply to compounds of Formula I$^{P2}$.

In some instances, the conjugate of formula IV is of the formula IV$^{P2}$:

$$L\text{-}(D^{LP2})_P \tag{IV$^{P2}$}$$

or a pharmaceutically acceptable salt or solvate thereof, wherein L is an antibody or antigen binding fragment thereof described herein (e.g. Ligand unit), D$^{LP2}$ is a topoisomerase I inhibitor (e.g. Drug Linker unit) that is of formula III$^{P2}$:

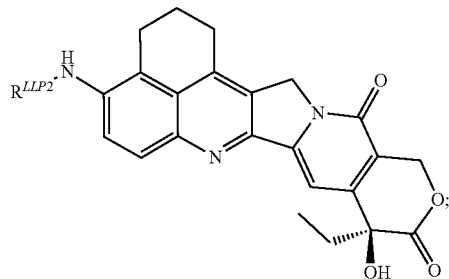

III$^{P2}$

R$^{LLP2}$ is a linker connected to the antibody or antigen binding fragment thereof (e.g. Ligand unit), wherein said linker is selected from (ia'):

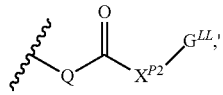

Ia$^{P2}$ where Q and X$^{P2}$ are as defined above and G$^{LL}$ is a linker connected to the antibody or antigen binding fragment thereof; and (ib'):

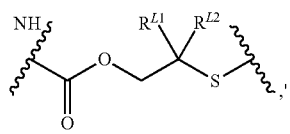

Ib where R$^{L1}$ and R$^{L2}$ are as defined above; and p is an integer of from 1 to 20.

Particularly suitable topoisomerase I inhibitors include those having the following formulas:

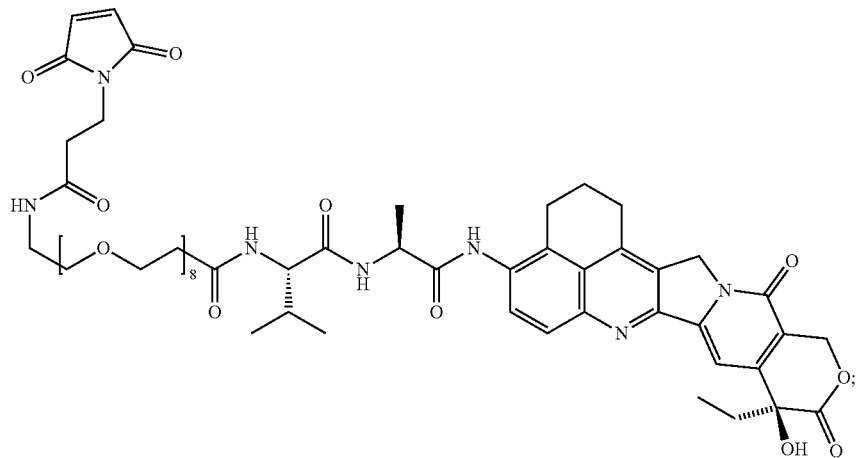

(SG3932)

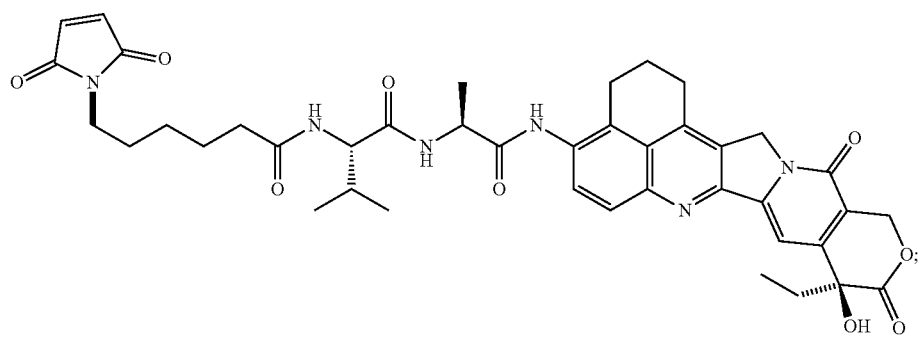

(SG4010)

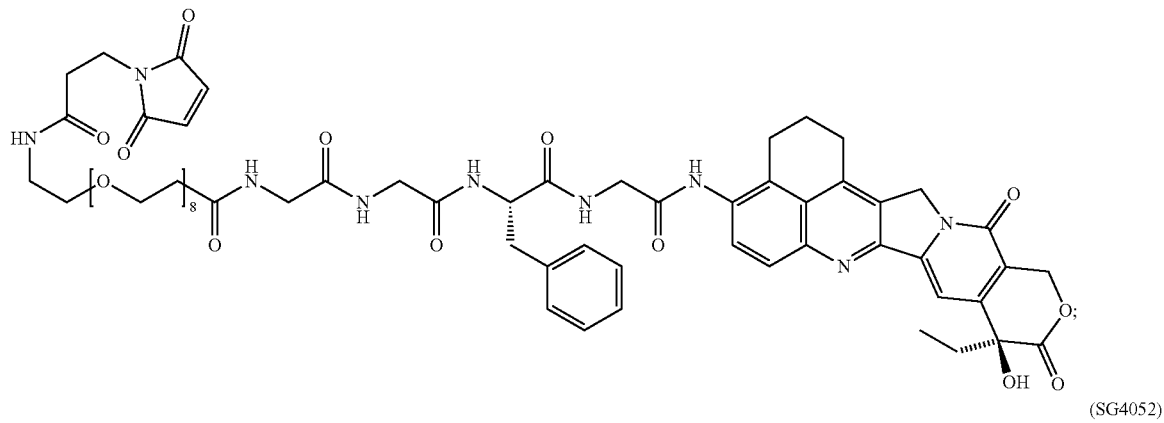
(SG4057)
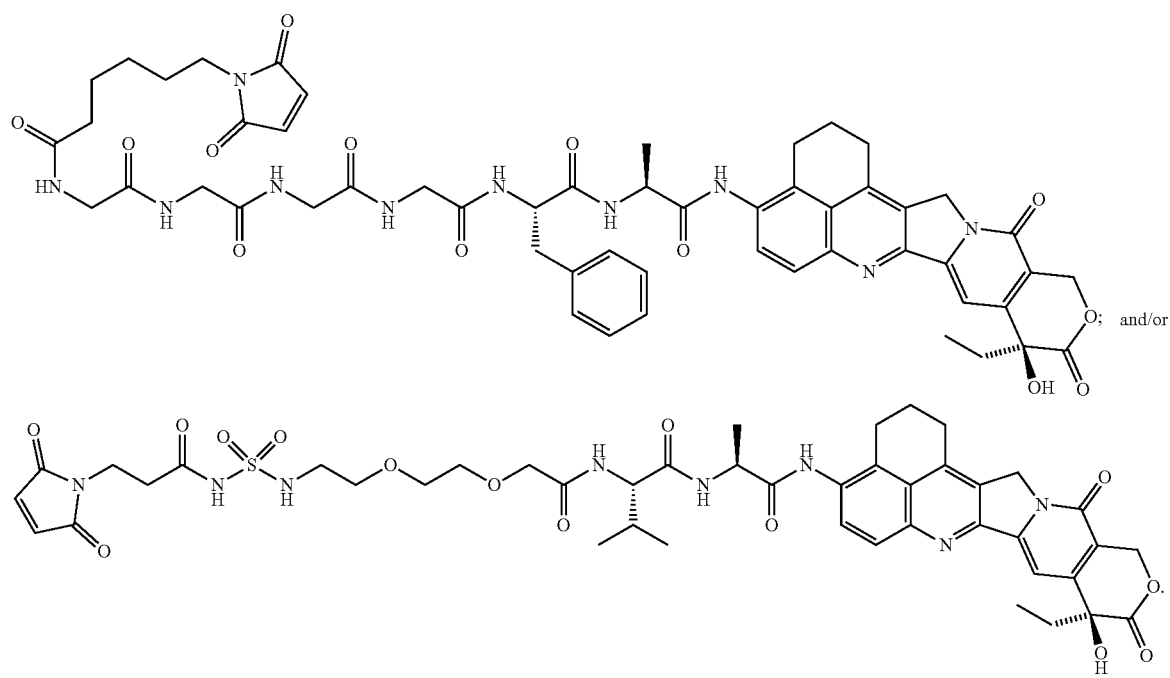
(SG4052)
and/or
SG3932 is particularly preferred. Thus, in preferable instance, an antibody molecule described herein is conjugated to a topoisomerase I inhibitor having the following formula (e.g. SG3932):
(SG3932)
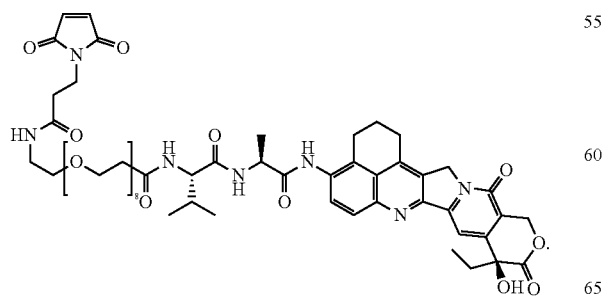

For the avoidance of doubt, the numeral '8' specifies that the structure within boxed parentheses is repeated eight times. Thus, another representation of SG3932 is:
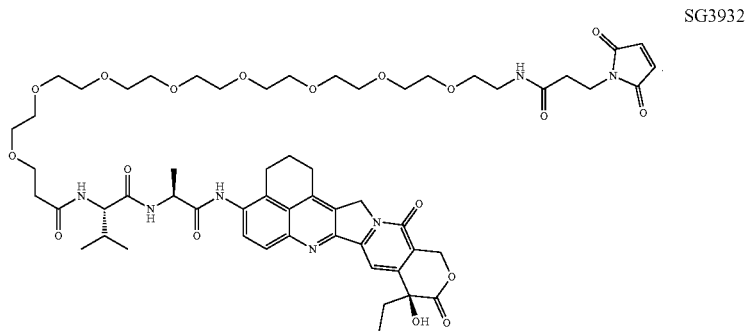
SG3932
Another representation of SG4010 is:
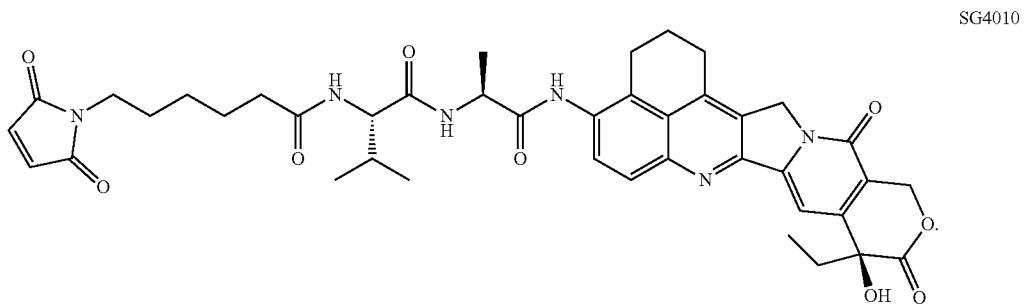 [SMILES: CC[C@@]1(O)C(=O)OCc2c1cc1n(c2=O)Cc2c-1nc1ccc(NC(=O)[C@H](C)NC(=O)[C@@H](NC(=O)CCCCCN3C(=O)C=CC3=O)C(C)C)c3c1c2CCC3]
SG4010
Another representation of SG4057 is:
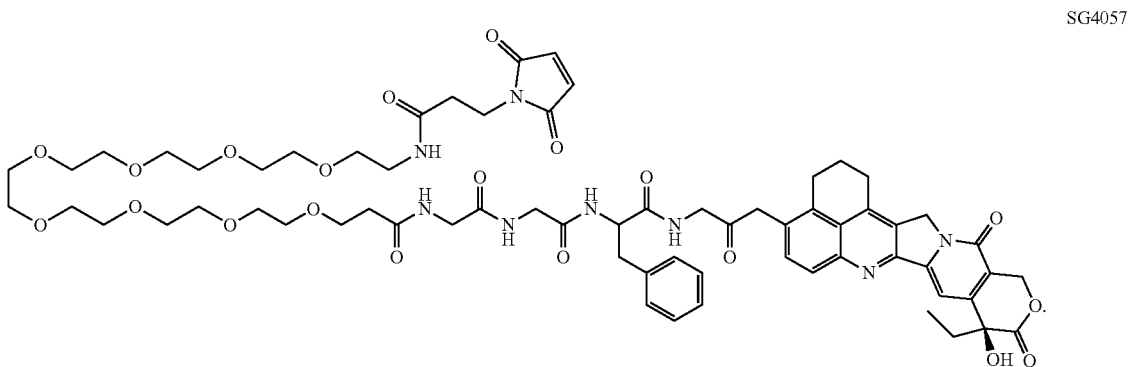 [SMILES: CC[C@@]1(O)C(=O)OCc2c1cc1n(c2=O)Cc2c-1nc1ccc(CC(=O)CNC(=O)C(Cc3ccccc3)NC(=O)CNC(=O)CNC(=O)CCOCCOCCOCCOCCOCCOCCOCCOCCNC(=O)CCN3C(=O)C=CC3=O)c3c1c2CCC3]
SG4057
Another representation of SG4052 is:
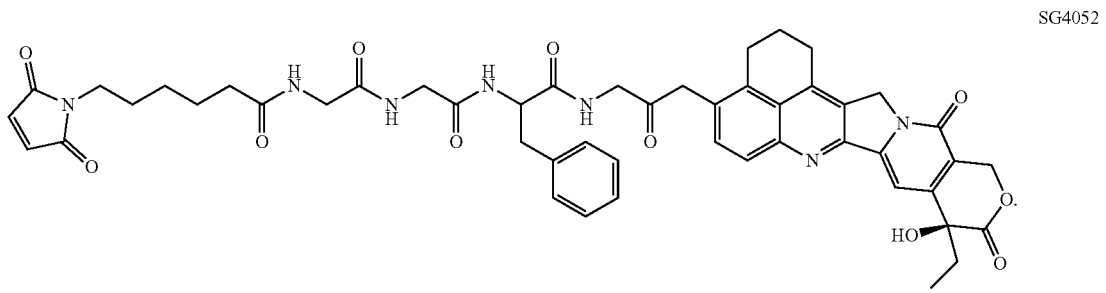 [SMILES: CC[C@@]1(O)C(=O)OCc2c1cc1n(c2=O)Cc2c-1nc1ccc(CC(=O)CNC(=O)C(Cc3ccccc3)NC(=O)CNC(=O)CNC(=O)CCCCCN3C(=O)C=CC3=O)c3c1c2CCC3]
SG4052

Any antibody or antigen binding fragment thereof described herein may be conjugated to one or more of said topoisomerase I inhibitor(s).

Synthesis of Topoisomerase I Inhibitors

For completion, certain general synthetic routes for the preparation of preferred topoisomerase I inhibitor(s) will now be described.

Compounds of formula I where $R^L$ is of formula Ia may be synthesised from a compound of Formula 2:

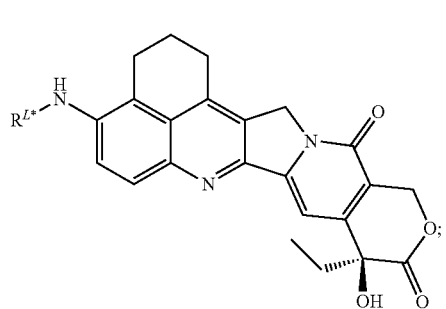

Formula 2 where $R^{L*}$ is —QH by linking a compound of Formula 3:

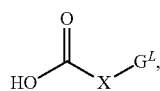

Formula 3 or an activated version thereof.

Such a reaction may be carried out under amide coupling conditions.

Compounds of Formula 2 may be synthesised by the deprotection of a compound of Formula 4:

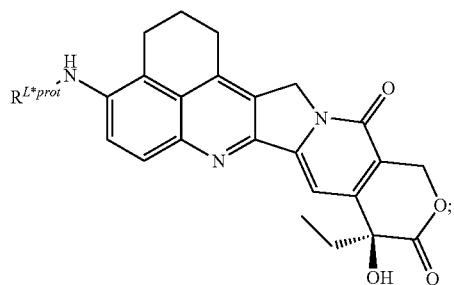

Formula 4 where $R^{L*prot}$ is -Q-Prot$^N$, where Prot$^N$ is an amine protecting group.

Compounds of Formula 4 may be synthesised by the coupling of a compound of Formula 5:

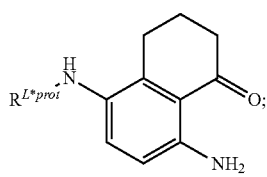

Formula 5 with the compound A3 using the Friedlander reaction.

Compounds of Formula 5 may be synthesised from compounds of Formula 6:

Formula 6 by removal of the trifluoroacetamide protecting group.

Compounds of Formula 6 may be synthesised by coupling: $R^{L*Prot}$-OH to the compound 17.

Compounds of formula I where $R^L$ is of formula Ia or Ib may be synthesised from the compound I11 by coupling of the compound $R^L$—OH, or an activated form thereof.

Amine Protecting Groups:

Amine protecting groups are well-known to those skilled in the art. Particular reference is made to the disclosure of suitable protecting groups in Greene's Protecting Groups in Organic Synthesis, Fourth Edition, John Wiley & Sons, 2007 (ISBN 978-0-471-69754-1), pages 696-871.

The drug loading (p) is the average number of drugs (e.g. tubulysin or topoisomerase inhibitor) per antibody molecule. In the compositions of the disclosure, drug loading ranges from 1 to 20 drugs (D) per antibody molecule. For example, drug loading may range from 1 to 10 drugs (D) per antibody molecule, i.e. where 1, 2, 3, 4, 5, 6, 7, 8, 9, or 10 drugs are covalently attached to the antibody molecule. Compositions of conjugates include collections of antibody molecules, conjugated with a range of drugs, from 1 to 10. Where the compounds of the disclosure are bound to lysines, drug loading may range from 1 to 80 drugs (D) per antibody molecule, although an upper limit of 40, 20, 10 or 8 may be preferred. Compositions of conjugates include collections of antibody molecules, conjugated with a range of drugs, from 1 to 80, 1 to 40, 1 to 20, 1 to 10 or 1 to 8.

The average number of drugs per antibody in preparations of conjugates from conjugation reactions may be characterized by conventional means such as UV, reverse phase HPLC, HIC, mass spectroscopy, ELISA assay, and electrophoresis. The quantitative distribution of conjugates in terms of p may also be determined. By ELISA, the averaged value of p in a particular preparation of conjugates may be determined (Hamblett, 2004; Sanderson, 2005). However, the distribution of p (drug) values is not discernible by the antibody-antigen binding and detection limitation of ELISA. Also, ELISA assay for detection of conjugates does not determine where the drug moieties are attached to the antibody molecule, such as the heavy chain or light chain fragments, or the particular amino acid residues. In some instances, separation, purification, and characterization of homogeneous conjugates where p is a certain value from conjugates with other drug loadings may be achieved by means such as reverse phase HPLC or electrophoresis. Such techniques are also applicable to other types of conjugates.

For some conjugates, p may be limited by the number of attachment sites on the antibody molecule. For example, an antibody molecule may have only one or several cysteine thiol groups, or may have only one or several sufficiently reactive thiol groups through which a linker may be attached.

Typically, fewer than the theoretical maximum of drug are conjugated to an antibody molecule during a conjugation reaction. An antibody molecule may contain, for example, many lysine residues that do not react with the linker (L). Only the most reactive lysine groups may react with an amine-reactive linker reagent. Also, only the most reactive cysteine thiol groups may react with a thiol-reactive linker reagent. Generally, antibody molecules do not contain many, if any, free and reactive cysteine thiol groups which may be linked to a drug moiety. Most cysteine thiol residues in the antibody molecules of the conjugates exist as disulfide bridges and must be reduced with a reducing agent such as dithiothreitol (DTT) or TCEP, under partial or total reducing conditions. The loading (drug/antibody ratio) of a conjugate may be controlled in several different manners, including: (i) limiting the molar excess of Drug Linker relative to antibody, (ii) limiting the conjugation reaction time or temperature, and (iii) partial or limiting reductive conditions for cysteine thiol modification.

Certain antibody molecules have reducible interchain disulfides, i.e. cysteine bridges. Antibody molecules may be made reactive for conjugation with linker reagents by treatment with a reducing agent such as DTT (dithiothreitol). Each cysteine bridge will thus form, theoretically, two reactive thiol nucleophiles. This process is also referred to as "classical conjugation" and is distinguished from methods such as where conjugation takes place at a cysteine that has been engineered into a specific site in the antibody molecule. Additional nucleophilic groups can be introduced into antibodies through the reaction of lysines with 2-iminothiolane (Traut's reagent) resulting in conversion of an amine into a thiol.

ADCs with drugs randomly conjugated to native cysteine residues are prepared by classical conjugation by partial reduction of the antibody followed by reaction with desired linker-drug. For example, the antibody at a concentration of 5 mg/mL may be partially reduced by addition of about 3 molar equivalents of DTT at pH 8.0, followed by incubation at about 37° C. for about 2 hours. The reduction reaction may then be chilled in ice and the excess DTT removed, for example, via diafiltration. The linker-drug can then be added at a linker—drug/thiol molar ratio of about 1:10. The conjugation reaction may be carried out in the presence of ~10% v/v of DMSO. After conjugation, excess free cysteine (about 2 fold molar ratio over linker-drug) can be added to quench unreacted linker-drug to produce the cysteine-linker-drug adduct. The reaction mixture can then purified (e.g., by hydrophobic interaction chromatography), and subjected to buffer-exchange into PBS. Drug load distribution can be determined using standard methods, such as hydrophobic interaction chromatography and reduced reverse phase chromatography, as described elsewhere.

Methods to prepare conjugates using direct conjugation at solvent-accessible thiols generated by reduction of the antibody molecule interchain disulphide bridges involving N-alkyl maleimide are known. Other methods conjugate the drug at primary amines of lysines using N-hydroxysuccinimide ester. Such methods are reviewed in, for example, Gébleux and Casi, Pharmacol Ther (2016) 167: 48-59, which is herein incorporated by reference in its entirety.

Separately or in addition to the classical conjugation methods described above, it is also possible to use site-specific conjugation, a method in which drug load and site of conjugation is controlled. This can be achieved by, for example, engineering cysteines at specific residues, replacement of residues with unnatural amino acids with bio-orthogonal reactivity or enzyme ligation approaches. One method of site-specific conjugation is described in Dimasi, 2017, which is herein incorporated by reference in its entirety and involves inserting cysteines into antibody molecules at particular positions.

Cysteine amino acids may be engineered at reactive sites in an antibody molecule and which do not form intrachain or intermolecular disulfide linkages (Junutula, 2008; Dornan, 2009; U.S. Pat. Nos. 7,521,541; 7,723,485; WO2009/052249). The engineered cysteine thiols may react with linkers or the drug-linker described herein which have thiol-reactive, electrophilic groups such as maleimide or alpha-halo amides to form conjugates with cysteine engineered antibody molecules and the drug. The location of the drug can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. If required, a drug loading near 2 can be achieved with near homogeneity of the conjugation product.

In some instances, the antibody molecule of the conjugate of the disclosure comprises a CH region and the drug is chemically conjugated at a cysteine amino acid inserted between positions 239 and 240 of the CH region, wherein the numbering of the constant region is as per the EU index. The connection between the antibody molecule and the drug may therefore be through this inserted cysteine amino acid and a terminal maleimide group on the linker.

Examples of CH regions that comprise a cysteine amino acid inserted between positions 239 and 240 of the CH region are SEQ ID NO: 43 and SEQ ID NO: 45. Examples of heavy chains comprising a CH region that comprises a cysteine amino acid inserted between positions 239 and 240 of the CH region are SEQ ID NOs: 50, 53 and 56.

In other instances, the antibody molecule of the conjugate does not comprise any amino acid residues inserted into the CH region. In particular instances, the antibody molecule of the conjugate does not comprise a cysteine amino acid inserted into the CH region (e.g. between positions 239 and 240, wherein the numbering of the constant region is as per the EU index). As demonstrated in the examples (e.g. Example 12), where classical conjugation is used to conjugate the drug-linker to native cysteines, the inserted cysteine is not necessary.

Examples of CH regions that do not comprise any amino acid residues inserted into the CH region are SEQ ID NO: 44, 46, 63 and 64. Examples of heavy chains comprising a CH region that do not comprise any amino acid residues inserted into the CH region are SEQ ID NOs: 51, 54, 57, 59 and 60.

Where more than one nucleophilic or electrophilic group of the antibody molecule reacts with a drug-linker intermediate, or linker reagent followed by drug reagent, then the resulting product is a mixture of conjugate compounds with a distribution of drug attached to an antibody, e.g. 1, 2, 3, etc. Liquid chromatography methods such as polymeric reverse phase (PLRP) and hydrophobic interaction (HIC) may separate compounds in the mixture by drug loading value. Preparations of conjugate with a single drug loading value (p) may be isolated, however, these single loading value conjugates may still be heterogeneous mixtures because the drug may be attached, via the linker, at different sites on the antibody molecule.

Thus the conjugate compositions of the disclosure include mixtures of antibody-drug conjugate compounds where the antibody has one or more drug moieties (e.g. tubulysin or topoisomerase inhibitor) and where the drug moieties may be attached to the antibody molecule at various amino acid residues.

In some instances, the average number of tubulysin drug moieties per antibody molecule is in the range 1 to 8. In some instances the range is selected from 1 to 6, 1 to 4, 1 to 3, preferably 1 to 2, more preferably 1.5 to 2, even more preferably 1.8 to 2, still more preferably 1.9 to 2.

As already described above, in some instances the antibody molecule of the ADC may comprise one or more mutations in the CH region(s) of the heavy chain(s) to reduce or abrogate binding of the antibody molecule to one or more Fcγ receptors. Thus, the first and/or second heavy chain of the ADCs described herein may comprise phenylalanine (F) at position 234, glutamic acid (E) at position 235, and serine (S) at position 331, wherein the numbering is as per the EU index.

Functional Properties of the Antibody Molecules and Conjugates

The antibody molecules and conjugates described herein may be characterised by reference to certain functional properties.

Binding Affinity

The antibody molecules and conjugates described herein may be characterised by the antigen-binding domain that binds EGFR having a particular affinity for EGFR and/or the antigen-binding domain that binds c-Met having a particular affinity for c-Met. The binding affinity of an antibody molecule or conjugate to a cognate antigen, such as human, mouse or cynomolgus EGFR or c-Met can be determined by surface plasmon resonance (SPR), using Biacore, for example. The binding affinity can be determined using an antibody molecule, for example as part of a bispecific antibody molecule that comprises a first antigen-binding domain that binds EGFR and a second antigen-binding domain that binds c-Met. Alternatively, the binding affinity can be determined using an antibody molecule that is monospecific for EGFR or c-Met. In some instances, the binding affinity is determined using BIACore as described in Example 2.1.

Binding affinity is typically measured by Kd (the equilibrium dissociation constant between the antigen-binding domain and its antigen). As is well understood, the lower the Kd value, the higher the binding affinity of the antigen-binding domain. For example, an antigen-binding domain that binds to a target with a Kd of 10 nM would be considered to be binding said target with a higher affinity than an antigen-binding domain that binds to the same target with a Kd of 100 nM.

Reference to human EGFR may refer to a polypeptide comprising the extracellular domain of EGFR, such as one having the amino acid sequence set forth in SEQ ID NO: 68. Reference to mouse EGFR may refer to a polypeptide produced from the molecule available from SinoBiological with catalogue #51091-M08H. Reference to cynomolgus EGFR may refer to the amino acid sequence set forth in SEQ ID NOs: 69. Reference to human c-Met may refer to a polypeptide having the amino acid sequence set forth in SEQ ID NO: 70. Reference to mouse c-Met may refer to a polypeptide having the amino acid sequence set forth in SEQ ID NO: 90 or to the polypeptide produced from the molecule available from SinoBiological with catalogue #50622-M08H. Reference to cynomolgus c-Met may refer to the amino acid sequence set forth in SEQ ID NO: 71.

EGFR Affinity

Antibody molecules and conjugates described herein may comprise an antigen-binding domain that binds to EGFR with a low affinity. EGFR is known to be expressed at low levels in normal tissues, e.g. the skin e.g. the skin. Antibody molecules and conjugates that bind to EGFR with a low-affinity are advantageously expected to display reduced on-target toxicity in normal tissues whilst still being able to target tumors expressing high levels of EGFR, resulting in an improved safety profile. Furthermore, as demonstrated herein, conjugates comprising this low affinity EGFR antigen-binding domain are more efficacious at treating cancer compared to conjugates comprising a higher affinity EGFR antigen-binding domain.

The antigen-binding domain that binds to EGFR may bind to human EGFR with an affinity having a Kd equal to or higher than 10 nM, 15 nM, 20 nM, 25 nM, 30 nM, 35 nM, or 40 nM. Alternatively, antigen-binding domain that binds to EGFR may bind to human EGFR with a Kd of between 10 and 100 nM, between 20 and 100 nM, between 30 and 100 nM, between 40 and 100 nM, between 10 and 80 nM, between 20 and 80 nM, between 30 and 80 nM, between 40 and 80 nM, between, between 10 and 70 nM, between 20 and 70 nM, between 30 and 70 nM, between 40 and 70 nM, between 10 and 60 nM, between 20 and 60 nM, between 30 and 60 nM, between 40 and 60 nM, between 10 and 50 nM, between 20 and 50 nM, between 30 and 50 nM, or between 40 and 50 nM.

The antigen-binding domain that binds to EGFR may bind to human EGFR with an affinity that is lower than the affinity that an antigen-binding domain comprising the heavy chain sequence and light chain sequence of antibody molecule QD6 set forth in SEQ ID NOs: 53 and 55, respectively.

For example, the antigen-binding domain that binds to EGFR may bind to human EGFR with an affinity having a Kd that is at least 2-fold, 3-fold, 4-fold, 5-fold, 6-fold, or 7-fold higher than the Kd that an antigen-binding domain comprising the heavy chain sequence and light chain sequence of antibody molecule QD6 set forth in SEQ ID NOs: 53 and 55, respectively, binds human EGFR. Alternatively, the antigen-binding domain that binds to EGFR may bind to human EGFR with an affinity having a Kd that is between 2- and 10-fold higher, between 3- and 10-fold higher, between 4- and 10-fold higher, between 5- and 10-fold higher, between 6- and 10-fold higher, between 7- and 10-fold higher, between 2- and 9-fold higher, between 3- and 9-fold higher, between 4- and 9-fold higher, between 5- and 9-fold higher, between 6- and 9-fold higher, between 7- and 9-fold higher, between 2- and 8-fold higher, between 3- and 8-fold higher, between 4- and 8-fold higher, between 5- and 8-fold higher, between 6- and 8-fold higher, between 7- and 8-fold higher than the Kd that an antigen-binding domain comprising the heavy chain sequence and light chain sequence of antibody QD6 set forth in SEQ ID NOs: 53 and 55, respectively, binds human EGFR.

The antigen-binding domain that binds to EGFR may bind to human EGFR with an affinity that is similar to the affinity that an antigen-binding domain comprising the variable heavy region sequence and variable light region sequence of antibody molecule RAA22 set forth in SEQ ID NOs: 16 and 20, respectively. For example, the antigen-binding domain that binds to EGFR may bind to human EGFR with an affinity having a Kd that is less than 5-fold different, less than 4-fold different, less than 3-fold different, less than 2-fold different, less than 1-fold different or less than 0.5-fold different than an antigen-binding domain comprising the variable heavy region sequence and variable light region sequence of antibody molecule RAA22 set forth in SEQ ID NOs: 16 and 20, respectively, binds human EGFR.

The antigen-binding domain that binds to EGFR may also bind to cynomolgus EGFR. For example, the antigen-binding domain that binds to EGFR may bind to cynomolgus EGFR with an affinity having a Kd that is less than 700 nM, less than 600 nM, less than 500 nM, less than 400 nM, less than 300 nM, or less than 250 nM. Alternatively, the antigen-binding domain that binds to EGFR may bind to cynomolgus EGFR with an affinity having a Kd of between 100 and 700 nM, between 100 and 600 nM, between 100 and 500 nM, between 100 and 400 nM, between 100 and 300 nM, between 150 and 250 nM, between 100 and 200 nM. The antigen-binding domain that binds to EGFR may bind to cynomolgus EGFR with a Kd that is less than or equal 10-, 9-, 8-, 7-, 6-, 5-, 4-, 3-fold higher Kd than the antigen-binding domain binds to human EGFR.

The antigen-binding domain that binds to EGFR may also bind to mouse EGFR. For example, the antigen-binding domain that binds to EGFR may bind to mouse EGFR with an affinity having a Kd that is less than 1 μM, less than 900 nM, less than 800 nM, less than 700 nM, less than 600 nM or less than 650 nM. Alternatively, the antigen-binding domain that binds to EGFR may bind to mouse EGFR with a Kd of between 100 nM and 1 μM, between 200 and 900 nM, between 300 and 800 nM, between 400 and 700 nM, between 400 and 600 nM, or between 450 and 550 nM.

Preferably, the antigen-binding domain that binds to EGFR is capable of binding human EGFR and cynomolgus EGFR. This cross-reactivity is advantageous, as it allows dosing and safety testing of the antibody molecules and conjugates to be performed in cynomolgus monkeys during preclinical development. Even more preferably, the antigen-binding domain that binds to EGFR is capable of binding human EGFR, cynomolgus EGFR and mouse EGFR. For example, the antigen-binding domain that binds EGFR may be capable of binding human EGFR, cynomolgus EGFR and mouse EGFR with the Kd values set out above (e.g. human EGFR with a Kd of between 10 and 100 nM, cynomolgus EGFR with a Kd of between 100 and 700 nM and mouse EGFR with a Kd of between 100 nM and 1 μM).

c-Met Affinity

The antigen-binding domain that binds to c-Met may bind to human c-Met with an affinity having a Kd of lower than 20 nM, 15 nM, 12 nM, 11 nM, 10 nM, 9 nM, 8 nM, 7 nM, 6 nM, 5 nM, 4 nM, 3 nM or 2.5 nM. Alternatively, antigen-binding domain that binds to c-Met may bind to human c-Met with an affinity having a Kd of between 1 and 20 nM, between 1 and 15 nM, between 1 and 10 nM, between 1 and 9 nM, between 1 and 8 nM, between 1 and 7 nM, between 1 and 6 nM, between 1 and 5 nM, between 1 and 4 nM, between 1 and 3 nM, between 1 and 2.5 nM, or between 2 and 2.5 nM.

The antigen-binding domain that binds to c-Met may bind to cynomolgus c-Met. For example, the antigen-binding domain that binds to c-Met may bind to cynomolgus c-Met with an affinity having a Kd that is lower than 30 nM, 25 nM, 20 nM, 15 nM, 10 nM, 9 nM, 8 nM, 7 nM, 6 nM, 5 nM, 4 nM, 3 nM, or 2.5 nM. Alternatively, antigen-binding domain that binds to c-Met may bind to cynomolgus c-Met with an affinity having a Kd of between 1 and 20 nM, between 1 and 15 nM, between 1 and 10 nM, between 1 and 9 nM, between 1 and 8 nM, between 1 and 7 nM, between 1 and 6 nM, between 1 and 5 nM, between 1 and 4 nM, between 1 and 3 nM, between 1 and 2.5 nM, or between 2 and 2.5 nM. The antigen-binding domain that binds to c-Met may bind to cynomolgus c-Met with an affinity having a Kd that is less than or equal 10-, 9-, 8-, 7-, 6-, 5-, 4-, 3-, 2-, 1-fold higher Kd than the antigen-binding domain binds to human c-Met.

Preferably, the antigen-binding domain that binds to c-Met is capable of binding human c-Met and cynomolgus c-Met. This cross-reactivity is advantageous, as it allows dosing and safety testing of the antibody molecules to be performed in cynomolgus monkeys during preclinical development. For example, the antigen-binding domain that binds c-Met may be capable of binding human c-Met and cynomolgus c-Met with the Kd values set out above (e.g. human c-Met with a Kd of between 1 and 20 nM and cynomolgus c-Met with a Kd of between 1 and 20 nM).

Specific Binding

The antibody molecules and conjugates described herein may comprise an antigen-binding domain that binds EGFR that is an antigen-binding domain that specifically binds EGFR. The antibody molecules and conjugates described herein may comprise an antigen-binding domain that binds c-Met that is an antigen-binding domain that specifically binds c-Met. The antibody molecules and conjugates described herein may comprise a first antigen-binding domain that binds EGFR, which is a first antigen-binding domain that specifically binds EGFR, and a second antigen-binding domain that binds c-Met, which is a first antigen-binding domain that specifically binds c-Met.

The term "specific" may refer to the situation in which the antigen-binding domain will not show any significant binding to molecules other than its specific binding partner(s), here EGFR or c-Met. Such molecules are referred to as "non-target molecules". The term "specific" is also applicable where the antibody molecule is specific for particular epitopes, such as epitopes on EGFR or c-Met, that are carried by a number of antigens in which case the antibody molecule will be able to bind to the various antigens carrying the epitope.

In some instances, an antibody molecule or conjugate is considered to not show any significant binding to a non-target molecule if the extent of binding to a non-target molecule is less than about 10% of the binding of the antibody to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the antibody molecule or conjugate described herein binds to EGFR and/or c-Met with an affinity that is at least 0.1 order of magnitude greater than the affinity towards another, non-target molecule. In some instances, the antibody molecule or conjugate of the present disclosure binds to EGFR and/or c-Met with an affinity that is one of at least 0.2, 0.3, 0.4, 0.5, 0.6, 0.7, 0.8, 0.9, 1.0, 1.5, or 2.0 orders of magnitude greater than the affinity towards another, non-target molecule.

EGFR is a member of the ErbB family of receptors, a subfamily of four closely related receptor tyrosine kinases: EGFR, HER2, HER3 and HER4. The RAA22 antigen-binding domain showed no binding to HER2, HER3 and HER4, demonstrating that this antigen-binding domain binds EGFR specifically. Thus, in a preferred instance, the antigen-binding domain that binds EGFR does not bind, or does not show any significant binding, to HER2, HER3 or HER4.

c-Met is a member of the subfamily of receptor tyrosine kinases that includes Ron and Sema 4a. The B09-GL antigen-binding domain showed no binding to Ron and Sema 4a, demonstrating that this antigen-binding domain binds c-Met specifically. Thus, in a preferred instance, the antigen-binding domain that binds c-Met does not bind, or does not show any significant binding, to Ron, Sema 4a.

Concurrent Engagement

The antibody molecules and conjugates comprising a first antigen-binding domain that binds EGFR and a second antigen-binding domain that binds c-Met described herein may be characterised by the ability of both the antigen-binding domains to concurrently engage their respective EGFR and c-Met targets. Antibody molecules and conjugates with the ability to concurrently engage EGFR and c-Met are expected to be advantageous, as numerous tumours are known to co-express both EGFR and c-Met and therefore can be targeted by antibody molecules of the disclosure. Thus, in some instances the antibody molecule or conjugate is able to concurrently engage EGFR and c-Met.

Concurrent engagement can be determined for example by an in vitro cytotoxicity assay using a cell line expresses roughly equal amounts of EGFR and c-Met and a conjugate comprising the antibody molecules with EGFR and c-Met antigen-binding domains. If the individual antigen-binding domains in the conjugate function independently to deliver the drug, blocking either target in this cell line would be expected to only modestly reduce the activity of the conjugate, shifting the IC50 by 2-fold or less, since the targets are present at similar levels. The EGFR and c-Met targets can be blocked in this assay by using, for example, a monospecific antibody molecule that binds the same region on either EGFR or c-Met, but lacks a drug that is able to induce cytotoxicity. For example, the monospecific antibody molecule may contain the same antigen-binding domain that binds EGFR, or the same antigen-binding domain that binds c-Met, as the conjugate being tested. If, on the other hand, the conjugate requires concurrent engagement to effectively deliver the conjugate into cells, blocking either target would be likely to have a greater impact on the activity of the conjugate. That is, the antibody molecule is considered to be able to engage both targets concurrently if there is a shift in IC50 by at least 2-fold, preferably at least 5-fold, even more preferably at least 10-fold after blocking either target when using this assay.

An additional method to determine concurrent engagement is to compare the activity of the bispecific EGFR-c-Met conjugate to monovalent, monospecific control conjugates in an in vitro cytotoxicity assay. The control conjugates comprise one antigen-binding domain to either EGFR or c-Met and one non-binding isotype antibody control antigen-binding domain. If each antigen-binding domain in the bispecific conjugate functions independently, the expected result would be that each monospecific control conjugate would only be modestly less potent than the bispecific conjugate, and the difference would be additive. Alternatively, if the two antigen-binding domains of the bispecific conjugate function synergistically by concurrent binding, one would expect larger differences in activity of the bispecific conjugate compared to the monospecific control antibodies. That is, the antibody molecule is considered to be able to engage both targets concurrently if the bispecific conjugate results in a shift in IC50 that is greater than the sum of the shifts in IC50 observed using the monospecific control conjugates.

Further details of these methods to measure concurrent engagement can be found in the examples.

Antibody Internalisation

The antibody molecules and conjugates described herein may be characterised by their ability to mediate efficient internalisation. This is particularly useful for conjugates, as it ensures the conjugate is internalised into the cell and delivered to lysosomes, where the antibody molecule is subsequently degraded and drug released into the cell, where it exerts its cellular effects, e.g. cytotoxicity.

Internalisation of an antibody molecule or conjugate by cells can be analysed by contacting live cells with the antibody molecule, and detecting the antibody molecule or conjugate after sufficient period of time for internalisation. Internalisation can be determined by detection of the localisation of the antibody molecule or conjugate. Where the antibody molecule or conjugate remains on the surface of the cell (e.g. is detected on the cell surface, and/or is not detected inside the cell), the antibody molecule or conjugate is determined not to have been internalised. Where the antibody molecule or conjugate is detected inside the cell (e.g. localised to the cytoplasm or a cellular organelle), the antibody molecule or conjugate is determined to have been internalised.

An exemplary method for visualising whether the antibody molecule or conjugate is able to mediate efficient internalisation involves labelling the antibody molecule with pH sensitive dyes that exhibit fluorescent at an acidic pH and adding these labelled antibody molecules or conjugates to cells. Internalisation into the cell can be detected by monitoring fluorescence. The antibody molecule or conjugate is considered able to mediate internalisation and delivery to lysosomes if the fluorescence observed is greater than that of a labelled non-binding control antibody molecule or conjugate over a certain time period, for example 48 hours. Further details of this method to visualise antibody internalisation can be found in the examples.

The antibody molecules or conjugates comprising a first antigen-binding domain that binds EGFR and a second antigen-binding domain that binds c-Met may be characterised by their ability to mediate more efficient internalisation when compared to the EGFR or c-Met monospecific controls. Antibody molecules and conjugates that exhibit this properties are expected to be advantageous, as they are expected to display greater selectivity to tumour cells co-expressing both targets and could minimise the impact of the antibody molecule in normal tissues that do not display significant levels of co-expression.

In Vitro Activity

The antibody molecules or conjugates described herein may be characterised by their cytotoxic activity, i.e. their ability to kill cells. Cytotoxic activity can be measured using an in vitro cell viability assay, such as the CellTiter-Glo® (Promega) assay, for example. In some instances, the cells are cells that expression both EGFR and c-Met.

Potency of an antibody molecule can be expressed as an IC50 value. IC50 is the median inhibitory concentration of an antibody molecule. In functional assays, IC50 is the concentration that reduces a biological response by 50% of its maximum. IC50 can be calculated by any number of means known in the art.

In some instances, the antibody molecules or conjugates described herein having cytotoxic activity have an IC50 of less than less than 4000 pM, less than 3500 pM, less than 3000 pM, less than 2500 pM, less than 2000 pM, less than 1500 pM, less than 1000 pM, less than 500 pM, less than 400 pM, less than 300 pM, less than 250 pM, less than 200 pM, less than 150 pM, or less than 100 pM when measured using an in vitro cell viability assay. In some instances, the antibody molecules or conjugates described herein may have an IC50 of between 60 and 500 pM.

In some instances, the antibody molecules or conjugates described herein are capable of increased killing of cells, e.g. tumor cells, that express significant amounts of both EGFR and c-Met compared to cells that express low levels of one or the other of EGFR and c-Met. Cells expressing significant amounts of both EGFR and c-Met may be determined by measuring relative receptor density at the cell surface. For example, cells expressing EGFR and c-Met at a relative receptor density at the cell surface of greater than 15,000 may be considered cells that express significant amounts of both EGFR and c-Met and cells that express one of EGFR and c-Met at a low relative receptor density at the cell surface of 15,000 or less. Relative EGFR and c-Met density can be measured, for example, using the Quantum MESF quantitative FACS assay kit as described in the examples.

Examples of cells that express significant amounts of both EGFR and c-Met may include NCI H596, HCC 827 GR Pool, A549, NCI H1792, NCI H1975, NCI H292 and NCI H358 cell lines. Examples of cells that express one of EGFR and c-Met at a low relative receptor density may include A427, NCI H23 and NCI H661 (Ag negative) cell lines. These cell lines are available through ATCC.

In some instances, the antibody molecules or conjugates described herein are capable of cytotoxic activity in cells that are resistant to cells that are resistant to tyrosine kinase inhibitors (TKIs). Examples of TKI resistant cells may include NCI H1975 (EGFR mutations: T790M, L858R) and HCC827 GR Pool (EGFR 4746-750 deletion+MET amplification).

In Vivo Activity

In some instances, the antibody molecules or conjugates described herein are capable of inhibiting the development or progression of a cancer.

The cancer may be a cancer that expressed both EGFR and c-Met. Cells of the cancer may express EGFR and c-Met at the cell surface. The cancer may e.g. lung cancer (such as Non-Small Cell Lung Cancer (NSCLC)), pancreatic cancer, breast cancer, colorectal cancer, gastric cancer, head and neck cancer, ovarian cancer or glioblastoma.

The ability of a given antibody molecule or conjugate to inhibit the development or progression of a cancer can be analysed e.g. using an in vivo model. For example, the in vivo model may involve measuring tumour growth in a patient derived xenograft (PDX) model. Further details of this exemplary method is described in the examples.

Inhibition of the development of a cancer may be inferred by observation of slower tumour growth or a decrease in tumour size following administration of the antibody molecule or conjugate, for example by measuring the tumour growth inhibition (% TGI). % TGI can be measured by comparing the size of the tumour measured at day 0 with the size of the tumour measured at the end of the study time for those subjects administered with the antibody molecule or conjugate, and comparing this to the tumour growth over the same time period for subjects administered with a control antibody molecule or conjugate. In this way, % TGI can be defined as Percent tumour growth versus Day 0 between treatment (TX) and control (C) groups, according to the formula: % $TGI=(1-(TX_{final}-TX_{initial})\ (C_{final}-C_{initial}))\times 100$.

In some instances, the antibody molecule or conjugate described herein has a % TGI of at least 50%, at least 55%, at least 60%, at least 65%, at least 70%, at least 75%, at least 80%, at least 85%, at least 90%, at least 95%, at least 96%, at least 97%, at least 98%, or at least 99%.

Inhibition of the development of a cancer may be inferred by observation of a delayed or prevented onset of, and/or reduced severity of, symptoms of the cancer in response to treatment with the antibody molecule. Inhibition of the progression of a cancer may be inferred by observation of delayed, prevented and/or reduced invasion and/or metastasis in response to treatment with the antibody molecule.

The antibody molecule described herein may be capable of inhibiting the development or progression of a cancer to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the development/progression of the cancer in the absence of treatment with the antibody molecule (or treatment with an appropriate control). In some instances, the antibody molecule described herein is capable of inhibiting the development or progression of a cancer to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of development/progression of the cancer in the absence of treatment with the antibody molecule (or treatment with an appropriate control).

In some instances the cancer comprise cancer cells that express high levels of EGFR and/or high levels of c-Met at the cell surface. Methods of measuring levels EGFR and c-Met are known in the art and include immunohistochemistry, for example.

In some instances, the antibody molecules or conjugates described herein are capable of increased inhibition of the development or progression of a cancer in cells that display high levels of both EGFR and c-Met compared to cells that express low levels of one or the other of EGFR and c-Met.

Nucleic Acids, Vectors, Host Cells, Expression and Purification

The present disclosure provides a nucleic acid molecule or molecules encoding an antibody molecule described herein. In some instances, a nucleic acid molecule comprises a polynucleotide sequence encoding a heavy chain variable region of an antibody molecule disclosed herein, a polynucleotide sequence encoding a light chain variable region of an antibody molecule disclosed herein, or both.

In some instances, the nucleic acid molecule or molecules are purified or isolated, e.g. from other nucleic acid, or naturally-occurring biological material. The skilled person would have no difficulty in preparing such nucleic acid molecules using methods well-known in the art.

The nucleic acid molecule or molecules may encode the VH domain and/or VL domain, preferably the VH domain and VL domain of: anti-EGFR antibody clone RAA22, anti-EGFR antibody clone QD6, anti-c-Met antibody clone B09-GL, preferably anti-EGFR antibody clone RAA22, or anti-c-Met antibody clone B09-GL. The VH and VL domain sequences of these antibodies are described herein. Where the nucleic acid encodes the VH and VL domain, or heavy and light chain, of an antibody molecule of the disclosure, the two domains or chains may be encoded on two separate nucleic acid molecules.

For example, the nucleic acid molecule(s) may comprise:
(i) the VH domain nucleic acid sequence of RAA22 set forth in SEQ ID NO: 17, and/or the VL domain nucleic acid sequence of RAA22 set forth in SEQ ID NO: 21;
(ii) the VH domain nucleic acid sequence of QD6 set forth in SEQ ID NO: 19, and/or the VL domain nucleic acid sequence of QD6 set forth in SEQ ID NO: 23; or
(iii) the VH domain nucleic acid sequence of B09-GL set forth in SEQ ID NO: 39, and/or the VL domain nucleic acid sequence of B09-GL set forth in SEQ ID NO: 41.

The nucleic acid molecule(s) may encode the heavy chain and/or light chain, preferably the heavy chain and light chain of: anti-EGFR antibody clone RAA22, anti-EGFR antibody clone QD6, anti-c-Met antibody clone B09-GL, preferably anti-EGFR antibody clone RAA22, or anti-c-Met antibody clone B09-GL. The heavy and light chain sequences of these antibody molecules are described herein.

The present disclosure also provides a vector comprising nucleic acid molecule encoding an antibody molecule described herein.

An isolated nucleic acid molecule may be used to express an antibody molecule of the disclosure. The nucleic acid will generally be provided in the form of a recombinant vector for expression. Another aspect of the disclosure thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NS0, or HEK cell, for example a HEK293 cell.

Another aspect of the disclosure provides a method of producing an antibody molecule of the disclosure comprising expressing a nucleic acid encoding the antibody molecule in a host cell and optionally isolating and/or purifying the antibody molecule thus produced. Methods for culturing host cells are well-known in the art. The method may further comprise isolating and/or purifying the antibody molecule. Techniques for the purification of recombinant antibody molecules are well-known in the art and include, for example HPLC, FPLC or affinity chromatography, e.g. using Protein A or Protein L. In some instances, purification may be performed using an affinity tag on antibody molecule. The method may also comprise formulating the antibody molecule into a pharmaceutical composition, optionally with a pharmaceutically acceptable excipient or other substance as described below.

Treatment

As explained above, co-expression of EGFR and c-Met is associated with many cancer types and antibody molecules that target both molecules and especially conjugates comprising such antibody molecules provide an opportunity for broad clinical benefit across multiple indications.

The antibody molecule or conjugate as described herein may thus be useful for therapeutic applications, in particular in the treatment of cancer.

An antibody molecule, conjugate or pharmaceutical composition as described herein may be used in a method of treatment of the human or animal body. Related aspects of the disclosure provide:
(i) an antibody molecule or conjugate described herein for use as a medicament,
(ii) an antibody molecule or conjugate described herein for use in a method of treatment of a disease or disorder,
(iii) an antibody molecule or conjugate described herein in the manufacture of a medicament for use in the treatment of a disease or disorder; and,
(iv) a method of treating a disease or disorder in an individual, wherein the method comprises administering to the individual a therapeutically effective amount of an antibody molecule or conjugate as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

A method of treatment as described may be comprise administering at least one further treatment to the individual in addition to the antibody molecule or conjugate. The antibody molecule or conjugate described herein may thus be administered to an individual alone or in combination with one or more other treatments. Where the antibody molecule or conjugate is administered to the individual in combination with another treatment, the additional treatment may be administered to the individual concurrently with, sequentially to, or separately from the administration of the antibody molecule or conjugate. Where the additional treatment is administered concurrently with the antibody molecule or conjugate, the antibody molecule and additional treatment may be administered to the individual as a combined preparation. For example, the additional therapy may be a known therapy or therapeutic agent for the disease to be treated.

Whilst an antibody molecule may be administered alone, antibody molecules or conjugates will usually be administered in the form of a pharmaceutical composition, which may comprise at least one component in addition to the antibody molecule or conjugate. Another aspect of the disclosure therefore provides a pharmaceutical composition comprising an antibody molecule or conjugate as described herein. A method comprising formulating an antibody molecule or conjugate into a pharmaceutical composition is also provided.

Pharmaceutical compositions may comprise, in addition to the antibody molecule or conjugate, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of antibody molecule, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody molecules are well known in the art (Ledermann, 1991; and Bagshawe, 1991). Specific dosages indicated herein, or in the Physician's Desk Reference (2003) as appropriate for an antibody molecule being administered, may be used. A therapeutically effective amount or suitable dose of an antibody molecule can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule.

In a preferred instance, an antibody molecule or conjugate as described herein may be for use in a method of treating cancer.

Cancer may be characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

The cancer may be a primary or a secondary cancer. Thus, an antibody molecule or conjugate as described herein may be for use in a method of treating cancer in an individual, wherein the cancer is a primary tumour and/or a tumour metastasis.

A tumour of a cancer to be treated using an antibody molecule or conjugate as described herein may co-express EGFR and c-Met. In one instance, the tumour may have been determined to co-expression EGFR and c-Met. Methods for determining the expression of a target are known in the art and include, for example, immunohistochemistry.

For example, the cancer to be treated using an antibody molecule or conjugate as described herein may be selected from the group consisting of: lung cancer (such as Non-Small Cell Lung Cancer (NSCLC)), pancreatic cancer, breast cancer, colorectal cancer, kidney cancer, gastric cancer, head and neck cancer, ovarian cancer or glioblastoma.

In a preferred instance, the cancer to be treated using an antibody molecule or conjugate as described herein is selected from the group consisting of: lung cancer (such as Non-Small Cell Lung Cancer (NSCLC)), pancreatic cancer, colon cancer, colorectal cancer and squamous cell carcinoma of head and neck (SCCHN or SQHN). In one instance, the cancer to be treated in non-small cell lung cancer (NSCLC). In one instance, the cancer is squamous cell carcinoma of head and neck (SCCHN).

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens.

Activating or enhancing immune responses to cancerous tumours in an individual may improve the capacity of the individual to resist cancer growth, in particular growth of a cancer already present the subject and/or decrease the propensity for cancer growth in the individual.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the disclosure in diverse forms thereof.

While the disclosure has been described in conjunction with the exemplary instances described above, many equivalent modifications and variations will be apparent to those skilled in the art when given this disclosure. Accordingly, the exemplary instances of the disclosure set forth above are considered to be illustrative and not limiting. Various changes to the described instances may be made without departing from the spirit and scope of the disclosure.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another instance includes from the one particular value and/or to the other particular value. Similarly, when values are expressed as approximations, by the use of the antecedent "about," it will be understood that the particular value forms another instance. The term "about" in relation to a numerical value is optional and means for example +/−10%.

EXAMPLES

Example 1—RAA22/B09 DuetMab Design and Construction

This examples describes the creation of bispecific antibody molecules that are capable of binding both EGFR and c-Met.

1.1 Isolation and Identification of Anti-cMET Antibody 0021U3-B09 cMET-specific scFv antibodies were isolated from a large naïve human scFv phage display library in a series of repeated panning selection cycles on recombinant mammalian expressed biotinylated monomeric human cMET (MedImmune) essentially as described (Vaughan, 1996). ScFvs from the round 2 of the selection output were expressed in the bacterial periplasm and screened for their ability to inhibit the binding of the human cMET receptor with the HGF ligand in a HGF:cMET HTRF® (Homogeneous Time-Resolved Fluorescence) ligand receptor inhibitory binding assay. Top hits exhibiting strong inhibitory effect were selected and subjected to DNA sequencing. Unique genes were then converted to human immunoglobulin G2 (IgG2) antibodies and produced in mammalian cells essentially as described (Persic; 1997). The purified antibodies were then ranked based on their inhibitory effect in the HGF:cMET HTRF® binding assay. The most potent antibody, 0021U3-B09, was selected for further characterization.

1.2 Optimization of Anti-cMET Antibody 0021U3-B09.

To minimize potential immunogenicity, non-Vernier framework residues (Foote and Winter 1992) in the variable framework regions of 0021U3-B09 were targeted specifically and altered to match the closest human germline sequence. In the VH region, seven amino acid residues were mutated to match the reference human germline sequence IGHV1-8*01. In the VL region, three residues were mutated to match the reference human germline sequence IGKV1-5*03. All residues in VH and VL regions were successfully changed to the germline residues without loss of activity. 0021U3-B09 was affinity optimized using a hybridization-based mutagenesis method essentially as described (Kunkel 1985). A large scFv library derived from 0021U3-B09 sequence was created by oligonucleotide-directed mutagenesis of the VH complementarity determining regions 3 (CDR3) using standard molecular biology techniques. The library was subjected to affinity-based solution phase selections to select variants with a higher affinity to human and cynomolgus cMET antigens. Crude scFv-containing periplasmic extracts from the CDR-targeted selection outputs were screened for improved inhibitory activity in the HGF:cMET HTRF® binding assay. Variants exhibiting significantly improved inhibitory effect compared to parent 0021U3-B09, were subjected to DNA sequencing and unique genes were converted to human IgG2. The purified antibodies were then ranked based on their inhibitory effect. The most potent antibody, B09-57, was selected for further characterization.

1.3 Isolation and Identification of Anti-EGFR Antibody Tdev-0004.

EGFR-specific scFv antibodies were isolated from a large naïve human scFv phage display library in a series of repeated panning selection cycles on recombinant mammalian expressed biotinylated monomeric human EGFR (MedImmune) essentially as described (Vaughan, 1996). ScFv-displaying phage from the round 3 of the selection output were screened for their binding to human and cynomolgus EGFR in ELISA. Top hits showing cross reactivity were selected and subjected to DNA sequencing. Unique genes were then converted to human immunoglobulin G1 (IgG1) antibodies and produced in mammalian cells essentially as described (Persic, 1997). The purified antibodies were then ranked based on their binding to the EGFR-expressing cell line, A431, by flow cytometry. Antibody Tdev-0004 exhibiting specific cell binding was selected for further characterization.

1.4 Optimization of Anti-EGFR Antibody Tdev-0004.

Variant RAA22 and QD6, were derived by optimizing the anti-EGFR Tdev-0004 mAb. The VL frameworks of Tdev-0004 had 100% match to the reference human germline sequence IGLV2-11*01/IGLJ2 (see https://www.ncbi.nlm.nih.gov/projects/igblast/Idlink.cgi?seqname=IGLV2-11*01&taxid=9606&dbname=IG_DB %2Fimgt.Homo_sapiens.V.f.orf.p), however, the VH frameworks had 79% homology with the closest human germline IGHV1-69*01/JH4 (see https://www.ncbi.nlm.nih.gov/projects/igblast/Idlink.cgi?seqname=IGHV1-69*01&taxid=9606&dbname=IG_DB %2Fimgt.Homo_sapiens.V.f.orf.p). To minimize potential immunogenicity, the VH region was initially fully germlined by mutating all 13 non-germline framework residues. Upon germlining, the binding of the fully germlined variant to cynomolgus EGFR was significantly impaired. To restore the binding to cynomolgus EGFR, four non-germline residues; K68, 173, R76 and T78 were selectively back mutated. Amino acid residues are numbered by Kabat numbering system (Kabat and Wu 1991). The resulting, partially germlined variant, named H4, was used as a template sequence for the affinity optimization. Variant H4 was affinity optimized by parsimonious mutagenesis of all six CDRs using a QuikChange Lightning Multi Site-Directed Mutagenesis Kit (Agilent), according to the manufacturer's instructions. Single amino acid mutagenized VH and VL libraries were expressed in bacteria as Fab fragments and screened for improved binding to human and cynomolgus EGFR in ELISA. Variants exhibiting improved binding compared to parent H4 were subjected to DNA sequencing and unique genes were converted to human IgG1. Variant RAA22 was identified with a single mutation in CDRH3. To further improve the affinity, individual positive mutations were combined to create a combinatorial library that was screened for variants with enhanced binding to human and cynomolgus EGFR. Variant QD6 was identified with four combined mutations in CDRL2, CDRL3 and CDRH3.

1.5 Generation of Monovalent Bispecific Anti-EGFR/cMET DuetMab Antibodies.

Figure 1A:
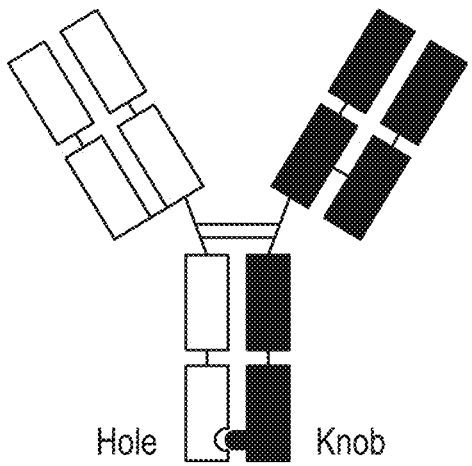
FIG. 1A. Graphical depiction of RAA22/B09-57. Shown are the Fabs of anti-EGFR RAA22, Fab of anti-cMET B09-57 and Hole and Knob heavy chains. The structural rendering is a composite of individual domain structures.
Figure 1B:
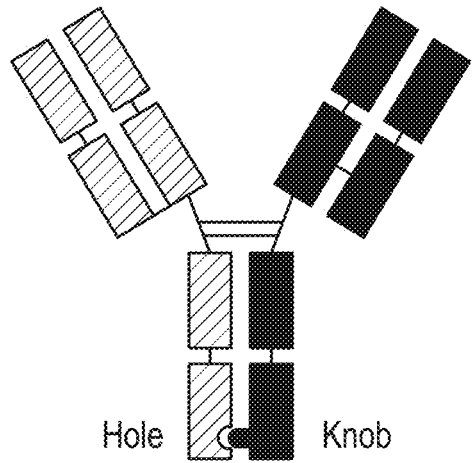
FIG. 1B. Graphical depiction of QD06/B09-57. Shown are the Fabs of anti-EGFR QD06, Fab of anti-cMET B09-57 and Hole and Knob heavy chains. The structural rendering is a composite of individual domain structures.

The variable domains of the anti-cMET mAb B09-57 and anti-EGFR mAbs RAA22 and QD6 were utilized for the construction of monovalent bispecific anti-EGFR/cMET antibodies on the backbone of the DuetMab platform (Mazor, 2015). Specifically, the VH gene of the anti-cMET B09-57 was inserted into a human gamma-1 constant heavy chain carrying the "Knob" mutation (T366W) and the alternative interchain cysteine mutations (F126C and C219V). The VL gene of B09-57 was inserted in frame into a human Kappa constant domain carrying the corresponding alternative interchain cysteine mutations (S121C and C214V) designed to pair with the "Knob" heavy chain. Similarly, the VH genes of the anti-EGFR RAA22 and affinity optimized QD6 were inserted into a human gamma-1 constant heavy chain carrying the "Hole" mutations (T366S, L368A, and Y407V), while the VL genes of RAA22 and B09-57 were inserted in frame into a human Lambda constant domain designed to pair with the "Hole" heavy chain. In addition, two residues in the CH3 domains of "Knob" and "Hole"

heavy chains were mutated to cysteine (S354C in "Knob" and Y349C in "Hole") to form a stabilizing disulfide bridge. The Fc domain was further engineered to carry a Cysteine insertion after Serine 239 (C239i/"Maia") designed to enable site-specific conjugation of maleimide-bearing cytotoxic drugs (Dimasi, 2017) Amino acid residues are numbered by Kabat numbering system (Kabat and Wu 1991). The assembled monovalent bispecific anti-EGFR/cMET DuetMab antibodies were designated as RAA22/B09-57 and QD6/B09-57 (FIG. 1). DuetMab antibodies were produced from mammalian cells as previously described (Mazor, 2017).

The amino acid sequences of the heavy and light chains of the DuetMabs produced according to this example are provided in the following table:

|  | RAA22/B09-57 | QD6/B09-57 |
|---|---|---|
| EGFR heavy chain | 56 | 53 |
| c-Met heavy chain | 50 | 50 |
| EGFR light chain | 58 | 55 |
| c-Met light chain | 52 | 52 |

Example 2—Biochemical and Biophysical Properties

This example tests various biochemical and biophysical properties of the RAA22, QD6 and B09-57 monoclonal antibodies and RAA22/B09-57 and QD6/B09-57 bispecific antibodies molecules, including their binding affinity to EGFR and c-Met, respectively and their ability to bind both antigens simultaneously.

2.1 Binding Affinity of DuetMabs and Parental mAbs for EGFR and cMET.

The kinetic rate constants ($k_{on}$ and $k_{off}$), and equilibrium dissociation constants ($K_D$) of EGFR-cMET DuetMAbs for recombinant human, cynomolgus monkey, and murine EGFR and cMET antigens were determined at 25° C. by SPR using an antibody capture assay on a BIAcore T200 instrument (GE Healthcare, Pittsburgh, PA). Mouse anti-human IgG was immobilized on a CM4 sensor chip with a final surface density of ~2000 resonance units (RUs). A reference flow cell surface was also prepared on this sensor chip using identical immobilization protocol. Test and control article antibodies were prepared at 5-20 nM in instrument buffer (HBS-EP buffer; 0.01M HEPES, pH 7.4, 0.15M NaCl, 3 mM EDTA, and 0.005% P-20), along with 3-fold serial dilutions of purified EGFR (0.27-200 nM human, 0.4-900 nM cyno, and 4-1000 nM murine) or cMET proteins (0.27 to 66 nM human and 0.27-22 nM cyno) in instrument buffer. A sequential approach was utilized for kinetic measurements. Antibodies were first injected over the capture surface, at a flow rate of 10 μL/minute. Once the binding of the captured antibody stabilized, a single concentration of the analyte was injected over both capture and reference surfaces, at a flow rate of 75 μL/minute. The resulting binding response curves yielded the association phase data. Following the injection of analyte, the flow was then switched back to instrument buffer for 15 minutes to permit the collection of dissociation phase data, followed by a 1-minute pulse of 10 mM glycine, pH 1.5, to regenerate the antibody-captured surface on the chip. Binding responses against test and control article antibodies were recorded from duplicate injections of each concentration of analyte. In addition, several buffer injections were interspersed throughout the injection series. Select buffer injections were used along with the reference cell responses to correct the raw data sets for injection artifacts and/or nonspecific binding interactions, commonly referred to as "double referencing". Corrected binding data were globally fit to a 1:1 binding model (Biacore T200 Evaluation software 2.0, GE Healthcare, Pittsburgh, PA). The calculated kinetic parameters ($k_{on}$ and $k_{off}$) and $K_D$ determined as $k_{off}/k_{on}$ are shown in Table 1.

TABLE 1

Kinetics of DuetMabs and parental IgGs to EGFR and cMET Antigens

| Antibody | Antigen | $K_{on}$ ($M^{-1}s^{-1}$) | $K_{off}$ ($s^{-1}$) | $K_D$ (nM) |
|---|---|---|---|---|
| RAA22 IgG | Human EGFR | $4.41 \times 10^4$ | $2.06 \times 10^{-3}$ | 46.6 |
|  | Cynomolgus monkey EGFR | $3.54 \times 10^4$ | $6.01 \times 10^{-3}$ | 169.8 |
|  | Mouse EGFR | $4.03 \times 10^4$ | $1.90 \times 10^{-2}$ | 488.0 |
|  | Human cMET | No binding detected at 200 nM | | |
|  | Cynomolgus monkey cMET |  |  |  |
|  | Mouse cMET |  |  |  |
| QD6 IgG | Human EGFR | $1.48 \times 10^5$ | $2.92 \times 10^{-4}$ | 2.0 |
|  | Cynomolgus monkey EGFR | $1.14 \times 10^5$ | $2.88 \times 10^{-4}$ | 2.5 |
|  | Mouse EGFR | $1.67 \times 10^5$ | $7.35 \times 10^{-4}$ | 4.4 |
|  | Human cMET | ND |  |  |
|  | Cynomolgus monkey cMET |  |  |  |
|  | Mouse cMET |  |  |  |
| B09-57 IgG | Human EGFR | No binding detected at 200 nM | | |
|  | Cynomolgus monkey EGFR |  |  |  |
|  | Mouse EGFR |  |  |  |
|  | Human cMET | $5.63 \times 10^5$ | $8.82 \times 10^{-4}$ | 1.6 |
|  | Cynomolgus monkey cMET | $1.04 \times 10^6$ | $1.94 \times 10^{-3}$ | 1.9 |
|  | Mouse cMET | No binding detected at 200 nM | | |
| RAA22/B09-57 DuetMab | Human EGFR | $4.47 \times 10^4$ | $2.01 \times 10^{-3}$ | 45.0 |
|  | Cynomolgus monkey EGFR | $2.78 \times 10^4$ | $5.48 \times 10^{-3}$ | 197.0 |

TABLE 1-continued

Kinetics of DuetMabs and parental IgGs to EGFR and cMET Antigens

| Antibody | Antigen | $K_{on}$ (M$^{-1}$s$^{-1}$) | $K_{off}$ (s$^{-1}$) | $K_D$ (nM) |
|---|---|---|---|---|
| | Mouse EGFR | 3.54 × 10$^4$ | 2.06 × 10$^{-2}$ | 575.4 |
| | Human cMET | 4.43 × 10$^5$ | 9.86 × 10$^{-4}$ | 2.2 |
| | Cynomolgus monkey cMET | 9.74 × 10$^5$ | 2.12 × 10$^{-3}$ | 2.2 |
| | Mouse cMET | ND | | |
| QD6/B09-57 DuetMab | Human EGFR | 6.35 × 10$^4$ | 3.74 × 10$^{-4}$ | 5.9 |
| | Cynomolgus monkey EGFR | 2.10 × 10$^5$ | 5.85 × 10$^{-4}$ | 2.8 |
| | Mouse EGFR | 1.26 × 10$^5$ | 7.80 × 10$^{-4}$ | 6.2 |
| | Human cMET | 4.25 × 10$^5$ | 6.96 × 10$^{-4}$ | 1.6 |
| | Cynomolgus monkey cMET | 9.58 × 10$^5$ | 2.06 × 10$^{-3}$ | 2.2 |
| | Mouse cMET | ND | | |

$^a$ND: not determined.
Kinetic measurements to soluble monomeric forms of EGFR and cMET were performed using a BIACore instrument.
$K_D$ were calculated as the ratio of $k_{off}/k_{on}$ from a non-linear fit of the data.

As can be seen from the above data, bispecific antibody molecule QD6/B09-57 binds human c-Met with a high affinity (~2 nM kD) and human EGFR with a high affinity (~6 nM kD), whilst bispecific antibody molecule RAA22/B09-57 binds human c-Met with a similarly high affinity (~2 nM kD) but binds human EGFR with a reduced affinity (~45 nM kD) in comparison to QD6/B09-57.

2.2 Concurrent Binding of DuetMabs to EGFR and cMET.

Figure 2:
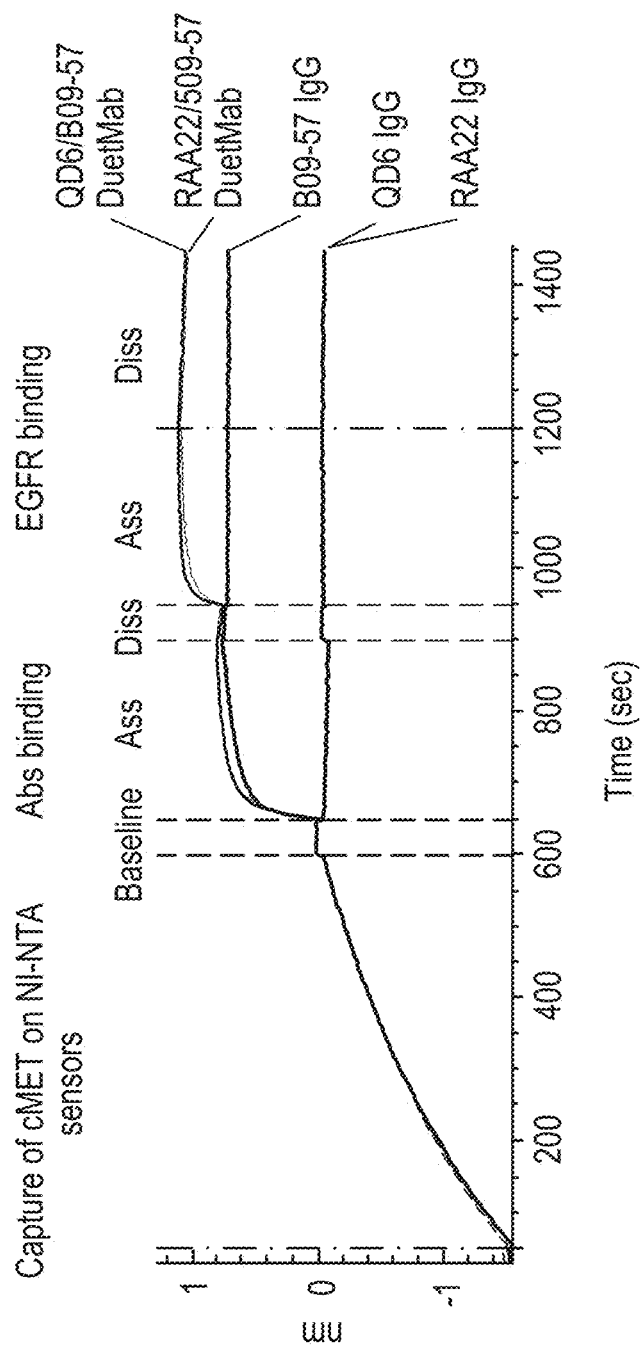
FIG. 2. Concurrent binding studies using antigen capture format were performed by Octet analysis. Sensors loaded with human cMET antigen were exposed to successive association and dissociation interactions first with antibodies then with human EGFR antigen. Ass=association; Diss=dissociation; NI-NTA=Nickel-nitrilotriacetic acid.

Concurrent binding studies to recombinant human EGFR and cMET proteins were measured by biolayer interferometry on an Octet384 instrument essentially as described (Mazor, 2015). Briefly, His-tagged cMET antigen at 5 μg/mL in assay buffer [PBS pH7.2, 3 mg/mL bovine serum albumin (BSA), 0.05% (v/v) Tween 20] was initially captured on NI-NTA biosensors. Following a washing step to remove any unbound protein, the respective loaded biosensors were subjected to successive association and dissociation interactions, first with 66 nM of the antibodies and then with the EGFR antigen at 500 nM. Association and dissociation curves were calculated from a non-linear fit of the data using the Octet384 software v.9.0. As shown in FIG. 2 the DuetMabs demonstrated simultaneous binding to both antigens while the parental anti-cMET IgG exhibited specific binding only to cMET and the two anti-EGFR IgGs exhibited no binding to the cMET loaded sensors.

2.3 EGFR and c-Met Specificity

Specificity for EGFR and cMET species paralogs and closely related family members was determined by ELISA. Briefly, antigen solutions were prepared in PBS at 1 μg/mL and 50 microliters was coated onto half area ELISA assay plates. Plates were washed and blocked with 1% BSA in PBS containing 0.005% Tween-20 (PBS-T) for one hour at room temperature. The wells were washed 4 times in PBS-T. As set out in FIG. 3, the primary antibodies used where: R374 (a non-binding IgG1 isotype control antibody), B09 (anti-cMET antibody), QD6 (anti-EGFR antibody), RAA22 (anti-EGFR antibody), QD6/B09 (bispecific EGFR/c-MET DuetMAb), RAA22/B09 (bispecific EGFR/c-MET DuetMAb), PaniX (anti-EGFR antibody), MetMab (anti-cMET antibody) and Mab11311 (anti-HER4 antibody). Wells were incubated with 50 microliters of the indicated primary antibodies diluted in PBS-T in a 1:3 dilution series, starting at 10 μg/mL and ending at 0.002 μg/mL, except for the HER4 binding mAb control, MAB1131, for which the series started at 1 μg/mL. The wells were washed 4 times in PBS-T, then 50 μl of goat anti-human Fab HRP-labeled secondary antibody, diluted 1:5000 in PBS-T, was added to each well and incubated for one hour at room temperature. 50 microliters of TMB substrate solution was added to all wells and incubated at room temperature for 5-30 min, until intense signal was observed in the positive control wells. 50 microliters of TMB stop solution was added to all wells and the absorbance was read at 450 nm on a SpectraMax M5 microplate reader. Data were analyzed in the SoftMax Pro 5 software and plotted using GraphPad Prism 7 graphing software.

Figure 3A:
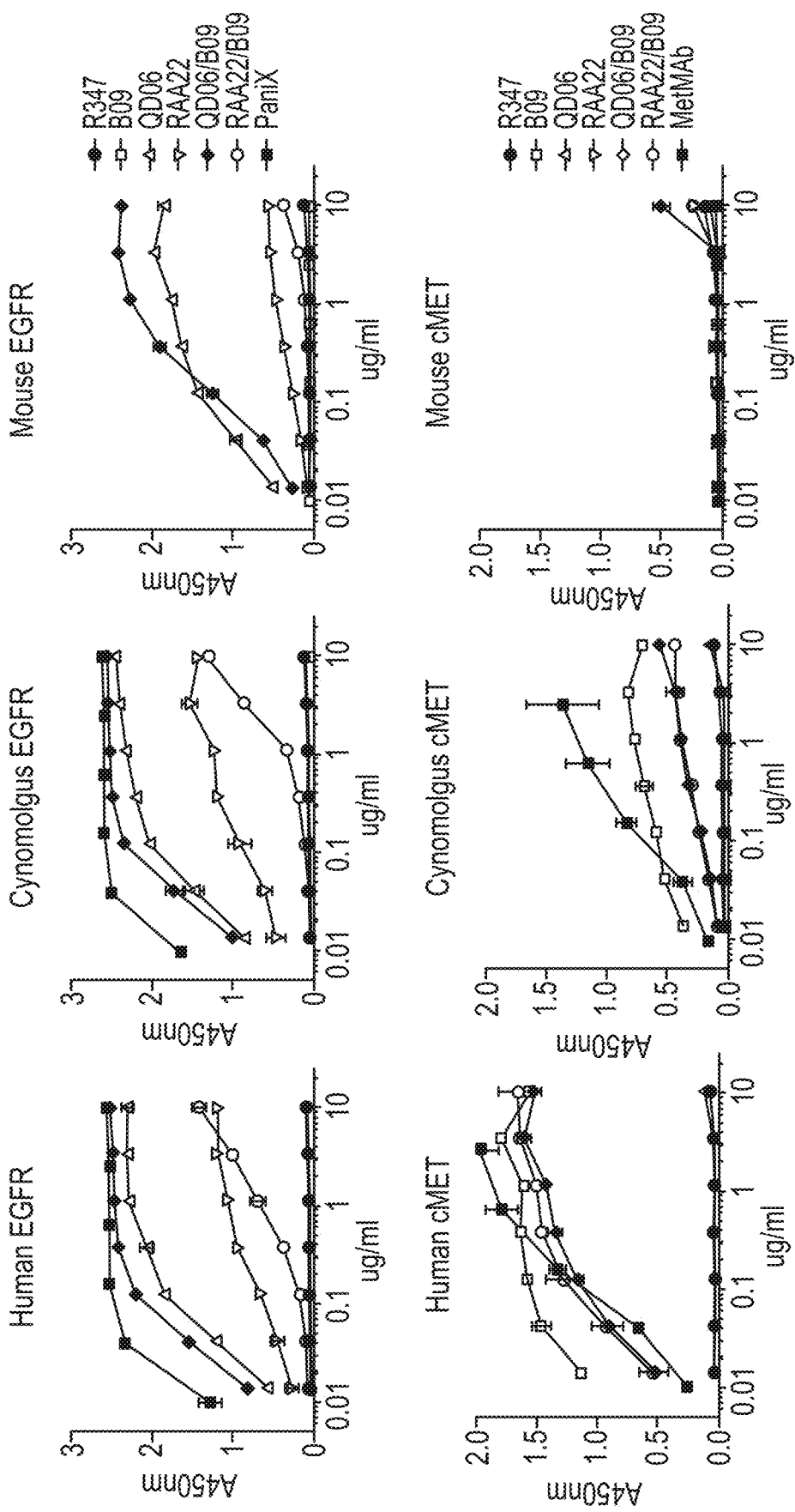
FIG. 3A. ELISA results showing EGFR and c-Met species cross reactivity. The high affinity monospecific EGFR IgG, QD6, as well as the monovalent bispecific EGFR/cMET DuetMAb, QD6/B09, bound to human, cynomolgus monkey, and mouse EGFR. The lowered affinity monospecific EGFR IgG, RAA22, bound more weakly to human, cynomolgus monkey, and mouse EGFR compared to QD6 and the corresponding monovalent bispecific EGFR/c-Met DuetMAb, RAA22/B09, showed still weaker binding to human and cynomolgus monkey EGFR relative to the bivalent parental IgG, RAA22, and nominal binding to mouse EGFR. The monospecific c-Met IgG, B09, as well as all of the bispecific variants, showed comparable binding to human and cynomolgus monkey c-Met but no detectable binding to mouse c-Met.

To determine the species cross reactivity, ELISA assays were carried out as described above. As shown in FIG. 3A, the high affinity EGFR IgG, QD6, as well as the monovalent bispecific EGFR/cMET DuetMAb, QD6/B09, bound to human, cynomolgus monkey, and mouse EGFR and gave robust signals in the ELISA assay. In contrast, the lowered affinity EGFR IgG, RAA22, bound more weakly to human, cynomolgus monkey, and mouse EGFR compared to QD6. Binding to mouse EGFR was weak, but detectable. The corresponding monovalent bispecific EGFR/cMET DuetMAb, RAA22/B09, showed still weaker binding to human and cynomolgus monkey EGFR relative to the bivalent parental IgG, RAA22, and nominal binding to mouse EGFR. The cMET IgG, B09, as well as all of the bispecific variants, showed comparable binding to human and cynomolgus monkey cMET. There was no detectable binding of any of the antibodies to mouse cMET. These results are consistent with the binding kinetics determined by surface plasmon resonance measurements on the BIAcore instrument (Table 1 above).

As shown in FIG. 3B none of the parental IgG or derivative bispecific antibodies showed appreciable binding to any of the EGFR HER family proteins, HER2, HER3, or HER4. Similarly, none of the antibodies showed significant binding to the cMET family members, Ron (CD136) or Semaphorin 3a.

These results demonstrate that the parental IgG's and the resulting bispecific antibodies bind specifically to their cognate targets, with no detectable binding to closely related family species.

Example 3—Monitoring Antibody Internalization and Trafficking to Acidified Compartments Using a pH Sensitive Dye The efficacy of antibody drug conjugates (ADC's) relies in part on the ability of the antibody to mediate efficient internalization and delivery to lysosomes, where the antibody is subsequently degraded. This lysosomal degradation thereby releases the cytotoxic warhead and allows it to exert its cellular effects on the target tumor cells. On the other hand, target expression in normal, non-tumor tissues can lead to toxicities that reduce the therapeutic window of the ADC. The design of the bispecific antibodies of the present disclosure are intended to minimize the impact of the ADC in normal tissues that exhibit little or no co-expression of the targets while maximizing the delivery of the ADC to tumor cells that co-express the two targets. To assess whether dual targeting using the EGFR affinity reduced bispecific antibody, RAA22/B09, provided a selectivity advantage relative to single target engagement, we carried out studies using pH sensitive dye labeled antibodies to compare internalization efficiency of the bispecific mAb versus the monovalent parental antibodies comprising the bispecific.

Visualization of antibody internalization and trafficking to acidified intracellular compartments, such as lysosomes and endosomes, was facilitated using antibodies labeled with pHAb pH sensitive dye (Promega). This dye exhibits very low fluorescence at pH>7, but becomes strongly fluorescent at acidic pH, reaching a maximum at approximately pH 5. Briefly, antibodies were labeled with pHAb amine reactive dye, according to the manufacturer's recommendations. The antibodies that were labeled were: R347 IgG1 isotype control, monovalent bispecific control antibodies anti-EGFR antibody RAA22/R347 and anti-cMET B09/R347, as well as EGFR/cMET monovalent bispecific antibody RAA22/B09. NCI-H1975 lung cancer cells, which co-express modest levels of EGFR (33,000 relative receptor density) and cMET (~50,000 relative receptor density), were plated into clear bottomed, black walled 96-well assay plates in 100 microliter volumes at a density of $2 \times 10^5$ cells/mL in RPMI growth medium supplemented with 10% fetal bovine serum. The plates were cultured in a humidified incubator overnight at 37° C. and 5% $CO_2$. The plates were then chilled on ice for 30 min prior to addition of pHAb labeled bispecific and monovalent control antibodies at various concentrations in pre-chilled growth medium. The cultures were chilled on ice for another 30 minutes, and then the fluorescence was read on an Operetta High Content Imaging system using the Cy3 filter and this initial reading was designated as time zero. The plates were moved back to the 37° C. incubator and additional readings were taken at 3, 6, 24, 30 and 48 hours.

A representative internalization experiment using pHAb labeled mAbs at 1.25 µg/mL to treat NCI H1975 cells is shown in FIG. 4. The non-binding IgG1 isotype control antibody, R347, showed no detectable fluorescence at any time point. The EGFR/cMET bispecific antibody, RAA22/B09, exhibited intracellular fluorescence by 3 hours and fluorescence intensity continued to increase out to 48 hours post treatment. The monovalent EGFR binding control antibody, RAA22/R347, showed very weak fluorescence starting at 24 hours, which did not increase dramatically by 48 hours. The monovalent monospecific cMET binding control antibody, B09/R347, showed modest fluorescence at 24 hours, increasing further by 48 hours. Nevertheless, the intensity of the fluorescent signal of the monospecific cMET antibody was modest compared to the bispecific RAA22/B09, suggesting that the bispecific antibody has greater internalization efficiency than the monospecific parental antibody in the dual target expressing cell line tested here. When the cells were treated with pHAb labeled mAbs at 0.625 µg/mL, the difference between bispecific antibody and monospecific controls was even more striking (FIG. 5). The monospecific antibodies showed very little fluorescence, even at 48 hours, while the bispecific RAA22/B09 antibody again showed intracellular fluorescence by 3 hours and fluorescence intensity continued to increase out to 48 hours post treatment. These results are consistent with the hypothesis that the dual targeting bispecific antibody mediates efficient internalization into cells co-expressing both EGFR and cMET. At the same time, the monospecific parental antibodies show a reduced uptake and fluorescence intensity compared to the bispecific antibody. A logical extension of these conclusions is to suggest that the bispecific antibody might behave more like the monospecific antibodies in tissues that express only one but not both targets, which is generally true for EGFR and cMET. Of particular note, the pHAb labeled lowered affinity EGFR control mAb, RAA22/R347, exhibited negligible uptake and fluorescence. This reduced binding to EGFR could minimize the impact of the ADC in normal tissues, such as the skin, which express significant levels of EGFR but little or no cMET.

Example 4—Monitoring Antibody Internalization Using Confocal Microscopy

Internalization kinetics of labeled DuetMabs: RAA22/B09 and QD6/B09 antibodies was assessed in vitro using live cell confocal fluorescence microscopy.

4.1 Materials and Methods

H1975 and HCC827 cells were from ATCC. RAA22/B09, QD6/B09, and single-arm derivatives were from MedImmune. QD6/B09 and single arm specific controls QD6/IgG and B09/IgG, with IgG Fab arms were derived from the non-specific human IgG1 NMGC were from MedImmune. RAA22/B09 and single-arm specific controls RAA22/IgG and B09/IgG derived from the non-specific human IgG1 R347, were from MedImmune. RPMI (11875-093), HEPES (15630106), sodium pyruvate (11360070), AlexaFluor® 647 (A-20186) Monoclonal Antibody Labeling Kits, Zeba™ Spin Desalting Columns (87767), and CellTracker™ Blue CMAC (C2110) were from Life Technologies (Carlsbad, CA). Accutase Cell Detachment Solution (423201) was from BioLegend (San Diego, CA). HyClone heat-inactivated fetal bovine serum (SH30071.03HI) was from GE Life Sciences (Marlborough, MA). PBS (21-040) was from Corning Incorporated (Corning, NY). FcR Blocking Reagent (130-059-901) was from Miltenyi Biotec Inc. (Auburn, CA). Polypropylene round-bottomed tubes (352063) were from BD Biosciences (San Jose, CA). CellCarrier 384-well microplates were from PerkinElmer Inc. (Cat #6007550, Waltham, MA).

Preparation of AlexaFluor Conjugates

Monoclonal antibodies were conjugated with AlexaFluor-647 dyes using the antibody labeling kits according to manufacturer instructions. In brief, 50-100 micrograms of an antibody in the sodium bicarbonate buffer, pH=8.3, were incubated with reactive dye reagents under gentle agitation at room temperature for 1 h. Unincorporated dyes were removed by size exclusion chromatography using Zeba™ Spin Desalting Columns with 40K MWCO equilibrated with 1×PBS according to manufacturer's instructions.

Culture and Preparation of Cells for Staining

Adherent H1975 or HCC827 cells were cultured in T-75 flasks in the CO2 incubators using media RPMI-1640 containing 10% fetal bovine serum (PBS) to 80-90% confluency after initial seeding. On the experiment day, adherent monolayers grown in T-75 flasks were dissociated into cell suspension using Accutase. Detached cells were washed twice with 1× PBS using centrifugation at 300×g for 5 min.

Cells were then resuspended into phenol-free RPMI at concentration of 2×106 cells/mL and used for staining.

Cell Staining for Imaging

Cell suspension at 2×106 cells/mL were incubated for 30 min with 1 μM CellTracker™ Blue CMAC prepared in phenol-free RPMI at 37° C. in the CO2 incubator. Unincorporated CellTracker™ Blue CMAC dye was removed by two washes with phenol-free RPMI using centrifugation at 300×g for 5 min at 4° C. Cells were then chilled on ice and blocked with the 10 ul FcR Blocking Reagent per 1×106 cells for 15 minutes. 2×10$^5$ cells were aliquoted into 5 mL round-bottomed tubes and incubated with fluorescent antibodies at a final concentration of 2.5 μg/mL. After removal of unbound fluorescent reagents by centrifugation at 4° C., cells were resuspended in phenol-free RPMI containing 100 mM HEPES, 1 mM sodium pyruvate, and 1% PBS. Cells were transferred into multiple wells of a 384-well imaging plate at a density of 50,00 cells per well, and briefly centrifuged at 2,200 rpm for 2 mM at 4° C. prior to image acquisition.

Acquisition of Cell Images Using Confocal Fluorescence Microscopy

Stained cells in imaging plates (384-well format) were either imaged on an Opera confocal fluorescence imaging system as previous described previously (Vainshtein, 2015) or transferred onto a Zeiss Axio Observer.Z1 inverted microscope with 40×/1.2NA LCIPlan Apo objective (Carl Zeiss Microscopy, Thornwood, NY). For experiments using the Zeiss microscope, the imaging environment was kept at 37° C. at 5% CO2 and 70% humidity using an Incubator XLmulti S DARK (PeCon Gmbh, Erbach, Germany). Samples were illuminated by 405, 488, 561, and 63 nm solid-state lasers (Carl Zeiss Microscopy, Thornwood, NY). A series of images was acquired at indicated times using a Yokogawa CSU-X1 Spinning Disk Unit (Yokogawa Electric Corporation, Tokyo, Japan) with Evolve 512 EMCCD (Photometrics, Tucson, AZ). Prior to image acquisition, exposure parameters, such as laser power, exposure times, camera gain, etc., were determined using an aliquot of the stained cells. Images were processed using ZEN 2.3 (Carl Zeiss Microscopy, Thornwood, NY) and analyzed using Columbus software (PerkinElmer, Waltham, MA).

Algorithm for Image Analysis of Internalization

The algorithm used for quantification of antibody internalization was described previously (Vainsthein, 2015), with the following updates and modifications. The reference channel used for iterative image processing originated from the CellTracker™ Blue CMAC (CTB) staining of cells. Signal channel still derived from the antibody-AlexaFluor-647 channels of the imagers. Images were processed by the algorithm using algorithm-defined parameters, which were initially set as default values and then optimized for each cell type and experiment. CTB staining of the image was used to identify cells using thresholding to detect a region on the image having a higher intensity than its surrounding based excluding areas with fluorescence intensity signals below the threshold. The remaining identified cell objects were designated "Total Cell". Cells were further selected filtering on morphology properties area (objects between 120-600 μm2) and roundness (>0.5). "Membrane Region" and "Cytoplasm Region" in the accepted cells were then constructed around the object boundaries using algorithm-defined parameters. Fluorescence intensity in each region was used to monitor antibody-associated AlexaFluor-647 signals. The fluorescence intensities of each region were reported as the mean of the sum of all pixels in accepted cells.

Accumulation of antibody-associated fluorescence in the cytoplasm was used to quantify kinetics of antibody internalization. To ensure comparability of results due to variability in cell staining and fluorescence intensity, cytoplasmic signals were normalized by the total cell signal at each time point and designated as the Internalized Fraction using the equation: Internalized Fraction=Intensity (cytoplasm)/ (Intensity (cytoplasm)+Intensity (membrane)). Internalization rate constants kint were calculated from internalization time course by curve fitting of the data using the equation: $F_{cyt}(t)=(1-e^{-k_{int} t}) \cdot F_{max,cyt}$, where $F_{max,cyt}$ is the maximal ratio cytoplasmic intensity per cell to total intensity per cell. The curve fitting of the data was conducted using Graphpad Prism (GraphPad Software, La Jolla, CA). The half-life of internalization (T½) was calculated as the ratio of ln(2) and kint.

4.2 In Vitro Internalization of RAA22/B09 and QD6/B09

Figure 6A:
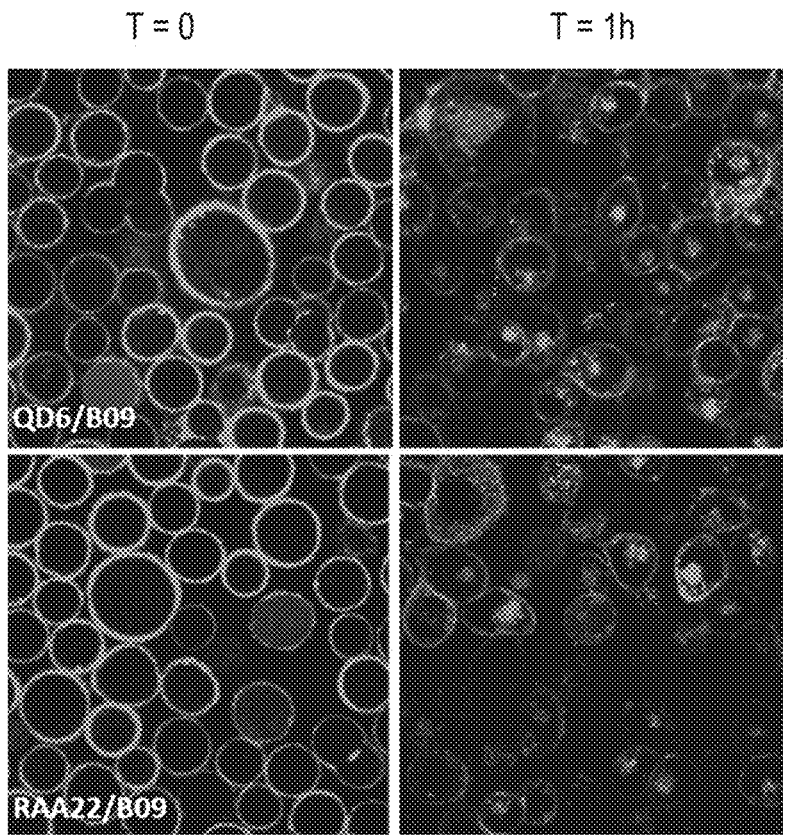
FIG. 6A. Kinetic of QD6/B09 and RAA22/B09 monoclonal antibody (mAb) internalization in H1975 cells. (a) Image overlays of cells labeled with CellTracker Blue CMAC for cytoplasm (blue) and with 2.5 ug/mL of QD6/B09-AlexaFluor647 (magenta, top panel) or 2.5 ug/mL of RAA22/B09AlexaFluor-647 (magenta, bottom panel) at the start of internalization and 1 hr after. Cells were labeled with CellTracker Blue CMAC, then bound with mAbs-AlexaFuor6457 at 2-8° C. and subjected to internalization condition: (37° C., 70% humidity and 5% CO2).
Figure 6B:
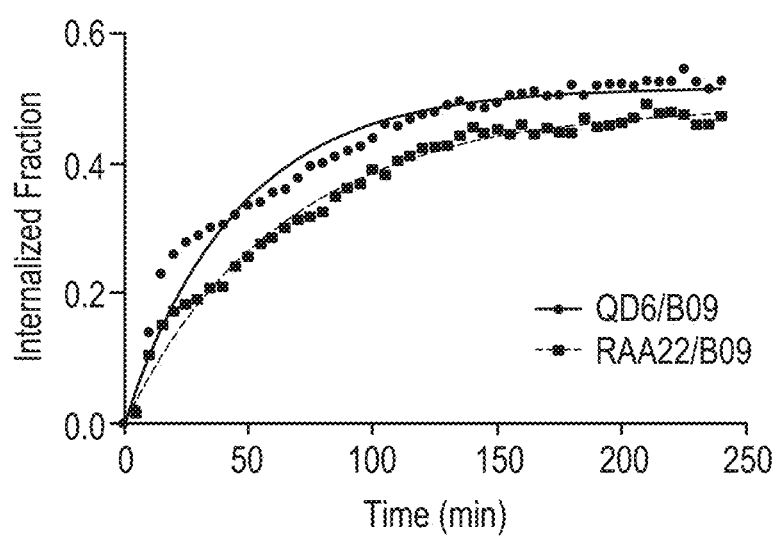
FIG. 6B. Kinetic of QD6/B09 and RAA22/B09 monoclonal antibody (mAb) internalization in H1975 cells. Time course of mAb-AlexaFluor647 internalization determined by quantitative analysis of kinetic images using the algorithm (Material and Methods). Kinetic images taken at 5-minute intervals were processed using the algorithm (Vainshtein, 2015) to determine antibody accumulation in cytoplasm. Antibody signals in cytoplasm normalized to antibody fluorescence in the cell (fraction in cytoplasm) for QD6/B09-AlexaFluor647 (red) versus RAA22/B09-AlexaFluor647 (blue) are shown for one of the three independent experiments. Internalization rate constant (kint) was calculated from the time course of internalization using the curve fitting with the equation $F_{cyt}(t)=(1-e^{-k_{int}-t}) F_{max,cyt}$ where $F_{max,cyt}$ is the maximal ratio cytoplasmic intensity per cell to total intensity per cell. $T_{1/2}$ calculated from $k_{int}$ was 37.5±10.6 min for QD6/B09 and 43.2±15.5 for RAA22/B09 (from n=3).

Internalization kinetics of AlexaFluor647 (AF647) primary-labeled DuetMabs: RAA22/B09 and QD6/B09 antibodies was assessed in vitro using the EGFR and c-MET expressing cell line, H1975. Each antibody was pre-bound to cells and antibody translocation from cell surface to cytoplasm was then monitored using live cell confocal fluorescence microscopy. FIG. 6 shows both antibodies localized primarily on the cell surface before (T=0) subjecting to internalization conditions and were translocated to the cytoplasm area (blue) after 1 hour (T=1 h). Kinetic images were taken every 5 min over the time course of internalization and were processed using quantitative algorithm (see above) to determine internalization kinetic constants and half-times. FIG. 6b shows very comparable internalization kinetic for QD6/B09 and RAA22/B09 with the half-times of 37.5±10.6 min and 43.2±15.5, respectively.

To evaluate the mode of antibody internalization and to investigate contribution of each arm to overall internalization of the DuetMabs, we evaluated internalization of single-arm specific control antibody molecules, QD6/IgG and B09/IgG, against duet QD6/B09, and RAA22/IgG and B09/IgG against duet RAA22/B09 in H1975 cells, which express both EGFR and c-MET. Since only one arm is specific for the target receptor, the control antibody can only internalize via one receptor eliminating dual receptor targeting and cross-linking as mode of internalization.

Figure 7A:
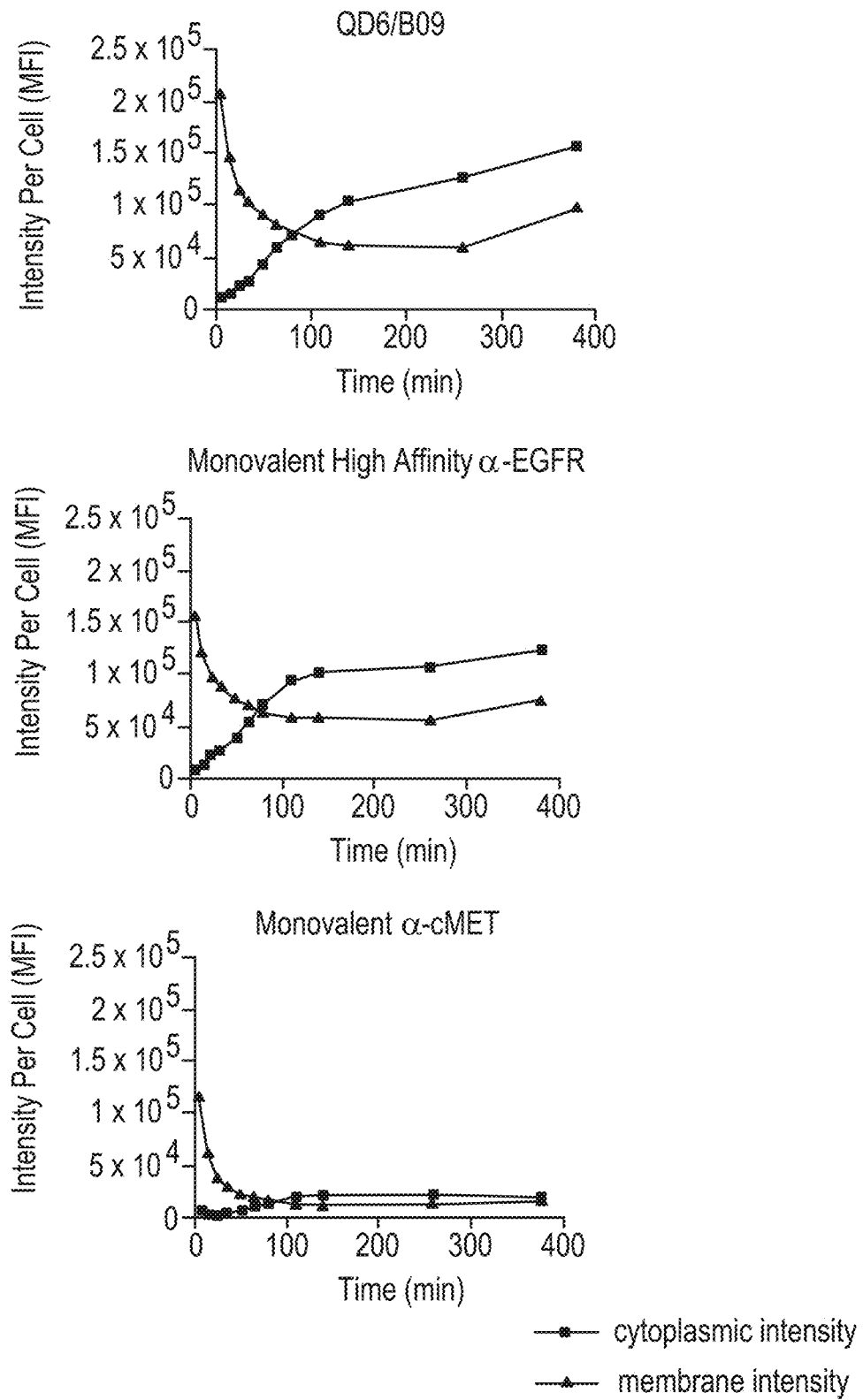
FIG. 7A. Internalization profiles of QD6/B09 DuetMab and its respective single-arm control antibodies. Internalization profiles are displayed via time course of the respective membrane and cytoplasm signals for each construct. QD6/B09 set was acquired using an Opera confocal fluorescence microscope.

Internalization profiles of QD6/B09 (FIG. 7A) and RAA22/B09 (FIG. 7B) rendered very similar patterns of congruent decrease of membrane mAb-F1647 signals with respective increase mAb-AF647 signals in the cytoplasm, a typical profile for internalization. However, their single-arm constructs showed very different internalization profiles. Single-arm QD6/IgG had a near-identical internalization time course as the QD6/B09 DuetMab (FIG. 7A, left and middle), indicating that internalization of QD6/B09 duet was mostly driven by EGFR-arm of the molecule with minimal contribution of B09-arm. Indeed, the B09/IgG construct showed very small level of internalization (FIG. 7B, right). The rapid and extensive decrease of the membrane signal corresponded to a very moderate increase of the cytoplasm signal, likely due to extensive dissociation of pre-bound B09/IgG from c-MET receptor on the cell surface. The dissociation of the antibody subsequently resulted in modest internalization of B09/IgG. These results revealed that internalization of QD6/B09 duet was mostly driven by the EGFR-arm of the molecule with minimal contribution of the B09-arm.

In contrast, RAA22/B09 DuetMab showed internalization profiles very different when compared to its single-arm control antibodies. As seen in FIG. 7B, cytoplasmic intensity values were 10.98- and 4.70-fold higher for RAA22/B09 DuetMab than RAA22-IgG and B09-IgG, respectively. While inefficient internalization of B09/IgG maybe attributed to its pronounced dissociation (discussed above), RAA22/IgG did undergo rapid internalization. However, due to the lower affinity of the EGFR-arm, the number of RAA22/IgG molecules were 10.98-fold less (based on fluorescent intensity) than for the RAA22-B09 DuetMab. The markedly increased amount of duet RAA22/B09 mAb entering the cytoplasm as opposed to the single-arm constructs demonstrated that both antibody arms must engage with target receptors to drive internalization. This finding shows that QD6/B09 and RAA22/B09 DuetMabs have different mechanisms of internalization, with QD6/B09 primarily driven by the EGFR-arm but RAA22/B09 requiring both EGFR and c-MET arms for engagement.

4.3 Internalization of RAA22/B09 in Cell Lines with Different Levels of Target Receptors Since binding of both EGFR and c-MET arms to target receptor promoted RAA22/B09 receptor internalization in H1975 cells, we examined if the increased number of EGFR and c-MET receptors would affect internalization properties. The respective receptor levels determined by Western Blot were 33,000 for EGFR and 50,000 for c-MET in H1975 cells and 790,000 for EGFR and 523,000 for c-MET in HCC827 cells. Internalization profiles of RAA22/B09 in H1975 (medium receptor) and HCC827 (high receptor) cells shows markedly increased internalization in HCC827 cells (FIG. 8).

As expected in correspondence to the 23.9-fold and 10.4-fold respective increases in overall levels of EGFR and c-MET RAA22/B09, binding to HCC827 cells were on average 8.9-fold higher than H1975 (T=0, $3.1 \times 10^7$ MFI versus $3.5 \times 10^6$ MFI). Internalization levels (judged by peak cytoplasmic intensity) was 21.7-fold higher in HCC827 cells, suggesting that significantly higher concentrations of antibody enter the cytoplasm in cells expressing high levels of target receptors. Importantly, in addition to the markedly different intensities, the internalization profiles (membrane and cytoplasm signals over time) were also significantly distinct between HCC827 and H1975 cells. In high expressing HCC827 cells, the decrease of RAA22/B09-AF647 membrane signal corresponded to the reciprocal increase of RAA22-B09 cytoplasm signal with total RAA22/B09 signal maintained over the time course, indicating strong dual arm antibody interaction with both receptors and subsequent internalization. In H1975 cells, there was a concurrent decrease of total and membrane intensity, indicating that portions of pre-bound antibody could have dissociated from cell surface and failed to internalize inside the cell. Similar profiles indicative of dissociation were observed for internalization of RAA22/IgG and B09/IgG in HCC827 cells where single arm engagement did not render effective binding and was prone to dissociation (FIGS. 9A and B). This data suggested that mixed mode of receptor interaction (single arm and dual arm engagement) is present when RAA22/B09 is subjected to internalization in H1975 cells. Together, these data suggest that target cell receptor expression levels are an important determinant of the extent and efficiency of RAA22/B09 internalization.

Example 5—Conjugation to Tubulysin AZ1508

5.1 Site Specific Conjugation

Conjugation of the tubulysin drug to the RAA22/B09 antibody molecule was carried out essentially as previously described in Thompson, 2016 and US20150291657A1.

5.2 Developability Assessment

Developability was assessed for both the unconjugated DuetMAb intermediate (cMet-EGFR DuetMAb, RAA22-B09) and for the antibody-drug conjugate (ADC) that consists of the DuetMAb conjugated to 2 molecules tubulysin AZ1508. The developability assessment for the tubulysin EGFR-cMET ADC comprised the evaluation of sequence liabilities, stability, biochemical/biophysical properties and manufacturability.

Sequence Liabilities

The amino acid sequence of RAA22-B09 was evaluated for the presence of known liabilities, including deamidation sites, oxidation sites and introduced glycosylation sites in the CDR region. The analysis did not reveal any sequence liabilities that were deemed high risk.

Stability

Stability studies were performed for the mAb intermediate RAA22-B09 at a concentration of 50 mg/ml in 20 mM Histidine, 240 mM sucrose, pH 6.0, and for the conjugated ADC at 5 mg/ml in 20 mM Histidine, 7% sucrose, pH 6.0. The material was filled in HDPE bottles.

Material was tested after undergoing 3× freeze-thaw cycles (from −80° C. to room temperature) and after incubation at 5° C., 25° C., and 40° C.

Samples were analyzed after 1 month; for materials stored at 5° C. and at 25° C. also after 2 months.

Visible particles were observed for the mAb intermediate. These particles were, however, deemed a low risk for development and can be easily removed by filtration prior to conjugation. The ADC remain practically free from visible particles.

No changes were observed over the course of the ADC stability studies at 5° C., 25° C., and 40° C. No increase in free drug content was observed.

Minimal changes in monomer purity were observed after storage at 5° C. and at 25° C. for both the mAb intermediate and the ADC.

The ADC retained cytotoxic activity after incubation at the indicated temperatures for 4 weeks. It was concluded that the ADC exhibits good thermal stability.

Biochemical/Biophysical Properties

The thermal melting temperature of mAb intermediate and ADC were determined by differential scanning calorimetry (DSC). It was found that conjugation does not decrease the melting temperature significantly. A homogenous population is observed post conjugation.

In conclusion, the cMET-EGFR mAb Intermediate (RAA22-B09-Maia) and the corresponding ADC with AZ1508 payload were deemed low risk with regard to developability.

5.3 Ex Vivo Stability Analysis of RAA22/B09-AZ1508 in Rat, Mouse, and Cynomolgus Monkey Serum RAA22/B09-AZ1508 was diluted in 0.2 μM filtered rat, mouse and cynomolgus serum to a final concentration of 200 μg/mL and incubated at 37 C for zero, one, three, and seven days. NHS-activated sepharose beads (GE Healthcare) were washed three times with 1×phosphate-buffered saline (PBS; pH 7.4), via centrifugation at 1×1000 g for one minute, to remove the isopropanol storage solution. One tenth the volume of sodium bicarbonate (1 M [v/v]) was added to the recombinant EGFR-ECD protein (2.12 mg/mL Lot #: C202020CT14C) and 6 mL of this mixture was incubated with 3 mL of washed NHS-activated sepharose beads. The bead mixture was incubated overnight at room temperature. The beads were washed three times with 1×PBS (pH 7.4) to remove unbound EGFR. The immobilization efficiency was determined to be 93% by comparing amount of bound versus starting amount of EGFR using an Agilent 1200 series HPLC and a Tosoh Bioscience TSKgel G3000 size-exclusion chromatography column following the manufacture's recommendation. RAA22/B09-AZ1508 was recovered from the serum by incubating 100 µL of the RAA22/B09-AZ1508-serum incubated mixture with 50 µL EGFR beads for 30 minutes at room temperature; followed by three sequential washes with 1×PBS buffer and elution with 100 µL antibody elution buffer (IgG elution buffer; Thermoscientific). The eluent was analyzed by rLCMS to calculate the amount of intact ADC remaining. Using reduced reverse phase mass spectrometry (rLCMS) on an Agilent 1290 series HPLC coupled to an Agilent 6520 Accurate-Mass TOF LC/MS with an electrospray ionization source, the ADC remaining was calculated using the peak height intensity obtained using Agilent the MassHunter data acquisition and chromatogram processing software. Approximately, 2 µg (35 µL) of reduced elutant was loaded onto a Poroshell 300SB-C3 column (2.1×75 mm, 255 Agilent) and eluted at a flow rate of 0.4 mL/min using a step gradient of 60% B after 6 minutes 256 (solvent A: 0.1% formic acid in water; solvent B: 0.1% formic acid in acetonitrile). The peak height intensity of the intact conjugated and unconjugated or modified ADC species was used to calculate the percent ADC remaining by dividing the intact conjugated peak height intensity by total ADC species peak height intensity. The results are shown in Table 2 below.

Antibody Labeling

PanIX, anti-EGFR-cMet and R347 purified antibodies were labeled using Alexa Fluor 647 Monoclonal Antibody Labeling Kit as per manufacturer instructions (Invitrogen Catalog no. A20186). Antibody concentration and fluorochrome to protein (F:P) ratio was calculated using a Nano-Drop ND-1000 Spectrophotomer.

Flow Cytometry

Cells were harvested and washed to a single cell suspension. Cell number and viability (>90%) was determined by Vi-Cell XLR Analyzer (Beckman Coulter). Cell concentration was adjusted to 5×106 cells/ml in ice cold FACS Buffer (Phosphate Buffered Saline pH 7.4, 5% FBS, 0.1% Sodium Azide) and plated into a 96 well u-bottom polystyrene plate, at 250,000 cells/well. Alexa 647 conjugated antibodies were serial diluted in cold FACS buffer at various concentrations (0.15-40 µg/mL) in duplicates to provide a binding curve. Cells and primary antibodies were incubated on wet ice for 20 minutes in dark. Cells were washed 2 times with cold FACS buffer and fixed in 200 µL ice cold 2% Paraformaldehyde (PFA). For data acquisition, the excitation and emission of Alexa 647 is 650/668 nm via the Red Laser 640 nm. Twenty-thousand events from each sample were collected by a Becton-Dickenson LSR II machine with FACSDiva™ software. Results were analyzed using FlowJo software.

TABLE 2

| % of conjugation after serum incubation | | | | % deacetylation after serum incubation | | | |
|---|---|---|---|---|---|---|---|
| RAA2/BO9-Maia-AZ1508 | Mouse | Rat | Cyno | RAA2/B09-Maia-AZ1508 | Mouse | Rat | Cyno |
| Time 0 | 93% | 93% | 92% | Time 0 | 3% | 4% | 3% |
| Day 1 | 91% | 91% | 91% | Day 1 | 7% | 12% | 8% |
| Day 3 | 90% | 86% | 86% | Day 3 | 15% | 40% | 36% |
| Day 7 | 84% | 83% | 84% | Day 7 | 40% | 41% | 37% |
| % of conjugation after serum incubation | | | | % deacetylation after serum incubation | | | |
| RAA2/BO9-Maia-AZ1508 | Mouse | Rat | Cyno | RAA2/B089-Maia-AZ1508 | Mouse | Rat | Cyno |
| Time 0 | 93% | 93% | 92% | Time 0 | 3% | 4% | 3% |
| Day 1 | 91% | 91% | 91% | Day 1 | 7% | 12% | 8% |
| Day 3 | 90% | 86% | 86% | Day 3 | 15% | 40% | 36% |
| Day 7 | 84% | 83% | 84% | Day 7 | 40% | 41% | 37% |

These data show the rate of deconjugation of the entire payload from the ADC and the metabolism of the ADC by liberation of the 0-acetyl group from the tubulysin warhead in mouse, rat, and cynomolgus monkey serum, ex vivo. The results demonstrate that there is less than or equal to 10% loss of the conjugated payload after one week at 37° C. when incubated with sera from any of the three species. The initial rate of de-O-acetylation of the tubulysin warhead from the ADC appears to differ slightly amongst the three species, but amount of de-O-acetylation at Day 7 is similar for all three species, at around 40%.

Example 6—ADC Cytotoxicity In Vitro

In this example the in vitro potency of EGFR/cMET bispecific ADC's was measured in a panel of cancer cell lines.

6.1 Quantitative FACS Characterisation of Cell Line Panel

FACS was carried out in order to quantify the relative EGFR and c-Met density in the cell lines tested.

Analysis of EGFR, EGFR-cMet; Quantum MESF (Molecules of Equivalent Soluble Fluorochrome)

The amount of EGFR, EGFR-cMet on the cells was assessed by employing Quantum Alexa Fluor 647 MESF beads (Catalog no. 647C, Bangs Laboratories) 10,000 events were acquired per sample (LSRII), utilizing the same flow cytometry settings as samples listed above. QuickCal program (www.bangslabs.com) was used to establish a standard curve relating channel value to fluorescence intensity in MESF units. Mean Fluorescence intensity (MFI) is directly proportional to the amount of fluorochrome present to calculate the number of molecules per cell. MESF calculated from the Quickcal program is divided by the antibody F:P ratio to give corrected ABC (Antibody Binding Capacity).

6.2 Methods to Determine ADC Cytotoxic Activity

The ADC Cytotoxic Activity was Tested in Multiple Cell Lines as Follows. Cells were Plated at a density of 10,000 cells per well of 96-well plates in a volume of 100 µL in their recommended culture media supplemented with 10% fetal bovine serum. A 3× concentration of each dose of antibody to be tested was prepared by serial dilution of the antibody stock in culture medium. Fifty microliters of each test article was added to cells in triplicate such that the final antibody concentration ranged from 60 nM to 0.0009 nM. The treated cells were cultured for 72 hours at 37 degrees C. in a humidified incubator. The metabolic activity was determined using CellTiter-Glo Luminescent Viability Assay from Promega according to manufacturer's instructions. Data were plotted as percent metabolic activity relative to untreated control. $IC_{50}$ values were determined using logistic non-linear regression analysis between the maximal viability (untreated cells) and the maximal response (peak inhibition) with GraphPad Prism software.

6.3 Results—In Vitro ADC Activity in Cell Line Panel

The in vitro potency of EGFR/cMET bispecific ADC's was measured in a panel of cancer cell lines using the CellTiter-Glo Luminescent Viability Assay. As shown in Table 3, both the higher affinity QD6/B09-AZ1508 and lowered affinity RAA22/B09-AZ1508 exhibited broad activity across cell lines with a range of target expression levels.

cific ADC function independently to deliver the ADC, blocking either target in this cell line would be expected to only modestly reduce the activity of the ADC, shifting the $IC_{50}$ by twofold or less, since the targets are present at similar levels. If, on the other hand, the ADC requires dual target engagement to effectively deliver the ADC into cells, blocking either target would be likely to have a greater impact on the activity of the bispecific ADC. In a related experiment, we compared the activity of the bispecific EGFR-cMET ADC to monovalent, monospecific control antibodies comprised of one binding arm to either EGFR or cMET and one non-binding isotype antibody control arm. Similarly, if each arm functions independently, the expected result would be that each monospecific control ADC would only be modestly less potent than the bispecific ADC, and the difference would be additive. Alternatively, if the two arms of the bispecific function synergistically, one would expect larger differences in activity of the bispecific ADC compared to the monospecific control antibodies.

7.1 Methods

The cytotoxic activity of ADC's were tested in the NCI-H1975 cell line as follows. Cells were plated at a density of

TABLE 3

In Vitro Activity of EGFR-cMET DuetMAb ADC's

| Cell Line | Relative EGFR density | Relative cMET density | High Affinity ADC QD6/B09-AZ1508 | | Lowered EGFR Affinity ADC RAA22/B09-AZ1508 | |
|---|---|---|---|---|---|---|
| | | | IC50 (pM) | Max % Inhibition | IC50 (pM) | Max % Inhibition |
| HCC 827 Parental | 1,513,899 | 236,933 | 96 | 79% | 132 | 55% |
| NCI H596 | 938,023 | 28,353 | 274 | 54% | 3,237 | 67% |
| HCC 827 GR Pool | 760,040 | 523,298 | 33 | 66% | 168 | 59% |
| A549 | 88,385 | 16,483 | 118 | 45% | 667 | 36% |
| NCI H1792 | 63,820 | 20,658 | 81 | 80% | 200 | 81% |
| NCI H1975 | 33,086 | 50, 339 | 178 | 65% | 255 | 65% |
| NCI H292 | 96,538 | 16,497 | 91 | 79% | 271 | 62% |
| A427 | 20,236 | 9,734 | 6,959 | 12% | 40,220 | 58% |
| NCI H358 | 15,065 | 16,429 | 168 | 29% | 3,017 | 30% |
| NCI H23 | 9,843 | 21,669 | >60,000 | ~5% | 8,096 | 46% |
| NCI H661 (Ag negative) | ND-9,906 | ND-8,114 | >60,000 | 0 | >66,667 | 10% |

Overall, the ADC with lowered affinity for EGFR showed comparable, though somewhat reduced, potency in a broad range of cell lines that co-express significant amounts of both EGFR and cMET. Generally, both ADC's showed reduced potency when one or the other target had a low relative receptor density at the cell surface of about 15,000 or less. This effect was more pronounced with the lowered affinity variant, which appeared more sensitive to lower levels of cMET.

Example 7—ADC Cytotoxicity In Vitro Proof of Concept (POC) Experiments

To further test the hypothesis that bispecific engagement of the lowered affinity EGFR-cMET antibody is required for optimal ADC delivery, we conducted in vitro experiments to determine the relative contribution of the individual antibody arms to the activity of the bispecific ADC. In the first experiment, we used an excess of unarmed parental antibodies to block either EGFR or cMET and then measured the activity of the bispecific EGFR-cMET ADC in an in vitro cytotoxicity assay. For this experiment, we used a cell line that expresses moderate levels of EGFR and cMET in roughly equal amounts. If the individual arms of the bispe- 10,000 cells per well of 96-well plates in a volume of 50 μL for the blocking experiment and 100 μL for the monovalent ADC experiment in their recommended culture media supplemented with 10% fetal bovine serum. For the unarmed mAb blocking experiments, 50 μL of a 300 μg/mL solution of either EGFR IgG (RAA22) or cMET IgG (B09) was added to the wells and pre-incubated for one hour at 37 degrees C. in a humidified incubator. A 3× concentration of each dose of antibody to be tested was prepared by 4× serial dilution of the antibody stock in culture medium. Fifty microliters of either media alone, isotype control IgG ADC (R347-AZ1508), or EGFR-cMET ADC (RAA22/B09-AZ1508) was added to cells in triplicate such that the final antibody concentration ranged from 67 nM down to 0.0009 nM. For the monovalent ADC experiment, 50 μL of 3× stocks of either isotype control ADC (R347-AZ1508), monovalent EGFR ADC (RAA22/R347-AZ1508), monovalent anti-cMET ADC (B09/R347-AZ1508), equimolar combinations of the monovalent ADC's, or EGFR-cMET ADC (RAA22/B09-AZ1508) was added in triplicate in a 4× dilution series starting at 60 nM and ending at 0.009 nM. The treated cells were cultured for 72 hours at 37 degrees C. in a humidified incubator. The metabolic activity was determined using CellTiter-Glo Luminescent Viability Assay from Promega according to manufacturer's instructions. Data were plotted as percent metabolic activity relative to untreated control. $IC_{50}$ values were determined using logistic non-linear regression analysis between the maximal viability (untreated cells) and the maximal response (peak inhibition) with GraphPad Prism software.

7.2 Results and Conclusions—In Vitro Proof of Concept for Dual Targeting (mAb Blocking Experiment and Monovalent ADC)

We conducted in vitro experiments to examine the relative contribution of the individual antibody arms to the cytotoxic activity of the bispecific ADC, as outlined above. As shown in the representative experiment in FIG. 10 pre-treatment of NCI H1975 cells with cMET IgG RAA22 resulted in a shift in $IC_{50}$ of the EGFR-cMET ADC (RAA22/B09-AZ1508) from approximately 60 pM to 3,480 pM, a difference of about 60 fold. Treatment with anti-cMET IgG B09 resulted in a shift in $IC_{50}$ to 680 pM, a difference of greater than 11 fold. Similarly, when NCI H1975 cells were treated with the monovalent monospecific EGFR ADC (RAA22/R347-AZ1508), the $IC_{50}$ was about 20,500 pM compared to 316 pM for the bispecific EGFR-cMET ADC, a difference of about 65 fold (FIG. 11). The $IC_{50}$ of the monovalent monospecific anti-cMET ADC (B09/R347-AZ1508) was 2,772 pM, a difference of about 13 fold compared to the bispecific antibody.

Collectively, these data suggest that efficient targeting of the EGFR-cMET ADC to tumor cells co-expressing both targets is largely driven by bispecific engagement of the ADC. Furthermore, these results show that the EGFR affinity reduced binding arm is insufficient to promote efficient ADC delivery in the absence of cMET binding, as demonstrated by the dramatic reduction of potency when the cMET arm is blocked by an unarmed antibody and by the weak cytotoxicity of the monovalent EGFR control ADC, RAA22/R347-AZ1508. Taken together, these results are consistent with the hypothesis that the reduced affinity of the EGFR binding arm of the bispecific ADC (RAA22/B09-AZ1508) will promote ADC delivery to EGFR and cMET co-expressing tumors, while exhibiting reduced cytotoxicity toward cells that primarily express only one of the targets. This effect is most prominent when only EGFR is available for engagement, which has implications for mitigating EGFR driven toxicities in normal organs, such as the skin, which expresses significant levels of EGFR but relatively little cMET.

Example 8—ADC In Vivo Pharmacology in Patient Derived Xenograft (PDX) Models

Patient derived xenograft (PDX) models of human cancer have become a well-established alternative to tumor cell line based tumor xenografts. PDX models are established from a patient's primary tumor tissue implanted directly into immunodeficient mice to yield in vivo propagated tumors in the mouse. The tumors thus derived are subsequently propagated in additional mice, without culturing in vitro, to establish a bank of low passage PDX tumor tissue which can be used to implant study mice. One key feature of PDX models is that they largely maintain the histological and genomic heterogeneity and preserve the gene expression profile of the corresponding original patient tumor. Compared to tumor cell line based xenograft models, which use clonal populations of tumor cells that have been adapted to growth in vitro, the characteristics of PDX models are intended to more accurately replicate the features of real human tumors, thus improving the predictive value of preclinical mouse models. Indeed, numerous studies have shown that the response and resistance profiles of PDX models to standard of care treatments closely correlate with clinical data in human subjects with a given tumor profile.

Despite the improvements that PDX models afford, there are limitations to standard in vivo pharmacology study designs, even when applied to PDX models. For each tumor model, a typical study tests a drug treatment at multiple dose levels, along with one or more positive or negative control compounds, with sufficient mice per treatment group to support intra-model statistics. The relatively large number of mice used for such a study design and the higher cost of PDX models can limit the number of tumor models that one can practically test for a given compound. An alternate/complementary approach to the traditional study design is the mouse PDX trial, a population based approach styled after human clinical trial design. In this approach, for each compound, a single mouse is typically treated at a single dose level established from prior dose range finding studies, with an optional treatment control group for each model. Due to the small number of mice required for each model, many PDX models can be tested, each representing a unique human tumor. Instead of relying on intra-model statistics, responses are evaluated across the entire population of tumor models tested. This approach can provide a more accurate estimate of response rate across a diverse range of target expression, molecular phenotypes, tumor subtypes, or other clinically relevant features of interest. Furthermore, the large number of unique models that one can test in a PDX trial can enable more meaningful exploratory genomics, transcriptomics, or expression profiling studies to begin the early search for correlates of response or resistance. For the exemplary study outlined here, we employed an "all-comers" approach, testing all the available NSCLC models at START Discovery, regardless of target expression level or molecular phenotype.

8.1 Methods

Mouse PDX trials were carried out at South Texas Accelerated Research Therapeutics (START, San Antonio, TX). START is accredited by AAALAC International (Association for the Assessment and Accreditation of Laboratory Animal Care International) and is compliant with the AstraZeneca Global Standard on Animal Care and Welfare. All models were developed at START. Patient-derived xenograft (START-PDX) models were established from viable human tumor tissue or fluid and have been serially passaged in animals a limited number of times to maintain tumor heterogeneity. Athymic Nude (Crl:NU(NCr)-Foxn1nu)/CB-17 Scid (CB17/Icr-Prkdcscid/IcrIcoCrl) mice were implanted unilaterally on the flank with tumor fragments harvested from host animals, each implanted from a specific passage lot. Pre-study tumor volumes were recorded beginning approximately one week prior to its estimated start date. When tumors reached the appropriate Tumor Volume Initiation (TVI) range (125-250 mm³), animals were randomized into treatment and control groups and intravenous (IV) dosing was initiated (Day 0); animals were followed individually throughout the study. Initial dosing began on Day 0; animals in all groups were dosed I.V. by weight (0.01 ml per gram; 10 ml/kg). Drug treated animals were dosed every 7 days for a total of 4 doses. Beginning on Day 0, tumor dimensions were measured by digital caliper and estimated tumor volumes were recorded for each treated and control animal; tumor volume was calculated using the formula: TV=width×length×0.52. Tumor growth observations continued for one week after the final dose. Each animal was sacrificed upon reaching the Tumor Volume (TV) endpoint (tumor volume≥1 cm$^3$) or the study time endpoint of 28 days, whichever came first. The observation period was extended for some PDX models with slow growing tumors. Tumor growth inhibition (% TGI) was defined as Percent tumor growth versus Day 0 between treatment (TX) and control (C) groups, according to the formula: % TGI=1−(TX$_{final}$−TX$_{initial}$)/(C$_{final}$−C$_{initial}$). Percent Tumor Regression was defined as the percentage tumor reduction of tumors in treated animals relative to the Day 0 tumor volume (day of initial dose), calculated at study endpoint according to the following formula: % Regression=(TX$_{final\ avg}$−TX$_{initial\ avg}$)/(TX$_{initial\ avg}$)×100.

8.2 Results and Conclusions

As shown in FIG. 12, both the high affinity EGFR-cMET ADC, QD6/B09-AZ1508, and the variant with lowered affinity for EGFR, RAA22/B09-AZ1508, induced tumor growth inhibition or regressions in numerous PDX models tested. Surprisingly, the lowered affinity ADC showed an overall trend of increased number and depth of responses observed, compared to the higher affinity ADC. This activity trend was slightly reversed for the PDX models that were least responsive to the lowered affinity ADC, which correlated somewhat to lower cMET expression. These observations raise the possibility that activity of the lowered affinity EGFR-cMET ADC is partially driven by cMET expression levels. The EGFR binding arm of both bispecific antibodies was derived from the same mouse EGFR cross reactive antibody (see Example 1). The intrinsic binding affinity of the QD6/B09 antibody toward mouse EGFR was approximately 6 nM, whereas the affinity of the RAA22/B09 bispecific antibody was approximately 575 nM. The unexpected improvement in the activity of the lowered EGFR affinity could be attributed to a reduced impact from the EGFR sink in normal tissues, such as the skin, resulting in higher overall circulating exposure of the ADC. Regardless, these data demonstrate that reducing the affinity toward EGFR of the EGFR-cMET bispecific antibody did not compromise the in vivo efficacy of the resulting ADC, but unexpectedly improved the activity compared to the higher affinity ADC.

8.3 PDX Study at Different Doses

A further experiment was carried out to test different doses of the ADCs in PDX models. This experiment was carried out as described in Example 8.1, except that individual mice reaching a tumor volume of ≥2 cm$^3$ were removed from the study and the final measurement included in the group mean until the mean reached volume endpoint or the study reached the time endpoint of 63 days. For the exemplified study, the high affinity EGFR-cMET ADC, QD6/B09-AZ1508, was tested at dose levels of 1 and 2 mg/kg and the variant with lowered affinity for EGFR, RAA22/B09-AZ1508, was tested at 1, 2, and 3 mg/kg.

Figure 13:
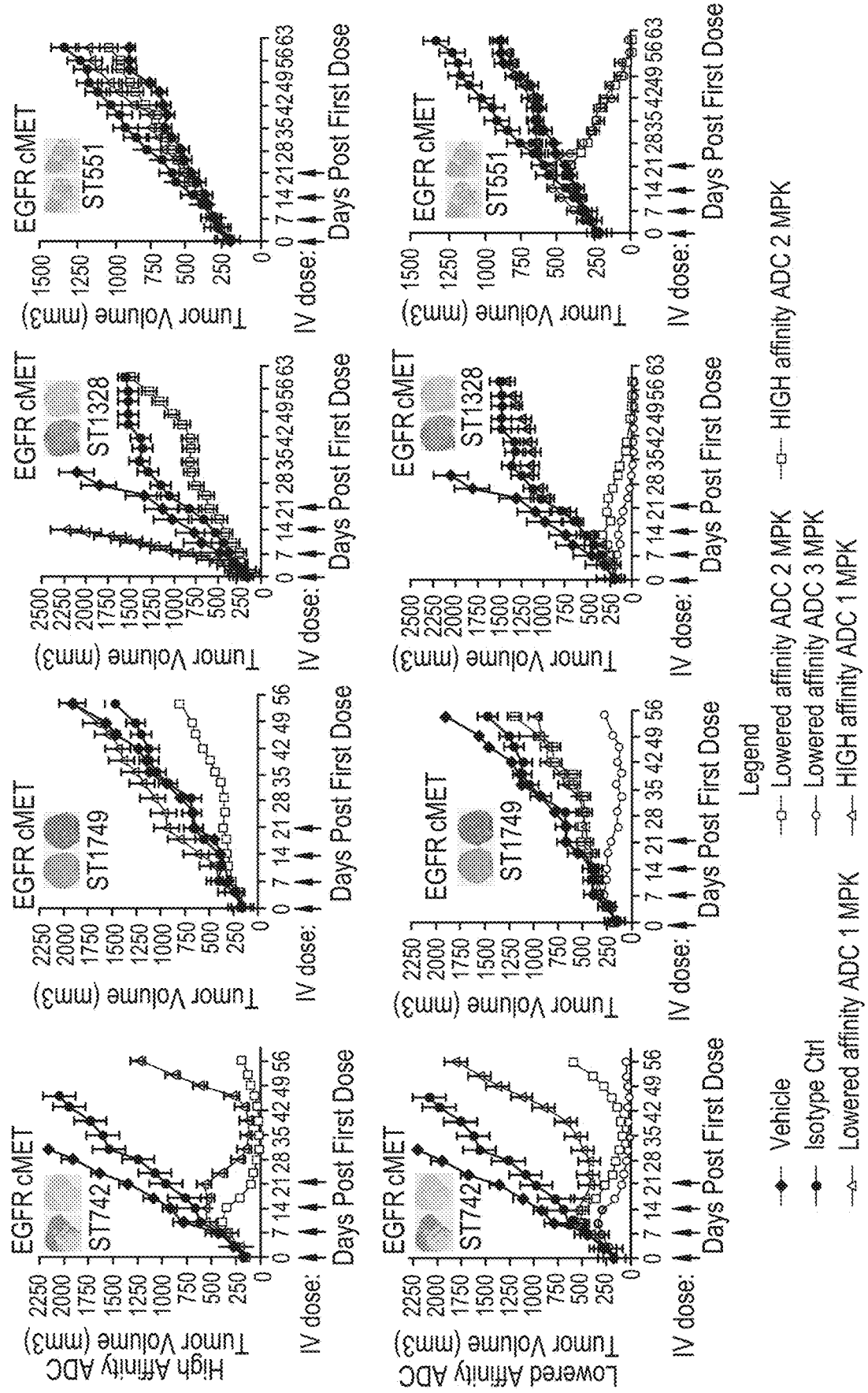

As demonstrated in FIG. 13, both the high affinity EGFR-cMET ADC, QD6/B09-AZ1508, and the variant with lowered affinity for EGFR, RAA22/B09-AZ1508, induced tumor growth inhibitory activity in PDX models at the tested doses. In accordance with the results described in Example 8.2 and shown in FIG. 12, the lowered affinity ADC was generally more efficacious than the high affinity ADC. In all four models tested, the lowered affinity ADC induced regressions at 2 or 3 mg/kg dose levels, demonstrating that the lowered affinity ADC is efficacious at modest doses. These data provide further evidence that reducing the affinity of the EGFR-cMET bispecific antibody toward EGFR did not reduce the in vivo efficacy of the resulting ADC, but rather improved the in vivo efficacy compared to the higher affinity ADC.

Example 9—ADC Efficacy in Orthotopic Pancreatic PDX Model

Subcutaneous in vivo tumor models are the mainstay for examining the efficacy of anti-cancer agents. However, this tumor implantation site is accompanied by a number of limitations that need to be considered when interpreting in vivo results. These deficiencies include, tumor vascularization and the lack of tissue-specific stroma in the growth and response of the tumor. To address these challenges, we compared the in vivo efficacy of both the High and Low affinity EGFR-cMET bispecific Antibody-Drug Conjugates in both subcutaneous and orthotopic models of a pancreatic PDX model MEDI-PANC-08. To track the growth of this tumor orthotopically, we developed a Luciferase expressing PDX variant (MEDI-PANC-08$^{LUC}$) whose growth could be tracked using Imaging.

9.1 Methods

All experiments were conducted in an AAALAC (Association for Assessment and Accreditation of Laboratory Animal Care) accredited facility, in accordance with MedImmune's IACUC (Institutional Animal Care and Use Committee) guidelines for humane treatment and care of laboratory animals. Animals were monitored daily for morbidity and mortality.

Subcutaneous PDX Model

The MEDI-PANC-08 pancreatic PDX model used in this study came from the Internal MedImmune PDX library. The PDX tumor was initially propagated in seed NSG (NOD.Cg-Prkdc$^{scid}$Il2rg$^{tm1Wjl}$/SzJ) mice, to generate sufficient tumor material to seed the efficacy study. Once tumors reached 800-1200 mm$^3$ the mice were humanely euthanized by $CO_2$ asphyxiation. Tumors were isolated under sterile conditions, cut into ~2 mm$^3$ pieces and implanted subcutaneously into the right flank of individual NSG mice using an 11-gauge trocar needle. Upon reaching ~150-250 mm3 in size, mice were randomized (based on tumor volume) into treatment groups and treated with the ADCs (Q1Wx4). Two EGFR-cMET bispecific ADCs were examined at 1, 2 and 3 mg/kg the QD6/B09 (high affinity) and RAA2/B09 (low affinity). An Isotype control ADC (R347-AZ1508) was also tested at 3 mg/kg. All Antibody-Drug Conjugates were diluted in buffer (25 mM Histidine, 7% Sucrose, 0.02% PS80, pH 6.0), immediately prior to use and administered i.v. via the tail vein. Tumor and body weight measurements were collected twice weekly and tumor volume calculated using the equation (L×W2)/2, where L and W refer to the length and width dimensions, respectively.

Orthotopic PDX Model

The luciferase expressing PDX model (MEDI-PANC-08$^{LUC}$) was grown subcutaneously in NSG seed mice and at a volume of 800-1200 mm$^3$ the tumors were harvested and cut into fragments of approximately 2 mm$^3$. The tumor fragments were subsequently sutured to the pancreas of NSG mice (Day Zero). Luciferase signal was determined weekly using the IVIS Spectrum In vivo Imaging system. Briefly, 10 minutes prior to imaging, 200 ul of luciferin dissolved in DPBS (15 mg/ml) was injected intra-peritoneally (i.p.). The mice were anesthetized under 3% isoflurane, laid on their right side and luminescence measured. Fourteen days after tumor implant, when luminescent signal was clearly detectable, the mice were randomized into their respective groups based on the luminescence. The mice were treated with Isotype control (R347-AZ1508, 3 mg/kg—Q1Wx4), Gemcitabine (75 mg/kg, Q2Dx5) and RAA2/B09 ADC (2 and 3 mg/kg—Q1Wx4). Luminescence was measured weekly. Study endpoints included body weight loss, deterioration of body condition and lethargy. Data were analyzed using the Living Image software (Perkin Elmer) and plotted as Average Radiance [p/s/cm2/sr] against time.

9.2 Results and Discussion

To assist in the selection of the appropriate EGFR affinity combination for the EGFR-CMET bispecific ADC, high and low affinity EGFR-cMET bispecific ADCs were compared in an in vivo efficacy study using the MEDI-PANC-08 pancreatic PDX model. As shown in Panels A and B of FIG. 14, a disparate difference was observed between the 2 molecules. The high affinity QD6/B09 ADC did not show efficacy at any of the 3 dose levels tested. Conversely, the low Affinity RAA2/B09 ADC produced complete tumor regression by day 65 followed by tumor re-growth at the 3 mg/kg dose level and tumor growth inhibition at 2 mg/kg.

Whilst subcutaneous tumor models have become the work-horse for in vivo efficacy studies, a major deficiency is that tumors are not grown at the site of origin and hence any drug response might not truly reflect of how patients will respond. To address this concern, an orthotopic model of pancreatic cancer was developed using the MEDI-PANC-08 tumor that had been transgenically modified to stably express luciferase. Following surgical implantation on the pancreas, tumors were allowed to establish and subsequently randomized based on luminescent signal. The mice were then treated with either the Low affinity RAA2/B09 EGFR-cMET ADC, isotype control or gemcitabine (a chemotherapy drug). Following treatment, the luminescence was measured weekly. As shown in Panel C of FIG. 14 the luminescence in the untreated and isotype control groups increases over time with animals removed from study due to poor body condition and large, palpable abdominal tumors. Gemcitabine showed an initial reduction in the luminescent signal reaching a nadir around day 21, after which the signal increased over time with the group removal from study at day 49. In the orthotopic model, both the 2 and 3 mg/kg dose levels of RAA2/B09 ADC caused a reduction in luminescent signal reaching close to background levels by day 60. In comparison to the subcutaneous study, the 2 mg/kg dose level demonstrated better activity producing tumor regressions. Necropsy of animals at the end of the study that showed tumors with luminescent signals close to background no longer showed visible tumor, hence supporting the correlation between luminescent signal and tumor volume.

In conclusion, the low Affinity EGFR-cMET RAA2/B09 ADC demonstrated improved efficacy compared to the high affinity QD6/B09 ADC in a subcutaneous PDX Pancreatic PDX model, with tumor regressions seen at 3 mg/kg. This efficacy was also observed in an orthotopic model using the same PDX tumor (MEDI-PANC-08) engineered to stably express luciferase. Using luminescence as a surrogate for tumor volume, RAA2/B09 ADC showed improved efficacy over the subcutaneous model producing tumor regressions at both 2 and 3 mg/kg.

Example 10—Safety and Pharmacokinetics

Pharmacokinetic (PK) analyses were carried out to compare the plasma PK parameters of the low and high affinity EGFR-cMET ADCs, including peak and total exposure, clearance, and half-life in mice and cynomolgus monkeys. A key aim was to determine whether reducing the affinity for EGFR would impact the circulating exposure of the EGFR-cMET bispecific ADC. PK samples were collected in mice and cynomolgus monkeys for both QD6/B09-57-AZ1508 and RAA/B09-57-AZ1508 across various dose levels. Non-compartmental analysis was performed to estimate PK parameters for QD6/B09-57-AZ1508 and RAA22/B09-57-AZ1508 based on total ADC concentrations across species and dose levels.

Overall, RAA22/B09-57-AZ1508 shows higher exposure and prolonged t½ compared to QD6/B09-57-AZ1508 in both mice and cynomolgus monkeys, suggesting improved PK in the lower affinity RAA22/B09-57-AZ1508.

10.1 Bioanalysis of Pre-Clinical PK Assay

The target compounds (QD6/B09-57-AZ1508 and RAA22/B09-57-AZ1508) concentration and the total antibody concentration was measured with one immuno capture LC-MS/MS assay. Briefly, a polyclonal anti-human antibody was conjugated to magnetic beads. Then 25 µL of plasma sample was diluted in PBS and incubated together with the magnetic beads. After capturing, the magnetic beads were washed multiple times before digested with trypsin under the presence of internal standards. The digestion was quenched with the addition of acid. The liquid content was then transferred to the injection plate.

The signature tryptic peptide on the human antibody Fc region and the cleaved warhead was separated using reversed phase chromatography (RPLC) followed with detection using multiple reaction monitoring (MRM). A signature peptide on the Fc region was used to calculate total Ab, while the digestion released warhead was used to calculate the ADCs. The internal standard used in this experiment are isotopically labeled peptide or protein (Si-luMAb, Sigma-Aldrich) or isotopically labeled warhead. The peak area ratio of the analyte against the internal standards was used to calculate against the standard curve.

The standard curves and QCs are prepared by spiking the target compounds at different levels into the same matrix as the samples. The quantification range covers 100 ng/mL-15,000 ng/mL, with the dilution QC covering up to 525,000 ng/mL. The standard curve was fitted with the simplest possible model. The accuracy and precision of the assay is within 20% for all levels except the lower limit of quantification (LLOQ), which is at 25%.

10.2 QD6/B09-57-AZ1508 PK in Mice

Mice studies included in the NCA analysis are summarized in Table 4.

TABLE 4

List of mice studies in RAA22/B09-57-AZ1508 and QD6/B09-57-AZ1508

| Study | Study Tile | Study design |
|---|---|---|
| 03-EGFR cMET-ADC-PK-15-003-A | Pharmacokinetics Study of CMET-EGFR-AZ1508 in Nude Mice (QD6/B09-57-AZ1508) | Single IV dose at 1, 3, 5, and 10 mg/kg; Plasma collections at 0.5, 4, 24, 48, 72, 144, & 240 hr; LC-MS/MS analysis of ADC and total Ab |
| RAA22/B09-AZ1508 mouse | Pharmacokinetics Study of cMET-EGFR DuetMAb | Single IV dose at 0.5, 1, 3, 5, and 10 mg/kg; Plasma collections at 0.5 hr, |

TABLE 4-continued

List of mice studies in RAA22/B09-57-AZ1508 and QD6/B09-57-AZ1508

| Study | Study Title | Study design |
|---|---|---|
| PK study - Oct. 2016 | RAA22/B09-AZ1508 in Nude Mice | 4 hr, 1 d, 2 d, 3 d, 6 d, 10 d, & 14 d; LC-MS/MS analysis of ADC and total Ab |

Mean PK concentration-time profiles in mice for RAA22/B09-57-AZ1508 and QD6/B09-57-AZ1508 are presented in FIG. 15.

Both RAA22/B09-57-AZ1508 and QD6/B09-57-AZ1508 exhibited linear PK in mice at the dose levels tested, with dose-proportional exposure ($C_{max}$ and AUC), comparable CL and $t_{1/2}$ observed at 0.5 mg/kg to 10 mg/kg for RAA22/B09-57-AZ1508 and at 1 mg/kg to 10 mg/kg for QD6/B09-57-AZ1508, respectively.

PK comparison between RAA22/B09-57-AZ1508 and QD6/B09-57-AZ1508 is assessed at 1, 3, 5, 10 mg/kg dose levels that were tested for both compounds and the mean PK parameters based on NCA is summarized in Table 5. The results demonstrated slower CL, higher exposure and prolonged $t_{1/2}$ in RAA22/B09-57-AZ1508, with mean AUC of RAA22/B09-57-AZ1508 showed 2- to 2.91-fold increase compared to QD6/B09-57-AZ1508; the mean $t_{1/2}$ ranged from 4.24 to 6.38 days for RAA22/B09-57-AZ1508 and from 2.57 to 3.33 days for QD6/B09-57-AZ1508, represented 1.27- to 2.32-fold increase in tin, for RAA22/B09-57-AZ1508.

TABLE 5

Mean NCA PK parameters by Dose levels between RAA22/B09-57-AZ1508 and QD6/B09-57-AZ1508 in Mice

| | 1 mg/kg | | 3 mg/kg | | 5 mg/kg | | 10 mg/kg | |
|---|---|---|---|---|---|---|---|---|
| Dose (mg/kg) molecule | RAA22/B09-57-AZ1508 | QD6/B09-57-AZ158 | RAA22/B09-57-AZ1508 | QD6/B09-57-AZ1508 | RAA22/B09-57-AZ1508 | QD6/B09-57-AZ1508 | RAA22/B09-57-AZ1508 | QD6/B09-57-AZ1508 |
| $C_{max}$ (mg/mL) | 12.8 | 11.3 | 51.1 | 31.0 | 90.7 | 44.8 | 198 | 134 |
| AUC (mg * day/mL) | 41.0 | 20.5 | 136 | 57.5 | 230 | 87.9 | 494 | 170 |
| t½ (day) | 5.97 | 2.57 | 4.24 | 3.33 | 6.38 | 3.28 | 5.31 | 2.95 |
| CL (mL/kg/day) | 20.8 | 45.7 | 20.0 | 46.9 | 18.5 | 50.8 | 17.3 | 53.8 |

10.3 QD6/B09-57-AZ1508 PK in Cynomolgus Monkeys

Cynomolgus monkey studies included in the NCA analysis is summarized in Table 6.

TABLE 6

List of cynomolgus monkey studies in RAA22/B09-57-AZ1508 and QD6/B09-57-AZ1508

| Study | Study Title | Study design |
|---|---|---|
| 20102256 | RAA22/B09-Maia-AZ1508: An Intravenous Repeat Dose Toxicity Study to Evaluate the Safety and Pharmacokinetics in Cynomolgus Monkeys | IV bolus injection Q3 Wk × 2 |
| 20067678 | An 8-Week Dose Range Finding Study of EGFR cMET by Intravenous Bolus Injection in Cynomolgus Monkeys | IV bolus injection Q3 Wk × 3 |
| 20067312 | A 8-Week Single Ascending Dose of EGFRcMet-ADC (EGFRcMet-1508) by Intravenous Route in Cynomolgus Monkeys | Single ascending IV dosing |

Mean PK concentration-time profiles in Cynomolgus monkeys for RAA22/B09-57-AZ1508 and QD6/B09-57-AZ1508 is presented in FIG. 16.

RAA22/B09-57-AZ1508 exhibited linear PK in cynomolgus monkeys at 2 mg/kg to 5 mg/kg, with dose-proportional exposure ($C_{max}$ and AUC), comparable CL and $t_{1/2}$ observed.

QD6/B09-57-AZ1508 exhibited non-linear PK in cynomolgus monkeys at 0.67 mg/kg to 3 mg/kg, with more than dose-proportional exposure (C. and AUC) shown, and faster CL and shorter $t_{1/2}$ observed at lower dose levels.

PK comparison between RAA22/B09-57-AZ1508 and QD6/B09-57-AZ1508 in cynomolgus monkeys is assessed at 2 and 3 mg/kg dose levels that were tested for both compounds and the mean PK parameters based on NCA is summarized in Table 7. The results demonstrated slower CL, higher exposure and prolonged $t_{1/2}$ in RAA22/B09-57-AZ1508, with mean AUC of RAA22/B09-57-AZ1508 showed 1.90- to 2.43-fold increase compared to QD6/B09-57-AZ1508; The mean $t_{1/2}$ were 4.30 to 5.90 days for RAA22/B09-57-AZ1508 and 0.969 to 1.07 days for QD6/B09-57-AZ1508, represented 4.44- to 5.51-fold increase in $t_{1/2}$ for RAA22/B09-57-AZ1508.

TABLE 7

Mean NCA PK parameters by Dose levels between RAA22/B09-57-AZ1508 and QD6/B09-57-AZ1508 in Monkeys

| | 2 mg/kg | | 3 mg/kg | |
|---|---|---|---|---|
| Dose (mg/kg) molecule | RAA22/B09-57-AZ1508 | QD6/B09-57-AZ1508* | RAA22/B09-57-AZ1508 | QD6/B09-57-AZ1508 |
| $C_{max}$ (mg/mL) | 59.1 | 47.5 | 86.6 | 73.3 |
| AUC (mg * day/mL) | 116 | 47.6 | 179 | 94.4 |
| $t^{1\!/\!2}$ (day) | 5.90 | 1.07 | 4.30 | 0.969 |
| CL (mL/kg/day) | 16.7 | 42.2 | 16.5 | 31.6 |

Taken together, these data demonstrate that the low affinity RAA22/B09-57-AZ1508 shows higher exposure and increased circulating half life compared to the high affinity QD6/B09-57-AZ1508 in both mice and cynomolgus monkeys. These data are consistent with the hypothesis that reducing the affinity for EGFR reduces the binding to EGFR present in normal tissue, thereby lessening the impact of the normal tissue sink and improving the plasma PK parameters.

Example 11—ADC with Topoisomerase I Inhibitor as Payload

An experiment was designed to test the efficacy and safety of the RAA22/B09-57 bispecific molecule conjugated to a different payload—a topoisomerase I inhibitor rather than the tubulysin used in the previous examples.

The DuetMab RAA22/B09 (with the "Maia" cysteine insertion after serine 239) bispecific antibody produced according to Example 1 was conjugated to the topoisomerase inhibitor SG3932 via "classical" conjugation to native cysteines in the bispecific antibody.

The efficacy of the EGFR/cMET topoisomerase I inhibitor ADC was investigated using a PDX trial. The PDX trial was carried out essentially as described above for Example 8 using a variety of different PDX models obtained from pancreatic, colon, NSCLC and squamous head and neck carcinoma (SQHN) tumors. Animals were injected with a single dose of the EGFR-cMET Maia Topo ADC at 10 mg/kg. The results of the PDX trial using the EGFR-cMET Maia Topo ADC are reported in FIG. 17.

As shown in FIG. 17, the EGFR-cMET Maia Topo ADC induced tumour growth inhibition or regression in numerous PDX models tested. Thus, these results demonstrate that RAA22/B09-57ADC containing the topoisomerase I inhibitor was efficacious in the PDX models representing multiple tumor types.

Example 12—Mutations to Improve PK of the ADC

The ADC with the topoisomerase I inhibitor produced and tested in Example 11 used the RAA22/B09 bispecific antibody containing the "Maia" cysteine insertion after serine 239. However, given that SG3932 conjugates to native cysteines, the Maia cysteine insertion is not necessary. We therefore sought to modify the RAA22/B09 Maia Topo ADC produced in Example 11 to remove this cysteine insertion.

It was also recognised that it may be possible to mitigate immune toxicities and improve pharmacokinetics if the effector functions of the Fc backbone were reduced or removed. We therefore also introduced the "triple mutant (TM)" of L234F/L235E/P331S (EU numbering) that has previously been shown to reduce Fc effector functions in antibody molecules (Organesyan, 2008; Hay, 2016).

The newly generated "EGFR-cMET TM" molecule, comprising variable regions from RAA22 and B09, with the 239i mutation removed and the TM introduced has the amino acid sequences set forth in the following table:

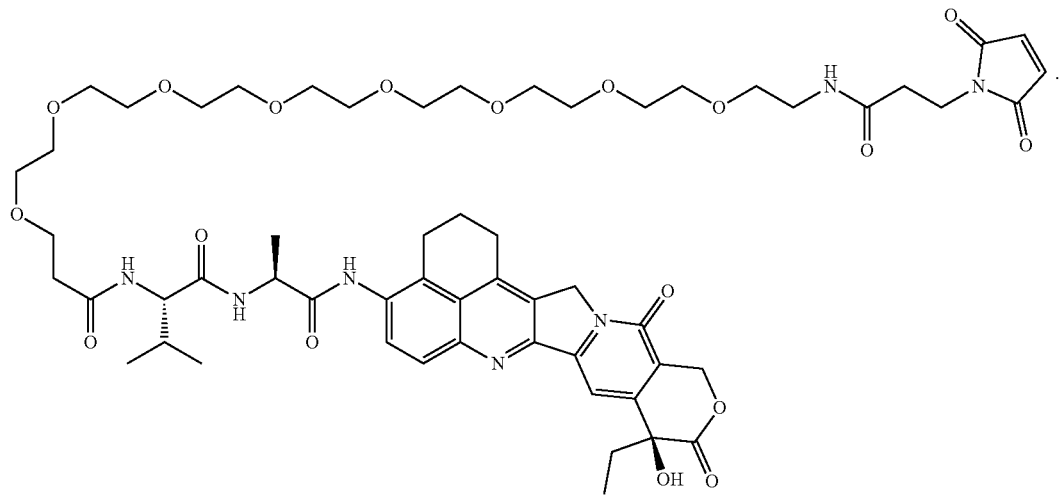

SG3932

| EGFR-cMET TM | |
|---|---|
| EGFR heavy chain | 59 |
| c-Met heavy chain | 60 |
| EGFR light chain | 61 |
| c-Met light chain | 62 |

For conjugation to SG3932, a 50 mM solution of Tris(2-carboxyethyl)phosphine (TCEP) in phosphate-buffered saline pH 7.4 (PBS) was added (12.5 molar equivalent/antibody) to a solution of EGFR-cMET TM bispecific antibody in reduction buffer containing PBS and 1 mM ethylenediaminetetraacetic acid (EDTA) and a final antibody concentration of ~3 mg/mL. The reduction mixture was allowed to incubate at 37° C. for 2 h in an orbital shaker with gentle (60 rpm) shaking. Reaction mixture was allowed to cool down to room temperature for 45 min SG3932 was then added as a DMSO solution (12.5 molar equivalent/antibody) for a 10% (v/v) final DMSO concentration. The solution was incubated for 2 hours at room temperature and then quenched by the addition of N-acetyl cysteine (5 micromoles/SG3932) and incubated at room temperature for 15 mM The reaction mixture filtered using 0.2 uM sterile filter and then stored at 2-8° C. overnight. Excess free drug was removed via Tangential Flow Filtration unit (TFF) using mPES, MidiKros® 30 kDa fiber filter with 375 cm² surface area, into buffer containing 30 mm Histidine, 30 mM Arginine, pH 6.8. Extent of free drug removal was monitored by UHPLC-RP using neat conjugate. After complete removal of free drug, ADC was buffer exchanged. ADC was filtered using 0.22 µm filter under sterile atmosphere and then polysorbate-80 was added to a final concentration of 0.02% (w/v).

UHPLC analysis on a Shimadzu Prominence system using a Thermo Scientific MAbPac 50 mm×2.1 mm column eluting with a gradient of water and acetonitrile on a reduced sample of ADC at 214 nm and 330 nm (SG3932 specific) revealed a drug-per-antibody ratio (DAR) of 6.0 molecules of SG3932 per antibody.

The efficacy of the EGFR-cMET TM ADC was investigated using a PDX trial. The PDX trial was carried out essentially as described above for Example 8 using a range of different PDX models obtained from pancreatic, colon, NSCLC and SQHN tumours. Animals were injected with a single dose of the EGFR-cMET TM ADC at 5 mg/kg. The results of the PDX trial using the EGFR-cMET TM ADC are reported in FIG. 18. Results from this experiment demonstrate that the EGFR-cMET TM ADC was able to induce tumour growth inhibition or regression in numerous PDX models tested The efficacy of the EGFR-cMET TM ADC ("TM ADC") was compared to the EGFR-cMET Maia Topo ADC ("Maia ADC") produced in Example 11 in PDX models SQHN-02 and PANC-08. The animals were doses with 2.5 mg/kg, 5 mg/kg or 10 mg/kg of each ADC and tumour growth monitored. Also included in this experiment was an untreated control ("untreated) and animal dosed with unconjugated EGFR-cMET TM (TM mAb). The results are shown in FIG. 19.

The results demonstrate that both EGFR-cMET TM ADC and EGFR-cMET Maia Topo ADC are similarly efficacious ("equipotent") at reducing tumour growth/inducing tumour regression at the range of doses tested. This suggests that the removal of the S239i mutation and abrogation of the Fc effector functions using the triple mutant does not negatively affect efficacy in these tumour models.

The EGFR-cMET TM ADC was also shown to be effective at reducing tumour growth in NSCLC tumours that express either wild type or mutant EGFR. Results demonstrate that the EGFR-cMET TM ADC is active in both wild type and mutant EGFR PDX models are shown in FIG. 20.

This is advantageous, as it indicates that the ADCs will be able to provide a benefit in multiple therapeutic settings and across a range of different EGFR genotypes.

Finally, pharmacokinetic (PK) studies were carried out in NOD-SCID mice to compare the EGFR-cMET TM ADC ("TM ADC") and the EGFR-cMET Maia Topo ADC ("Maia ADC") produced in Example 11. The Experiment was carried out largely as described in Example 10.

Representative results of these PK studies are provided in FIG. 21. As reported in this figure, the EGFR-cMET TM ADC exhibited a greater half-life ($t_{1/2}$=5.0 days) and reduced drug clearance (CL=14.8 ml/day/kg) when compared to the EGFR-cMET Maia Topo ADC ($t_{1/2}$=3.0 days; CL=39.7 ml/day/kg). Thus, the results indicate that the EGFR-cMET TM ADC described here shows improve PK compared to the EGFR-cMET Maia Topo ADC produced in Example 10. A similar improvement in PK was also observed when comparing the unconjugated EGFR-cMET TM antibody ("TM mAb") to the unconjugated EGFR-cMET Maia ("Maia ADC").

Example 13—EGFR and cMet Receptor Degradation after Treatment with EGFR-CMET TOP1i TM ADC Antibody mediated receptor degradation was performed by Western blot analysis as follows: HCC827 GR pool cells were plated in 12 well culture plates (Corning/Costar) at $6 \times 10^5$ cells/well in 2 ml of RPMI (Gibco) media containing 10% heat inactivated fetal bovine serum (HI FBS, Gibco). The cells were allowed to adhere and grow overnight at 37° C. with 5% $CO_2$ incubator. Next day morning, The growth media was carefully aspirated away, and the cells were treated with 1 mL of fresh growth media containing the test mAbs identified in Table 9, each at a final concentration of 10 micrograms per mL. The cells were incubated at 37° C. in a humidified growth chamber at 5% $CO_2$ for 24 hours. Then the media was aspirated away carefully and the cells were washed once with 2 mL of Dulbecco's Phosphate Buffered Saline without calcium and magnesium (DPBS). The cells were lysed by the addition of 150 microliters of M-per mammalian protein extraction reagent (Thermo Scientific) containing Complete Protease Inhibitor Cocktail (Roche) and PhosStop phosphatase inhibitor cocktail (Roche). To facilitate more complete lysis, the plates were transferred to −80° C. and subjected to one freeze-thaw cycle. The resulting lysates were transferred to microcentrifuge tubes and cellular debris was removed by centrifugation for 10 minutes at maximum speed (14,000 RPM) at 4° C. microcentrifuge, transferred supernatant to clean microcentrifuge tubes and stored at −80° C. prior to analysis. Protein concentration were measured by using Pierce BCA Protein Assay Kit (Thermo Scientific).

For Western blot analysis 4× LDS (Invitrogen) and 10× Sample Reducing Agent (Invitrogen) were used to prepare the samples to reached final protein concentration 10 microgram protein (1× LDS and 1× sample reducing agent) in 16 microliter volume. Samples were heated for 10 minutes at 95° C., then cooled to room temperature and centrifuged briefly. 10 microgram protein per sample were loaded, onto 4-12% Bis-Tris gels (NuPage, Invitrogen), in MOPS buffer and subjected to electrophoresis for one hour at 200 V constant voltage. The separated proteins were transferred onto the membrane [Polyvinylidene difluoride (PDVF) using an iBlot transfer apparatus (Invitrogen), according to the manufacturer's protocol. The blots were blocked with Pierce protein free T20 (PBS) blocking buffer (Thermo Scientific) for one hour at room temperature. Then Incubated with primary specific antibody for overnight at 4° C. (1:4, 500 dilutions of total cMET; 1:2,500 dilution of Total EGFR and 1:15,000 beta-actin] (Cell Signaling Technologies) in blocking buffer. The specifically bound antibodies were detected with horseradish peroxidase (HRP) labeled secondary antibodies (Jackson Immunoresearch) using SuperSignal West Dura ECL reagent (Pierce/Thermo Scientific). Images were captured with GE Image Quant LAS 4000.

TABLE 9

Test mAbs used in receptor degradation analysis

| Reagent | Description |
|---|---|
| R347-TM hIgG | Control IgG |
| RAA22/R347 EGFR mAb | EGFR dummy arm mAb comprising EGFR-binding VH and VL domains of SEQ ID Nos: 18 and 20, respectively, and R347 VH and VL domain sequences, as opposed to a cMet binding arm, and no TOP1i pay load |
| B09/R347 cMET mAb | cMet dummy arm mAb, comprising cMet-binding VH and VL domains of SEQ ID Nos: 38 and 40, respectively, and R347 VH and VL domain sequences as opposed to a EGFR binding arm and no TOP1i payload |
| EGFR/cMET bispecific mAb | comprising the EGFR-binding VH and VL domains of SEQ ID Nos: 18 and 20, respectively and cMet-binding VH and VL domains of SEQ ID Nos: 38 and 40, respectively, but no TOP1i pay load |
| EGFR-cMet TOP1i TM ADC | comprising a $1^{st}$ heavy chain of SEQ ID NO: 59, a $2^{nd}$ heavy chain of SEQ ID NO: 60, a $1^{st}$ light chain of SEQ ID NO: 61 and a $2^{nd}$ light chain of SEQ ID NO: 62, plus TOP1i payload SG3932 |
| Amivantamab | as described in e.g., claim 1 of US9593164B2 |

The results, shown in FIG. 22, indicate than the R347 dummy arm mAbs or their combination do not induce significant receptor downmodulation, while the bispecific does. This is consistent with the hypothesis that the mAb internalization is optimal when both the EGFR and cMet targets are engaged. Moreover, EGFR-cMET mAb appears to cause some degradation of cMet and a comparable amount of EGFR degradation to EGFR-cMet TOP1i TM ADC. In addition, EGFR-cMet TOP1i TM ADC appears to induce more cMet degradation than amivantamab (a recently approved EGFR-cMet bispecific that is reported to induce receptor degradation).

REFERENCES

A number of publications are cited above in order to more fully describe and disclose the disclosure and the state of the art to which the disclosure pertains. Full citations for these references are provided below. The entirety of each of these references is incorporated herein.

| | |
|---|---|
| Altschul, 1990 | Altschul, S.F. et al., Basic local alignment search tool., J Mol Biol. 1990, 215(3): 403-10. |
| Altschul, 1997 | Altschul, S.F. et al. Gapped BLAST and PSI-BLAST: a new generation of protein database search programs. Nucl. Acids Res., 1997, 25 3389-3402 |
| Andreev, 2017 | Andreev, J., et al., Bispecific Antibodies and Antibody-Drug Conjugates (ADCs) Bridging HER2 and Prolactin Receptor Improve Efficacy of HER2 ADCs. Molecular cancer therapeutics, 2017. |
| Angevin, 2017 | Angevin, E., et al., Phase 1 study of ABBV-399, a c-Met antibody-drug conjugate (ADC), as monotherapy and in combination with erlotinib in patients (pts) with non-small cell lung cancer (NSCLC). Journal of Clinical Oncology, 2017. 35(15_suppl): p. 2509-2509. |
| Ariyawutyakorn, 2016 | Ariyawutyakorn, W., S. Saichaemchan, and M. Varella-Garcia, Understanding and Targeting MET Signaling in Solid Tumors - Are We There Yet? Journal of Cancer, 2016. 7(6): p. 633-649. |
| Arteaga, 2014 | Arteaga, C.L. and J.A. Engelman, ERBB receptors: from oncogene discovery to basic science to mechanism-based cancer therapeutics. Cancer Cell, 2014. 25(3): p. 282-303. |
| Bachleitner-Hofmann, 2008 | Bachleitner-Hofmann, T., et al., HER kinase activation confers resistance to MET tyrosine kinase inhibition in MET oncogene-addicted gastric cancer cells. Mol Cancer Ther, 2008. 7: p. 3499-3508. |
| Bagshawe, 1991 | Bagshawe et al. Antibody-enzyme conjugates can generate cytotoxic drugs from inactive precursors at tumor sites. Antibody, Immunoconjugates and Radiopharmaceuticals, 1991, 4: 915-922 |
| Bardelli, 2013 | Bardelli, A., et al., Amplification of the MET Receptor Drives Resistance to Anti-EGFR Therapies in Colorectal Cancer. Cancer Discovery, 2013. 3(6): p. 658-673. |
| Bardia, 2017 | Bardia et al. Efficacy and Safety of Anti-Trop-2 Antibody Drug Conjugate Sacituzumab Govitecan (IMMU-132) in Heavily Pretreated Patients With Metastatic Triple-Negative Breast Cancer. J Clin Oncol. 2017, 35(19): 2141-2148 |
| Bean, 2007 | Bean, J., et al., MET amplification occurs with or without T790M mutations in EGFR mutant lung tumors with acquired resistance to gefitinib or erlotinib. Proceedings of the National Academy of Sciences of the United States of America, 2007. 104(52): p. 20932-20937. |
| Beck, 2017 | Beck, A., et al. Strategies and challenges for the next generation of antibody-drug conjugates., Nature Reviews Drug Discovery, 2017, 16, pp. 315-337 |

-continued

| | |
|---|---|
| Belalcazar, 2010 | Belalcazar, A., et al., Targeting the Met pathway in lung cancer. Expert review of anticancer therapy, 2012. 12(4): p. 519-528. |
| Benedettini, 2010 | Benedettini, E., et al., Met activation in non-small cell lung cancer is associated with de novo resistance to EGFR inhibitors and the development of brain metastasis. The American journal of pathology, 2010. 177(1): p. 415-423. |
| Bertotti, 2015 | Bertotti, A. and F. Sassi, Molecular Pathways: Sensitivity and Resistance to Anti-EGFR Antibodies. Clinical Cancer Research, 2015. |
| Birchmeier, 2003 | Birchmeier, C., et al., Met, metastasis, motility and more. Nat Rev Mol Cell Biol, 2003. 4: p. 915-925. |
| Boccaccio, 2014 | Boccaccio, C., P. Luraghi, and P.M. Comoglio, MET-Mediated Resistance to EGFR Inhibitors: An Old Liaison Rooted in Colorectal Cancer Stem Cells. 2014. p. 3647-3651. |
| Bouattour, 2018 | Bouattour, M., et al., Recent developments of c-Met as a therapeutic target in hepatocellular carcinoma. Hepatology (Baltimore, Md.), 2018. 67(3): p. 1132-1149. |
| Bouchard, 2014 | Bouchard, H., C. Viskov, and C. Garcia-Echeverria, Antibody-drug conjugates-a new wave of cancer drugs. Bioorg Med Chem Lett, 2014. 24(23): p. 5357-63. |
| Brinkmann, 2017 | Brinkmann, U. and R.E. Kontermann, The making of bispecific antibodies. MAbs, 2017. 9(2): p. 182-212. |
| Calvo, 2017 | Calvo, E., et al., Preliminary results from a phase 1 study of the antibody-drug conjugate ABBV-221 in patients with solid tumors likely to express EGFR. Journal of Clinical Oncology, 2017. 35(15_suppl): p. 2510-2510. |
| Cappuzzo, 2009 | Cappuzzo, F., et al., Increased MET gene copy number negatively affects survival of surgically resected non-small-cell lung cancer patients. J Clin Oncol, 2009. 27(10): p. 1667-74. |
| Cardillo, 2015 | Cardillo et al. Sacituzumab Govitecan (IMMU-132), an Anti-Trop-2/SN-38 Antibody-Drug Conjugate: Characterization and Efficacy in Pancreatic, Gastric, and Other Cancers. Bioconjug Chem., 2015, 26(5): 919-31 |
| Cecchi, 2012 | Cecchi, F., D.C. Rabe, and D.P. Bottaro, Targeting the HGF/Met signaling pathway in cancer therapy. Expert opinion on therapeutic targets, 2012. 16(6): p. 553-572. |
| Chan, 2017 | Chan, D.L.H., et al., Epidermal growth factor receptor (EGFR) inhibitors for metastatic colorectal cancer. Cochrane Database Syst Rev, 2017. 6: p. CD007047. |
| Chong, 2013 | Chong, C.R. and P.A. Janne, The quest to overcome resistance to EGFR-targeted therapies in cancer. Nature medicine, 2013. 19(11): p. 1389-1400. |
| Chothia, 1987 | Chothia, C. and Lesk, A.M., Canonical structures for the hypervariable regions of immunoglobulins. J. Mol. Biol. 1987, 196: 901-917 |
| Choueiri, 2017 | Choueiri, T.K., et al., Biomarker-Based Phase II Trial of Savolitinib in Patients With Advanced Papillary Renal Cell Cancer. J Clin Oncol, 2017. 35(26): p. 2993-3001. |
| Comer, 2018 | Comer, F., C. Gao, and S. Coats, Bispecific and Biparatopic Antibody Drug Conjugates, in Innovations for Next-Generation Antibody-Drug Conjugates, M. Damelin, Editor. 2018, Springer International Publishing: Cham. p. 267-280. |
| Corso, 2010 | Corso, S., et al., Activation of HER family members in gastric carcinoma cells mediates resistance to MET inhibition. Molecular Cancer, 2010. 9(1): p. 121. |
| Cunningham, 2004 | Cunningham, D., et al., Cetuximab monotherapy and cetuximab plus irinotecan in irinotecan-refractory metastatic colorectal cancer. N Engl J Med, 2004. 351(4): p. 337-45. |
| De Bacco, 2012 | De Bacco, F., et al., The MET Oncogene Is a Functional Marker of a Glioblastoma Stem Cell Subtype. Cancer research, 2012. 72(17): p. 4537-4550. |
| de Goeij, 2016 | de Goeij, B.E.C.G. and J.M. Lambert, New developments for antibody-drug conjugate-based therapeutic approaches. Antigen processing * Special section: New concepts in antibody therapeutics, 2016. 40: p. 14-23. |
| Dimasi, 2017 | Dimasi et al. Efficient Preparation of Site-Specific Antibody-Drug Conjugates Using Cysteine Insertion. Mol Pharmaceuticals, 2017, 14(5) 1501-1516 |
| Dokala, 2005 | Dokala, A. and S.S. Thakur, Extracellular region of epidermal growth factor receptor: a potential target for anti-EGFR drug discovery. Oncogene, 2016. 36: p. 2337. |
| Domling, 2005 | Domling et al. Myxobacterial epothilones and tubulysins as promising anticancer agents. Mol. Diversity, 2005 9: 141-147 |
| Donaghy, 2016 | Donaghy, H., Effects of antibody, drug and linker on the preclinical and clinical toxicides of antibody-drug conjugates. MAbs, 2016. 8(4): p. 659-71. |
| Dornan, 2009 | Dornan et al., Therapeutic potential of an anti-CD79b antibody-drug conjugate, anti-CD79b-vc-MMAE, for the treatment of non-Hodgkin lymphoma. Blood, 2009, 114(13): 2721-2729 |
| Dubowchik, 2002 | Dubowchik et al., Cathepsin B-labile dipeptide linkers for lysosomal release of doxorubicin from internalizing immunoconjugates: model studies of enzymatic drug release and antigen-specific in vitro anticancer activity, Bioconjugate Chemistry, 2002, 13,855-869 |
| Engelman, 2007 | Engelman, J.A., et al., MET amplification leads to gefitinib resistance in lung cancer by activating ERBB3 signaling. Science, 2007. 316: p. 1039-1043. |
| Fan, 2015 | Fan, G.W., et al., Bispecific antibodies and their applications. Journal of Hematology & Oncology, 2015. 8. |

-continued

| | |
|---|---|
| Garber, 2014 | Garber, K., MET inhibitors start on road to recovery. Nature reviews.Drug discovery, 2014.13(8): p. 563-565. |
| Gherardi, 2013 | Gherardi et al., Functional map and domain structure of MET, the product of the c-met protooncogene and receptor for hepatocyte growth factor/scatter factor. Proc Natl Acad Sci U.S.A, 2003, 100(21): 12039-12044 |
| Giordano, 1989 | Giordano, S., et al., Tyrosine kinase receptor indistinguishable from the c-met protein. Nature, 1989. 339: p. 155-156. |
| Gisterek, 2011 | Gisterek, I., et al., Prognostic role ofc-met expression in breast cancer patients. Rep Pract Oncol Radiother, 2011.16(5): p. 173-7. |
| Gou, 2016 | Gou, L.Y., et al., The coexistence of MET over-expression and an EGFR T790M mutation is related to acquired resistance to EGFR tyrosine kinase inhibitors in advanced non-small cell lung cancer. Oncotarget, 2016. |
| Guo, 2008 | Guo, A., et al., Signaling networks assembled by oncogenic EGFR and c-Met. Proceedings of the National Academy of Sciences, 2008.105(2): p. 692-697. |
| Guo, 2014 | Guo, B., et al., Prognostic value of MET gene copy number and protein expression in patients with surgically resected non-small cell lung cancer: a meta-analysis of published literatures. PLoS One, 2014. 9(6): p. e99399. |
| Hamblett, 2004 | Hamblett et al., Effects of drug loading on the antitumor activity of a monoclonal antibody drug conjugate. Clin. Cancer Res., 2004, 10: 7063-7070 |
| Haura, 2013 | Haura, E.B. and M.A. and Smith, Signaling Control by Epidermal Growth Factor Receptor and MET: Rationale for Cotargeting Strategies in Lung Cancer. Journal of Clinical Oncology, 2013. 31(32): p. 4148. |
| Hay, 2016 | Hay et al., Targeting CD73 in the tumor microenvironment with MEDI9447. Oncoimmunology, 2016 5(8): e1208875. |
| Hinrichs, 2015 | Hinrichs, M.J. and R. Dixit, Antibody Drug Conjugates: Nonclinical Safety Considerations. AAPS J, 2015. 17(5): p. 1055-64. |
| Huang, 2014 | Huang, L., et al., MET expression plays differing roles in non-small-cell lung cancer patients with or without EGFR mutation. Journal of thoracic oncology: official publication of the International Association for the Study of Lung Cancer, 2014. 9(5): p. 725-728. |
| Jimeno, 2009 | Jimeno, A., et al., KRAS mutations and sensitivity to epidermal growth factor receptor inhibitors in colorectal cancer: practical application of patient selection. J Clin Oncol, 2009. 27(7): p. 1130-6. |
| Jun, 2013 | Jun, H.J., R.T. Bronson, and A. Charest, Inhibition of EGFR induces a c-MET driven stem cell population in Glioblastoma. Stem cells (Dayton, Ohio), 2013. |
| Junutula, 2008 | Junutula, et al., Site-specific conjugation of a cytotoxic drug to an antibody improves the therapeutic index. Nature Biotech., 2008, 26(8): 925-932 |
| Junutula, 2016 | Junutula, J.R. and H.P. Gerber, Next-Generation Antibody-Drug Conjugates (ADCs) for Cancer Therapy. ACS Med Chem Lett, 2016. 7(11): p. 972-973. |
| Kabat, 1991 | Kabat, E.A. et al. Sequences of Proteins of Immunological Interest, 5th Ed. Public Health Service, National Institutes of Health, Bethesda, MD, 1991 |
| Karamouzis, 2009 | Karamouzis, M.V., P.A. Konstantinopoulos, and A.G. Papavassiliou, Targeting MET as a strategy to overcome crosstalk-related resistance to EGFR inhibitors. The Lancet Oncology, 2009. 10(7): p. 709-717. |
| Kim, 2017a | Kim, J.H., B.J. Kim, and H.S. Kim, Clinicopathological impacts of high c-Met expression in head and neck squamous cell carcinoma: a meta-analysis and review. Oncotarget, 2017. 8(68): p. 113120-113128. |
| Kim, 2017b | Kim, J.H., B.J. Kim, and H.S. Kim, Clinicopathological impacts of high c-Met expression in renal cell carcinoma: a meta-analysis and review. Oncotarget, 2017. 8(43): p. 75478-75487. |
| Kim, 2017c | Kim, J.H., et al., Prognostic value ofc-Met overexpression in hepatocellular carcinoma: a meta-analysis and review. Oncotarget, 2017. 8(52): p. 90351-90357. |
| Klein, 2012 | Klein et al. Progress in overcoming the chain association issue in bispecific heterodimeric IgG antibodies. MAbs, 2012, 4: 653-63 |
| Knickelbein, 2015 | Knickelbein, K. and L. Zhang, Mutant KRAS as a critical determinant of the therapeutic response of colorectal cancer. Genes Dis, 2015. 2(1): p. 4-12. |
| Kondo, 2013 | Kondo, S., et al., Clinical impact ofc-Met expression and its gene amplification in hepatocellular carcinoma. International journal of clinical oncology, 2013. 18(2): p. 207-213. |
| Kontermann, 2015 | Kontermann, R.E. and U. Brinkmann, Bispecific antibodies. Drug Discov Today, 2015. 20(7): p. 838-47. |
| Lacouture, 2006 | Lacouture, M.E., Mechanisms of cutaneous toxicides to EGFR inhibitors. Nature reviews.Cancer, 2006. 6(10): p. 803-812. |
| Lambert, 2017 | Lambert, J.M. and C.Q. Morris, Antibody-Drug Conjugates (ADCs) for Personalized Treatment of Solid Tumors: A Review. Adv Ther, 2017. 34(5): p. 1015-1035. |
| Ledermann, 1991 | Ledermann et al. A phase-I study of repeated therapy with radiolabelled antibody to carcinoembryonic antigen using intermittent or continuous administration of cyclosporin A to suppress the immune response. Int. J. Cancer, 1991, 47: 659-664 |
| LeFranc, 2015 | LeFranc, M.P. et al., IMGT ®, the international ImMunoGeneTics information system ®, 25years on., Nucleic Acids Res. 2015, 43(Database issue): D413-22. |
| Li, 2011 | Li, C., et al., c-Met Is a Marker of Pancreatic Cancer Stem Cells and Therapeutic Target. Gastroenterology, 2011.141(6): p. 2218-2227.e5. |
| Liska, 2011 | Liska, D., et al., HGF Rescues Colorectal Cancer Cells from EGFR Inhibition via MET Activation. Clinical Cancer Research, 2011. 17(3): p. 472-482. |

| | -continued |
|---|---|
| Liu, 2015 | Liu, Y., et al., Prognostic value of c-Met in colorectal cancer: a meta-analysis. World J Gastroenterol, 2015. 21(12): p. 3706-10. |
| Lü, 2017 | Lü, Y.F. and Z.M. Wang, Research progress in the technology evolution and action modes of bispecific antibodies. Chinese Journal of New Drugs, 2017. 26(20): p. 2431-2438. |
| Luraghi, 2014 | Luraghi, P., et al., MET Signaling in Colon Cancer Stem-like Cells Blunts the Therapeutic Response to EGFR Inhibitors. Cancer research, 2014. 74(6): p. 1857-1869. |
| Madoz-Gúrpide, 2016 | Madoz-Gúrpide, J., et al., Activation of MET pathway predicts poor outcome to cetuximab in patients with recurrent or metastatic head and neck cancer. 2016. p. 1-13. |
| Marano, 2015 | Marano, L., et al., c-Met targeting in advanced gastric cancer: An open challenge. Cancer letters, 2015. 365(1): p. 30-36. |
| Mazor, 2017 | Mazor, Y., et al., Enhanced tumor-targeting selectivity by modulating bispecific antibody binding affinity and format valence. Sci Rep, 2017. 7: p. 40098. |
| Mazor, 2015 | Mazor, Y., et al., Insights into the molecular basis of a bispecific antibody's target selectivity. MAbs, 2015. 7(3): p. 461-9. |
| McDermott, 2010 | McDermott, U., et al., Acquired Resistance of Non-Small Cell Lung Cancer Cells to MET Kinase Inhibition Is Mediated by a Switch to Epidermal Growth Factor Receptor Dependency. Cancer research, 2010. 70(4): p. 1625-1634. |
| Miyamoto, 2011 | Miyamoto, M., et al., Prognostic significance of overexpression of c-Met oncoprotein in cholangiocarcinoma. British journal of cancer, 2011. 105(1): p. 131-138. |
| Mo, 2017 | Mo, H.N. and P. Liu, Targeting MET in cancer therapy. Chronic Dis Transl Med, 2017. 3(3): p. 148-153. |
| Moores, 2016 | Moores, S.L., et al., A Novel Bispecific Antibody Targeting EGFR and cMet that is Effective Against EGFR Inhibitor- Resistant Lung Tumors. Cancer research, 2016. |
| Nasiri, 2018 | Nasiri, H., et al., Antibody-drug conjugates: promising and efficient tools for targeted cancer therapy. J Cell Physiol, 2018. |
| Neuberger, 1988 | Neuberger et al., 1988, 8th International Biotechnology Symposium Part 2, 792-799 |
| Nicholson, 2001 | Nicholson, R.I., J.M. Gee, and M.E. Harper, EGFR and cancer prognosis. Eur J Cancer, 2001. 37: p. 9-15. |
| Ogitani, 2016a | Ogitani et al. Wide application of a novel topoisomerase I inhibitor-based drug conjugation technology. Bioorg Med Chem Lett. 2016, 26(20): 5069-5072 |
| Ogitani, 2016b | Ogitani et al. DS-8201a, A Novel HER2-Targeting ADC with a Novel DNA Topoisomerase I Inhibitor, Demonstrates a Promising Antitumor Efficacy with Differentiation from T-DM1. Clin Cancer Res. 2016, 22(20): 5097-5108 |
| Organ, 2011 | Organ, S.L. and M.S. Tsao, An overview of the c-MET signaling pathway. Therapeutic advances in medical oncology, 2011. 3(1 Suppl): p. S7-S19. |
| Organesyan, 2008 | Organesyan et al. Structural characterization of a human Fc fragment engineered for lack of effector functions. Acta Crystallogr D Biol Crystallogr. 2008 ;64(Pt 6): 700-4. |
| Ou, 2016 | Ou, S.-H.I., N. Agarwal, and S.M. Ali, High MET amplification level as a resistance mechanism to osimertinib (AZD9291) in a patient that symptomatically responded to crizotinib treatment post-osimertinib progression. Lung Cancer, 2016. 98(Supplement C): p. 59-61. |
| Pearson, 1988 | Pearson and Lipman, Improved tools for biological sequence comparison. PNAS USA, 1988, 85: 2444-2448 |
| Persic, 1997 | Persic et al. An integrated vector system for the eukaryotic expression of antibodies or their fragments after selection from phage display libraries. Gene, 1997, 187: 9-18. |
| Peters, 2012 | Peters, S. and A.A. Adjei, MET: a promising anticancer therapeutic target. Nature reviews.Clinical oncology, 2012. 9(6): p. 314-326. |
| Philips, 2016 | Phillips, A.C., et al., ABT-414, an Antibody-Drug Conjugate Targeting a Tumor-Selective EGFR Epitope. Molecular Cancer Therapeutics, 2016. 15(4): p. 661-669. |
| Philips, 2018 | Phillips, A.C., et al., Characterization of ABBV-221, a Tumor-Selective EGFR Targeting Antibody Drug Conjugate. Mol Cancer Ther, 2018. |
| Prat, 1991 | Prat, M., et al., The receptor encoded by the human c-MET oncogene is expressed in hepatocytes, epithelial cells and solid tumors. International journal of cancer .Journal international du cancer, 1991. 49(3): p. 323-328. |
| Puri, 2008 | Puri, N. and R. Salgia, Synergism of EGFR and c-Metpathways, cross-talk and inhibition, in non-small cell lung cancer. J Carcinog, 2008. 7: p. 9. |
| Remon, 2018 | Remon, J., et al., Osimertinib and other third-generation EGFR TKI in EGFR-mutant NSCLC patients. Ann Oncol, 2018. 29(suppl_l): p. i20-i27. |
| Retter, 2005 | Retter, I., et al., "VBASE2, an integrative Vgene database." Nucl. Acids Res. 2005, 33 (suppl 1): D671-D674 |
| Rho, 2009 | Rho, J.K., et al., The role of MET activation in determining the sensitivity to epidermal growth factor receptor tyrosine kinase inhibitors. Molecular cancer research : MCR, 2009. 7(10): p. 1736-1743. |
| Ridgway, 1996 | Ridgway et al., 'Knobs-into-holes' engineering of antibody CH3 domains for heavy chain heterodimerization. Protein Eng., 1996, 9: 617-621 |

-continued

| | |
|---|---|
| Rocha-Lima, 2007 | Rocha-Lima, C.M., et al., EGFR targeting of solid tumors. Cancer control: journal of the Moffitt Cancer Center, 2007. 14(3): p. 295-304. |
| Sacco, 2015 | Sacco, J.J. and M.J. Clague, Dysregulation of the Met pathway in non-small cell lung cancer: implications for drug targeting and resistance. Transl Lung Cancer Res, 2015. 4(3): p. 242-52. |
| Saltz, 2004 | Saltz, L.B., et al., Phase II trial of cetuximab in patients with refractory colorectal cancer that expresses the epidermal growth factor receptor. J Clin Oncol, 2004. 22(7): p. 1201-8. |
| Sanderson, 2005 | Sanderson et al., In vivo drug-linker stability of an anti-CD30 dipeptide-linked auristatin immunoconjugate. Clin. Cancer Res. 2005, 11: 843-852 |
| Sau, 2017 | Sau, S., et al., Advances in antibody-drug conjugates: A new era of targeted cancer therapy. Drug Discov Today, 2017. 22(10): p. 1547-1556. |
| Sellmann, 2016 | Sellmann, C., et al., Balancing Selectivity and Efficacy of Bispecific EGFR x c-MET Antibodies and Antibody-Drug Conjugates. Journal of Biological Chemistry, 2016. |
| Seshacharyulu, 2012 | Seshacharyulu, P., et al., Targeting the EGFR signaling pathway in cancer therapy. Expert Opinion on Therapeutic Targets, 2012. 16(1): p. 15-31. |
| Sierra, 2011 | Sierra, J.R. and M.-S. Tsao, c-MET as a potential therapeutic target and biomarker in cancer. Therapeutic Advances in Medical Oncology, 2011. 3(1 suppl): p. S21-S35. |
| Smith, 1981 | Smith and Waterman, Identification of common molecular subsequences. J. Moi Biol. 1981, 147: 195-197 |
| Sohn, 2014 | Sohn, J., et al., cMET Activation and EGFR-Directed Therapy Resistance in Triple-Negative Breast Cancer. Journal of Cancer, 2014. 5(9): p. 745-753. |
| Suda, 2010 | Suda, K., et al., Reciprocal and complementary role of MET amplification and EGFR T790M mutation in acquired resistance to kinase inhibitors in lung cancer. Clinical cancer research : an official journal of the American Association for Cancer Research, 2010. 16(22): p. 5489-5498. |
| Thompson, 2016 | Thompson et al. Rational design, biophysical and biological characterization of site-specific antibody-tubulysin conjugates with improved stability, efficacy and pharmacokinetics. J Control Release. 2016, 236: 100-16. |
| Tolcher, 2014 | Tolcher, A., et al., 342 A phase $^{+1}\!/_{\!2}$ study evaluating the safety, pharmacokinetics and efficacy of ABT-414 in subjects with advanced solid tumors likely to over-express the epidermal growth factor receptor (EGFR). European Journal of Cancer, 2014. 50: p. ill. |
| Tolcher, 2014 | Tolcher, A.W., Antibody drug conjugates: lessons from 20 years of clinical experience. Annals of oncology : official journal of the European Society for Medical Oncology, 2016. |
| Troiani, 2016 | Troiani, T., et al., Therapeutic value of EGFR inhibition in CRC and NSCLC: 15 years of clinical evidence. ESMO open, 2016. 1(5): p. e000088. |
| Trusolino, 2010 | Trusolino, L., A. Bertotti, and P. Comoglio, MET signalling: principles and functions in development, organ regeneration and cancer. Nature reviews .Molecular cell biology, 2010.11(12): p. 834. |
| Vainshtein, 2015 | Vainshtein et al., Quantitative measurement of the target-mediated internalization kinetics of biopharmaceuticals, PharmRes., 2015. 32: 286-299. |
| Vaughan, 1996 | Vaughan, et al., Human antibodies with sub-nanomolar affinities isolated from a large non-immunizedphage display library, Nat Biotechnol,. 1996. 14: p. 309 |
| Vecchione, 2011 | Vecchione, L., et al., EGFR-targeted therapy. Special Issue - Gastroenterology, 2011. 317(19): p. 2765-2771. |
| Vsiansky, 2018 | Vsiansky, V., et al., Prognostic role ofc-Met in head and neck squamous cell cancer tissues: a meta-analysis. Scientific Reports, 2018. 8(1): p. 10370. |
| Wang, 2018 | Wang, X. et al., IgG Fc engineering to modulate antibody effector functions Protein Cell. 2018;9(1): 63-73 |
| Wang, 2017 | Wang, J., et al., ABBV-399, a c-Met Antibody-Drug Conjugate that Targets Both MET-Amplified and c-Met-Overexpressing Tumors, Irrespective of MET Pathway Dependence. Clinical cancer research : an official journal of the American Association for Cancer Research, 2017. 23(4): p. 992-1000. |
| Wu, 2017 | Wu, Y.-L., et al., Does c-Met remain a rational target for therapy in patients with EGFR TKI-resistant non-small cell lung cancer? Cancer Treatment Reviews, 2017. 61: p. 70-81. |
| Xu, 2016 | Xu, Y.P., et al., C-Met as a Molecular Marker for Esophageal Squamous Cell Carcinoma and Its Association with Clinical Outcome. Journal of Cancer, 2016. 7(5): p. 587-594. |
| Yan, 2015 | Yan, S., et al., Prognostic significance ofc-Met in breast cancer: a meta-analysis of 6010 cases. Diagn Pathol, 2015. 10: p. 62. |
| Zhang, 2016 | Zhang, Y., Z. Du, and M. Zhang, Biomarker development in MET-targeted therapy. Oncotarget, 2016. 7(24): p. 37370-37389. |
| Zhang, 2015 | Zhang, Y.W., Promise and challenges on the horizon of MET-targeted cancer therapeutics. World J Biol Chem, 2015. 6(2): p. 16-27. |
| Zucali, 2008 | Zucali, P.A., et al., Role of cMET expression in non-small-cell lung cancer patients treated with EGFR tyrosine kinase inhibitors. Annals of Oncology, 2008.19(9): p. 1605-1612. |

For standard molecular biology techniques, see Sambrook, J., Russel, D. W. *Molecular Cloning, A Laboratory Manual.* 3 ed. 2001, Cold Spring Harbor, NY: Cold Spring Harbor Laboratory Press

---

Sequence annex

---

CDR sequences for anti-EGFR antibody clone RAA22
HCDR1 - DNDFS (SEQ ID NO: 1)
HCDR2 - AIVAVFRTETYAQKFQD (SEQ ID NO: 2)
HCDR3 - RLMSAISGPGAPLLM (SEQ ID NO: 3)
LCDR1 - TGTSSDVGGYNYVS (SEQ ID NO: 4)
LCDR2 - DVSKRPS (SEQ ID NO: 5)
LCDR3 - SSYTSSDTLEI (SEQ ID NO: 6)

CDR sequences for anti-EGFR antibody clone QD6
HCDR1 - DNDFS (SEQ ID NO: 1)
HCDR2 - AIVAVVRTETYAQKFQD (SEQ ID NO: 7)
HCDR3 - RLMSAISGPGAPLLM (SEQ ID NO: 3)
LCDR1 - TGTSSDVGGYNYVS (SEQ ID NO: 4)
LCDR2 - DVSERPS (SEQ ID NO: 66)
LCDR3 - FSYTSSDTLEI (SEQ ID NO: 67)

FR sequences for anti-EGFR antibody clones RAA22 and QD6
HFR1 - QVQLVQSGAEVKKPGSSVKVSCKASGGTFS (SEQ ID NO: 8)
HFR2 - WVRQAPGQGLEWMG (SEQ ID NO: 9)
HFR3 - RVKITADISTRTTYMELSSLRSEDTAVYYCAR (SEQ ID NO: 10)
HFR4 - WGQGTLVTVSS (SEQ ID NO: 11)
LFR1 - QSALTQPRSVSGSPGQSVTISC (SEQ ID NO: 12)
LFR2 - WYQQHPGKAPKLMIY (SEQ ID NO: 13)
LFR3 - GVPDRFSGSKSGNTASLTISGLQAEDEADYYC (SEQ ID NO: 14)
LFR4 - FGGGTKLTVL (SEQ ID NO: 15)

Amino acid sequence of the variable heavy (VH) resion of anti-EGFR antibody clone RAA22 (SEQ ID NO: 16)
QVQLVQSGAEVKKPGSSVKVSCKASGGTFSDNDFSWVRQAPGQGLEWMGAIVAVFRT
ETYAQKFQDRVKITADISTRTTYMELSSLRSEDTAVYYCARRLMSAISGPGAPLLMWGQ
GTLVTVSS Nucleic acid sequence of the VH region of anti-EGFR antibody clone RAA22 (SEQ ID NO: 17):
CAGGTGCAGCTGGTGCAGTCTGGGGCCGAAGTGAAGAAACCCGGCAGCAGCGTGAA
GGTGTCCTGTAAAGCCAGCGGCGGCACCTTCAGCGACAACGACTTTAGCTGGGTCC
GACAGGCCCCTGGACAGGGCCTGGAATGGATGGGAGCCATCGTGGCCGTGTTCCGG
ACAGAGACATACGCCCAGAAATTCCAGGACAGAGTGAAAATCACCGCCGACATCAG
CACCAGAACCACCTACATGGAACTGAGCAGCCTGAGAAGCGAGGACACCGCCGTGT
ACTACTGCGCCAGACGGCTGATGTCTGCCATCTCTGGACCTGGCGCTCCTCTGCTCA
TGTGGGGACAGGGAACACTGGTCACCGTGTCCAGC Amino acid sequence of the VH region of anti-EGFR antibody clone QD6 (SEQ ID NO: 18):
QVQLVQSGAEVKKPGSSVKVSCKASGGTFSDNDFSWVRQAPGQGLEWMGAIVAVVRT
ETYAQKFQDRVKITADISTRTTYMELSSLRSEDTAVYYCARRLMSAISGPGAPLLMWGQ
GTLVTVSS Nucleic acid sequence of the VH region of anti-EGFR antibody clone QD6 (SEQ ID NO: 19):
CAGGTGCAGCTGGTGCAGTCTGGGGCCGAAGTGAAGAAACCCGGCAGCAGCGTGAA
GGTGTCCTGTAAAGCCAGCGGCGGCACCTTCAGCGACAACGACTTTAGCTGGGTCC
GACAGGCCCCTGGACAGGGCCTGGAATGGATGGGAGCCATCGTGGCCGTGGTCCGG
ACAGAGACATACGCCCAGAAATTCCAGGACAGAGTGAAAATCACCGCCGACATCAG
CACCAGAACCACCTACATGGAACTGAGCAGCCTGAGAAGCGAGGACACCGCCGTGT
ACTACTGCGCCAGACGGCTGATGTCTGCCATCTCTGGACCTGGCGCTCCTCTGCTCA
TGTGGGGACAGGGAACACTGGTCACCGTGTCCAGC Amino acid sequence of the variable light (VL) region of anti-EGFR antibody clone RAA22 (SEQ ID NO: 20):
QSALTQPRSVSGSPGQSVTISCTGTSSDVGGYNYVSWYQQHPGKAPKLMIYDVSKRPSG
VPDRFSGSKSGNTASLTISGLQAEDEADYYCSSYTSSDTLEIFGGGTKLTVL Nucleic acid sequence of the VL region of anti-EGFR antibody clone RAA22 (SEQ ID NO: 21):
CAGTCTGCCCTGACTCAGCCTCGCTCAGTGTCCGGGTCTCCTGGACAGTCAGTCACC
ATCTCCTGCACTGGAACCAGCAGTGATGTTGGTGGTTATAACTATGTCTCCTGGTAC
CAACAGCACCCAGGCAAAGCCCCCAAACTCATGATTTATGATGTCAGTAAGCGGCC
CTCAGGGGTCCCTGATCGCTTCTCTGGCTCCAAGTCTGGCAACACGGCCTCCCTGAC
CATCTCTGGGCTCCAGGCTGAGGACGAGGCTGATTATTACTGCAGTTCATATACAAG
CAGCGACACTCTCGAAATATTCGGCGGAGGGACCAAGCTGACCGTCCTA Amino acid sequence of the VL region of anti-EGFR antibody clone QD6 (SEQ ID NO: 22):
QSALTQPRSVSGSPGQSVTISCTGTSSDVGGYNYVSWYQQHPGKAPKLMIYDVSERPSG
VPDRFSGSKSGNTASLTISGLQAEDEADYYCFSYTSSDTLEIFGGGTKLTVL -continued Sequence annex Nucleic acid sequence of the VL region of anti-EGFR antibody clone QD6 (SEQ ID NO: 23):
CAGTCTGCCCTGACTCAGCCTCGCTCAGTGTCCGGGTCTCCTGGACAGTCAGTCACC
ATCTCCTGCACTGGAACCAGCAGTGATGTTGGTGGTTATAACTATGTCTCCTGGTAC
CAACAGCACCCAGGCAAAGCCCCCAAACTCATGATTTATGATGTCAGTGAACGGCC
CTCAGGGGTCCCTGATCGCTTCTCTGGCTCCAAGTCTGGCAACACGGCCTCCCTGAC
CATCTCTGGGCTCCAGGCTGAGGACGAGGCTGATTATTACTGCTTCTCATATACAAG
CAGCGACACTCTCGAAATATTCGGCGGAGGGACCAAGCTGACCGTCCTA CDR sequences for anti-c-Met antibody clone B09-GL
HCDR1 - DYYIH (SEQ ID NO: 24)
HCDR2 - WMNPNSGNTGYAQKFQG (SEQ ID NO: 25)
HCDR3 - GQGYTHS (SEQ ID NO: 26)
LCDR1 - RASEGIYHWLA (SEQ ID NO: 27)
LCDR2 - KASSLAS (SEQ ID NO: 28)
LCDR3 - QQYSNYPPT (SEQ ID NO: 29)

FR sequences for anti-c-Met antibody clone B09-GL
HFR1 - QVQLVQSGAEVKKPGASVKVSCKASGYTFT (SEQ ID NO: 30)
HFR2 - WVRQATGQGLEWMG (SEQ ID NO: 31)
HFR3 - RVTMTRDTSISTAYMELSSLRSEDTAVYYCAR (SEQ ID NO: 32)
HFR4 - WGQGTMVTVSS (SEQ ID NO: 33)
LFR1 - DIQMTQSPSTLSASVGDRVTITC (SEQ ID NO: 34)
LFR2 - WYQQKPGKAPKLLIY (SEQ ID NO: 35)
LFR3 - GVPSRFSGSGSGTEFTLTISSLQPDDFATYYC (SEQ ID NO: 36)
LFR4 - FGGGTKLEIK (SEQ ID NO: 37)

Amino acid sequence of the variable heavy (VH) region of anti-c-Met antibody clone B09-GL
(SEQ ID NO: 38):
QVQLVQSGAEVKKPGASVKVSCKASGYTFTDYYIHWVRQATGQGLEWMGWMNPNSG
NTGYAQKFQGRVTMTRDTSISTAYMELSSLRSEDTAVYYCARGQGYTHSWGQGTMVT
VSS Nucleic acid sequence of the VH region of anti-c-Met antibody clone B09-GL (SEQ ID NO: 39):
CAAGTGCAGCTGGTGCAGTCTGGCGCCGAAGTGAAGAAACCTGGCGCCAGCGTGAA
GGTCAGCTGCAAGGCCAGCGGCTACACCTTCACCGACTACTACATCCACTGGGTCCG
CCAGGCCACAGGCCAGGGACTGGAATGGATGGGCTGGATGAACCCCAACAGCGGC
AACACCGGCTACGCCCAGAAATTCCAGGGCAGAGTGACCATGACCCGGGACACCAG
CATCAGCACCGCCTACATGGAACTGAGCAGCCTGCGGAGCGAGGACACCGCCGTGT
ACTACTGTGCCAGAGGCCAGGGCTACACCCACAGCTGGGGCCAGGGCACCATGGTC
ACAGTGTCCAGC Amino acid sequence of the variable light (VL) region of anti-c-Met antibody clone B09-GL
(SEQ ID NO: 40):
DIQMTQSPSTLSASVGDRVTITCRASEGIYHWLAWYQQKPGKAPKLLIYKASSLASGVPS
RFSGSGSGTEFTLTISSLQPDDFATYYCQQYSNYPPTFGGGTKLEIK Nucleic acid sequence of the VL region of anti-c-Met antibody clone B09-GL (SEQ ID NO: 41):
GACATCCAGATGACCCAGAGCCCCAGCACCCTGAGCGCCAGCGTCGGCGACAGAGT
GACCATCACCTGTCGGGCCAGCGAGGGCATCTACCACTGGCTGGCCTGGTATCAGC
AGAAGCCCGGCAAGGCCCCCAAGCTGCTGATCTACAAGGCCAGCAGCCTGGCCAGC
GGAGTCCCTAGCAGATTTTCTGGCAGCGGCAGCGGCACCGAGTTCACCCTGACCATC
AGCAGCCTGCAGCCCGACGACTTCGCCACCTACTACTGCCAGCAGTACAGCAACTA
CCCCCCCACCTTCGGCGGAGGCACCAAGCTGGAAATCAAG Amino acid sequence of a human immunoglobulin G1 heavy chain constant (CH) region (SEQ
ID NO: 42):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDK
SRWQQGNVFSCSVMHEALHNHYTQKSLSLSPGK Amino acid sequence of a human immunoglobulin G1 CH region modified to include "Knob"
mutation, interchain cysteine mutations, a cysteine to form a stabilizing disulfide bridge and with
a cysteine insertion (SEQ ID NO: 43):
Following substitutions are underlined:
"Knob" mutation (T366W); interchain cysteine mutations (F126C and C219V); stabilizing
cysteine mutation (S354C); and cysteine insertion (C239i), where numbering of residues is
according to EU index.
ASTKGPSVCPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSVDKTHTCPPCPAPELLGG
PSCVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPC
REEMTKNQVSLWCLVKGFYPSDIAVEWESNGQPENNYKTTPPVLDSDGSFFLYSKLTV
DKSRWQQGNVFSCSVMHEALHNHYTQKSLSLSPG

Sequence annex

Amino acid sequence of a human immunoglobulin G1 CH region modified to include "Knob" mutation, interchain cysteine mutations, a cysteine to form a stabilizing disulfide bridge and without a cysteine insertion (SEQ ID NO: 44):
Following substitutions are underlined:
"Knob" mutation (T366W); interchain cysteine mutations (F126C and C219V); and stabilizing cysteine mutation (S354C), where numbering of residues is according to EU index.
ASTKGPSVCPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSVDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPCR
EEMTKNQVSLWCLVKGFYPSDIAVEWESNGQPENNYKTTPPVLDSDGSFFLYSKLTVD
KSRWQQGNVFSCSVMHEALHNHYTQKSLSLSPG Amino acid sequence of a human immunoglobulin G1 CH region modified to include "Hole" mutations, a cysteine to form a stabilizing disulfide bridge and with a cysteine insertion (SEQ ID NO: 45):
Following substitutions are underlined:
"Hole" mutations (T366S, L368A, and Y407V); stabilizing cysteine mutation (Y349C); and cysteine insertion (C239i), where numbering of residues is according to EU index.
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSCVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVCTLPPS
REEMTKNQVSLSCAVKGFYPSDIAVEWESNGQPENNYKTTPPVLDSDGSFFLVSKLTVD
KSRWQQGNVFSCSVMHEALHNHYTQKSLSLSPGK Amino acid sequence of a human immunoglobulin G1 CH region modified to include "Hole" mutations, a cysteine to form a stabilizing disulfide bridge and without a cysteine insertion (SEQ ID NO: 46):
Following substitutions are underlined:
"Hole" mutations (T366S, L368A, and Y407V); and stabilizing cysteine mutation (Y349C), where numbering of residues is according to EU index.
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVCTLPPSR
EEMTKNQVSLSCAVKGFYPSDIAVEWESNGQPENNYKTTPPVLDSDGSFFLVSKLTVDK
SRWQQGNVFSCSVMHEALHNHYTQKSLSLSPGK Amino acid sequence of a wild-type human immunoglobulin kappa constant region (SEQ ID NO: 47):
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC Amino acid sequence of a human immunoglobulin kappa constant region modified to include S121C and C214V substitutions (SEQ ID NO: 48):
Following substitutions are underlined:
S121C and C214V, wherein numbering is according to EU index
RTVAAPSVFIFPPCDEQLKSGTASVVCLLNNFYPREAKVQWKVDNALQSGNSQESVTEQ
DSKDSTYSLSSTLTLSKADYEKHKVYACEVTHQGLSSPVTKSFNRGEV Amino acid sequence of a human immunoglobulin lambda constant region (SEQ ID NO: 49):
GQPKAAPSVTLFPPSSEELQANKATLVCLISDFYPGAVTVAWKADSSPVKAGVETTTPS
KQSNNKYAASSYLSLTPEQWKSHRSYSCQVTHEGSTVEKTVAPTECS Amino acid sequence of the heavy chain of anti-c-Met antibody clone B09-GL with cysteine insertion (SEQ ID NO: 50):
Following substitutions are underlined:
"Knob" mutation (T366W); interchain cysteine mutations (F126C and C219V); stabilizing cysteine mutation (S354C); and cysteine insertion (C239i), where numbering of residues is according to EU index.
QVQLVQSGAEVKKPGASVKVSCKASGYTFTDYYIHWVRQATGQGLEWMGWMNPNSG
NTGYAQKFQGRVTMTRDTSISTAYMELSSLRSEDTAVYYCARGQGYTHSWGQGTMVT
VSSASTKGPSVCPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSVDKTHTCPPCPAPE
LLGGPSCVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPCREEMTKNQVSLWCLVKGFYPSDIAVEWESNGQPENNYKTTPPVLDSDGSFFLY
SKLTVDKSRWQQGNVFSCSVMHEALHNHYTQKSLSLSPG Amino acid sequence of the heavy chain of anti-c-Met antibody clone B09-GL without cysteine insertion (SEQ ID NO: 51):
Following substitutions are underlined:
"Knob" mutation (T366W); interchain cysteine mutations (F126C and C219V); and stabilizing cysteine mutation (S354C), where numbering of residues is according to EU index.
QVQLVQSGAEVKKPGASVKVSCKASGYTFTDYYIHWVRQATGQGLEWMGWMNPNSG

```
NTGYAQKFQGRVTMTRDTSISTAYMELSSLRSEDTAVYYCARGQGYTHSWGQGTMVT
VSSASTKGPSVCPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSVDKTHTCPPCPAPE
LLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYT
LPPCREEMTKNQVSLWCLVKGFYPSDIAVEWESNGQPENNYKTTPPVLDSDGSFFLYSK
LTVDKSRWQQGNVFSCSVMHEALHNHYTQKSLSLSPG
```

Amino acid sequence of the light chain of anti-c-Met antibody clone B09-GL (SEQ ID NO: 52):
Following substitutions are underlined:
S121C and C214V, wherein numbering is according to EU index
```
DIQMTQSPSTLSASVGDRVTITCRASEGIYHWLAWYQQKPGKAPKLLIYKASSLASGVPS
RFSGSGSGTEFTLTISSLQPDDFATYYCQQYSNYPPTFGGGTKLEIKRTVAAPSVFIFPPCD
EQLKSGTASVVCLLNNFYPREAKVQWKVDNALQSGNSQESVTEQDSKDSTYSLSSTLTL
SKADYEKHKVYACEVTHQGLSSPVTKSFNRGEV
```

Amino acid sequence of the heavy chain of anti-EGFR antibody clone QD6 with cysteine insertion (SEQ ID NO: 53):
Following substitutions are underlined:
"Hole" mutations (T366S, L368A, and Y407V); stabilizing cysteine mutation (Y349C); and cysteine insertion (C239i), where numbering of residues is according to EU index.
```
QVQLVQSGAEVKKPGSSVKVSCKASGGTFSDNDFSWVRQAPGQGLEWMGAIVAVVRT
ETYAQKFQDRVKITADISTRTTYMELSSLRSEDTAVYYCARRLMSAISGPGAPLLMWGQ
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPC
PAPELLGGPSCVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVCTLPPSREEMTKNQVSLSCAVKGFYPSDIAVEWESNGQPENNYKTTPPVLDSDGSFF
LVSKLTVDKSRWQQGNVFSCSVMHEALHNHYTQKSLSLSPGK
```

Amino acid sequence of the heavy chain of anti-EGFR antibody clone QD6 without cysteine insertion (SEQ ID NO: 54):
Following substitutions are underlined:
"Hole" mutations (T366S, L368A, and Y407V); and stabilizing cysteine mutation (Y349C), where numbering of residues is according to EU index.
```
QVQLVQSGAEVKKPGSSVKVSCKASGGTFSDNDFSWVRQAPGQGLEWMGAIVAVVRT
ETYAQKFQDRVKITADISTRTTYMELSSLRSEDTAVYYCARRLMSAISGPGAPLLMWGQ
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQ
VCTLPPSREEMTKNQVSLSCAVKGFYPSDIAVEWESNGQPENNYKTTPPVLDSDGSFFL
VSKLTVDKSRWQQGNVFSCSVMHEALHNHYTQKSLSLSPGK
```

Amino acid sequence of the light chain of anti-EGFR antibody clone QD6 (SEQ ID NO: 55):
```
QSALTQPRSVSGSPGQSVTISCTGTSSDVGGYNYVSWYQQHPGKAPKLMIYDVSERPSG
VPDRFSGSKSGNTASLTISGLQAEDEADYYCFSYTSSDTLEIFGGGTKLTVLGQPKAAPS
VTLFPPSSEELQANKATLVCLISDFYPGAVTVAWKADSSPVKAGVETTTPSKQSNNKYA
ASSYLSLTPEQWKSHRSYSCQVTHEGSTVEKTVAPTECS
```

Amino acid sequence of the heavy chain of anti-EGFR antibody clone RAA22 with cysteine insertion (SEQ ID NO: 56):
Following substitutions are underlined:
"Hole" mutations (T366S, L368A, and Y407V); stabilizing cysteine mutation (Y349C); and cysteine insertion (C239i), where numbering of residues is according to EU index.
```
QVQLVQSGAEVKKPGSSVKVSCKASGGTFSDNDFSWVRQAPGQGLEWMGAIVAVFRT
ETYAQKFQDRVKITADISTRTTYMELSSLRSEDTAVYYCARRLMSAISGPGAPLLMWGQ
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPC
PAPELLGGPSCVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVCTLPPSREEMTKNQVSLSCAVKGFYPSDIAVEWESNGQPENNYKTTPPVLDSDGSFF
LVSKLTVDKSRWQQGNVFSCSVMHEALHNHYTQKSLSLSPGK
```

Amino acid sequence of the heavy chain of anti-EGFR antibody clone RAA22 without cysteine insertion (SEQ ID NO: 57):
Following substitutions are underlined:
"Hole" mutations (T366S, L368A, and Y407V); and stabilizing cysteine mutation (Y349C), where numbering of residues is according to EU index.
```
QVQLVQSGAEVKKPGSSVKVSCKASGGTFSDNDFSWVRQAPGQGLEWMGAIVAVFRT
ETYAQKFQDRVKITADISTRTTYMELSSLRSEDTAVYYCARRLMSAISGPGAPLLMWGQ
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPC
PAPELLGGPSCVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVCTLPPSREEMTKNQVSLSCAVKGFYPSDIAVEWESNGQPENNYKTTPPVLDSDGSFF
LVSKLTVDKSRWQQGNVFSCSVMHEALHNHYTQKSLSLSPGK
```

Sequence annex

Amino acid sequence of the light chain of anti-EGFR antibody clone RAA22 (SEQ ID NO: 58):
QSALTQPRSVSGSPGQSVTISCTGTSSDVGGYNYVSWYQQHPGKPKLMIYDVSKRPSG
VPDRFSGSKSGNTASLTISGLQAEDEADYYCSSYTSSDTLEIFGGGTKLTVLGQPKAAPS
VTLFPPSSEELQANKATLVCLISDFYPGAVTVAWKADSSPVKAGVETTTPSKQSNNKYA
ASSYLSLTPEQWKSHRSYSCQVTHEGSTVEKTVAPTECS Amino acid sequence of the heavy chain of anti-EGFR in "EGFR-cMET TM" antibody (SEQ ID NO: 59):
Following substitutions are underlined:
Triple mutation (TM; L234F, L235E and P331S); "Knob" mutation (T366W); interchain
cysteine mutations (F126C and C219V); stabilizing cysteine mutation (S354C), where
numbering of residues is according to EU index.
QVQLVQSGAEVKKPGSSVKVSCKASGGTFSDNDFSWVRQAPGQGLEWMGAIVAVFRT
ETYAQKFQDRVKITADISTRTTYMELSSLRSEDTAVYYCARRLMSAISGPGAPLLMWGQ
GTLVTVSSASTKGPSVCPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSVDKTHTCPP
CPAPEFEGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPASIEKTISKAKGQPREP
QVYTLPPCREEMTKNQVSLWCLVKGFYPSDIAVEWESNGQPENNYKTTPPVLDSDGSF
FLYSKLTVDKSRWQQGNVFSCSVMHEALHNHYTQKSLSLSPGK Amino acid sequence of the heavy chain of anti-c-Met in "EGFR-cMET TM" antibody (SEQ ID NO: 60):
Following substitutions are underlined:
Triple mutation (TM; L234F, L235E and P331S); "Hole" mutations (T366S, L368A, and
Y407V); and stabilizing cysteine mutation (Y349C), where numbering of residues is according
to EU index.
QVQLVQSGAEVKKPGASVKVSCKASGYTFTDYYIHWVRQATGQGLEWMGWMNPNSG
NTGYAQKFQGRVTMTRDTSISTAYMELSSLRSEDTAVYYCARGQGYTHSWGQGTMVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEF
EGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPASIEKTISKAKGQPREPQVCT
LPPSREEMTKNQVSLSCAVKGFYPSDIAVEWESNGQPENNYKTTPPVLDSDGSFFLVSKL
TVDKSRWQQGNVFSCSVMHEALHNHYTQKSLSLSPGK Amino acid sequence of the light chain of anti-EGFR in "EGFR-cMET TM" antibody (SEQ ID NO: 61):
Following substitutions are underlined:
S121C and C214V, wherein numbering is according to EU index
QSALTQPRSVSGSPGQSVTISCTGTSSDVGGYNYVSWYQQHPGKAPKLMIYDVSKRPSG
VPDRFSGSKSGNTASLTISGLQAEDEADYYCSSYTSSDTLEIFGGGTKLTVLGQPKAAPS
VTLFPPCSEELQANKATLVCLISDFYPGAVTVAWKADSSPVKAGVETTTPSKQSNNKYA
ASSYLSLTPEQWKSHRSYSCQVTHEGSTVEKTVAPTEVS Amino acid sequence of the light chain of anti-c-Met in "EGFR-cMET TM" antibody (SEQ ID NO: 62):
DIQMTQSPSTLSASVGDRVTITCRASEGIYHWLAWYQQKPGKAPKLLIYKASSLASGVPS
RFSGSGSGTEFTLTISSLQPDDFATYYCQQYSNYPPTFGGGTKLEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC Amino acid sequence of a human immunoglobulin G1 CH region modified to include "knob"
mutations, a cysteine to form a stabilizing disulfide bridge, without a cysteine insertion and with
the TM (SEP ID NO: 63):
Following substitutions are underlined:
Triple mutation (TM; L234F, L235E and P331S); "Knob" mutation (T366W); interchain
cysteine mutations (F126C and C219V); stabilizing cysteine mutation (S354C), where
numbering of residues is according to EU index.
ASTKGPSVCPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSVDKTHTCPPCPAPEFEG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPASIEKTISKAKGQPREPQVYTLPPC
REEMTKNQVSLWCLVKGFYPSDIAVEWESNGQPENNYKTTPPVLDSDGSFFLYSKLTV
DKSRWQQGNVFSCSVMHEALHNHYTQKSLSLSPGK Amino acid sequence of a human immunoglobulin G1 CH region modified to include "Hole"
mutations, a cysteine to form a stabilizing disulfide bridge, without a cysteine insertion and with
the TM (SEP ID NO: 64):
Following substitutions are underlined:
Triple mutation (TM; L234F, L235E and P331S); "Hole" mutations (T366S, L368A, and
Y407V); and stabilizing cysteine mutation (Y349C), where numbering of residues is according
to EU index.
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEFEGG
PSVFLFPPKPKDTLMISRTPEVTCVVVDVSHEDPEVKFNWYVDGVEVHNAKTKPREEQY

| Sequence annex |
| --- |

NSTYRVVSVLTVLHQDWLNGKEYKCKVSNKALPASI EKTISKAKGQPREPQVCTLPPSR
EEMTKNQVSLSCAVKGFYPSDIAVEWESNGQPENNYKTTPPVLDSDGSFFLVSKLTVDK
SRWQQGNVFSCSVMHEALHNHYTQKSLSLSPGK

Amino acid sequence of a human immunoglobulin lambda constant region modified to include
S121C and C214V substitutions (SEQ ID NO: 65):
GQPKAAPSVTLFPPCSEELQANKATLVCLISDFYPGAVTVAWKADSSPVKAGVETTTPS
KQSNNKYAASSYLSLTPEQWKSHRSYSCQVTHEGSTVEKTVAPTEVS Amino acid sequence of the human EGFR extracellular domain (SEQ ID NO: 68):
LEEKKVCQGTSNKLTQLGTFEDHFLSLQRMFNNCEVVLGNLEITYVQRNYDLSFLKTIQ
EVAGYVLIALNTVERIPLENLQIIRGNMYYENSYALAVLSNYDANKTGLKELPMRNLQE
ILHGAVRFSNNPALCNVESIQWRDIVSSDFLSNMSMDFQNHLGSCQKCDPSCPNGSCWG
AGEENCQKLTKIICAQQCSGRCRGKSPSDCCHNQCAAGCTGPRESDCLVCRKFRDEATC
KDTCPPLMLYNPTTYQMDVNPEGKYSFGATCVKKCPRNYVVTDHGSCVRACGADSYE
MEEDGVRKCKKCEGPCRKVCNGIGIGEFKDSLSINATNIKHFKNCTSISGDLHILPVAFRG
DSFTHTPPLDPQELDILKTVKEITGFLLIQAWPENRTDLHAFENLEIIRGRTKQHGQFSLA
VVSLNITSLGLRSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFVENSECIQCH
PECLPQAMNITCTGRGPDNCIQCAHYIDGPHCVKTCPAGVMGENNTLVWKYADAGHV
CHLCHPNCTYGCTGPGLEGCPTNGPKIPS Amino acid sequence of the cynomolgus monkey EGFR extracellular domain (SEQ ID NO: 69):
LEEKKVCQGTSNKLTQLGTFEDHFLSLQRMFNNCEVVLGNLEITYVQRNYDLSFLKTIQ
EVAGYVLIALNTVERIPLENLQIIRGNMYYENSYALAVLSNYDANKTGLKELPMRNLQE
ILHGAVRFSNNPALCNVESIQWRDIVSSEFLSNMSMDFQNHLGSCQKCDPSCPNGSCWG
AGEENCQKLTKIICAQQCSGRCRGKSPSDCCHNQCAAGCTGPRESDCLVCRKFRDEATC
KDTCPPLMLYNPTTYQMDVNPEGKYSFGATCVKKCPRNYVVTDHGSCVRACGADSYE
MEEDGVRKCKKCEGPCRKVCNGIGIGEFKDTLSINATNIKHFKNCTSISGDLHILPVAFR
GDSFTHTPPLDPQELDILKTVKEITGFLLIQAWPENRTDLHAFENLEIIRGRTKQHGQFSL
AVVSLNITSLGLRSLKEISDGDVIISGNKNLCYANTINWKKLFGTSSQKTKIISNRGENSC
KATGQVCHALCSPEGCWGPEPRDCVSCQNVSRGRECVDKCNILEGEPREFVENSECIQC
HPECLPQVMNITCTGRGPDNCIQCAHYIDGPHCVKTCPAGVMGENNTLVWKYADAGH
VCHLCHPNCTYGCTGPGLEGCARNGPKIPS Amino acid sequence of the human c-Met extracellular domain (SEQ ID NO: 70):
ECKEALAKSEMNVNMKYQLPNFTAETPIQNVILHEHHIFLGATNYIYVLNEEDLQKVAE
YKTGPVLEHPDCFPCQDCSSKANLSGGVWKDNINMALVVDTYYDDQLISCGSVNRGTC
QRHVFPHNHTADIQSEVHCIFSPQIEEPSQCPDCVVSALGAKVLSSVKDRFINFFVGNTIN
SSYFPDHPLHSISVRRLKETKDGFMFLTDQSYIDVLPEFRDSYPIKYVHAFESNNFIYFLT
VQRETLDAQTFHTRIIRFCSINSGLHSYMEMPLECILTEKRKKRSTKKEVFNILQAAYVSK
PGAQLARQIGASLNDDILFGVFAQSKPDSAEPMDRSAMCAFPIKYVNDFFNKIVNKNNV
RCLQHFYGPNHEHCFNRTLLRNSSGCEARRDEYRTEFTTALQRVDLFMGQFSEVLLTSIS
TFIKGDLTIANLGTSEGRFMQVVVSRSGPSTPHVNFLLDSHPVSPEVIVEHTLNQNGYTL
VITGKKITKIPLNGLGCRHFQSCSQCLSAPPFVQCGWCHDKCVRSEECLSGTWTQQICLP
AIYKVFPNSAPLEGGTRLTICGWDFGFRRNNKFDLKKTRVLLGNESCTLTLSESTMNTLK
CTVGPAMNKHFNMSIIISNGHGTTQYSTFSYVDPVITSISPKYGPMAGGTLLTLTGNYLN
SGNSRHISIGGKTCTLKSVSNSILECYTPAQTISTEFAVKLKIDLANRETSIFSYREDPIVYE
IHPTKSFISGGSTITGVGKNLNSVSVPRMVINVHEAGRNFTVACQHRSNSEIICCTTPSLQ
QLNLQLPLKTKAFFMLDGILSKYFDLIYVHNPVFKPFEKPVMISMGNENVLEIKGNDIDP
EAVKGEVLKVGNKSCENIHLHSEAVLCTVPNDLLKLNSELNIEWKQAISSTVLGKVIVQP
DQNFT Amino acid sequence of the cynomolgus monkey c-Met extracellular domain (SEQ ID NO: 71):
ECKEALAKSEMNVNMKYQLPNFTAETAIQNVILHEHHIFLGATNYIYVLNEEDLQKVAE
YKTGPVLEHPDCFPCQDCSSKANLSGGVWKDNINMALVVDTYYDDQLISCGSVNRGTC
QRHVFPHNHTADIQSEVHCIFSPQIEEPNQCPDCVVSALGAKVLSSVKDRFINFFVGNTIN
SSYFPHHPLHSISVRRLKETKDGFMFLTDQSYIDVLPEFRDSYPIKYIHAFESNNFIYFLTV
QRETLNAQTFHTRIIRFCSLNSGLHSYMEMPLECILTEKRKKRSTKKEVFNILQAAYVSK
PGAQLARQIGASLNDDILFGVFAQSKPDSAEPMDRSAMCAFPIKYVNDFFNKIVNKNNV
RCLQHFYGPNHEHCFNRTLLRNSSGCEARRDEYRAEFTTALQRVDLFMGQFSEVLLTSIS
TFVKGDLTIANLGTSEGRFMQVVVSRSGPSTPHVNFLLDSHPVSPEVIVEHPLNQNGYTL
VVTGKKITKIPLNGLGCRHFQSCSQCLSAPPFVQCGWCHDKCVRSEECPSGTWTQQICLP
AIYKVFPTSAPLEGGTRLTICGWDFGFRRNNKFDLKKTRVLLGNESCTLTLSESTMNTLK
CTVGPAMNKHFNMSIIISNGHGTTQYSTFSYVDPIITSISPKYGPMAGGTLLTLTGNYLNS
GNSRHISIGGKTCTLKSVSNSILECYTPAQTISTEFAVKLKIDLANRETSIFSYREDPIVYEI
HPTKSFISGGSTITGVGKNLHSVSVPRMVINVHEAGRNFTVACQHRSNSEIICCTTPSLQQ
LNLQLPLKTKAFFMLDGILSKYFDLIYVHNPVFKPFEKPVMISMGNENVLEIKGNDIDPE
AVKGEVLKVGNKSCENIHLHSEAVLCTVPNDLLKLNSELNIEWKQAISSTVLGKVIVQP
DQNFT

SEQUENCE LISTING

```
Sequence total quantity: 71
SEQ ID NO: 1                    moltype = AA   length = 5
FEATURE                         Location/Qualifiers
source                          1..5
                                mol_type = protein
                                note = HCDR1
                                organism = synthetic construct
SEQUENCE: 1
DNDFS                                                                        5

SEQ ID NO: 2                    moltype = AA   length = 17
FEATURE                         Location/Qualifiers
source                          1..17
                                mol_type = protein
                                note = HCDR2
                                organism = synthetic construct
SEQUENCE: 2
AIVAVFRTET YAQKFQD                                                          17

SEQ ID NO: 3                    moltype = AA   length = 15
FEATURE                         Location/Qualifiers
source                          1..15
                                mol_type = protein
                                note = HCDR3
                                organism = synthetic construct
SEQUENCE: 3
RLMSAISGPG APLLM                                                            15

SEQ ID NO: 4                    moltype = AA   length = 14
FEATURE                         Location/Qualifiers
source                          1..14
                                mol_type = protein
                                note = LCDR1
                                organism = synthetic construct
SEQUENCE: 4
TGTSSDVGGY NYVS                                                             14

SEQ ID NO: 5                    moltype = AA   length = 7
FEATURE                         Location/Qualifiers
source                          1..7
                                mol_type = protein
                                note = LCDR2
                                organism = synthetic construct
SEQUENCE: 5
DVSKRPS                                                                      7

SEQ ID NO: 6                    moltype = AA   length = 11
FEATURE                         Location/Qualifiers
source                          1..11
                                mol_type = protein
                                note = SSYTSSDTLEI
                                organism = synthetic construct
SEQUENCE: 6
SSYTSSDTLE I                                                                11

SEQ ID NO: 7                    moltype = AA   length = 17
FEATURE                         Location/Qualifiers
source                          1..17
                                mol_type = protein
                                note = HCDR2
                                organism = synthetic construct
SEQUENCE: 7
AIVAVVRTET YAQKFQD                                                          17

SEQ ID NO: 8                    moltype = AA   length = 30
FEATURE                         Location/Qualifiers
source                          1..30
                                mol_type = protein
                                note = HFR1
                                organism = synthetic construct
SEQUENCE: 8
QVQLVQSGAE VKKPGSSVKV SCKASGGTFS                                            30

SEQ ID NO: 9                    moltype = AA   length = 14
FEATURE                         Location/Qualifiers
source                          1..14
                                mol_type = protein
                                note = HFR2
```

-continued

```
SEQUENCE: 9
WVRQAPGQGL EWMG                                                       14

SEQ ID NO: 11           moltype = AA   length = 32
FEATURE                 Location/Qualifiers
source                  1..32
                        mol_type = protein
                        note = HFR3
                        organism = synthetic construct
SEQUENCE: 10
RVKITADIST RTTYMELSSL RSEDTAVYYC AR                                   32

SEQ ID NO: 11           moltype = AA   length = 11
FEATURE                 Location/Qualifiers
source                  1..11
                        mol_type = protein
                        note = HFR4
                        organism = synthetic construct
SEQUENCE: 11
WGQGTLVTVS S                                                          11

SEQ ID NO: 12           moltype = AA   length = 22
FEATURE                 Location/Qualifiers
source                  1..22
                        mol_type = protein
                        note = LFR1
                        organism = synthetic construct
SEQUENCE: 12
QSALTQPRSV SGSPGQSVTI SC                                              22

SEQ ID NO: 13           moltype = AA   length = 15
FEATURE                 Location/Qualifiers
source                  1..15
                        mol_type = protein
                        note = LFR2
                        organism = synthetic construct
SEQUENCE: 13
WYQQHPGKAP KLMIY                                                      15

SEQ ID NO: 14           moltype = AA   length = 32
FEATURE                 Location/Qualifiers
source                  1..32
                        mol_type = protein
                        note = LFR3
                        organism = synthetic construct
SEQUENCE: 14
GVPDRFSGSK SGNTASLTIS GLQAEDEADY YC                                   32

SEQ ID NO: 15           moltype = AA   length = 10
FEATURE                 Location/Qualifiers
source                  1..10
                        mol_type = protein
                        note = LFR4
                        organism = synthetic construct
SEQUENCE: 15
FGGGTKLTVL                                                            10

SEQ ID NO: 16           moltype = AA   length = 124
FEATURE                 Location/Qualifiers
source                  1..124
                        mol_type = protein
                        note = Amino acid sequence of the variable heavy (VH)
                         region of anti-EGFR antibody clone RAA22
                        organism = synthetic construct
SEQUENCE: 16
QVQLVQSGAE VKKPGSSVKV SCKASGGTFS DNDFSWVRQA PGQGLEWMGA IVAVFRTETY     60
AQKFQDRVKI TADISTRTTY MELSSLRSED TAVYYCARRL MSAISGPGAP LLMWGQGTLV    120
TVSS                                                                 124

SEQ ID NO: 17           moltype = DNA   length = 372
FEATURE                 Location/Qualifiers
source                  1..372
                        mol_type = other DNA
                        note = Nucleic acid sequence of the VH region of anti-EGFR
                         antibody clone RAA22
                        organism = synthetic construct
SEQUENCE: 17
caggtgcagc tggtgcagtc tggggccgaa gtgaagaaac ccggcagcag cgtgaaggtg     60
```

```
tcctgtaaag ccagcggcgg caccttcagc gacaacgact ttagctgggt ccgacaggcc    120
cctggacagg gcctggaatg gatgggagcc atcgtggccg tgttccggac agagacatac    180
gcccagaaat tccaggacag agtgaaaatc accgccgaca tcagcaccag aaccacctac    240
atggaactga gcagcctgag aagcgaggac accgccgtgt actactgcgc cagacggctg    300
atgtctgcca tctctggacc tggcgctcct ctgctcatgt ggggacaggg aacactggtc    360
accgtgtcca gc                                                        372

SEQ ID NO: 18           moltype = AA  length = 124
FEATURE                 Location/Qualifiers
source                  1..124
                        mol_type = protein
                        note = Amino acid sequence of the VH region of anti-EGFR
                          antibody clone QD6
                        organism = synthetic construct
SEQUENCE: 18
QVQLVQSGAE VKKPGSSVKV SCKASGGTFS DNDFSWVRQA PGQGLEWMGA IVAVVRTETY    60
AQKFQDRVKI TADISTRTTY MELSSLRSED TAVYYCARRL MSAISGPGAP LLMWGQGTLV    120
TVSS                                                                 124

SEQ ID NO: 19           moltype = DNA  length = 372
FEATURE                 Location/Qualifiers
source                  1..372
                        mol_type = other DNA
                        note = Nucleic acid sequence of the VH region of anti-EGFR
                          antibody clone QD6
                        organism = synthetic construct
SEQUENCE: 19
caggtgcagc tggtgcagtc tggggccgaa gtgaagaaac ccggcagcag cgtgaaggtg    60
tcctgtaaag ccagcggcgg caccttcagc gacaacgact ttagctgggt ccgacaggcc    120
cctggacagg gcctggaatg gatgggagcc atcgtggccg tgttccggac agagacatac    180
gcccagaaat tccaggacag agtgaaaatc accgccgaca tcagcaccag aaccacctac    240
atggaactga gcagcctgag aagcgaggac accgccgtgt actactgcgc cagacggctg    300
atgtctgcca tctctggacc tggcgctcct ctgctcatgt ggggacaggg aacactggtc    360
accgtgtcca gc                                                        372

SEQ ID NO: 20           moltype = AA  length = 111
FEATURE                 Location/Qualifiers
source                  1..111
                        mol_type = protein
                        note = Amino acid sequence of the variable light (VL)
                          region of anti-EGFR antibody clone RAA22
                        organism = synthetic construct
SEQUENCE: 20
QSALTQPRSV SGSPGQSVTI SCTGTSSDVG GYNYVSWYQQ HPGKAPKLMI YDVSKRPSGV    60
PDRFSGSKSG NTASLTISGL QAEDEADYYC SSYTSSDTLE IFGGGTKLTV L             111

SEQ ID NO: 21           moltype = DNA  length = 333
FEATURE                 Location/Qualifiers
source                  1..333
                        mol_type = other DNA
                        organism = synthetic construct
SEQUENCE: 21
cagtctgccc tgactcagcc tcgctcagtg tccgggtctc ctggacagtc agtcaccatc    60
tcctgcactg gaaccagcag tgatgttggt ggttataact atgtctcctg gtaccaacag    120
cacccaggca aagcccccaa actcatgatt tatgatgtca gtaagcggcc ctcaggggtc    180
cctgatcgct tctctggctc caagtctggc aacacggcct ccctgaccat ctctgggctc    240
caggctgagg acgaggctga ttattactgc agttcatata caagcagcga cactctcgaa    300
atattcggcg gagggaccaa gctgaccgtc cta                                 333

SEQ ID NO: 22           moltype = AA  length = 111
FEATURE                 Location/Qualifiers
source                  1..111
                        mol_type = protein
                        note = Amino acid sequence of the VL region of anti-EGFR
                          antibody clone QD6
                        organism = synthetic construct
SEQUENCE: 22
QSALTQPRSV SGSPGQSVTI SCTGTSSDVG GYNYVSWYQQ HPGKAPKLMI YDVSERPSGV    60
PDRFSGSKSG NTASLTISGL QAEDEADYYC FSYTSSDTLE IFGGGTKLTV L             111

SEQ ID NO: 23           moltype = DNA  length = 333
FEATURE                 Location/Qualifiers
source                  1..333
                        mol_type = other DNA
                        note = Nucleic acid sequence of the VL region of anti-EGFR
                          antibody clone QD6
                        organism = synthetic construct
SEQUENCE: 23
cagtctgccc tgactcagcc tcgctcagtg tccgggtctc ctggacagtc agtcaccatc    60
```

```
tcctgcactg gaaccagcag tgatgttggt ggttataact atgtctcctg gtaccaacag    120
cacccaggca aagcccccaa actcatgatt tatgatgtca gtgaacggcc ctcaggggtc    180
cctgatcgct tctctggctc caagtctggc aacacggcct ccctgaccat ctctgggctc    240
caggctgagg acgaggctga ttattactgc ttctcatata caagcagcga cactctcgaa    300
atattcggcg gagggaccaa gctgaccgtc cta                                 333

SEQ ID NO: 24           moltype = AA   length = 5
FEATURE                 Location/Qualifiers
source                  1..5
                        mol_type = protein
                        note = HCDR1
                        organism = synthetic construct
SEQUENCE: 24
DYYIH                                                                 5

SEQ ID NO: 25           moltype = AA   length = 17
FEATURE                 Location/Qualifiers
source                  1..17
                        mol_type = protein
                        note = HCDR2
                        organism = synthetic construct
SEQUENCE: 25
WMNPNSGNTG YAQKFQG                                                   17

SEQ ID NO: 26           moltype = AA   length = 7
FEATURE                 Location/Qualifiers
source                  1..7
                        mol_type = protein
                        note = HCDR3
                        organism = synthetic construct
SEQUENCE: 26
GQGYTHS                                                               7

SEQ ID NO: 27           moltype = AA   length = 11
FEATURE                 Location/Qualifiers
source                  1..11
                        mol_type = protein
                        note = LCDR1
                        organism = synthetic construct
SEQUENCE: 27
RASEGIYHWL A                                                         11

SEQ ID NO: 28           moltype = AA   length = 7
FEATURE                 Location/Qualifiers
source                  1..7
                        mol_type = protein
                        note = LCDR2
                        organism = synthetic construct
SEQUENCE: 28
KASSLAS                                                               7

SEQ ID NO: 29           moltype = AA   length = 9
FEATURE                 Location/Qualifiers
source                  1..9
                        mol_type = protein
                        note = LCDR3
                        organism = synthetic construct
SEQUENCE: 29
QQYSNYPPT                                                             9

SEQ ID NO: 30           moltype = AA   length = 30
FEATURE                 Location/Qualifiers
source                  1..30
                        mol_type = protein
                        note = HFR1
                        organism = synthetic construct
SEQUENCE: 30
QVQLVQSGAE VKKPGASVKV SCKASGYTFT                                     30

SEQ ID NO: 31           moltype = AA   length = 14
FEATURE                 Location/Qualifiers
source                  1..14
                        mol_type = protein
                        note = HFR2
                        organism = synthetic construct
SEQUENCE: 31
WVRQATGQGL EWMG                                                      14

SEQ ID NO: 32           moltype = AA   length = 32
```

```
FEATURE                 Location/Qualifiers
source                  1..32
                        mol_type = protein
                        note = HFR3
                        organism = synthetic construct
SEQUENCE: 32
RVTMTRDTSI STAYMELSSL RSEDTAVYYC AR                              32

SEQ ID NO: 33           moltype = AA  length = 11
FEATURE                 Location/Qualifiers
source                  1..11
                        mol_type = protein
                        note = HFR4
                        organism = synthetic construct
SEQUENCE: 33
WGQGTMVTVS S                                                     11

SEQ ID NO: 34           moltype = AA  length = 23
FEATURE                 Location/Qualifiers
source                  1..23
                        mol_type = protein
                        note = LFR1
                        organism = synthetic construct
SEQUENCE: 34
DIQMTQSPST LSASVGDRVT ITC                                        23

SEQ ID NO: 35           moltype = AA  length = 15
FEATURE                 Location/Qualifiers
source                  1..15
                        mol_type = protein
                        note = LFR2
                        organism = synthetic construct
SEQUENCE: 35
WYQQKPGKAP KLLIY                                                 15

SEQ ID NO: 36           moltype = AA  length = 32
FEATURE                 Location/Qualifiers
source                  1..32
                        mol_type = protein
                        note = LFR3
                        organism = synthetic construct
SEQUENCE: 36
GVPSRFSGSG SGTEFTLTIS SLQPDDFATY YC                              32

SEQ ID NO: 37           moltype = AA  length = 10
FEATURE                 Location/Qualifiers
source                  1..10
                        mol_type = protein
                        note = LFR4
                        organism = synthetic construct
SEQUENCE: 37
FGGGTKLEIK                                                       10

SEQ ID NO: 38           moltype = AA  length = 116
FEATURE                 Location/Qualifiers
source                  1..116
                        mol_type = protein
                        note = Amino acid sequence of the variable heavy (VH)
                          region of anti-c-Met antibody clone B09-GL
                        organism = synthetic construct
SEQUENCE: 38
QVQLVQSGAE VKKPGASVKV SCKASGYTFT DYYIHWVRQA TGQGLEWMGW MNPNSGNTGY 60
AQKFQGRVTM TRDTSISTAY MELSSLRSED TAVYYCARGQ GYTHSWGQGT MVTVSS    116

SEQ ID NO: 39           moltype = DNA  length = 348
FEATURE                 Location/Qualifiers
source                  1..348
                        mol_type = other DNA
                        note = Nucleic acid sequence of the VH region of anti-c-Met
                          antibody clone B09-GL
                        organism = synthetic construct
SEQUENCE: 39
caagtgcagc tggtgcagtc tggcgccgaa gtgaagaaac ctggcgccag cgtgaaggtc 60
agctgcaagg ccagcggcta caccttcacc gactactaca tccactgggt ccgccaggcc 120
acaggccagg gactgaatg gatgggctgg atgaacccca acagcggcaa caccggctac 180
gcccagaaat tccagggcag agtgaccatg acccggggaca ccagcatcag caccgcctac 240
atggaactga gcagcctgcg gagcgaggac accgccgtgt actactgtgc cagaggccag 300
ggctacaccc acagctgggg ccagggcacc atggtcacag tgtccagc            348
```

| | | |
|---|---|---|
| SEQ ID NO: 40 | moltype = AA length = 107 | |
| FEATURE | Location/Qualifiers | |
| source | 1..107 | |
| | mol_type = protein | |
| | note = Amino acid sequence of the variable light (VL) | |
| | region of anti-c-Met antibody clone B09-GL | |
| | organism = synthetic construct | |
| SEQUENCE: 40 | | |
| DIQMTQSPST LSASVGDRVT ITCRASEGIY HWLAWYQQKP GKAPKLLIYK ASSLASGVPS | | 60 |
| RFSGSGSGTE FTLTISSLQP DDFATYYCQQ YSNYPPTFGG GTKLEIK | | 107 |

| | | |
|---|---|---|
| SEQ ID NO: 41 | moltype = DNA length = 321 | |
| FEATURE | Location/Qualifiers | |
| source | 1..321 | |
| | mol_type = other DNA | |
| | note = Nucleic acid sequence of the VL region of anti-c-Met | |
| | antibody clone B09-GL | |
| | organism = synthetic construct | |
| SEQUENCE: 41 | | |
| gacatccaga tgacccagag ccccagcacc ctgagcgcca gcgtcggcga cagagtgacc | | 60 |
| atcacctgtc gggccagcga gggcatctac cactggctgg cctggtatca gcagaagccc | | 120 |
| ggcaaggccc ccaagctgct gatctacaag gccagcagcc tggccagcga agtccctagc | | 180 |
| agatttctg gcagcggcag cggcaccgag ttcaccctga ccatcagcag cctgcagccc | | 240 |
| gacgacttcg ccacctacta ctgccagcag tacagcaact accccccac cttcggcgga | | 300 |
| ggcaccaagc tggaaatcaa g | | 321 |

| | | |
|---|---|---|
| SEQ ID NO: 42 | moltype = AA length = 330 | |
| FEATURE | Location/Qualifiers | |
| source | 1..330 | |
| | mol_type = protein | |
| | note = Amino acid sequence of a human immunoglobulin G1 | |
| | heavy chain constant | |
| | organism = synthetic construct | |
| SEQUENCE: 42 | | |
| ASTKGPSVFP LAPSSKSTSG GTAALGCLVK DYFPEPVTVS WNSGALTSGV HTFPAVLQSS | | 60 |
| GLYSLSSVVT VPSSSLGTQT YICNVNHKPS NTKVDKKVEP KSCDKTHTCP PCPAPELLGG | | 120 |
| PSVFLFPPKP KDTLMISRTP EVTCVVVDVS HEDPEVKFNW YVDGVEVHNA KTKPREEQYN | | 180 |
| STYRVVSVLT VLHQDWLNGK EYKCKVSNKA LPAPIEKTIS KAKGQPREPQ VYTLPPSRDE | | 240 |
| LTKNQVSLTC LVKGFYPSDI AVEWESNGQP ENNYKTTPPV LDSDGSFFLY SKLTVDKSRW | | 300 |
| QQGNVFSCSV MHEALHNHYT QKSLSLSPGK | | 330 |

| | | |
|---|---|---|
| SEQ ID NO: 43 | moltype = AA length = 330 | |
| FEATURE | Location/Qualifiers | |
| source | 1..330 | |
| | mol_type = protein | |
| | note = Amino acid sequence of a human immunoglobulin G1 CH | |
| | region modified to include 'Knob' mutation, interchain | |
| | cysteine mutations, a cysteine to form a stabilizing | |
| | disulfide bridge and with a cysteine insertion | |
| | organism = synthetic construct | |
| SEQUENCE: 43 | | |
| ASTKGPSVCP LAPSSKSTSG GTAALGCLVK DYFPEPVTVS WNSGALTSGV HTFPAVLQSS | | 60 |
| GLYSLSSVVT VPSSSLGTQT YICNVNHKPS NTKVDKRVEP KSCDKTHTCP PCPAPELLGG | | 120 |
| PSCVFLFPPK PKDTLMISRT PEVTCVVVDV SHEDPEVKFN WYVDGVEVHN AKTKPREEQY | | 180 |
| NSTYRVVSVL TVLHQDWLNG KEYKCKVSNK ALPAPIEKTI SKAKGQPREP QVYTLPPCRE | | 240 |
| EMTKNQVSLW CLVKGFYPSD IAVEWESNGQ PENNYKTTPP VLDSDGSFFL YSKLTVDKSR | | 300 |
| WQQGNVFSCS VMHEALHNHY TQKSLSLSPG | | 330 |

| | | |
|---|---|---|
| SEQ ID NO: 44 | moltype = AA length = 329 | |
| FEATURE | Location/Qualifiers | |
| source | 1..329 | |
| | mol_type = protein | |
| | note = Amino acid sequence of a human immunoglobulin G1 CH | |
| | region modified to include 'Knob' mutation, interchain | |
| | cysteine mutations, a cysteine to form a stabilizing | |
| | disulfide bridge and without a cysteine insertion | |
| | organism = synthetic construct | |
| SEQUENCE: 44 | | |
| ASTKGPSVCP LAPSSKSTSG GTAALGCLVK DYFPEPVTVS WNSGALTSGV HTFPAVLQSS | | 60 |
| GLYSLSSVVT VPSSSLGTQT YICNVNHKPS NTKVDKRVEP KSCDKTHTCP PCPAPELLGG | | 120 |
| PSVFLFPPKP KDTLMISRTP EVTCVVVDVS HEDPEVKFNW YVDGVEVHNA KTKPREEQYN | | 180 |
| STYRVVSVLT VLHQDWLNGK EYKCKVSNKA LPAPIEKTIS KAKGQPREPQ VYTLPPCREE | | 240 |
| MTKNQVSLWC LVKGFYPSDI AVEWESNGQP ENNYKTTPPV LDSDGSFFLY SKLTVDKSRW | | 300 |
| QQGNVFSCSV MHEALHNHYT QKSLSLSPG | | 329 |

| | | |
|---|---|---|
| SEQ ID NO: 45 | moltype = AA length = 331 | |
| FEATURE | Location/Qualifiers | |
| source | 1..331 | |
| | mol_type = protein | |

```
                    note = Amino acid sequence of a human immunoglobulin G1 CH
                      region modified to include 'Hole' mutations, a cysteine to
                      form a stabilizing disulfide bridge and with a cysteine
                      insertion
                    organism = synthetic construct
SEQUENCE: 45
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSCVFLFPPK PKDTLMISRT PEVTCVVVDV SHEDPEVKFN WYVDGVEVHN AKTKPREEQY    180
NSTYRVVSVL TVLHQDWLNG KEYKCKVSNK ALPAPIEKTI SKAKGQPREP QVCTLPPSRE    240
EMTKNQVSLS CAVKGFYPSD IAVEWESNGQ PENNYKTTPP VLDSDGSFFL VSKLTVDKSR    300
WQQGNVFSCS VMHEALHNHY TQKSLSLSPG K                                   331

SEQ ID NO: 46           moltype = AA  length = 330
FEATURE                 Location/Qualifiers
source                  1..330
                        mol_type = protein
                        note = Amino acid sequence of a human immunoglobulin G1 CH
                          region modified to include 'Hole' mutations, a cysteine to
                          form a stabilizing disulfide bridge and without a cysteine
                          insertion
                        organism = synthetic construct
SEQUENCE: 46
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VCTLPPSREE    240
MTKNQVSLSC AVKGFYPSDI AVEWESNGQP ENNYKTTPPV LDSDGSFFLV SKLTVDKSRW    300
QQGNVFSCSV MHEALHNHYT QKSLSLSPGK                                    330

SEQ ID NO: 47           moltype = AA  length = 107
FEATURE                 Location/Qualifiers
source                  1..107
                        mol_type = protein
                        note = Amino acid sequence of a wild-type human
                          immunoglobulin kappa constant region (
                        organism = synthetic construct
SEQUENCE: 47
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                 107

SEQ ID NO: 48           moltype = AA  length = 107
FEATURE                 Location/Qualifiers
source                  1..107
                        mol_type = protein
                        note = Amino acid sequence of a human immunoglobulin kappa
                          constant region modified to include S121C and C214V
                          substitutions
                        organism = synthetic construct
SEQUENCE: 48
RTVAAPSVFI FPPCDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEV                 107

SEQ ID NO: 49           moltype = AA  length = 106
FEATURE                 Location/Qualifiers
source                  1..106
                        mol_type = protein
                        note = Amino acid sequence of a human immunoglobulin lambda
                          constant region
                        organism = synthetic construct
SEQUENCE: 49
GQPKAAPSVT LFPPSSEELQ ANKATLVCLI SDFYPGAVTV AWKADSSPVK AGVETTTPSK     60
QSNNKYAASS YLSLTPEQWK SHRSYSCQVT HEGSTVEKTV APTECS                  106

SEQ ID NO: 50           moltype = AA  length = 446
FEATURE                 Location/Qualifiers
source                  1..446
                        mol_type = protein
                        note = Amino acid sequence of the heavy chain of anti-c-Met
                          antibody clone B09-GL with cysteine insertion
                        organism = synthetic construct
SEQUENCE: 50
QVQLVQSGAE VKKPGASVKV SCKASGYTFT DYYIHWVRQA TGQGLEWMGW MNPNSGNTGY     60
AQKFQGRVTM TRDTSISTAY MELSSLRSED TAVYYCARGQ GYTHSWGQGT MVTVSSASTK    120
GPSVCPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSVD KTHTCPPCPA PELLGGPSCV    240
FLFPPKPKDT LMISRTPEVT CVVVDVSHED PEVKFNWYVD GVEVHNAKTK PREEQYNSTY    300
```

```
RVVSVLTVLH QDWLNGKEYK CKVSNKALPA PIEKTISKAK GQPREPQVYT LPPCREEMTK    360
NQVSLWCLVK GFYPSDIAVE WESNGQPENN YKTTPPVLDS DGSFFLYSKL TVDKSRWQQG    420
NVFSCSVMHE ALHNHYTQKS LSLSPG                                        446

SEQ ID NO: 51            moltype = AA  length = 445
FEATURE                  Location/Qualifiers
source                   1..445
                         mol_type = protein
                         note = Amino acid sequence of the heavy chain of anti-c-Met
                           antibody clone B09-GL without cysteine insertion
                         organism = synthetic construct
SEQUENCE: 51
QVQLVQSGAE VKKPGASVKV SCKASGYTFT DYYIHWVRQA TGQGLEWMGW MNPNSGNTGY     60
AQKFQGRVTM TRDTSISTAY MELSSLRSED TAVYYCARGQ GYTHSWQGT MVTVSSASTK    120
GPSVCPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSVD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPCREEMTKN    360
QVSLWCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 52            moltype = AA  length = 214
FEATURE                  Location/Qualifiers
source                   1..214
                         mol_type = protein
                         note = Amino acid sequence of the light chain of anti-c-Met
                           antibody clone B09-GL
                         organism = synthetic construct
SEQUENCE: 52
DIQMTQSPST LSASVGDRVT ITCRASEGIY HWLAWYQQKP GKAPKLLIYK ASSLASGVPS     60
RFSGSGSGTE FTLTISSLQP DDFATYYCQQ YSNYPPTFGG GTKLEIKRTV AAPSVFIFPP    120
CDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEV                                214

SEQ ID NO: 53            moltype = AA  length = 455
FEATURE                  Location/Qualifiers
source                   1..455
                         mol_type = protein
                         note = Amino acid sequence of the heavy chain of anti-EGFR
                           antibody clone QD6 without cysteine insertion
                         organism = synthetic construct
SEQUENCE: 53
QVQLVQSGAE VKKPGSSVKV SCKASGGTFS DNDFSWVRQA PGQGLEWMGA IVAVVRTETY     60
AQKFQDRVKI TADISTRTTY MELSSLRSED TAVYYCARRL MSAISGPGAP LLMWGQGTLV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK RVEPKSCDKT HTCPPCPAPE    240
LLGGPSCVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALPAPI EKTISKAKGQ PREPQVCTLP    360
PSREEMTKNQ VSLSCAVKGF YPSDIAVEWE SNGQPENNYK TTPPVLDSDG SFFLVSKLTV    420
DKSRWQQGNV FSCSVMHEAL HNHYTQKSLS LSPGK                              455

SEQ ID NO: 54            moltype = AA  length = 454
FEATURE                  Location/Qualifiers
source                   1..454
                         mol_type = protein
                         note = Amino acid sequence of the heavy chain of anti-EGFR
                           antibody clone QD6 without cysteine insertion
                         organism = synthetic construct
SEQUENCE: 54
QVQLVQSGAE VKKPGSSVKV SCKASGGTFS DNDFSWVRQA PGQGLEWMGA IVAVVRTETY     60
AQKFQDRVKI TADISTRTTY MELSSLRSED TAVYYCARRL MSAISGPGAP LLMWGQGTLV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK RVEPKSCDKT HTCPPCPAPE    240
LLGGPSVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPAPIE KTISKAKGQP REPQVCTLPP    360
SREEMTKNQV SLSCAVKGFY PSDIAVEWES NGQPENNYKT TPPVLDSDGS FFLVSKLTVD    420
KSRWQQGNVF SCSVMHEALH NHYTQKSLSL SPGK                               454

SEQ ID NO: 55            moltype = AA  length = 217
FEATURE                  Location/Qualifiers
source                   1..217
                         mol_type = protein
                         note = Amino acid sequence of the light chain of anti-EGFR
                           antibody clone QD6
                         organism = synthetic construct
SEQUENCE: 55
QSALTQPRSV SGSPGQSVTI SCTGTSSDVG GYNYVSWYQQ HPGKAPKLMI YDVSERPSGV     60
PDRFSGSKSG NTASLTISGL QAEDEADYYC FSYTSSDTLE IFGGGTKLTV LGQPKAAPSV    120
TLFPPSSEEL QANKATLVCL ISDFYPGAVT VAWKADSSPV KAGVETTTPS KQSNNKYAAS    180
```

```
SYLSLTPEQW KSHRSYSCQV THEGSTVEKT VAPTECS                                 217

SEQ ID NO: 56           moltype = AA  length = 455
FEATURE                 Location/Qualifiers
source                  1..455
                        mol_type = protein
                        note = Amino acid sequence of the heavy chain of anti-EGFR
                          antibody clone RAA22 with cysteine insertion
                        organism = synthetic construct
SEQUENCE: 56
QVQLVQSGAE VKKPGSSVKV SCKASGGTFS DNDFSWVRQA PGQGLEWMGA IVAVFRTETY          60
AQKFQDRVKI TADISTRTTY MELSSLRSED TAVYYCARRL MSAISGPGAP LLMWGQGTLV         120
TVSSASTKGP SVFPLAPSSK STSGGTAALG CLVKDYFPEP VTVSWNSGAL TSGVHTFPAV         180
LQSSGLYSLS SVVTVPSSSL GTQTYICNVN HKPSNTKVDK RVEPKSCDKT HTCPPCPAPE         240
LLGGPSCVFL FPPKPKDTLM ISRTPEVTCV VVDVSHEDPE VKFNWYVDGV EVHNAKTKPR         300
EEQYNSTYRV VSVLTVLHQD WLNGKEYKCK VSNKALPAPI EKTISKAKGQ PREPQVCTLP         360
PSREEMTKNQ VSLSCAVKGF YPSDIAVEWE SNGQPENNYK TTPPVLDSDG SFFLVSKLTV         420
DKSRWQQGNV FSCSVMHEAL HNHYTQKSLS LSPGK                                   455

SEQ ID NO: 57           moltype = AA  length = 455
FEATURE                 Location/Qualifiers
source                  1..455
                        mol_type = protein
                        note = Amino acid sequence of the heavy chain of anti-EGFR
                          antibody clone RAA22 without cysteine insertion
                        organism = synthetic construct
SEQUENCE: 57
QVQLVQSGAE VKKPGSSVKV SCKASGGTFS DNDFSWVRQA PGQGLEWMGA IVAVFRTETY          60
AQKFQDRVKI TADISTRTTY MELSSLRSED TAVYYCARRL MSAISGPGAP LLMWGQGTLV         120
TVSSASTKGP SVFPLAPSSK STSGGTAALG CLVKDYFPEP VTVSWNSGAL TSGVHTFPAV         180
LQSSGLYSLS SVVTVPSSSL GTQTYICNVN HKPSNTKVDK RVEPKSCDKT HTCPPCPAPE         240
LLGGPSCVFL FPPKPKDTLM ISRTPEVTCV VVDVSHEDPE VKFNWYVDGV EVHNAKTKPR         300
EEQYNSTYRV VSVLTVLHQD WLNGKEYKCK VSNKALPAPI EKTISKAKGQ PREPQVCTLP         360
PSREEMTKNQ VSLSCAVKGF YPSDIAVEWE SNGQPENNYK TTPPVLDSDG SFFLVSKLTV         420
DKSRWQQGNV FSCSVMHEAL HNHYTQKSLS LSPGK                                   455

SEQ ID NO: 58           moltype = AA  length = 217
FEATURE                 Location/Qualifiers
source                  1..217
                        mol_type = protein
                        note = Amino acid sequence of the light chain of anti-EGFR
                          antibody clone RAA22
                        organism = synthetic construct
SEQUENCE: 58
QSALTQPRSV SGSPGQSVTI SCTGTSSDVG GYNYVSWYQQ HPGKAPKLMI YDVSKRPSGV          60
PDRFSGSKSG NTASLTISGL QAEDEADYYC SSYTSSDTLE IFGGGTKLTV LGQPKAAPSV         120
TLFPPSSEEL QANKATLVCL ISDFYPGAVT VAWKADSSPV KAGVETTTPS KQSNNKYAAS         180
SYLSLTPEQW KSHRSYSCQV THEGSTVEKT VAPTECS                                 217

SEQ ID NO: 59           moltype = AA  length = 454
FEATURE                 Location/Qualifiers
source                  1..454
                        mol_type = protein
                        note = Amino acid sequence of the heavy chain of anti-EGFR
                          in 'EGFR-cMET TM' antibody
                        organism = synthetic construct
SEQUENCE: 59
QVQLVQSGAE VKKPGSSVKV SCKASGGTFS DNDFSWVRQA PGQGLEWMGA IVAVFRTETY          60
AQKFQDRVKI TADISTRTTY MELSSLRSED TAVYYCARRL MSAISGPGAP LLMWGQGTLV         120
TVSSASTKGP SVCPLAPSSK STSGGTAALG CLVKDYFPEP VTVSWNSGAL TSGVHTFPAV         180
LQSSGLYSLS SVVTVPSSSL GTQTYICNVN HKPSNTKVDK RVEPKSVDKT HTCPPCPAPE         240
FEGGPSVFLF PPKPKDTLMI SRTPEVTCVV VDVSHEDPEV KFNWYVDGVE VHNAKTKPRE         300
EQYNSTYRVV SVLTVLHQDW LNGKEYKCKV SNKALPASIE KTISKAKGQP REPQVYTLPP         360
CREEMTKNQV SLWCLVKGFY PSDIAVEWES NGQPENNYKT TPPVLDSDGS FFLYSKLTVD         420
KSRWQQGNVF SCSVMHEALH NHYTQKSLSL SPGK                                    454

SEQ ID NO: 60           moltype = AA  length = 446
FEATURE                 Location/Qualifiers
source                  1..446
                        mol_type = protein
                        note = Amino acid sequence of the heavy chain of anti-c-Met
                          in 'EGFR-cMET TM' antibody
                        organism = synthetic construct
SEQUENCE: 60
QVQLVQSGAE VKKPGASVKV SCKASGYTFT DYYIHWVRQA TGQGLEWMGW MNPNSGNTGY          60
AQKFQGRVTM TRDTSISTAY MELSSLRSED TAVYYCARGQ GYTHSWGQGT MVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKRVEPKSCD KTHTCPPCPA PEFEGGPSVF         240
LFPPKPKDTL MISRTPEVTC VVVDVSHEDP EVKFNWYVDG VEVHNAKTKP REEQYNSTYR         300
```

```
VVSVLTVLHQ DWLNGKEYKC KVSNKALPAS IEKTISKAKG QPREPQVCTL PPSREEMTKN   360
QVSLSCAVKG FYPSDIAVEW ESNGQPENNY KTTPPVLDSD GSFFLVSKLT VDKSRWQQGN   420
VFSCSVMHEA LHNHYTQKSL SLSPGK                                       446

SEQ ID NO: 61              moltype = AA  length = 217
FEATURE                    Location/Qualifiers
source                     1..217
                           mol_type = protein
                           note = Amino acid sequence of the light chain of anti-EGFR
                             in 'EGFR-cMET TM' antibody
                           organism = synthetic construct
SEQUENCE: 61
QSALTQPRSV SGSPGQSVTI SCTGTSSDVG GYNYVSWYQQ HPGKAPKLMI YDVSKRPSGV   60
PDRFSGSKSG NTASLTISGL QAEDEADYYC SSYTSSDTLE IFGGGTKLTV LGQPKAAPSV   120
TLFPPCSEEL QANKATLVCL ISDFYPGAVT VAWKADSSPV KAGVETTTPS KQSNNKYAAS   180
SYLSLTPEQW KSHRSYSCQV THEGSTVEKT VAPTEVS                           217

SEQ ID NO: 62              moltype = AA  length = 214
FEATURE                    Location/Qualifiers
source                     1..214
                           mol_type = protein
                           note = Amino acid sequence of the light chain of anti-c-Met
                             in 'EGFR-cMET TM' antibody
                           organism = synthetic construct
SEQUENCE: 62
DIQMTQSPST LSASVGDRVT ITCRASEGIY HWLAWYQQKP GKAPKLLIYK ASSLASGVPS   60
RFSGSGSGTE FTLTISSLQP DDFATYYCQQ YSNYPPTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 63              moltype = AA  length = 330
FEATURE                    Location/Qualifiers
source                     1..330
                           mol_type = protein
                           note = Amino acid sequence of a human immunoglobulin G1 CH
                             region modified to include 'knob' mutations, a cysteine to
                             form a stabilizing disulfide bridge, without a cysteine
                             insertion and with the TM
                           organism = synthetic construct
SEQUENCE: 63
ASTKGPSVCP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSVDKTHTCP PCPAPEFEGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPASIEKTIS KAKGQPREPQ VYTLPPCREE   240
MTKNQVSLWC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 64              moltype = AA  length = 330
FEATURE                    Location/Qualifiers
source                     1..330
                           mol_type = protein
                           note = Amino acid sequence of a human immunoglobulin G1 CH
                             region modified to include 'Hole' mutations, a cysteine to
                             form a stabilizing disulfide bridge, without a cysteine
                             insertion and with the TM
                           organism = synthetic construct
SEQUENCE: 64
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEFEGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPASIEKTIS KAKGQPREPQ VCTLPPSREE   240
MTKNQVSLSC AVKGFYPSDI AVEWESNGQP ENNYKTTPPV LDSDGSFFLV SKLTVDKSRW   300
QQGNVFSCSV MHEALHNHYT QKSLSLSPGK                                   330

SEQ ID NO: 65              moltype = AA  length = 106
FEATURE                    Location/Qualifiers
source                     1..106
                           mol_type = protein
                           note = Amino acid sequence of a human immunoglobulin lambda
                             constant region modified to include S121C and C214V
                             substitutions
                           organism = synthetic construct
SEQUENCE: 65
GQPKAAPSVT LFPPCSEELQ ANKATLVCLI SDFYPGAVTV AWKADSSPVK AGVETTTPSK   60
QSNNKYAASS YLSLTPEQWK SHRSYSCQVT HEGSTVEKTV APTEVS                 106

SEQ ID NO: 66              moltype = AA  length = 7
FEATURE                    Location/Qualifiers
source                     1..7
```

```
                        mol_type = protein
                        note = LCDR2
                        organism = synthetic construct
SEQUENCE: 66
DVSERPS                                                                  7

SEQ ID NO: 67           moltype = AA   length = 11
FEATURE                 Location/Qualifiers
source                  1..11
                        mol_type = protein
                        note = LCDR3
                        organism = synthetic construct
SEQUENCE: 67
FSYTSSDTLE I                                                            11

SEQ ID NO: 68           moltype = AA   length = 621
FEATURE                 Location/Qualifiers
source                  1..621
                        mol_type = protein
                        note = Amino acid sequence of the human EGFR extracellular
                          domain
                        organism = synthetic construct
SEQUENCE: 68
LEEKKVCQGT SNKLTQLGTF EDHFLSLQRM FNNCEVVLGN LEITYVQRNY DLSFLKTIQE   60
VAGYVLIALN TVERIPLENL QIIRGNMYYE NSYALAVLSN YDANKTGLKE LPMRNLQEIL  120
HGAVRFSNNP ALCNVESIQW RDIVSSDFLS NMSMDFQNHL GSCQKCDPSC PNGSCWGAGE  180
ENCQKLTKII CAQQCSGRCR GKSPSDCCHN QCAAGCTGPR ESDCLVCRKF RDEATCKDTC  240
PPLMLYNPTT YQMDVNPEGK YSFGATCVKK CPRNYVVTDH GSCVRACGAD SYEMEEDGVR  300
KCKKCEGPCR KVCNGIGIGE FKDSLSINAT NIKHFKNCTS ISGDLHILPV AFRGDSFTHT  360
PPLDPQELDI LKTVKEITGF LLIQAWPENR TDLHAFENLE IIRGRTKQHG QFSLAVVSLN  420
ITSLGLRSLK EISDGDVIIS GNKNLCYANT INWKKLFGTS GQKTKIISNR GENSCKATGQ  480
VCHALCSPEG CWGPEPRDCV SCRNVSRGRE CVDKCNLLEG EPREFVENSE CIQCHPECLP  540
QAMNITCTGR GPDNCIQCAH YIDGPHCVKT CPAGVMGENN TLVWKYADAG HVCHLCHPNC  600
TYGCTGPGLE GCPTNGPKIP S                                            621

SEQ ID NO: 69           moltype = AA   length = 621
FEATURE                 Location/Qualifiers
source                  1..621
                        mol_type = protein
                        note = Amino acid sequence of the cynomolgus monkey EGFR
                          extracellular domain
                        organism = synthetic construct
SEQUENCE: 69
LEEKKVCQGT SNKLTQLGTF EDHFLSLQRM FNNCEVVLGN LEITYVQRNY DLSFLKTIQE   60
VAGYVLIALN TVERIPLENL QIIRGNMYYE NSYALAVLSN YDANKTGLKE LPMRNLQEIL  120
HGAVRFSNNP ALCNVESIQW RDIVSSEFLS NMSMDFQNHL GSCQKCDPSC PNGSCWGAGE  180
ENCQKLTKII CAQQCSGRCR GKSPSDCCHN QCAAGCTGPR ESDCLVCRKF RDEATCKDTC  240
PPLMLYNPTT YQMDVNPEGK YSFGATCVKK CPRNYVVTDH GSCVRACGAD SYEMEEDGVR  300
KCKKCEGPCR KVCNGIGIGE FKDTLSINAT NIKHFKNCTS ISGDLHILPV AFRGDSFTHT  360
PPLDPQELDI LKTVKEITGF LLIQAWPENR TDLHAFENLE IIRGRTKQHG QFSLAVVSLN  420
ITSLGLRSLK EISDGDVIIS GNKNLCYANT INWKKLFGTS SQKTKIISNR GENSCKATGQ  480
VCHALCSPEG CWGPEPRDCV SCQNVSRGRE CVDKCNILEG EPREFVENSE CIQCHPECLP  540
QVMNITCTGR GPDNCIQCAH YIDGPHCVKT CPAGVMGENN TLVWKYADAG HVCHLCHPNC  600
TYGCTGPGLE GCARNGPKIP S                                            621

SEQ ID NO: 70           moltype = AA   length = 908
FEATURE                 Location/Qualifiers
source                  1..908
                        mol_type = protein
                        note = Amino acid sequence of the human c-Met extracellular
                          domain
                        organism = synthetic construct
SEQUENCE: 70
ECKEALAKSE MNVNMKYQLP NFTAETPIQN VILHEHHIFL GATNYIYVLN EEDLQKVAEY   60
KTGPVLEHPD CFPCQDCSSK ANLSGGVWKD NINMALVVDT YYDDQLISCG SVNRGTCQRH  120
VFPHNHTADI QSEVHCIFSP QIEEPSQCPD CVVSALGAKV LSSVKDRFIN FFVGNTINSS  180
YFPDHPLHSI SVRRLKETKD GFMFLTDQSY IDVLPEFRDS YPIKYVHAFE SNNFIYFLTV  240
QRETLDAQTF HTRIIRFCSI NSGLHSYMEM PLECILTEKR KKRSTKKEVF NILQAAYVSK  300
PGAQLARQIG ASLNDDILFG VFAQSKPDSA EPMDRSAMCA FPIKYVNDFF NKIVNKNNVR  360
CLQHFYGPNH EHCFNRTLLR NSSGCEARRD EYRTEFTTAL QRVDLFMGQF SEVLLTSIST  420
FIKGDLTIAN LGTSEGRFMQ VVVSRSGPST PHVNFLLDSH PVSPEVIVEH TLNQNGYTLV  480
ITGKKITKIP LNGLGCRHFQ SCSQCLSAPP FVQCGWCHDK CVRSEECLSG TWTQQICLPA  540
IYKVFPNSAP LEGGTRLTIC GWDFGFRRNN KFDLKKTRVL LGNESCTLTL SESTMNTLKC  600
TVGPAMNKHF NMSIIISNGH GTTQYSTFSY VDPVITSISP KYGPMAGGTL LTLTGNYLNS  660
GNSRHISIGG KTCTLKSVSN SILECYTPAQ TISTEFAVKL KIDLANRETS IFSYREDPIV  720
YEIHPTKSFI SGGSTITGVG KNLNSVSVPR MVINVHEAGR NFTVACQHRS NSEIICCTTP  780
SLQQLNLQLP LKTKAFFMLD GILSKYFDLI YVHNPVFKPF EKPVMISMGN ENVLEIKGND  840
IDPEAVKGEV LKVGNKSCEN IHLHSEAVLC TVPNDLLKLN SELNIEWKQA ISSTVLGKVI  900
VQPDQNFT                                                           908
```

```
SEQ ID NO: 71          moltype = AA  length = 908
FEATURE                Location/Qualifiers
source                 1..908
                       mol_type = protein
                       note = Amino acid sequence of the cynomolgus monkey c-Met
                         extracellular domain
                       organism = synthetic construct
SEQUENCE: 71
ECKEALAKSE MNVNMKYQLP NFTAETAIQN VILHEHHIFL GATNYIYVLN EEDLQKVAEY   60
KTGPVLEHPD CFPCQDCSSK ANLSGGVWKD NINMALVVDT YYDDQLISCG SVNRGTCQRH  120
VFPHNHTADI QSEVHCIFSP QIEEPNQCPD CVVSALGAKV LSSVKDRFIN FFVGNTINSS  180
YFPHHPLHSI SVRRLKETKD GFMFLTDQSY IDVLPEFRDS YPIKYIHAFE SNNFIYFLTV  240
QRETLNAQTF HTRIIRFCSL NSGLHSYMEM PLECILTEKR KKRSTKKEVF NILQAAYVSK  300
PGAQLARQIG ASLNDDILFG VFAQSKPDSA EPMDRSAMCA FPIKYVNDFF NKIVNKNNVR  360
CLQHFYGPNH EHCFNRTLLR NSSGCEARRD EYRAEFTTAL QRVDLFMGQF SEVLLTSIST  420
FVKGDLTIAN LGTSEGRFMQ VVVSRSGPST PHVNFLLDSH PVSPEVIVEH PLNQNGYTLV  480
VTGKKITKIP LNGLGCRHFQ SCSQCLSAPP FVQCGWCHDK CVRSEECPSG TWTQQICLPA  540
IYKVFPTSAP LEGGTRLTIC GWDFGFRRNN KFDLKKTRVL LGNESCTLTL SESTMNTLKC  600
TVGPAMNKHF NMSIIISNGH GTTQYSTFSY VDPIITSISP KYGPMAGGTL LTLTGNYLNS  660
GNSRHISIGG KTCTLKSVSN SILECYTPAQ TISTEFAVKL KIDLANRETS IFSYREDPIV  720
YEIHPTKSFI SGGSTITGVG KNLHSVSVPR MVINVHEAGR NFTVACQHRS NSEIICCTTP  780
SLQQLNLQLP LKTKAFFMLD GILSKYFDLI YVHNPVFKPF EKPVMISMGN ENVLEIKGND  840
IDPEAVKGEV LKVGNKSCEN IHLHSEAVLC TVPNDLLKLN SELNIEWKQA ISSTVLGKVI  900
VQPDQNFT                                                          908
```

The invention claimed is:

1. An antibody molecule comprising:
a first antigen-binding domain that binds epidermal growth factor receptor (EGFR); and
a second antigen-binding domain that binds c-Met, wherein the first antigen-binding domain comprises:
(i) a heavy chain variable (VH) region comprising the following complementarity determining regions (CDRs):
HCDR1 having the amino acid sequence of SEQ ID NO: 1
HCDR2 having the amino acid sequence of SEQ ID NO: 2
HCDR3 having the amino acid sequence of SEQ ID NO: 3; and
(ii) a light chain variable (VL) region comprising the following CDRs:
LCDR1 having the amino acid sequence of SEQ ID NO: 4
LCDR2 having the amino acid sequence of SEQ ID NO: 5
LCDR3 having the amino acid sequence of SEQ ID NO: 6.

2. The antibody molecule according to claim 1, wherein the first antigen-binding domain comprises:
a VH region comprising an amino acid sequence having at least 70%, at least 80%, at least 90%, or at least 95% sequence identity to the amino acid sequence of SEQ ID NO: 16; and
a VL region comprising an amino acid sequence having at least 70%, at least 80%, at least 90%, or at least 95% sequence identity to the amino acid sequence of SEQ ID NO: 20.

3. The antibody molecule according to claim 1, wherein the second antigen-binding domain comprises:
(i) a heavy chain variable (VH) region comprising the following complementarity determining regions (CDRs):
HCDR1 having the amino acid sequence of SEQ ID NO: 24
HCDR2 having the amino acid sequence of SEQ ID NO: 25
HCDR3 having the amino acid sequence of SEQ ID NO: 26; and
(ii) a light chain variable (VL) region comprising the following CDRs:
LCDR1 having the amino acid sequence of SEQ ID NO: 27
LCDR2 having the amino acid sequence of SEQ ID NO: 28
LCDR3 having the amino acid sequence of SEQ ID NO: 29.

4. The antibody molecule according to claim 3, wherein the second antigen-binding domain comprises:
a VH region comprising an amino acid sequence having at least 70%, at least 80%, at least 90%, or at least 95% sequence identity to the amino acid sequence of SEQ ID NO: 38; and
a VL region comprising an amino acid sequence having at least 70%, at least 80%, at least 90%, or at least 95% sequence identity to the amino acid sequence of SEQ ID NO: 40.

5. The antibody molecule according to claim 1, wherein antibody molecule comprises:
a first heavy chain, wherein the first heavy chain comprises the VH region of the first antigen-binding domain, and a first heavy chain constant (CH) region or a fragment thereof;
a first light chain, wherein the first light chain comprises the VL region of the first antigen-binding domain, and a first light chain constant (CL) region or a fragment thereof;
a second heavy chain, wherein the second heavy chain comprises the VH region of the second antigen-binding domain, and a second heavy chain constant (CH) region or a fragment thereof; and
a second light chain, wherein the second light chain comprises the VL region of the second antigen-binding domain, and a second light chain constant (CL) region or a fragment thereof.

6. The antibody molecule according to claim 5, wherein the first and second heavy chain form a heterodimer, optionally wherein one of the first and second heavy chains comprises a cysteine (C) residue at position 354 and a tryptophan (W) residue at position 366 and the other heavy chain comprises a cysteine (C) residue at position 349, a valine (V) residue at position 407, a serine (S) at position 366 and an alanine (A) at position 368, wherein the numbering of the constant region is as per the EU index.

7. The antibody molecule according to claim 5, wherein the antibody molecule comprises:
  (a) a modified CH region, wherein the modified CH region comprises a substitution of a native non-cysteine amino acid to a cysteine amino acid; and
  (b) a modified corresponding CL region, wherein the modified CL comprises a substitution of a native non-cysteine amino acid to a cysteine amino acid, wherein either;
    (i) the first heavy chain comprises the modified CH region and the first light chain comprises the modified corresponding CL region; or
    (ii) the second heavy chain comprises the modified CH region and the second light chain comprises the modified corresponding CL region, and
  wherein the substituted cysteine of the modified CH region and the substituted cysteine of the modified corresponding light chain can form a disulphide bond.

8. The antibody molecule according to claim 7, wherein the modified CH region comprises a substitution of a native non-cysteine amino acid to a cysteine amino acid at position 126; and the modified corresponding CL region comprises a substitution of a native non-cysteine amino acid to a cysteine amino acid at position 121, wherein the numbering of the constant region is as per the EU index.

9. The antibody molecule according to claim 5, wherein the first and/or second CH region comprise a mutation to reduce or abrogate binding of the antibody molecule to one or more Fcγ receptors.

10. The antibody molecule according to claim 5, wherein the first and/or second CH region comprises a phenylalanine at position 234, glutamic acid at position 235, and serine at position 331, wherein the numbering of the constant region is as per the EU index.

11. The antibody molecule according to claim 5, wherein the first CH region comprises an amino acid sequence having at least 90%, 91%, 92%, 93%, 94%, 95%, 96%, 97%, 98%, 99%, or 100% sequence identity to the sequence set forth in SEQ ID NOs: 45, 46 or 63; and the second CH region comprises an amino acid sequence having at least 90%, 91%, 92%, 93%, 94%, 95%, 96%, 97%, 98%, 99%, or 100% sequence identity to the sequence set forth in SEQ ID NO: 43, 44 or 64, and optionally wherein the first CL region comprises an amino acid sequence having at least 90%, 91%, 92%, 93%, 94%, 95%, 96%, 97%, 98%, 99%, or 100% sequence identity to the sequence set forth in SEQ ID NO: 49 or 65; and the second CL region comprises an amino acid sequence having at least 90%, 91%, 92%, 93%, 94%, 95%, 96%, 97%, 98%, 99%, or 100% sequence identity to the sequence set forth in SEQ ID NO: 47 or 48.

12. The antibody molecule according to claim 11, wherein the first CH region comprises an amino acid sequence having at least 90%, 91%, 92%, 93%, 94%, 95%, 96%, 97%, 98%, 99%, or 100% sequence identity to the sequence set forth in SEQ ID NO: 63; and the second CH region comprises an amino acid sequence having at least 90%, 91%, 92%, 93%, 94%, 95%, 96%, 97%, 98%, 99%, or 100% sequence identity to the sequence set forth in SEQ ID NO: 64, and wherein the first CL region comprises an amino acid sequence having at least 90%, 91%, 92%, 93%, 94%, 95%, 96%, 97%, 98%, 99%, or 100% sequence identity to the sequence set forth in SEQ ID NO: 65; and the second CL region comprises an amino acid sequence having at least 90%, 91%, 92%, 93%, 94%, 95%, 96%, 97%, 98%, 99%, or 100% sequence identity to the sequence set forth in SEQ ID NO: 47.

13. The antibody molecule according to claim 11, wherein the first heavy chain comprises an amino acid sequence having at least 90%, 91%, 92%, 93%, 94%, 95%, 96%, 97%, 98%, 99%, or 100% sequence identity to the sequence set forth in SEQ ID NOs: 56, 57 or 59; and the second heavy chain comprises an amino acid sequence having at least 90%, 91%, 92%, 93%, 94%, 95%, 96%, 97%, 98%, 99%, or 100% sequence identity to the sequence set forth in SEQ ID NOs: 50, 51 or 60, and optionally wherein the first light chain comprises an amino acid sequence having at least 90%, 91%, 92%, 93%, 94%, 95%, 96%, 97%, 98%, 99%, or 100% sequence identity to the sequence set forth in SEQ ID NO: 58 or 61; and the second light chain comprises an amino acid sequence having at least 90%, 91%, 92%, 93%, 94%, 95%, 96%, 97%, 98%, 99%, or 100% sequence identity to the sequence set forth in SEQ ID NO: 52 or 62.

14. The antibody molecule according to claim 12, wherein the first heavy chain comprises an amino acid sequence having the sequence set forth in SEQ ID NO: 59; the second heavy chain comprises an amino acid sequence having the sequence set forth in SEQ ID NO: 60; the first light chain comprises an amino acid sequence having the sequence set forth in SEQ ID NO: 61; and the second light chain comprises an amino acid sequence having the sequence set forth in SEQ ID NO: 62.

15. A conjugate comprising the antibody molecule of claim 1 conjugated to a drug.

16. The conjugate according to claim 15, wherein the drug is a topoisomerase I inhibitor having formula A*

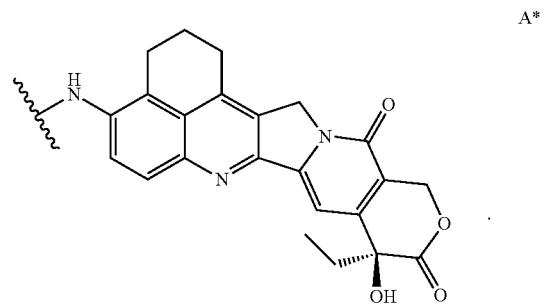 [SMILES: *Nc1ccc2nc3c(c4c2c1CCC4)Cn1c-3cc2c(c1=O)COC(=O)[C@]2(O)CC]

17. The conjugate according to claim 16, wherein the topoisomerase I inhibitor has formula I:

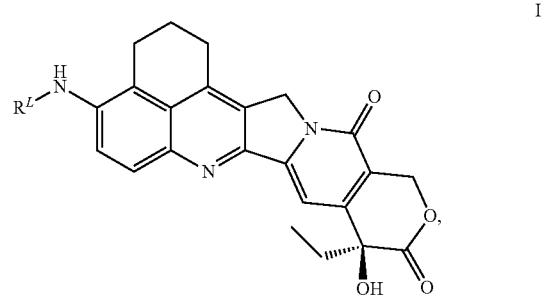

or a salt or solvates thereof, wherein $R^L$ is a linker for connection to the antibody molecule, optionally wherein said linker is selected from:

(ia):

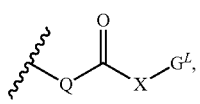

wherein
Q is:

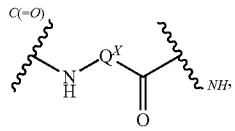

where $Q^X$ is such that Q is an amino-acid residue, a dipeptide residue, a tripeptide residue or a tetrapeptide residue;
X is:

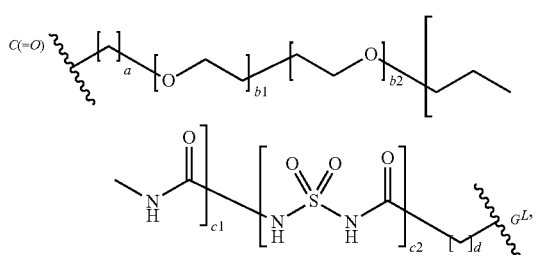

where a=0 to 5, b1=0 to 16, b2=0 to 16, c1=0 or 1, c2=0 or 1, d=0 to 5, wherein at least b1 or b2=0 (i.e. only one of b1 and b2 may not be 0) and at least c1 or c2=0 (i.e. only one of c1 and c2 may not be 0);
$G^L$ is a linker for connecting to the antibody molecule; or (ib):

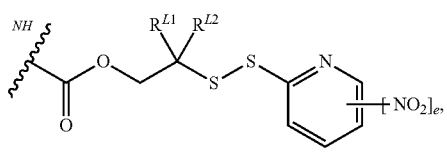

where $R^{L1}$ and $R^{L2}$ are independently selected from H and methyl, or together with the carbon atom to which they are bound form a cyclopropylene or cyclobutylene group; and
e is 0 or 1.

18. The conjugate of claim 15 having the formula IV:

or a pharmaceutically acceptable salt or solvate thereof, wherein:
L is the antibody molecule;
$D^L$ is drug having a linker; and
p is an integer from 1 to 20.

19. The conjugate according to claim 18, wherein p is a range selected from 2 to 8, 3 to 7, 4 to 7 or 5 to 7.

20. The conjugate according to claim 18, wherein $D^L$ is a topoisomerase I inhibitor having a linker that is of formula III:

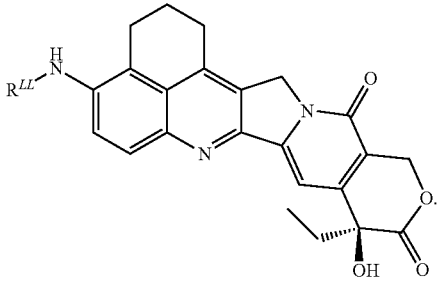

$R^{LL}$ is a linker connected to the antibody molecule, wherein the linker is selected from (Ia'):

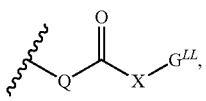

where Q is

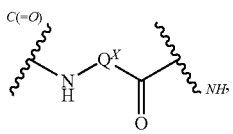

where $Q^X$ is such that Q is an amino-acid residue, a dipeptide residue, a tripeptide residue or a tetrapeptide residue;
X is:

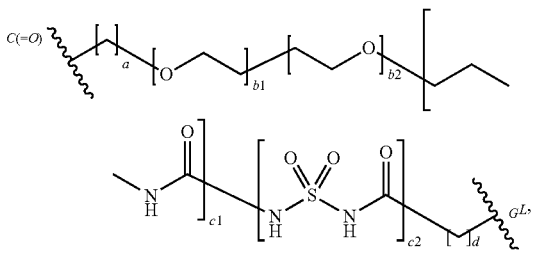

where a=0 to 5, b1=0 to 16, b2=0 to 16, c1=0 or 1, c2=0 or 1, d=0 to 5, wherein at least b1 or b2=0 (i.e. only one of b1 and b2 may not be 0) and at least c1 or c2=0 (i.e. only one of c1 and c2 may not be 0);
and GEL is a linker connected to the antibody molecule; and (Ib'):

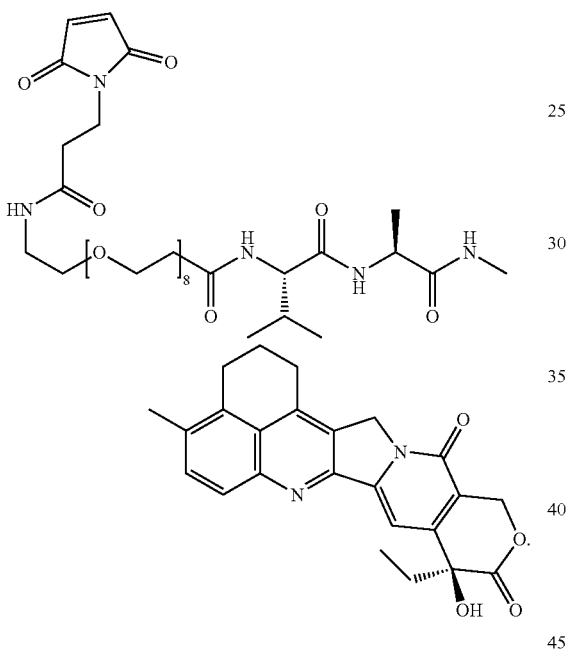

where $R^{L1}$ and $R^{L2}$ independently selected from H and methyl, or together with the carbon atom to which they are bound to form a cyclopropylene or cyclobutylene group.

21. The conjugate of claim 15, wherein the antibody molecule is conjugated to a topoisomerase I inhibitor having the following formula:

(SG3932)

22. A pharmaceutical composition comprising the conjugate according to claim 15, and a pharmaceutically acceptable carrier.

23. A nucleic acid encoding an antibody molecule according to claim 1.

24. An expression vector comprising the nucleic acid of claim 23.

25. A recombinant host cell comprising the nucleic acid according to claim 23.

26. A conjugate, comprising:
(a) an antibody molecule comprising a first antigen-binding domain that binds epidermal growth factor receptor (EGFR) wherein the first antigen-binding domain comprises:
(i) a heavy chain variable (VH) region comprising the following complementarity determining regions (CDRs):
HCDR1 having the amino acid sequence of SEQ ID NO: 1

HCDR2 having the amino acid sequence of SEQ ID NO: 2
HCDR3 having the amino acid sequence of SEQ ID NO: 3; and
(ii) a light chain variable (VL) region comprising the following CDRs:
LCDR1 having the amino acid sequence of SEQ ID NO: 4
LCDR2 having the amino acid sequence of SEQ ID NO: 5
LCDR3 having the amino acid sequence of SEQ ID NO: 6, and
a second antigen-binding domain that binds c-Met wherein the second antigen-binding domain comprises:
(i) a heavy chain variable (VH) region comprising the following complementarity determining regions (CDRs):
HCDR1 having the amino acid sequence of SEQ ID NO: 24
HCDR2 having the amino acid sequence of SEQ ID NO: 25
HCDR3 having the amino acid sequence of SEQ ID NO: 26; and
(ii) a light chain variable (VL) region comprising the following CDRs:
LCDR1 having the amino acid sequence of SEQ ID NO: 27
LCDR2 having the amino acid sequence of SEQ ID NO: 28
LCDR3 having the amino acid sequence of SEQ ID NO: 29; and
(b) a topoisomerase I inhibitor having the following formula:

(SG3932)

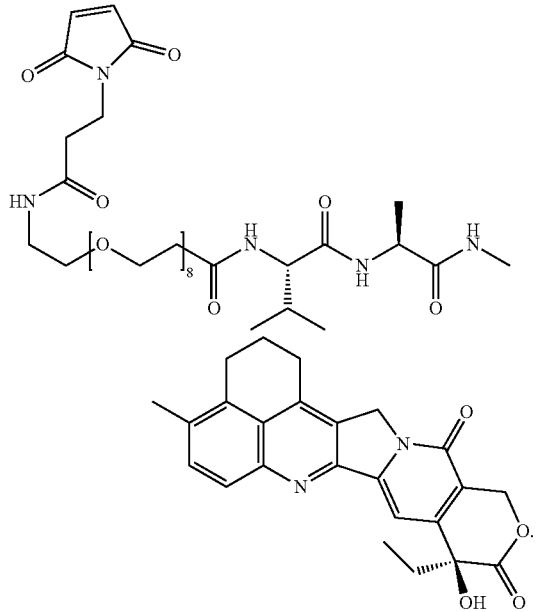

27. A conjugate according to claim 26 wherein the drug-antibody ratio is 6.

* * * * *